United States Patent
Maheshwari et al.

(10) Patent No.: US 9,150,844 B2
(45) Date of Patent: Oct. 6, 2015

(54) PROTEIN FUSION CONSTRUCTS POSSESSING THROMBOLYTIC AND ANTICOAGULANT PROPERTIES

(76) Inventors: Neeraj Maheshwari, Chandigarh (IN); Girish Sahni, Chandigarh (IN)

( * ) Notice: Subject to any disclaimer, the term of this patent is extended or adjusted under 35 U.S.C. 154(b) by 0 days.

(21) Appl. No.: 13/814,412

(22) PCT Filed: Aug. 5, 2011

(86) PCT No.: PCT/IB2011/001825
§ 371 (c)(1),
(2), (4) Date: Feb. 5, 2013

(87) PCT Pub. No.: WO2012/017310
PCT Pub. Date: Feb. 9, 2012

(65) Prior Publication Data
US 2013/0136731 A1    May 30, 2013

(30) Foreign Application Priority Data

Aug. 5, 2010 (IN) ............... 1845/DEL/2010

(51) Int. Cl.
| | | |
|---|---|---|
| C07K 14/315 | (2006.01) | |
| C07K 14/47 | (2006.01) | |
| C07K 19/00 | (2006.01) | |
| A61K 38/17 | (2006.01) | |
| C12N 9/48 | (2006.01) | |
| C12N 1/19 | (2006.01) | |
| C12N 1/21 | (2006.01) | |
| C12N 15/62 | (2006.01) | |
| A61K 38/16 | (2006.01) | |
| C12N 9/52 | (2006.01) | |
| C12N 9/72 | (2006.01) | |
| C07K 14/745 | (2006.01) | |
| A61K 38/00 | (2006.01) | |

(52) U.S. Cl.
CPC ............ *C12N 9/48* (2013.01); *A61K 38/166* (2013.01); *A61K 38/1709* (2013.01); *C07K 14/3153* (2013.01); *C07K 14/7455* (2013.01); *C12N 9/52* (2013.01); *C12N 9/6459* (2013.01); *C12Y 304/21069* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,256,770 A | | 10/1993 | Glaser et al. |
| 5,403,734 A | * | 4/1995 | Mulvihill et al. ............ 435/226 |
| 5,434,073 A | * | 7/1995 | Dawson et al. ............ 435/216 |
| 5,466,668 A | | 11/1995 | Glaser et al. |
| 5,516,659 A | | 5/1996 | Nii et al. |
| 5,830,700 A | * | 11/1998 | Irani ............ 435/69.7 |
| 6,133,011 A | | 10/2000 | Wnendt et al. |
| 7,622,457 B2 | | 11/2009 | Light et al. |
| 2003/0092627 A1 | | 5/2003 | Petersen et al. |
| 2003/0186883 A1 | | 10/2003 | Light et al. |
| 2005/0260598 A1 | | 11/2005 | Sahni et al. |
| 2008/0019985 A1 | | 1/2008 | Light et al. |
| 2008/0171852 A9 | | 7/2008 | Kim et al. |
| 2010/0034804 A1 | | 2/2010 | Kumar et al. |

FOREIGN PATENT DOCUMENTS

WO    WO 9010081 A1 *  9/1990

OTHER PUBLICATIONS

Wang et al., A fusion protein with improved thrombolytic effect and low bleeding risk, Thromb. Haemost., 2009 102, 1194-1203.*
Myers et al., Construction and characterization of a chimeric protein consisting of tissue-type plasminogen activator and the epidermal growth factor-like regions of thrombomodulin, Fibrinolysis, 1994, 8, 229-37.*
Blann et al., ABC of antithrombotic therapy, Brit. Med. J., 2002, 325, 762-765.*
Mundada et al., Structure-function analysis of the streptokinase amino terminus, J. Biol. Chem., 2003, 278, 24421-27.*
Smith et al., Fibrinolysis with acyl-enzymes, Nature, 1981, 290, 505-08.*
Wen et al., Human thrombomodulin, Biochemistry, 1987, 26, 4350-57.*
UniProt Accession No. P00779, 2010, www.uniprot.org.*
Banerjee et al., Streptokinase, Biotech. Adv., 2004, 22, 287-307.*
Hayashi, Further Localization of Binding Sites for Thrombin and Protein C in Human Thrombomodulin, Journal of Biological Chemistry, 265:33, pp. 20156-20159, 1990.
Novokhatny, Domain Structure and Domain-Domain Interactions of Recombinant Tissue Plasminogen Activator, The Journal of Biological Chemistry, 266:20, pp. 12994-13002, 1991.
Butenas et al., "Blood Coagulation," Biochemistry (Moscow), 67(1): 3-12, (2002) (Translated from Biokhimiya, vol. 67 (1): 5-15, 2002).
Dahlback et al., "The anticoagulant protein C pathway," FEBS Letters, 579: 3310-3316 (2005).
De Renzo et al., "Interaction of Streptokinase and Human Plasminogen," The Journal of Biological Chemistry, 242(10): 2428-2434 (1967).
Esmon et al., "Identification of an endothelial cell cofactor for thrombin-catalyzed activation of protein C," Proc. Natl. Acad. Sci. USA 78(4): 2249-2252 (1981).

(Continued)

*Primary Examiner* — Rebecca Prouty
*Assistant Examiner* — Todd M Epstein

(57) ABSTRACT

The present invention discloses novel hybrid proteins that have both plasminogen activator and anti-thrombotic properties, including clot specific action, that renders these as highly advantageous for the treatment of circulatory disorders involving fibrin clot formation due to underlying tissue damage in the blood vessels leading to myocardial infarction, strokes etc. Also disclosed are new proteins, and methods of obtaining the same, that help to dissolve blood clots by activating plasminogen in a plasmin or thrombin dependent manner and also inhibit both the activity and generation of thrombin through the intrinsic pathway of blood coagulation.

38 Claims, 21 Drawing Sheets

(56) References Cited

OTHER PUBLICATIONS

Esmon, "The Roles of Protein C and Thrombomodulin in the Regulation of Blood Coagulation," The Journal of Biological Chemistry, 264(9): 4743-4746 (1989).
Grella et al., "Activation of Human Plasminogen by Staphylokinase. Direct Evidence That Preformed Plasmin is Necessary for Activation to Occur," Blood 89: 1585-1589 (1997).
Haskel et al., "Prevention of arterial reocclusion after thrombolysis with recombinant lipoprotein-associated coagulation inhibitor," Circulation 84: 821-827 (1991).
Hogg et al., "Fibrin monomer protects thrombin from inactivation by heparin-antithrombin III: Implications for heparin efficacy," Proc. Natl. Acad. Sci. USA, 86: 3619-3623 (1989).
Kurosawa et al., "A 10-kDa Cyanogen Bromide Fragment from the Epidermal Growth Factor Homology Domain of Rabbit Thrombomodulin Contains the Primary Thrombin Binding Site," The Journal of Biological Chemistry, 263(13): 5993-5996 (1988).
Kurosawa et al., "Proteolytic Formation and Properties of Functional Domains of Thrombomodulin," The Journal of Biological Chemistry, 262(5): 2206-2212 (1987).
Lee et al., "Activation/inactivation of human factor V by plasmin," Blood, 73(1): 185-190 (1989).
Liu et al., "The Binding of Thrombin by Fibrin," The Journal of Biological Chemistry, 254(20): 10421-10425 (1979).
Lougheed et al., "Thrombin inhibition by cyclic peptides from thrombomodulin," Protein Science, 4: 773-780 (1995).
Loy et al., "Domain Interactions between Streptokinase and Human Plasminogen," Biochemistry 40: 14686-14695 (2001).
Malke et al., "Streptokinase: Cloning, expression, and excretion by Escherichia coli," Proc. Nati. Acad. Sci. Usa, 81: 3557-3561 (1984).
Mehta et al., "Bridge-Overlap-Extension PCR Method for Constructing Chimeric Genes," BioTechniques 26:1082-1086 (1999).
Meininger et al., "Synthesis, activity, and preliminary structure of the fourth EGF-like domain of thrombomodulin," Protein Science, 4: 1683-1695 (1999).
Nagendra Nath Reddy et al., "Mechanism of Activation of Human Plasminogen by Streptokinase: Presence of active center is streptokinase-Plasminogen Complex," The Journal of Biological Chemistry, 247:1683-1691 (1972).
Norden et al., "Increasing gene dosage greatly enhances recombinant expression of aquaporins in *Pichia pastoris*," BMC Biotechnology, 11:47 (2011).
Ohman et al., "Consequences of reocclusion after successful reperfusion therapy in acute myocardial infarction. TAMI Study Group," Circulation 82:781-791 (1990).
Parry et al., "Molecular mechanisms of plasminogen activation: bacterial cofactors provide clues," TIBS 25: 53-59 (2000).
Ramchuran et al., "The methylotrophic yeast *Pichia pastoris* as a host for the expression and production of thermostable xylanase from the bacterium *Rhodothermus marinus*," FEMS Yeast Research 5: 839-850 (2005).
Sazonova et al., "The Mechanism of a Bacterial Plasminogen Activator Intermediate between Streptokinase and Staphylokinase," The Journal of Biological Chemistry, 276(16): 12609-12613 (2001).
Schaller et al., "The plasmin-antiplasmin system: structural and functional aspects," Cell. Mol. Life Sci., 68:785-801 (2011).
Sharma et al., "Preparation of Electro-Competent *E. coli* Using Salt-Free Growth Medium," BioTechniques 20:42-44 (1996).
Stearns et al., "Microthrombomodulin. Residues 310-486 from the epidermal growth factor precursor homology domain of thrombomodulin will accelerate protein C activation," The Journal of Biological Chemistry, 264(6): 3352-3356 (1989).
Szemraj et al., "A new recombinant thrombolytic and antithrombotic agent with higher fibrin affinity—a staphylokinase variant. 1. in vitro study," Journal of Thrombosis and Haemostasis, 3(10): 2156-2165 (2005).
Vali et al., "Localization of the Binding Site on Fibrin for the Secondary Binding Site of Thrombin," Biochemistry, 27: 1956-1963 (1988).
Wang et al., "Crystal Structure of the Catalytic Domain of Human Plasmin Complexed with Streptokinase," Science, 281: 1662-1665 (1998).
Wang et al., "Crystal structure of streptokinase beta-domain," FEBS Letters, 459: 85-89 (1999).
Wang et al., "Two-Stage PCR Protocol Allowing Introduction of Multiple Mutations, Deletions and Insertions Using QuikChange Site-Directed Mutagenesis," BioTechniques 26:680-682 (1999).
Weitz et al., "Clot-bound thrombin is protected from inhibition by heparin-antithrombin III but is susceptible to inactivation by antithrombin III-independent inhibitors," J Clin Invest, 86(2): 385-391 (1990).
Weitz et al., "Thrombin Binds to Soluble Fibrin Degradation Products Where it is Protected From Inhibition by Heparin-Antithrombin but Susceptible to Inactivation by Antithrombin-Independent Inhibitors," Circulation 97: 544-552 (1998).
Wohl et al., "Steady State Kinetics of Activation of Human and Bovine Plasminogens by Streptokinase and Its Equimolar Complexes with Various Activated Forms of Human Plasminogen," The Journal of Biological Chemistry, 253 (5): 1402-1407 (1978).
Yadav et al., "Probing the primary structural determinants of streptokinase inter-domain linkers by site-specific substitution and deletion mutagenesis," Biochimica et Biophysica Acta, 1804: 1730-1737 (2010).
Bajaj et al., "Activation of Human Plasminogen by Equimolar Levels of Streptokinase," The Journal of Biological Chemistry, 252(2): 492-498 (1977).
Boxrud et al., "Resolution of Conformational Activation in the Kinetic Mechanism of Plasminogen Activation by Streptokinase," The Journal of Biological Chemistry, 279(35): 36633-36641 (2004).
Buck et al., "Interaction of streptokinase and human plasminogen. V. Studies on the nature and mechanism of formation of the enzymatic site of the activator complex," The Journal of Biological Chemistry, 243(13):3648-3654 (1968).
Grignani, Guido, et al., "Current Concepts in Coronary Thrombolysis", Haematologica; 79:475-482 (1994).
Gardell, Stephen J., "The Search for the Ideal Thrombolytic Agent: Maximize the Benefit and Minimize the Risk", Toxicologic Pathology 21:190-198 (1993).

* cited by examiner

Figure 1.
Schematic Representation of Various Constructs
(A)
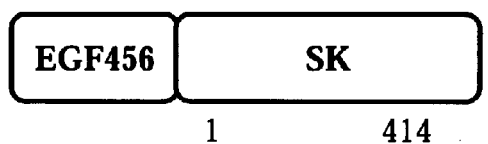
Fig. 1(A)
(B)
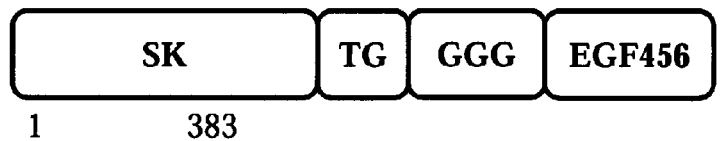
Fig. 1(B)
(C)
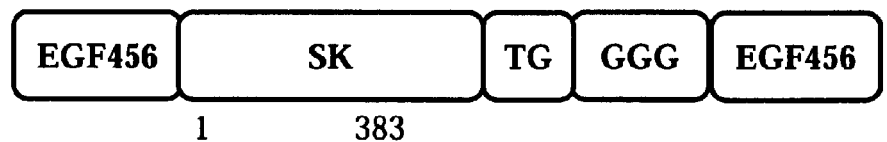
Fig. 1(C)
(D)
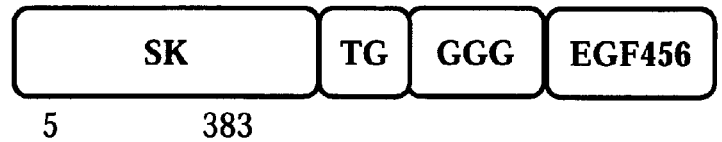
Fig. 1(D)

Schematic Representation of Various Constructs (cont,d)

(E)

(F)

(G)

(H)

Schematic Representation of Various Constructs

(I) | EGF 456 | Finger domain | egf | kringle1 | kringle2 | CD | EGF456 |

Fig. 1(I)

(J) | Finger domain | egf | kringle1 | kringle2 | CD | EGF 456 |

Fig. 1(J)

(K) | EGF 456 | Finger domain | egf | kringle1 | kringle2 | CD |

Fig. 1(K)

Schematic Representation of Various Constructs (Fig. 1, cont,d)

(L)

(M)

(N)

(O)

(P)

Schematic representation of various fusion gene Constructs (cont,d)

(Q)

(R)

(S)

(T)

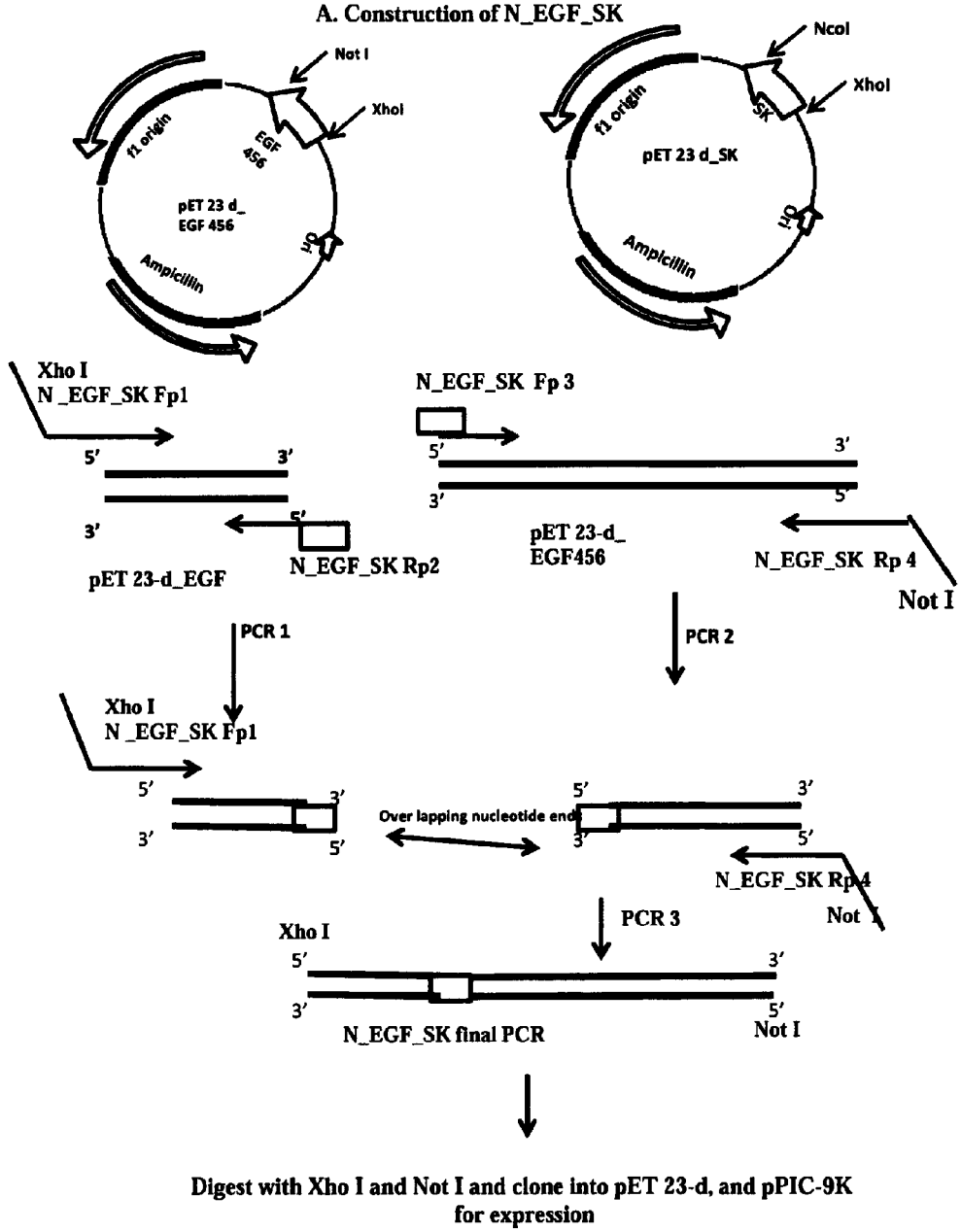

Fig. 2 B. Construction of SK_EGF
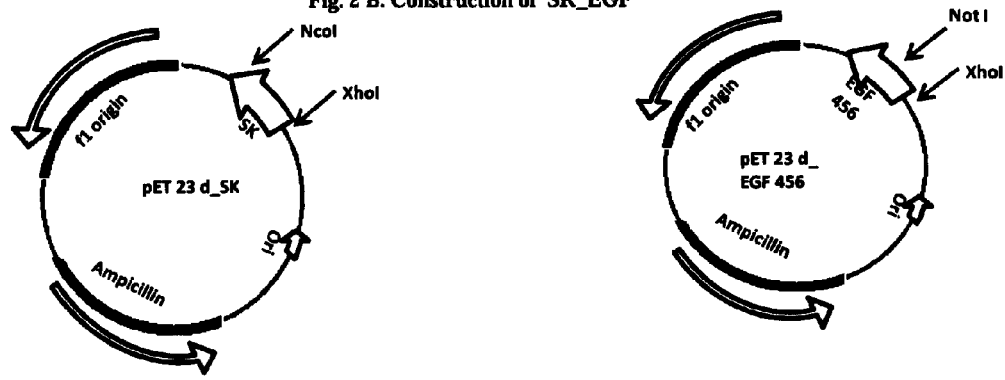
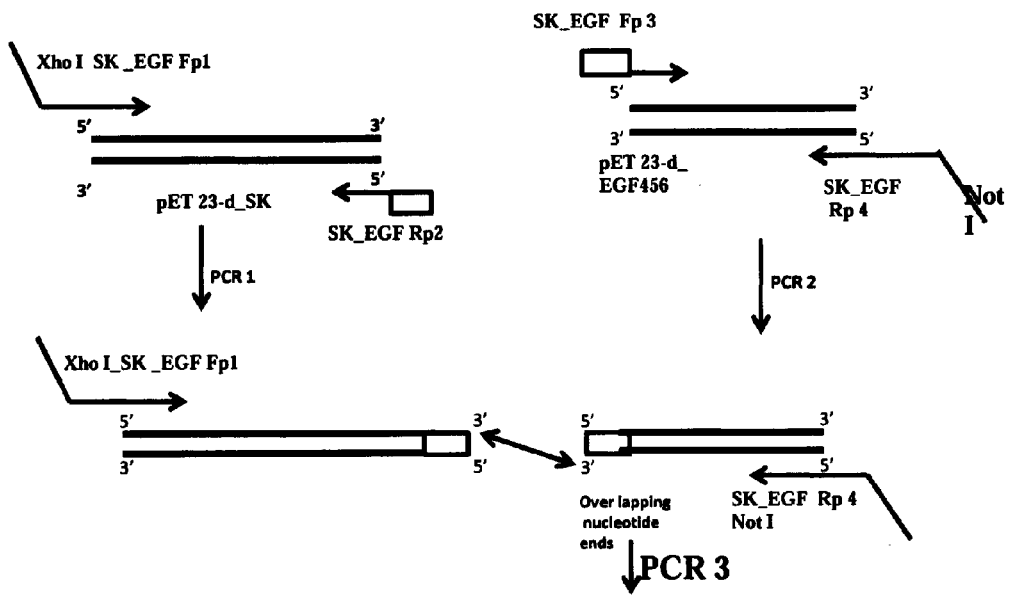
Digest with Xho I and Not I and cloned into pET 23-d and pPIC-9K
for expression

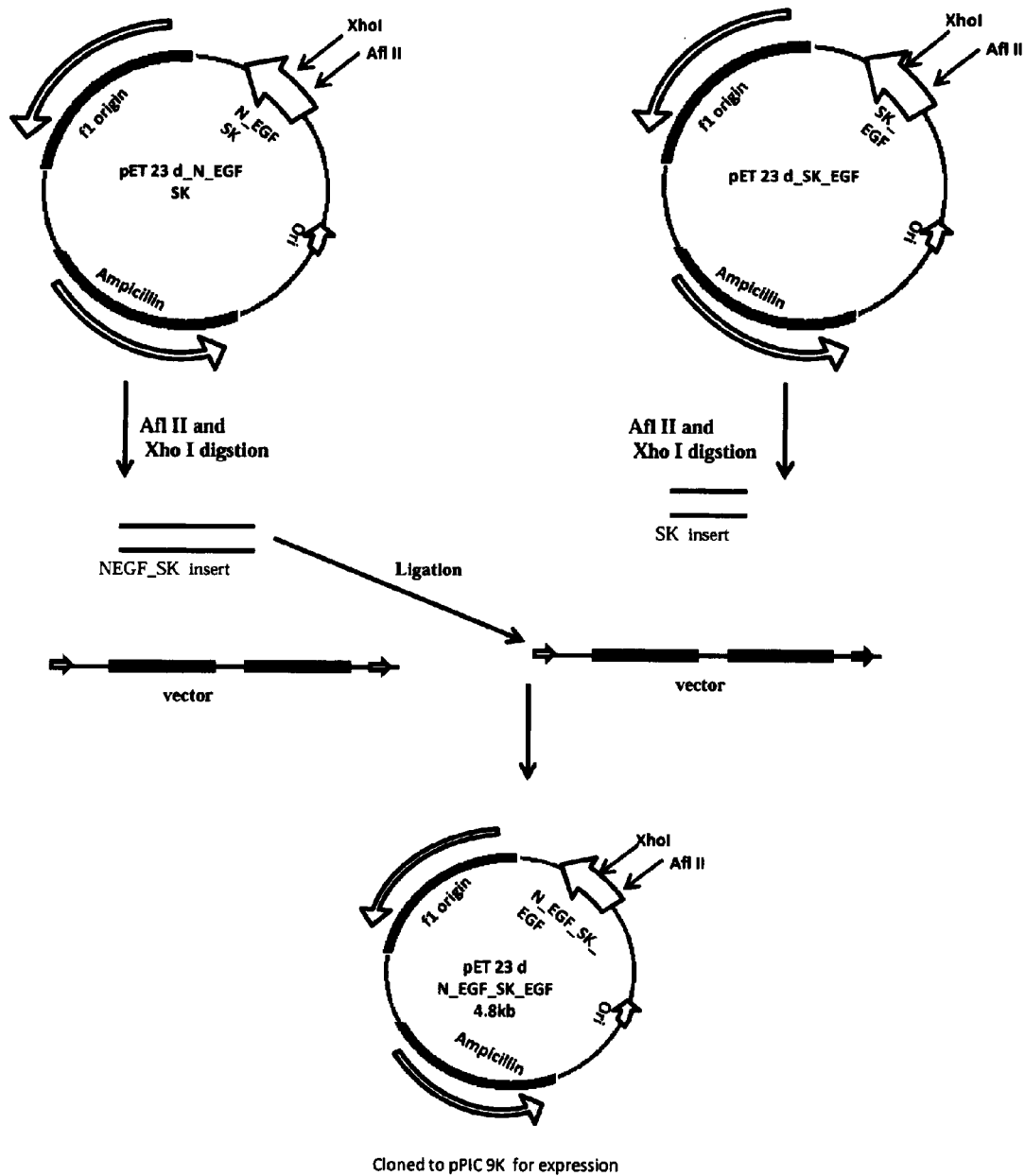

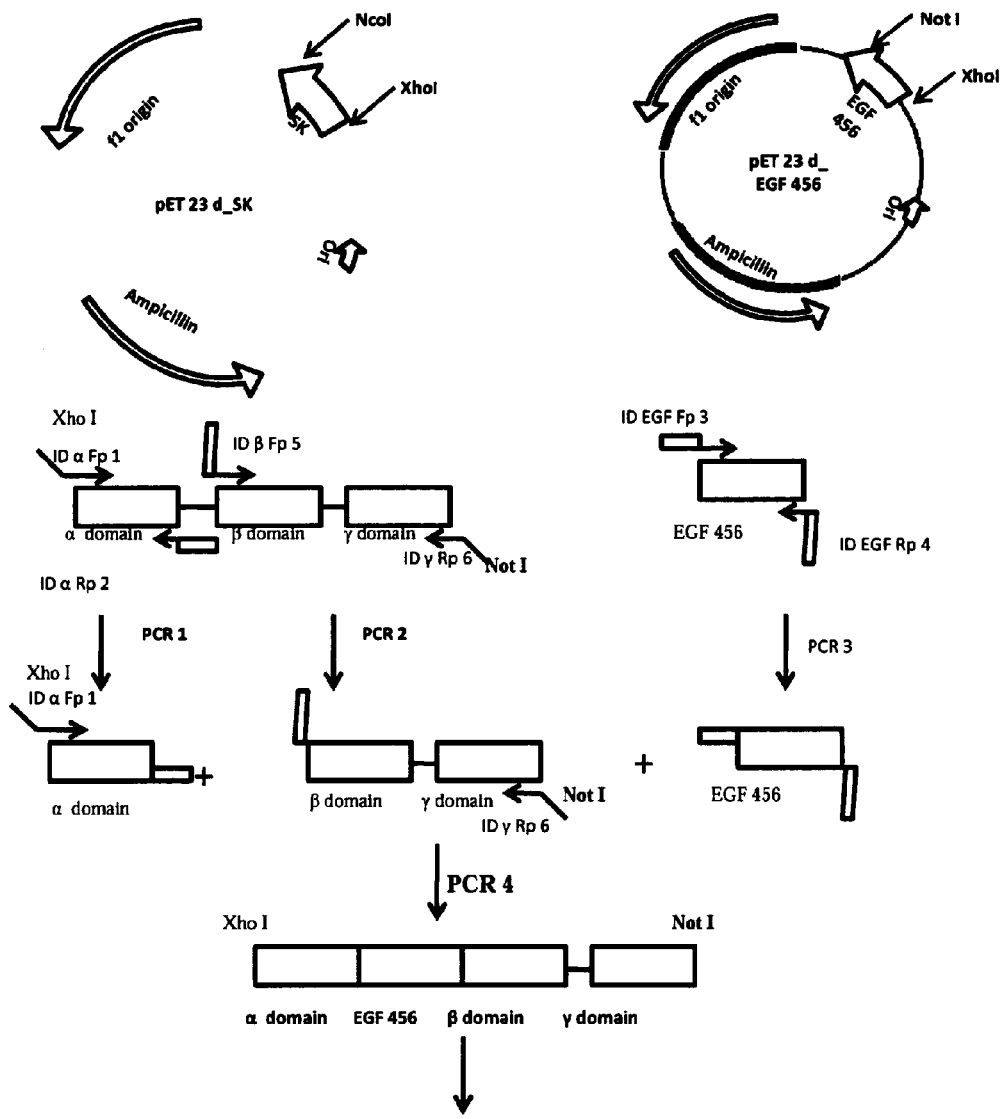

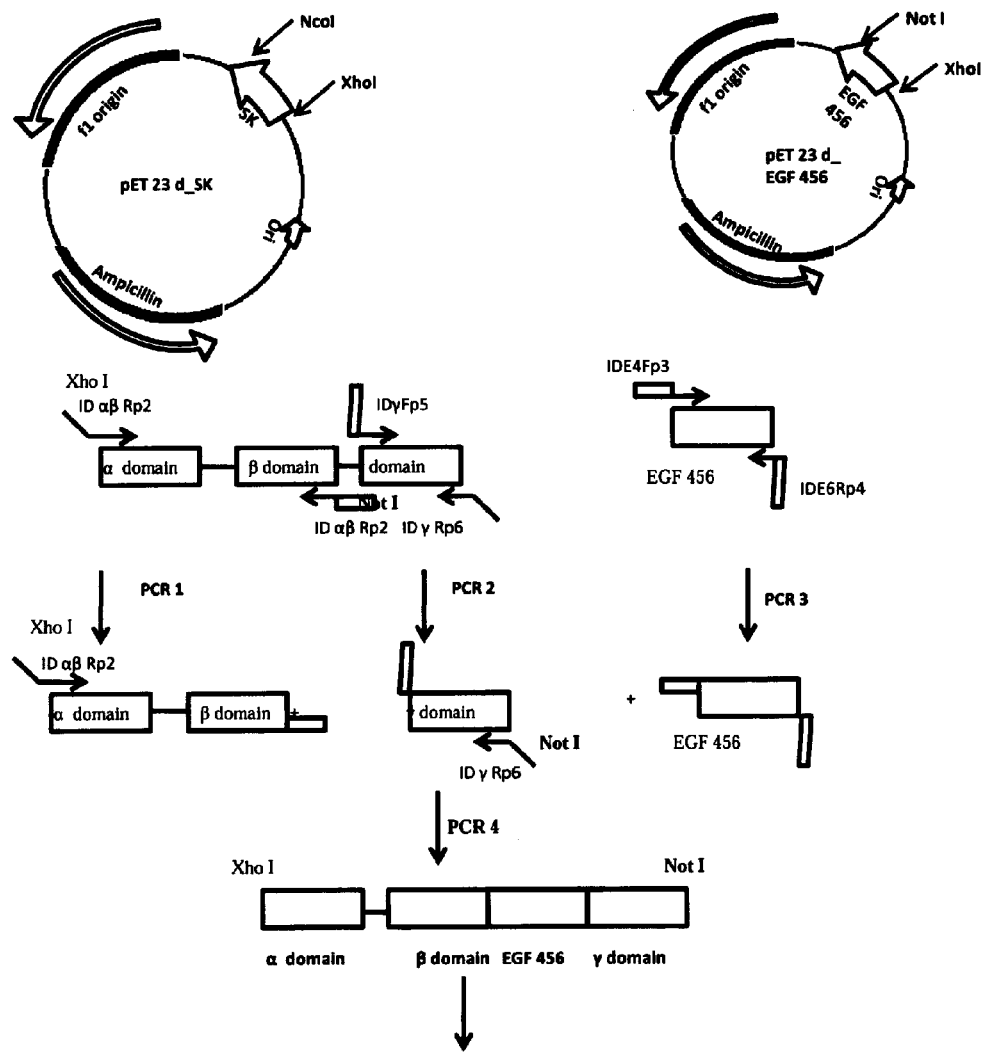
Fig. 2 E. Interdomain SK _ EGF (where EGF456 introduced between the junction of β and γ domain)
Digest with Xho I and Not I and ligated wnto pET-23-d and pPIC-9K

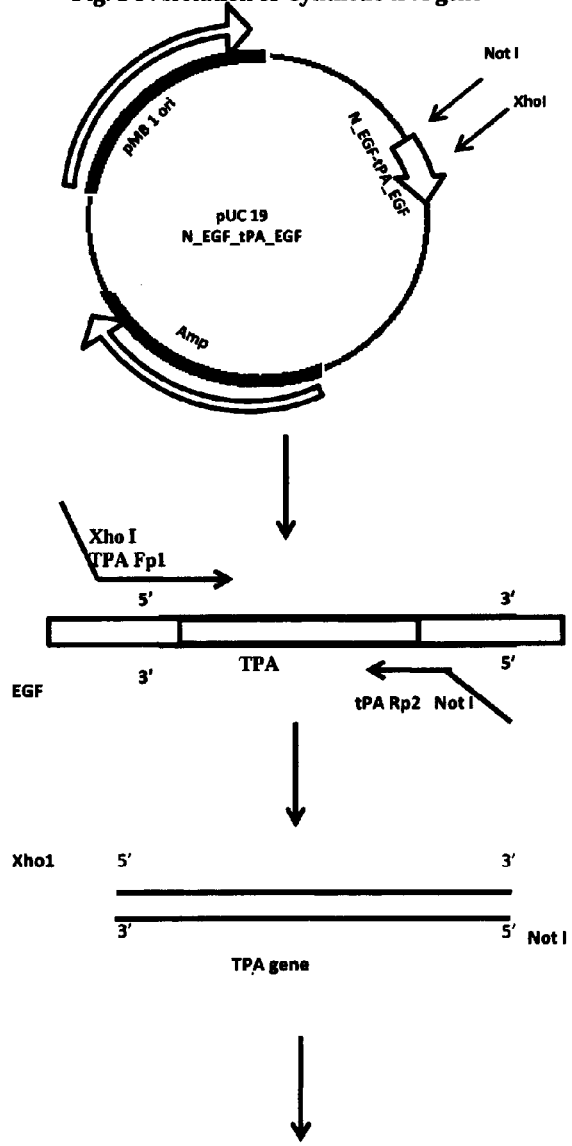
Fig. 2 F. Isolation of synthetic tPA gene
tPA gene (synthetically prepared and cloned in pUC 19 vector) was digested with Xho I and Not I and cloned into pET23-d, and pPIC-9K for expression

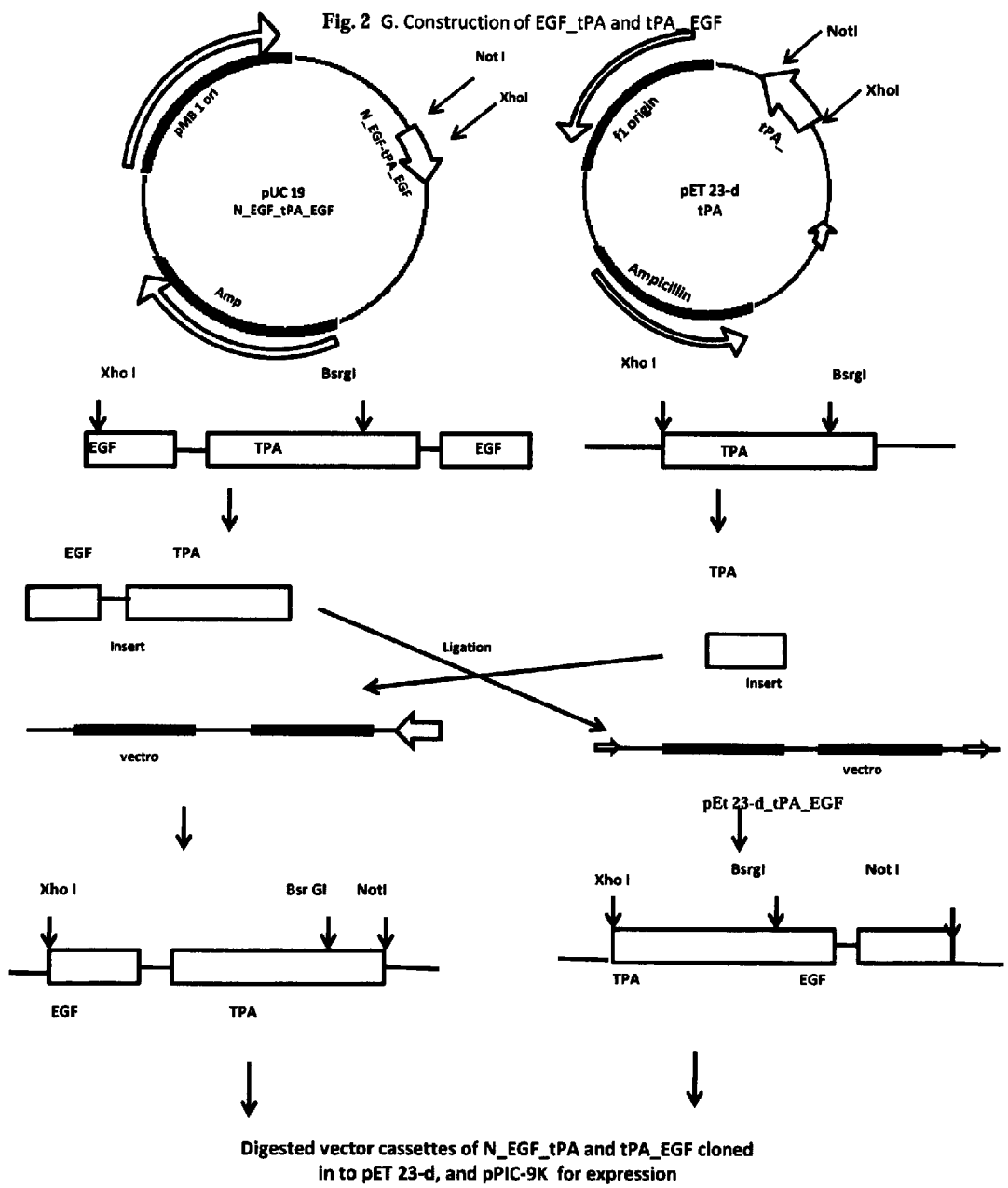

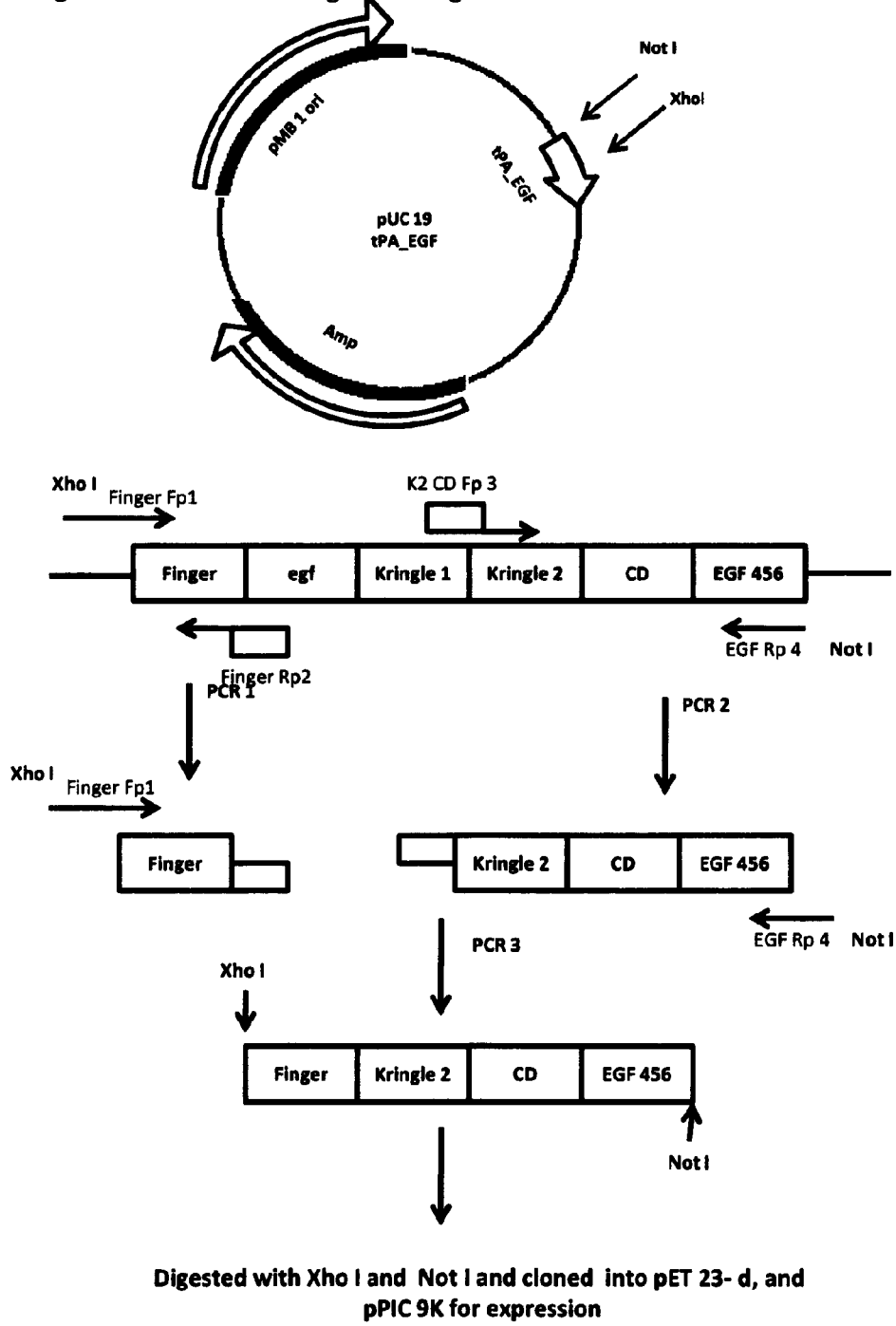
Fig. 2 H. Construction of egf and kringle 1 deleted tPA_EGF construct
Digested with Xho I and Not I and cloned into pET 23- d, and pPIC 9K for expression

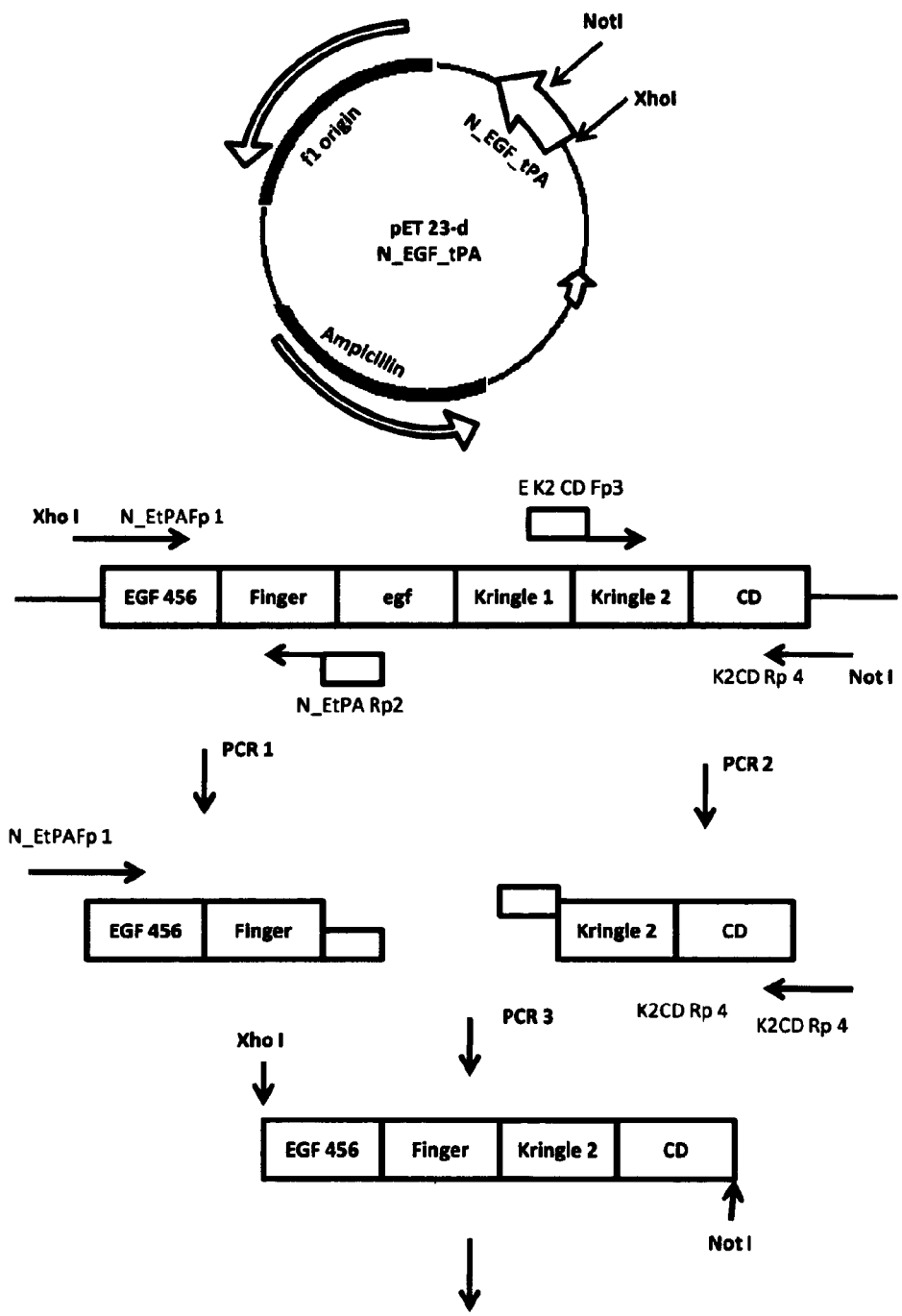
Fig. 2 I. Construction of egf and kringle 1 deleted N_EGF_tPA construct
Digested with Xho I and Not I and cloned into pET 23- d, and pPIC 9K for expression

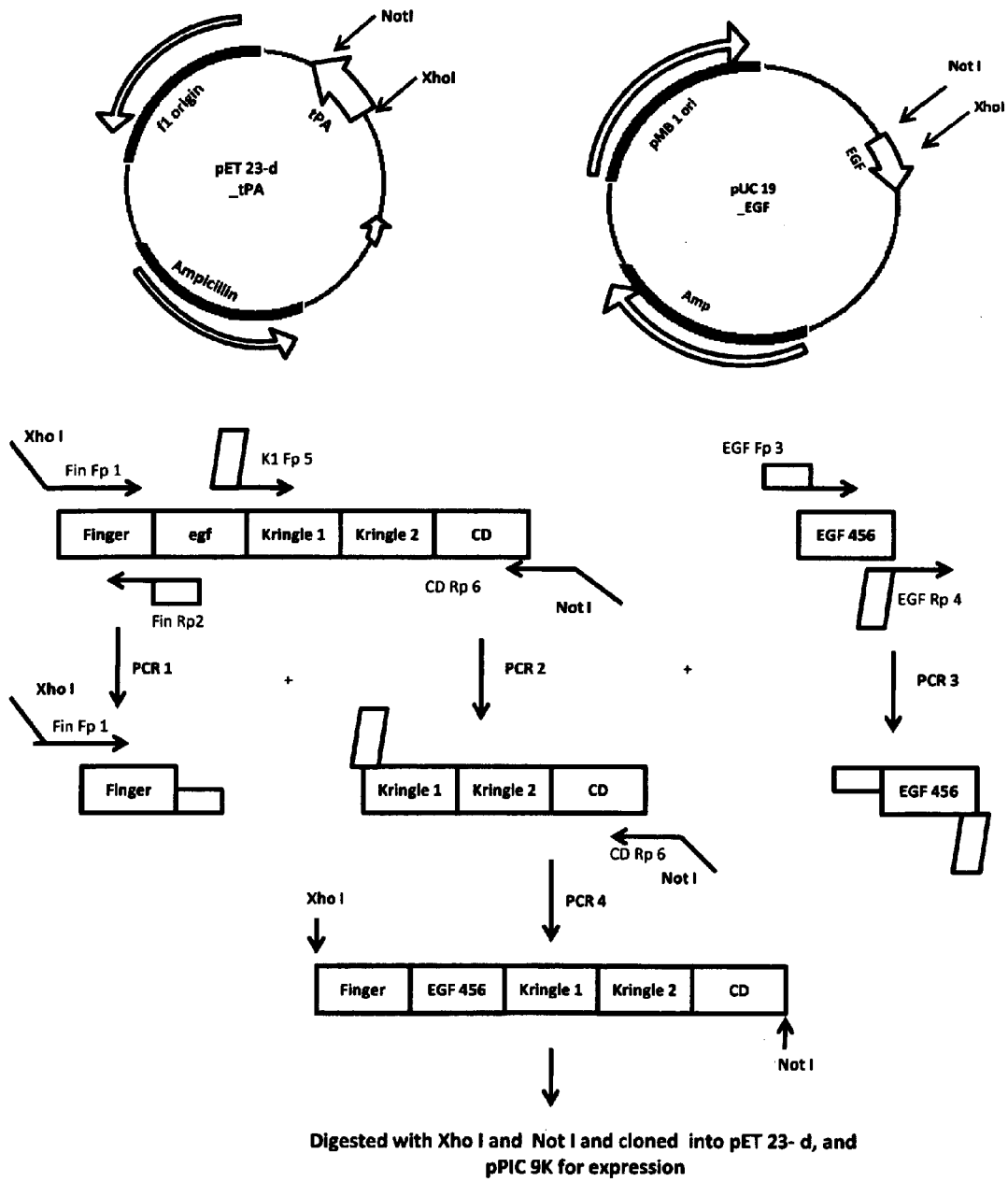
Fig. 2 J. Interdomain EGF _tPA (where egf of tPA is repalced with EGF 456)

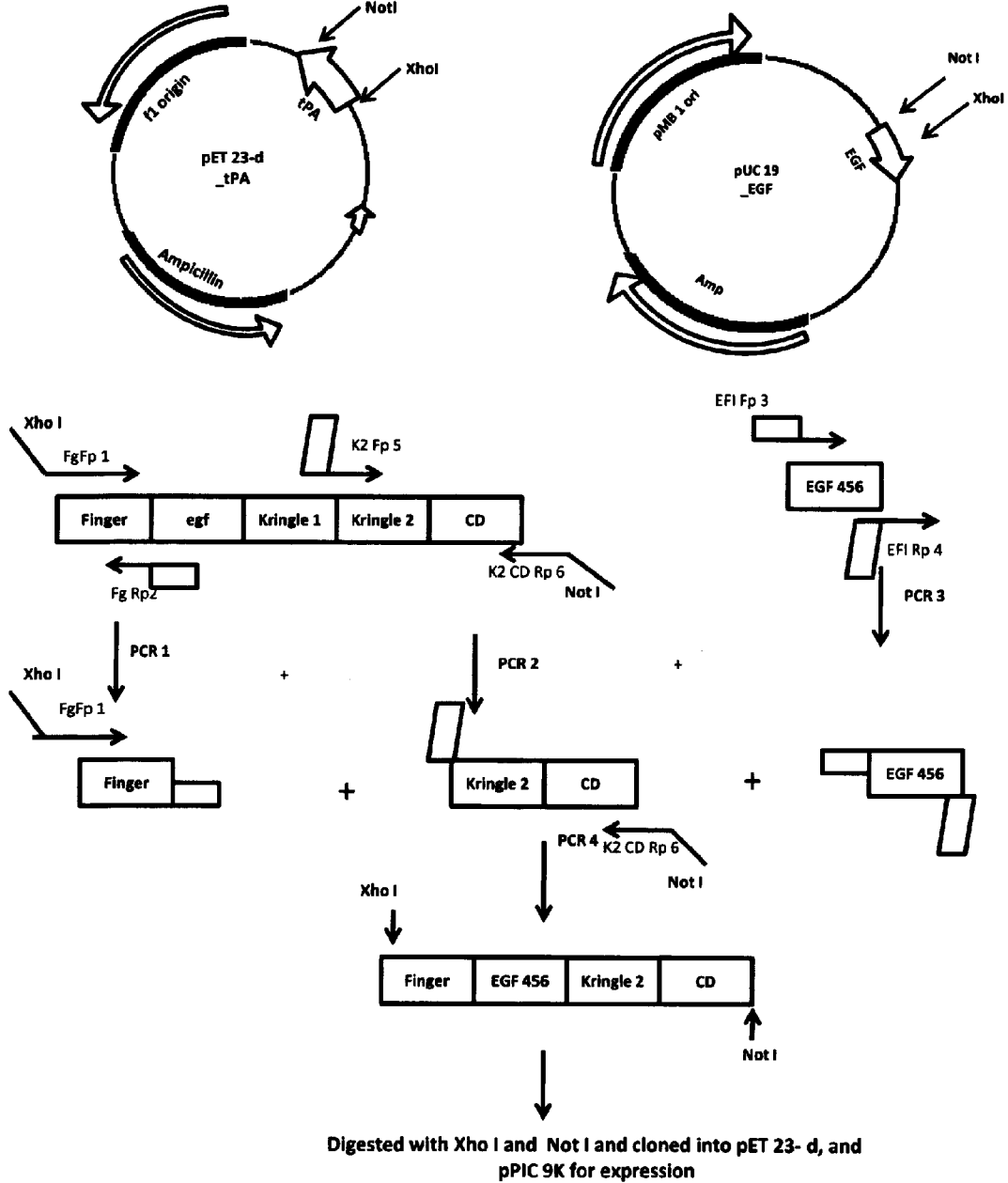

SEQUENCE LISTING

```
<160> NUMBER OF SEQ ID NOS: 137

<210> SEQ ID NO 1
<211> LENGTH: 1245
<212> TYPE: DNA
<213> ORGANISM: Artificial Sequence
<220> FEATURE:
<223> OTHER INFORMATION: Streptococcus equisimilis

<400> SEQUENCE: 1
attgctggac ctgagtggct gctagaccgt ccatctgtca acaacagcca attagttgtt      60
agcgttgctg gtactgttga ggggacgaat caagacatta gtcttaaatt ttttgaaatc     120
gatctaacat cacgacctgc tcatggagga aagacagagc aaggcttaag tccaaaatca     180
aaaccatttg ctactgatag tggcgcgatg tcacataaac ttgagaaagc tgacttacta     240
aaggctattc aagaacaatt gatcgctaac gtccacagta acgacgacta ctttgaggtc     300
attgattttg caagcgatgc aaccattact gatcgaaacg gcaaggtcta ctttgctgac     360
aaagatggtt cggtaacctt gccgacccaa cctgtccaag aattttttgct aagcggacat     420 gtgcgcgtta gaccatataa agaaaaacca atacaaaacc aagcgaaatc tgttgatgtg     480
gaatatactg tacagtttac tcccttaaac cctgatgacg atttcagacc aggtctcaaa     540
gatactaagc tattgaaaac actagctatc ggtgacacca tcacatctca agaattacta     600
gctcaagcac aaagcatttt aaacaaaaac cacccaggct atacgattta tgaacgtgac     660
tcctcaatcg tcactcatga caatgacatt ttccgtacga ttttaccaat ggatcaagag     720
tttacttacc gtgttaaaaa tcgggaacaa gcttatagga tcaataaaaa atctggtctg     780
aatgaagaaa taaacaacac tgacctgatc tctgagaaat attcgtcct taaaaagggg     840 gaaaagccgt atgatccctt tgatcgcagt cacttgaaac tgttcaccat caaatacgtt     900
gatgtcgata ccaacgaatt gctaaaagt gagcagctct taacagctag cgaacgtaac     960
ttagacttca gagatttata cgatcctcgt gataaggcta aactactcta caacaatctc    1020
gatgcttttg gtattatgga ctatacctta actgaaaag tagaggataa tcacgatgac    1080
accaaccgta tcataaccgt ttatatgggc aagcgacccg aaggagagaa tgctagctat    1140
catttagcct atgataaaga tcgttatacc gaagaagaac gagaagttta cagctacctg    1200
cgttatacag ggacacctat acctgataac cctaacgaca aataa                    1245

<210> SEQ ID NO 2
<211> LENGTH: 354
<212> TYPE: DNA
```

<213> ORGANISM: Artificial Sequence
<220> FEATURE:
<223> OTHER INFORMATION: Homo sapiens

<400> SEQUENCE: 2

```
gtggacccgt gcttcagagc caactgcgag taccagtgcc agccccctgaa ccaaactagc      60
tacctctgcg tctgcgccga gggcttcgcg cccattcccc acgagccgca caggtgccag     120
atgttttgca accagactgc ctgtccagcc gactgcgacc ccaacaccca ggctagctgt     180
gagtgccctg aaggctacat cctggacgac ggtttcatct gcacggacat cgacgagtgc     240
gaaaacggcg gcttctgctc cggggtgtgc acaacctcc ccgtaccttt cgagtgcatc     300
tgcgggcccg actcggccct tgcccgccac attggcaccg actgtgactc cggc           354
```

<210> SEQ ID NO 3
<211> LENGTH: 1605
<212> TYPE: DNA
<213> ORGANISM: Artificial Sequence
<220> FEATURE:
<223> OTHER INFORMATION: Interdoamin SK_EGF between alpha and Beta

<400> SEQUENCE: 3

```
attgctggac ctgagtggct gctagaccgt ccatctgtca caacagcca attagttgtt       60
agcgttgctg gtactgttga ggggacgaat caagacatta gtcttaaatt ttttgaaatc     120
gatctaacat cacgacctgc tcatggagga agacagagc aaggcttaag tccaaaatca     180
aaaccatttg ctactgatag tggcgcgatg tcacataaac ttgagaaagc tgacttacta     240
aaggctattc aagaacaatt gatcgctaac gtccacagta acgacgacta ctttgaggtc     300
attgattttg caagcgatgc aaccattact gatcgaaacg gcaaggtcta ctttgctgac     360
aaagatggtt cggtaacctt gccgacccaa cctgtccaag aatttttgct aagcggacat     420
gtgcgcgtta gaccatataa agaaaaacca atacaaaacc aagcgaaatc tgagcccgtg     480
gacccgtgct tcagagccaa ctgcgagtac cagtgccagc ccctgaacca aactagctac     540
ctctgcgtct gcgccgaggg cttcgcgccc attcccacg agccgcacag gtgccagatg     600
ttttgcaacc agactgcctg tccagccgac tgcgacccca cacccaggc tagctgtgag     660
tgccctgaag gctacatcct ggacgacggt ttcatctgca cggacatcga cgagtgcgaa     720
aacggcggct tctgctccgg ggtgtgccac aacctcccg taccttcga gtgcatctgc     780
gggcccgact cggcccttgc cgccacatt ggcactgact gtgactccgg cgttgatgtg     840
gaatatactg tacagtttac tcccttaaac cctgatgacg atttcagacc aggtctcaaa     900
gatactaagc tattgaaaac actagctatc ggtgacacca tcacatctca agaattacta     960
gctcaagcac aaagcatttt aaacaaaaac cacccaggct atacgattta tgaacgtgac    1020
tcctcaatcg tcactcatga caatgacatt ttccgtacga ttttaccaat ggatcaagag    1080
tttacttacc gtgttaaaaa tcgggaacaa gcttatagga tcaataaaaa atctggtctg    1140
aatgaagaaa taaacaacac tgacctgatc tctgagaaat attacgtcct aaaaaagggg    1200
gaaaagccgt atgatccctt tgatcgcagt cacttgaaac tgttcaccat caaatacgtt    1260
gatgtcgata ccaacgaatt gctaaaaagt gagcagctct taacagctag cgaacgtaac    1320
ttagacttca gagatttata cgatcctcgt gataaggcta actactcta caacaatctc    1380
gatgcttttg gtattatgga ctataccta actggaaaag tagaggataa tcacgatgac    1440
accaaccgta tcataaccgt ttatatgggc aagcgacccg aaggagagaa tgctagctat    1500
catttagcct atgataaaga tcgttatacc gaagaagaac gagaagttta cagctacctg    1560
```
cgttatacag ggacacctat acctgataac cctaacgaca aataa                     1605

<210> SEQ ID NO 4
<211> LENGTH: 1599
<212> TYPE: DNA
<213> ORGANISM: Artificial Sequence
<220> FEATURE:
<223> OTHER INFORMATION: N_EGF_SK, fusion at the N-terminal of SK

<400> SEQUENCE: 4

```
gtggacccgt gcttcagagc caactgcgag taccagtgcc agcccctgaa ccaaactagc       60
tacctctgcg tctgcgccga gggcttcgcg cccattcccc acgagccgca caggtgccag      120
atgttttgca accagactgc ctgtccagcc gactgcgacc ccaacaccca ggctagctgt      180
gagtgccctg aaggctacat cctggacgac ggtttcatct gcacggacat cgacgagtgc      240
gaaaacggcg gcttctgctc cggggtgtgc cacaacctcc ccggtacctt cgagtgcatc      300
tgcgggcccg actcggccct tgcccgccac attggcaccg actgtgactc cggcattgct      360
ggacctgagt ggctgctaga ccgtccatct gtcaacaaca gccaattagt tgttagcgtt      420
gctggtactt ttgagggac gaatcaagac attagtctta aattttttga aatcgatcta      480
acatcacgac ctgctcatgg aggaaagaca gagcaaggct taagtccaaa atcaaaacca      540
tttgctactg atagtggcgc gatgtcacat aaacttgaga agctgactt actaaaggct      600
attcaagaac aattgatcgc taacgtccac agtaacgacg actactttga ggtcattgat      660
tttgcaagcg atgcaaccat tactgatcga acggcaagg tctactttgc tgacaaagat      720
ggttcggtaa ccttgccgac ccaacctgtc caagaatttt tgctaagcgg acatgtgcgc      780
gttagaccat ataagaaaa accaatacaa aaccaagcga atctgttga tgtggaatat      840
actgtacagt ttactcccct taaaccctgat gacgatttca gaccaggtct caaagatact      900
aagctattga aaacactagc tatcggtgac accatcacat ctcaagaatt actagctcaa      960
gcacaaagca ttttaaacaa aaaccaccca ggctatacga tttatgaacg tgactcctca     1020
atcgtcactc atgacaatga cattttccgt acgattttac caatggatca agagtttact     1080
taccgtgtta aaaatcggga acaagcttat aggatcaata aaaaatctgg tctgaatgaa     1140
gaaataaaca acactgacct gatctctgag aaatattacg tccttaaaaa aggggaaaag     1200
ccgtatgatc cctttgatcg cagtcacttg aaactgttca ccatcaaata cgttgatgtc     1260
gataccaacg aattgctaaa agtgagcag ctcttaacag ctagcgaacg taacttagac     1320
ttcagagatt tatacgatcc tcgtgataag gctaaactac tctacaacaa tctcgatgct     1380
tttggtatta tggactatac cttaactgga aaagtagagg ataatcacga tgacaccaac     1440
cgtatcataa ccgtttatat gggcaagcga cccgaaggag agaatgctag ctatcattta     1500
gcctatgata agatcgtta taccgaagaa gaacgagaag tttacagcta cctgcgttat     1560
acagggacac ctatacctga taaccctaac gacaaataa                            1599
```

<210> SEQ ID NO 5
<211> LENGTH: 1245
<212> TYPE: DNA
<213> ORGANISM: Artificial Sequence
<220> FEATURE:
<223> OTHER INFORMATION: INTERDOMAIN BETA AND GAMMA

<400> SEQUENCE: 5

```
attgctggac ctgagtggct gctagaccgt ccatctgtca acaacagcca attagttgtt       60
```

```
agcgttgctg gtactgttga ggggacgaat caagacatta gtcttaaatt tttgaaatc    120
gatctaacat cacgacctgc tcatggagga agacagagc aaggcttaag tccaaaatca    180
aaaccatttg ctactgatag tggcgcgatg tcacataaac ttgagaaagc tgacttacta   240
aaggctattc aagaacaatt gatcgctaac gtccacagta acgacgacta ctttgaggtc   300
attgattttg caagcgatgc aaccattact gatcgaaacg gcaaggtcta ctttgctgac   360
aaagatggtt cggtaacctt gccgacccaa cctgtccaag aattttttgct aagcggacat  420
gtgcgcgtta gaccatataa agaaaaacca atacaaaacc aagcgaaatc tgttgatgtg   480
gaatatactg tacagtttac tccctttaaac cctgatgacg atttcagacc aggtctcaaa  540
gatactaagc tattgaaaac actagctatc ggtgacacca tcacatctca agaattacta   600
gctcaagcac aaagcatttt aaacaaaaac cacccaggct atacgattta tgaacgtgac   660
tcctcaatcg tcactcatga caatgacatt ttccgtacga ttttaccaat ggatcaagag   720
ttacttacc gtgttaaaaa tcgggaacaa gcttatagga tcaataaaaa atctggtctg    780
aatgaagaaa taacaacac tgacctgatc tctgagaaat attacgtcct aaaaaaggg    840
gaaaagccgt atgatccctt tgatcgcagt cacttgaaaac tgttcaccat caaatacgtt   900
gatgtcgata ccaacgaatt gctaaaaagt gagcagctct taacagctag cgaacgtaac   960
ttagacttca gagatttata cgatcctcgt gataaggcta aactactcta caacaatctc  1020
gatgcttttg gtattatgga ctataccttta actggaaaag tagaggataa tcacgatgac 1080
accaaccgta tcataaccgt ttatatgggc aagcgacccg aaggagagaa tgctagctat  1140
catttagcct atgataaaga tcgttatacc gaagaagaac gagaagttta cagctacctg  1200
cgttatacag ggacacctat acctgataac cctaacgaca aataa                    1245

<210> SEQ ID NO 6
<211> LENGTH: 1530
<212> TYPE: DNA
<213> ORGANISM: Artificial Sequence
<220> FEATURE:
<223> OTHER INFORMATION: SK_EGF, Fusion at the C-terminal of SK

<400> SEQUENCE: 6
attgctggac ctgagtggct gctagaccgt ccatctgtca acaacagcca attagttgtt    60
agcgttgctg gtactgttga ggggacgaat caagacatta gtcttaaatt tttgaaatc    120
gatctaacat cacgacctgc tcatggagga agacagagc aaggcttaag tccaaaatca   180
aaaccatttg ctactgatag tggcgcgatg tcacataaac ttgagaaagc tgacttacta   240
aaggctattc aagaacaatt gatcgctaac gtccacagta acgacgacta ctttgaggtc   300
attgattttg caagcgatgc aaccattact gatcgaaacg gcaaggtcta ctttgctgac   360
aaagatggtt cggtaacctt gccgacccaa cctgtccaag aattttttgct aagcggacat  420
gtgcgcgtta gaccatataa agaaaaacca atacaaaacc aagcgaaatc tgttgatgtg   480
gaatatactg tacagtttac tccctttaaac cctgatgacg atttcagacc aggtctcaaa  540
gatactaagc tattgaaaac actagctatc ggtgacacca tcacatctca agaattacta   600
gctcaagcac aaagcatttt aaacaaaaac cacccaggct atacgattta tgaacgtgac   660
tcctcaatcg tcactcatga caatgacatt ttccgtacga ttttaccaat ggatcaagag   720
ttacttacc gtgttaaaaa tcgggaacaa gcttatagga tcaataaaaa atctggtctg    780
aatgaagaaa taacaacac tgacctgatc tctgagaaat attacgtcct aaaaaaggg    840
gaaaagccgt atgatccctt tgatcgcagt cacttgaaaac tgttcaccat caaatacgtt   900
```

```
gatgtcgata ccaacgaatt gctaaaaagt gagcagctct taacagctag cgaacgtaac    960
ttagacttca gagatttata cgatcctcgt gataaggcta aactactcta caacaatctc   1020
gatgcttttg gtattatgga ctataccttac actggaaaag tagaggataa tcacgatgac   1080
accaaccgta tcataaccgt ttatatgggc aagcgacccg aaggagagaa tgctagctat   1140
catttagccg gtggcggaca agctcaacaa attgtggtgg acccgtgctt cagagccaac   1200
tgcgagtacc agtgccagcc cctgaaccaa actagctacc tctgcgtctg cgccgagggc   1260
ttcgcgccca ttccccacga gccgcacagg tgccagatgt tttgcaacca gactgcctgt   1320
ccagccgact gcgaccccaa cacccaggct agctgtgagt gccctgaagg ctacatcctg   1380
gacgacggtt tcatctgcac ggacatcgac gagtgcgaaa acggcggctt ctgctccggg   1440
gtgtgccaca acctccccgg taccttcgag tgcatctgcg ggcccgactc ggcccttgcc   1500
cgccacattg gcaccgactg tgactccggc                                    1530
```

<210> SEQ ID NO 7
<211> LENGTH: 1884
<212> TYPE: DNA
<213> ORGANISM: Artificial Sequence
<220> FEATURE:
<223> OTHER INFORMATION: N_EGF_SK_EGF, fusion at the N and C-terminal
      of SK

<400> SEQUENCE: 7

```
gtggacccgt gcttcagagc caactgcgag taccagtgcc agcccctgaa ccaaactagc     60
tacctctgcg tctgcgccga gggcttcgcg cccattcccc acgagccgca caggtgccag    120
atgttttgca accagactgc ctgtccagcc gactgcgacc ccaacaccca ggctagctgt    180
gagtgccctg aaggctacat cctggacgac ggtttcatct gcacggacat cgacgagtgc    240
gaaaacggcg gcttctgctc cggggtgtgc cacaacctcc ccggtaccttcgagtgcatc    300 tgcgggcccg actcggccct tgcccgccac attggcaccg actgtgactc cggcattgct   360
ggacctgagt ggctgctaga ccgtccatct gtcaacaaca gccaattagt tgttagcgtt   420
gctggtactt ttgagggggac gaatcaagac attagtctta aatttttga atcgatcta    480 acatcacgac ctgctcatgg aggaaagaca gagcaaggct taagtccaaa atcaaaacca   540
tttgctactg atagtggcgc gatgtcacat aaacttgaga aagctgactt actaaaggct   600
attcaagaac aattgatcgc taacgtccac agtaacgacg actactttga ggtcattgat   660
tttgcaagcg atgcaaccat tactgatcga acggcaaggt ctactttgc tgacaaagat   720 ggttcggtaa ccttgccgac ccaacctgtc caagaatttt tgctaagcgg acatgtgcgc   780
gttagaccat ataagaaaaa accaataca aaccaagcga atctgttga tgtggaatat    840 actgtacagt ttactcccct taaaccctgat gacgatttca gaccaggtct caaagatact   900
aagctattga aaacactagc tatcggtgac accatcacat ctcaagaatt actagctcaa   960
gcacaaagca ttttaaacaa aaaccaccca ggctatacga tttatgaacg tgactcctca   1020
atcgtcactc atgacaatga catttcccgt acgatttac caatggatca agagttact    1080 taccgtgtta aaaatcggga caagcttat aggatcaata aaaatctgg tctgaatgaa   1140 gaaataaaca acactgacct gatctctgag aaatattacg tccttaaaaa aggggaaaag   1200
ccgtatgatc cctttgatcg cagtcacttg aaactgttca ccatcaaata cgttgatgtc   1260
gataccaacg aattgctaaa aagtgagcag ctcttaacag ctagcgaacg taacttagac   1320
ttcagagatt tatacgatcc tcgtgataag gctaaactac tctacaacaa tctcgatgct   1380
```

```
tttggtatta tggactatac cttaactgga aaagtagagg ataatcacga tgacaccaac    1440
cgtatcataa ccgtttatat gggcaagcga cccgaaggag agaatgctag ctatcattta    1500
gccggtggcg acaagctca acaaattgtg gtggaccgt gcttcagagc caactgcgag      1560
taccagtgcc agcccctgaa ccaaactagc tacctctgcg tctgcgccga gggcttcgcg    1620
cccattcccc acgagccgca caggtgccag atgttttgca accagactgc ctgtccagcc    1680
gactgcgacc ccaacaccca ggctagctgt gagtgccctg aaggctacat cctggacgac    1740
ggtttcatct gcacggacat cgacgagtgc gaaaacggcg gcttctgctc cggggtgtgc    1800
cacaacctcc ccgtaccttt cgagtgcatc tgcgggcccg actcggccct tgcccgccac    1860
attggcaccg actgtgactc cggc                                          1884

<210> SEQ ID NO 8
<211> LENGTH: 354
<212> TYPE: DNA
<213> ORGANISM: Artificial Sequence
<220> FEATURE:
<223> OTHER INFORMATION: EGF 456 ARTIFICIAL

<400> SEQUENCE: 8 gttgacccttt gctttagagc caactgtgaa taccaatgcc agcctttgaa ccagacctca    60
tacttgtgtg tttgtgccga gggttttgca ccaattcctc atgaaccaca cagatgtcaa    120
atgttctgca accagactgc ctgtccagca gactgcgatc ctaatacaca agcttcttgt    180
gagtgccctg aaggatacat cttggatgac ggttttattt gtactgacat cgatgagtgc    240
gaaaacggtg gattttgtag tggtgtttgc cataatcttc caggaacctt cgaatgtatt    300
tgcggtcctg actctgcctt ggcaagacac atcggaactg actgtgattc cgga          354

<210> SEQ ID NO 9
<211> LENGTH: 1617
<212> TYPE: DNA
<213> ORGANISM: Artificial Sequence
<220> FEATURE:
<223> OTHER INFORMATION: ARTIFICIALLY SYNTHESIZED TPA

<400> SEQUENCE: 9
caagagattc atgctagatt cagaagaggt gctagatcct accaggtcat ttgtagagat    60
gaaaagacac aaatgatcta tcaacagcac cagtcatggc ttagacctgt tttgagaagt    120
aacagagtcg agtactgttg gtgcaattct ggtagagccc aatgtcatag tgttccagtc    180
aaatcatgta gtgaacctag atgctttaac ggtggaactt gtcaacaggc tttgtacttc    240
tctgatttcg tttgtcaatg cccagaggga ttcgctggta atgttgcga aattgacacc     300 agagctactt gttacgaaga tcagggaatc tcatatagag gtacatggtc taccgctgag    360
tccggagccg aatgtactaa ctggaattct ccgctttgg cccaaaaacc atactctggt     420
agaagacctg atgctattag acttggtttg ggaaaccaca attattgcag aaatccagac    480
agagattcta agccttggtg ttacgttttt aaggccggaa atattcaag tgaattctgt      540 tccaccctg catgctcaga gggtaacagt gattgttact ttggtaatgg atctgcttat     600
agaggaaccc attccttgac tgagtcaggt gccagttgtc ttccatggaa ctcaatgatt    660
ttgatcggaa aagtttacac tgcacaaaat cctagtgcac aggctcttgg tttgggaaag    720
cataactact gtagaaatcc agacggagat gccaaacctt ggtgtcacgt tcttaagaac    780
agaagattga catgggaata ctgtgacgtc ccatcttgtt ccacctgcgg tttgagacaa    840
```

```
tactcacaac ctcagtttag aattaaaggt ggattgttcg ctgatatcgc ctctcatcca      900
tggcaggctg ccattttttgc taagcacaga agatccctg gagagagatt cctttgtggt    960
ggaattttga tctcttcctg ctggattttg tccgcagctc actgttttca agaaagattc   1020
ccacctcatc accttacagt tatcttggga agaacctaca gagttgtccc aggtgaagag   1080
gaacagaagt ttgaggttga aaaatacatt gtccataagg agttcgatga cgatacttat   1140
gacaatgata tcgcactttt gcaattgaag tctgattcaa gtagatgtgc tcaggaatct   1200
tccgttgtca gaactgtttg tttgccacct gctgaccttc aattgcctga ttggacagag   1260
tgtgaacttt ctggttacgg aaaacacgaa gccttgtctc cattttattc cgagagactt   1320
aaggaagcac atgttagatt gtatccttca agtagatgta catcccaaca ccttttgaac   1380
agaactgtca cagacaatat gttgtgtgct ggagatacca gatcaggtgg accacaagcc   1440
aacttgcatg acgcatgcca gggagatagt ggtggacctc ttgtttgttt gaatgacggt   1500
agaatgactc ttgtcggaat tatctcttgg ggtttgggat gtggtcaaaa agatgttcca   1560
ggtgtctaca ctaaggttac aaactatttg gactggatca gagataacat gagacca     1617
```

<210> SEQ ID NO 10
<211> LENGTH: 2325
<212> TYPE: DNA
<213> ORGANISM: Artificial Sequence
<220> FEATURE:
<223> OTHER INFORMATION: N_EGF_TPA_EGF, Fusion at the N and C terminal
      of TPA

<400> SEQUENCE: 10

```
gtcgatccat gttttagagc taattgcgag tatcaatgcc agcctcttaa ccaaacttct      60
tatttgtgtg tttgcgcaga gggttttgct cctatcccac acgagcctca tagatgccag    120
atgttttgca accagaccgc atgtccagct gactgcgatc ctaatactca agcttcctgt   180
gagtgccctg aaggttacat tttggacgat ggattcattt gcaccgatat tgacgaatgt   240
gagaacggtg gattttgttc aggagtttgc cacaatttgc caggtacatt cgaatgtatt   300
tgtggacctg atagtgctct tgccagacat attggaacag attgtgactc cggtcaagag   360
attcatgcta gattcagaag aggtgctaga tcctaccagg tcatttgtag atgaaaaag   420 acacaaatga tctatcaaca gcaccagtca tggcttagac ctgttttgag aagtaacaga   480
gtcgagtact gttggtgcaa ttctggtaga gcccaatgtc atagtgttcc agtcaaatca   540
tgtagtgaac ctagatgctt taacggtgga acttgtcaac aggctttgta cttctctgat   600
ttcgtttgtc aatgcccaga gggattcgct ggtaaatgtt gcgaaattga caccagagct   660
acttgttacg aagatcaggg aatctcatat agaggtacat ggtctaccgc tgagtccgga   720
gccgaatgta ctaactggaa ttcttccgct ttggcccaaa aaccatactc tggtagaaga   780
cctgatgcta ttagacttgg tttgggaaac acaattatt gcagaaatcc agacagagat   840
tctaagcctt ggtgttacgt tttttaaggcc ggaaaatatt caagtgaatt ctgttccacc   900
cctgcatgct cagagggtaa cagtgattgt tactttggta atggatctgc ttatagagga   960
acccattcct tgactgagtc aggtgccagt tgtcttccat ggaactcaat gattttgatc  1020
ggaaaagttt acactgcaca aaatcctagt gcacaggctc ttggtttggg aaagcataac  1080
tactgtagaa atccagacgg agatgccaaa ccttggtgtc acgttcttaa gaacagaaga  1140
ttgacatggg aatactgtga cgtcccatct tgttccacct gcggtttgag acaatactca  1200
caacctcagt ttagaattaa aggtggattg ttcgctgata tcgcctctca tccatggcag  1260
```

-continued

```
gctgccattt tgctaagca cagaagatcc cctggagaga gattcctttg tggtggaatt      1320
ttgatctctt cctgctggat tttgtccgca gctcactgtt ttcaagaaag attcccacct      1380
catcacctta cagttatctt gggaagaacc tacagagttg tcccaggtga agaggaacag      1440
aagtttgagg ttgaaaaata cattgtccat aaggagttcg atgacgatac ttatgacaat      1500
gatatcgcac ttttgcaatt gaagtctgat tcaagtagat gtgctcagga atcttccgtt      1560
gtcagaactg tttgtttgcc acctgctgac cttcaattgc ctgattggac agagtgtgaa      1620 cttttctggtt acggaaaaca cgaagccttg tctccatttt attccgagag acttaaggaa      1680
gcacatgtta gattgtatcc ttcaagtaga tgtacatccc aacaccttt gaacagaact      1740 gtcacagaca atatgttgtg tgctggagat accgatcag gtggaccaca agccaacttg      1800
catgacgcat gccagggaga tagtggtgga cctcttgttt gtttgaatga cggtagaatg      1860
actcttgtcg gaattatctc ttggggtttg ggatgtggtc aaaaagatgt tccaggtgtc      1920
tacactaagg ttacaaacta tttggactgg atcagagata acatgagacc agtcgatcca      1980
tgttttagag ctaattgcga gtatcaatgc cagcctctta ccaaacttc ttatttgtgt      2040 gtttgcgcag agggttttgc tcctatccca cacgagcctc atagatgcca gatgtttgc      2100 aaccagaccg catgtccagc tgactgcgat cctaatactc aagcttcctg tgagtgccct      2160
gaaggttaca ttttggacga tggattcatt tgcaccgata ttgacgaatg tgagaacggt      2220
ggattttgtt caggagtttg ccacaatttg ccaggtacat cgaatgtat ttgtggacct      2280 gatagtgctc ttgccagaca tattggaaca gattgtgact ccggt                    2325
```

<210> SEQ ID NO 11
<211> LENGTH: 1971
<212> TYPE: DNA
<213> ORGANISM: Artificial Sequence
<220> FEATURE:
<223> OTHER INFORMATION: N_EGF_TPA, fusion at the N-teminal of TPA

<400> SEQUENCE: 11

```
gtcgatccat gttttagagc taattgcgag tatcaatgcc agcctcttaa ccaaacttct       60
tatttgtgtg tttgcgcaga gggttttgct cctatcccac acgagcctca tagatgccag      120
atgttttgca accagaccgc atgtccagct gactgcgatc ctaatactca agcttcctgt      180
gagtgccctg aaggttacat tttggacgat ggattcattt gcaccgatat tgacgaatgt      240
gagaacggtg gattttgttc aggagtttgc cacaatttgc caggtacatt cgaatgtatt      300
tgtggacctg atagtgctct tgccagacat attggaacag attgtgactc cggtcaagag      360
attcatgcta gattcagaag aggtgctaga tcctaccagg tcatttgtag agatgaaaag      420
acacaaatga tctatcaaca gcaccagtca tggcttagac tgttttgag aagtaacaga      480 gtcgagtact gttggtgcaa ttctggtaga gcccaatgtc atagtgttcc agtcaaatca      540
tgtagtgaac ctagatgctt taacggtgga acttgtcaac aggctttgta cttctctgat      600
ttcgtttgtc aatgcccaga gggattcgct ggtaaatgtt gcgaaattga caccagagct      660
acttgttacg aagatcaggg aatctcatat agaggtacat ggtctaccgc tgagtccgga      720
gccgaatgta ctaactggaa ttcttccgct ttggcccaaa aaccatactc tggtagaaga      780
cctgatgcta ttagacttgg tttgggaaac cacaattatt gcagaaatcc agacagagat      840
tctaagcctt ggtgttacgt ttttaaggcc ggaaaatatt caagtgaatt ctgttccacc      900
cctgcatgct cagagggtaa cagtgattgt tactttggta tggatctgc ttatagagga      960 acccattcct tgactgagtc aggtgccagt tgtcttccat ggaactcaat gattttgatc     1020
```

```
ggaaaagttt acactgcaca aaatcctagt gcacaggctc ttggtttggg aaagcataac   1080
tactgtagaa atccagacgg agatgccaaa ccttggtgtc acgttcttaa gaacagaaga   1140
ttgacatggg aatactgtga cgtcccatct tgttccacct gcggtttgag acaatactca   1200
caacctcagt ttagaattaa aggtggattg ttcgctgata tcgcctctca tccatggcag   1260
gctgccattt tgctaagca cagaagatcc cctggagaga gattcctttg tggtggaatt   1320
ttgatctctt cctgctggat tttgtccgca gctcactgtt ttcaagaaag attcccacct   1380
catcacctta cagttatctt gggaagaacc tacagagttg tcccaggtga agaggaacag   1440
aagtttgagg ttgaaaaata cattgtccat aaggagttcg atgacgatac ttatgacaat   1500
gatatcgcac ttttgcaatt gaagtctgat tcaagtagat gtgctcagga atcttccgtt   1560
gtcagaactg tttgtttgcc acctgctgac cttcaattgc ctgattggac agagtgtgaa   1620 cttctctggtt acggaaaaca cgaagccttg tctccatttt attccgagag acttaaggaa   1680
gcacatgtta gattgtatcc ttcaagtaga tgtacatccc aacacctttt gaacagaact   1740
gtcacagaca atatgttgtg tgctggagat accagatcag gtggaccaca agccaacttg   1800
catgacgcat gccagggaga tagtggtgga cctcttgttt gtttgaatga cggtagaatg   1860
actcttgtcg gaattatctc ttgggggtttg ggatgtggtc aaaaagatgt tccaggtgtc   1920
tacactaagg ttacaaacta tttggactgg atcagagata acatgagacc a           1971

<210> SEQ ID NO 12
<211> LENGTH: 1971
<212> TYPE: DNA
<213> ORGANISM: Artificial Sequence
<220> FEATURE:
<223> OTHER INFORMATION: TPA_EGF, fusion at the C-terminal of TPA

<400> SEQUENCE: 12
caagagattc atgctagatt cagaagaggt gctagatcct accaggtcat ttgtagagat     60
gaaaagacac aaatgatcta tcaacagcac cagtcatggc ttagacctgt tttgagaagt    120
aacagagtcg agtactgttg gtgcaattct ggtagagccc aatgtcatag tgttccagtc    180
aaatcatgta gtgaacctag atgctttaac ggtggaactt gtcaacaggc tttgtacttc    240
tctgatttcg tttgtcaatg cccagaggga ttcgctggta atgttgcga aattgacacc     300 agagctactt gttacgaaga tcagggaatc tcatatagag gtacatggtc taccgctgag    360
tccggagccg aatgtactaa ctggaattct tccgctttgg cccaaaaacc atactctggt    420
agaagacctg atgctattag acttggtttg gaaaccacaa ttattgcag aaatccagac     480 agagattcta agccttggtg ttacgttttt aaggccggaa atattcaag tgaattctgt     540 tccaccctg catgctcaga gggtaacagt gattgttact tggtaatgg atctgcttat     600 agaggaaccc attccttgac tgagtcaggt gccagttgtc ttccatggaa ctcaatgatt    660
ttgatcggaa agtttacac tgcacaaaat cctagtgcac aggctcttgg tttgggaaag    720
cataactact gtagaaatcc agacggagat gccaaaccttt ggtgtcacgt tcttaagaac   780
agaagattga catgggaata ctgtgacgtc ccatcttgtt ccacctgcgg tttgagacaa    840
tactcacaac ctcagtttag aattaaaggt ggattgttcg ctgatatcgc ctctcatcca    900
tggcaggctg ccattttgc taagcacaga gatcccctg agagagatt cctttgtggt      960 ggaattttga tctcttcctg ctggattttg tccgcagctc actgttttca gaaagattc    1020 ccacctcatc accttacagt tatcttggga agaacctaca gagttgtccc aggtgaagag    1080
```

```
gaacagaagt tgaggttga aaaatacatt gtccataagg agttcgatga cgatacttat    1140
gacaatgata tcgcactttt gcaattgaag tctgattcaa gtagatgtgc tcaggaatct    1200
tccgttgtca gaactgtttg tttgccacct gctgaccttc aattgcctga ttggacagag    1260
tgtgaacttt ctggttacgg aaaacacgaa gccttgtctc cattttattc cgagagactt    1320
aaggaagcac atgttagatt gtatccttca agtagatgta catcccaaca ccttttgaac    1380
agaactgtca cagacaatat gttgtgtgct ggagatacca gatcaggtgg accacaagcc    1440
aacttgcatg acgcatgcca gggagatagt ggtggacctc ttgtttgttt gaatgacggt    1500
agaatgactc ttgtcggaat tatctcttgg ggtttgggat gtggtcaaaa agatgttcca    1560
ggtgtctaca ctaaggttac aaactatttg gactggatca gagataacat gagaccagtc    1620
gatccatgtt ttagagctaa ttgcgagtat caatgccagc ctcttaacca aacttcttat    1680
ttgtgtgttt gcgcagaggg ttttgctcct atcccacacg agcctcatag atgccagatg    1740
ttttgcaacc agaccgcatg tccagctgac tgcgatccta atactcaagc ttcctgtgag    1800
tgccctgaag gttacatttt ggacgatgga ttcatttgca ccgatattga cgaatgtgag    1860
aacggtggat tttgttcagg agtttgccac aatttgccag gtacattcga atgtatttgt    1920
ggacctgata gtgctcttgc cagacatatt ggaacagatt gtgactccgg t              1971
```

<210> SEQ ID NO 13
<211> LENGTH: 1860
<212> TYPE: DNA
<213> ORGANISM: Artificial Sequence
<220> FEATURE:
<223> OTHER INFORMATION: ID EGF TPA DEL EGF

<400> SEQUENCE: 13

```
caagagattc atgctagatt cagaagaggt gctagatcct accaggtcat ttgtagagat      60
gaaaagacac aaatgatcta tcaacagcac cagtcatggc ttagacctgt tttgagaagt     120
aacagagtcg agtactgttg gtgcaattct ggtagagccc aatgtcatag tgttccagtt     180
aaatcagttg acccttgctt tagagccaac tgtgaatacc aatgccagcc tttgaaccag     240
acctcatact gtgtgtttg tgccgagggt tttgcaccaa ttcctcatga accacacaga     300
tgtcaaatgt tctgcaacca gactgcctgt ccagcagact gcgatcctaa tacacaagct     360
tcttgtgagt gccctgaagg atacatcttg gatgacggtt ttatttgtac tgacatcgat     420
gagtgcgaaa acggtggatt ttgtagtggt gtttgccata atcttccagg aaccttcgaa     480
tgtatttgcg gtcctgactc tgccttggca agacatatag gtactgactg tgattccgga     540
accagagcta cttgttacga agatcaggga atctcatata gaggtacatg gtctaccgct     600
gagtccggag ccgaatgtac taactggaat tcttccgctt tggcccaaaa accatactct     660
ggtagaagac ctgatgctat tagacttggt ttgggaaacc acaattattg cagaaatcca     720
gacagagatt ctaagccttg gtgttacgtt tttaaggccg gaaaatattc aagtgaattc     780
tgttccaccc ctgcatgctc agagggtaac agtgattgtt actttggtaa tggatctgct     840
tatagaggaa cccattcctt gactgagtca ggtgccagtt gtcttccatg gaactcaatg     900
attttgatcg gaaaagttta cactgcacaa aatcctagtg cacaggctct ggtttgggga     960
aagcataact actgtagaaa tccagacgga gatgccaaac cttggtgtca cgttcttaag    1020
aacagaagat tgacatggga atactgtgac gtcccatctt gttccacctg cggttttgaga    1080 caatactcac aacctcagtt tagaattaaa ggtggattgt tcgctgatat cgcctctcat    1140
ccatggcagg ctgccatttt tgctaagcac agaagatccc ctggagagag attcctttgt    1200
```

```
ggtggaattt tgatctcttc ctgctggatt ttgtccgcag ctcactgttt tcaagaaaga    1260
ttcccacctc atcaccttac agttatcttg ggaagaacct acagagttgt cccaggtgaa    1320
gaggaacaga agtttgaggt tgaaaaatac attgtccata aggagttcga tgacgatact    1380
tatgacaatg atatcgcact tttgcaattg aagtctgatt caagtagatg tgctcaggaa    1440
tcttccgttg tcagaactgt tgtttgcca cctgctgacc ttcaattgcc tgattggaca    1500
gagtgtgaac tttctggtta cggaaaacac gaagccttgt ctccatttta ttccgagaga    1560
cttaaggaag cacatgttag attgtatcct tcaagtagat gtacatccca cacctttg     1620 aacagaactg tcacagacaa tatgttgtgt gctggagata ccagatcagg tggaccacaa    1680
gccaacttgc atgacgcatg ccagggagat agtggtggac ctcttgtttg tttgaatgac    1740
ggtagaatga ctcttgtcgg aattatctct tggggtttgg gatgtggtca aaaagatgtt    1800
ccaggtgtct acactaaggt tacaaactat ttggactgga tcagagataa catgagacca    1860
```

<210> SEQ ID NO 14
<211> LENGTH: 1593
<212> TYPE: DNA
<213> ORGANISM: Artificial Sequence
<220> FEATURE:
<223> OTHER INFORMATION: ID EGF TPA DEL EGF K1

<400> SEQUENCE: 14

```
caagagattc atgctagatt cagaagaggt gctagatcct accaggtcat tgtagagat      60 gaaaagacac aaatgatcta tcaacagcac cagtcatggc ttagacctgt tttgagaagt    120
aacagagtcg agtactgttg gtgcaattct ggtagagccc aatgtcatag tgttccagtt    180
aaatcagttg acccttgctt tagagccaac tgtgaatacc aatgccagcc tttgaaccag    240
acctcatact gtgtgtttg tgccgagggt tttgcaccaa ttcctcatga accacacaga    300
tgtcaaatgt tctgcaacca gactgcctgt ccagcagact gcgatcctaa tacacaagct    360
tcttgtgagt gccctgaagg atacatcttg gatgacggtt ttatttgtac tgacatcgat    420
gagtgcgaaa acggtggatt tgtagtgggt gtttgccata atcttccagg aaccttcgaa    480
tgtatttgcg gtcctgactc tgccttggca agacatattg gtactgattg tgattccgga    540
aacagtgatt gttactttgg taatggatct gcttatagag gaacccattc cttgactgag    600
tcaggtgcca gttgtcttcc atggaactca atgattttga tcggaaaagt ttacactgca    660
caaaatccta gtgcacaggc tcttggtttg gaaagcata actactgtag aaatccagac    720
ggagatgcca aaccttggtg tcacgttctt aagaacagag attgacatg ggaatactgt    780 gacgtcccat cttgttccac ctgcggtttg agacaatact cacaacctca gtttagaatt    840
aaaggtggat tgttcgctga tatcgcctct catccatggc aggctgccat tttgctaag    900 cacagaagat cccctggaga gagattcctt tgtggtggaa ttttgatctc ttcctgctgg    960
attttgtccg cagctcactg ttttcaagaa agattcccac ctcatcacct acagttatc    1020 ttgggaagaa cctacagagt gtcccaggt gaagaggaac agaagtttga ggttgaaaaa    1080
tacattgtcc ataaggagtt cgatgacgat acttatgaca atgatatcgc acttttgcaa    1140
ttgaagtctg attcaagtag atgtgctcag gaatcttccg ttgtcagaac tgtttgtttg    1200
ccacctgctg accttcaatt gcctgattgg acagagtgtg aactttctgg ttacggaaaa    1260
cacgaagcct gtctccatt ttattccgag agacttaagg aagcacatgt tagattgtat    1320
ccttcaagta gatgtacatc ccaacacctt ttgaacagaa ctgtcacaga caatatgttg    1380
```

```
tgtgctggag ataccagatc aggtggacca caagccaact tgcatgacgc atgccaggga    1440
gatagtggtg gacctcttgt ttgtttgaat gacggtagaa tgactcttgt cggaattatc    1500
tcttggggtt tgggatgtgg tcaaaaagat gttccaggtg tctacactaa ggttacaaac    1560
tatttggact ggatcagaga taacatgaga cca                                 1593
```

<210> SEQ ID NO 15
<211> LENGTH: 1593
<212> TYPE: DNA
<213> ORGANISM: Artificial Sequence
<220> FEATURE:
<223> OTHER INFORMATION: N_EGF DEL EGF K1

<400> SEQUENCE: 15

```
gttgacccct tgcttcagagc caactgtgaa taccaatgcc agcctttgaa ccagacctca     60
tacttgtgtg tttgtgccga gggttttgca ccaattcctc atgaaccaca cagatgtcaa    120
atgttctgca accagactgc ctgtccagca gactgcgatc ctaatacaca agcttcttgt    180
gagtgccctg aaggatacat cttggatgac ggttttattt gtactgacat cgatgagtgc    240
gaaaacggtg gattttgtag tggtgtttgc cataatcttc caggaaccct cgaatgtatt    300
tgcggtcctg actctgcctt ggcaagacac atcggaactg actgtgattc cggacaagag    360
attcatgcta gattcagaag aggtgctaga tcctaccagg tcatttgtag agatgaaaag    420
acacaaatga tctatcaaca gcaccagtca tggcttagac tgttttgag aagtaacaga    480 gtcgagtact gttggtgcaa ttctggtaga gcccaatgtc atagtgttcc agtcaagtca    540
aatagtgatt gttactttgg taatggatct gcttatagag aacccattc cttgactgag    600 tcaggtgcca gttgtcttcc atggaactca atgatttga tcggaaaagt ttacactgca    660
caaaatccta gtgcacaggc tcttggtttg ggaaagcata actactgtag aaatccagac    720
ggagatgcca accttggtg tcacgttctt aagaacagaa gattgacatg gaatactgt    780 gacgtcccat cttgttccac ctgccggtttg agacaatact cacaacctca gtttagaatt    840
aaaggtggat tgttcgctga tatcgcctct catccatggc aggctgccat ttttgctaag    900
cacagaagat cccctggaga gagattcctt tgtggtggaa ttttgatctc ttcctgctgg    960
attttgtccg cagctcactg ttttcaagaa agattcccac ctcatcacct tacagttatc   1020 ttggaagaa cctacagagt tgtcccaggt gaagaggaac agaagtttga ggttgaaaaa    1080
tacattgtcc ataaggagtt cgatgacgat acttatgaca atgatatcgc acttttgcaa    1140
ttgaagtctg attcaagtag atgtgctcag gaatcttccg ttgtcagaac tgttgtttg    1200 ccacctgctg accttcaatt gcctgattgg acagagtgtg aactttctgg ttacggaaaa    1260
cacgaagcct tgtctccatt ttattccgag agacttaagg aagcacatgt tagattgtat   1320
ccttcaagta gatgtacatc ccaacacctt ttgaacagaa ctgtcacaga caatatgttg    1380
tgtgctggag ataccagatc aggtggacca caagccaact tgcatgacgc atgccaggga   1440
gatagtggtg gacctcttgt ttgtttgaat gacggtagaa tgactcttgt cggaattatc    1500
tcttggggtt tgggatgtgg tcaaaaagat gttccaggtg tctacactaa ggttacaaac   1560
tatttggact ggatcagaga taacatgaga cca                                1593
```

<210> SEQ ID NO 16
<211> LENGTH: 1593
<212> TYPE: DNA
<213> ORGANISM: Artificial Sequence
<220> FEATURE:
<223> OTHER INFORMATION: TPA _EGF DEL EGF AND K1

<400> SEQUENCE: 16

```
caagagattc atgctagatt cagaagaggt gctagatcct accaggtcat ttgtagagat      60
gaaaagacac aaatgatcta tcaacagcac cagtcatggc ttagacctgt tttgagaagt     120
aacagagtcg agtactgttg gtgcaattct ggtagagccc aatgtcatag tgttccagtc     180
aagtcaaata gtgattgtta ctttggtaat ggatctgctt atagaggaac ccattccttg     240
actgagtcag gtgccagttg tcttccatgg aactcaatga ttttgatcgg aaaagtttac     300
actgcacaaa atcctagtgc acaggctctt ggtttgggaa agcataacta ctgtagaaat     360
ccagacggag atgccaaacc ttggtgtcac gttcttaaga acagaagatt gacatgggaa     420
tactgtgacg tcccatcttg ttccacctgc ggtttgagac aatactcaca acctcagttt     480
agaattaaag gtggattgtt cgctgatatc gcctctcatc catggcaggc tgccattttt     540
gctaagcaca agatccccc tggagagaga ttcctttgtg gtggaatttt gatctcttcc     600
tgctggattt tgtccgcagc tcactgtttt caagaaagat tcccacctca tcaccttaca     660
gttatcttgg gaagaaccta cagagttgtc ccaggtgaag aggaacagaa gtttgaggtt     720
gaaaaataca ttgtccataa ggagttcgat gacgatactt atgacaatga tatcgcactt     780
ttgcaattga agtctgattc aagtagatgt gctcaggaat cttccgttgt cagaactgtt     840
tgtttgccac ctgctgacct tcaattgcct gattggacag agtgtgaact ttctggttac     900
ggaaaacacg aagccttgtc tccatttat tccgagagac ttaaggaagc acatgttaga     960
ttgtatcctt caagtagatg tacatcccaa caccttttga acagaactgt cacagacaat    1020
atgttgtgtg ctggagatac cagatcaggt ggaccacaag ccaacttgca tgacgcatgc    1080
cagggagata gtggtggacc tcttgtttgt ttgaatgacg gtagaatgac tcttgtcgga    1140
attatctctt ggggtttggg atgtggtcaa aaagatgttc caggtgtcta cactaaggtt    1200
acaaactatt tggactggat cagagataac atgagaccag tcgatccatg ttttagagct    1260
aattgcgagt atcaatgcca gcctcttaac caaacttctt atttgtgtgt ttgcgcagag    1320
ggttttgctc ctatcccaca cgagcctcat agatgccaga tgttttgcaa ccagaccgca    1380
tgtccagctg actgcgatcc taatactcaa gcttcctgtg agtgccctga aggttacatt    1440
ttggacgatg gattcatttg caccgatatt gacgaatgtg agaacggtgg attttgttca    1500
ggagtttgcc acaatttgcc aggtacattc gaatgtattt gtggacctga tagtgctctt    1560
gccagacata ttggaacaga ttgtgactca ggt                                  1593
```

<210> SEQ ID NO 17
<211> LENGTH: 414
<212> TYPE: DNA
<213> ORGANISM: Artificial Sequence
<220> FEATURE:
<223> OTHER INFORMATION: SAK

<400> SEQUENCE: 17

```
atgtcaagtt cattcgacaa aggaaaatat aaaaaaggcg atgacgcgag ttatttttgaa      60
ccaacaggcc cgtatttgat ggtaaatgtg actggagttg atagtaaagg aaatgaattg     120
ctatcccctc attatgtcga gtttcctatt aaacctggga ctacacttac aaaagaaaaa     180
attgaatact atgtcgaatg gcattagat gcgacagcat ataagagtt tagagtagtt     240
gaattagatc caagcgcaaa gatcgaagtc acttattatg ataagaataa gaaaaagaa     300
gaaacgaagt ctttccctat aacagaaaaa ggttttgttg tcccagattt atcagagcat     360
```

| attaaaaacc ctggattcaa cttaattaca aaggttgtta tagaaaagaa ataa | 414 |

<210> SEQ ID NO 18
<211> LENGTH: 762
<212> TYPE: DNA
<213> ORGANISM: Artificial Sequence
<220> FEATURE:
<223> OTHER INFORMATION: N_EGF_SAK, fusion at the N-terminal of SAK

<400> SEQUENCE: 18

| gtggacccgt gcttcagagc caactgcgag taccagtgcc agcccctgaa ccaaactagc | 60 |
| tacctctgcg tctgcgccga gggcttcgcg cccattcccc acgagccgca caggtgccag | 120 |
| atgttttgca accagactgc ctgtccagcc gactgcgacc ccaacaccca ggctagctgt | 180 |
| gagtgccctg aaggctacat cctggacgac ggtttcatct gcacggacat cgacgagtgc | 240 |
| gaaaacggcg gcttctgctc cggggtgtgc cacaacctcc ccggtacctt cgagtgcatc | 300 |
| tgcgggcccg actcggccct tgcccgccac attggcaccg actgtgactc cggctcaagt | 360 |
| tcattcgaca aggaaaaata taaaaaaggc gatgacgcga gttatttga accaacaggc | 420 |
| ccgtatttga tggtaaatgt gactggagtt gatagtaaag gaaatgaatt gctatcccct | 480 |
| cattatgtcg agtttcctat aaacctggg actacactta caaagaaaaa aattgaatac | 540 |
| tatgtcgaat gggcattaga tgcgacagca tataagagt ttagagtagt tgaattagat | 600 |
| ccaagcgcaa agatcgaagt cacttattat gataagaata gaaaaaaga gaaacgaag | 660 |
| tctttcccta acagaaaaa aggttttgtt gtcccagatt tatcagagca tattaaaaac | 720 |
| cctggattca acttaattac aaaggttgtt atagaaaaga aa | 762 |

<210> SEQ ID NO 19
<211> LENGTH: 768
<212> TYPE: DNA
<213> ORGANISM: Artificial Sequence
<220> FEATURE:
<223> OTHER INFORMATION: SAK_EGF, fusion at the C-terminal of SAK

<400> SEQUENCE: 19

| tcaagttcat tcgacaaagg aaaatataaa aaaggcgatg acgcgagtta ttttgaacca | 60 |
| acaggcccgt atttgatggt aaatgtgact ggagttgata gtaaaggaaa tgaattgcta | 120 |
| tcccctcatt atgtcgagtt tcctattaaa cctgggacta cacttacaaa agaaaaaatt | 180 |
| gaatactatg tcgaatgggc attagatgcg acagcatata agagtttag agtagttgaa | 240 |
| ttagatccaa gcgcaaagat cgaagtcact tattatgata gaataagaa aaaagaagaa | 300 |
| acgaagtctt tccctataac agaaaaaggt tttgttgtcc cagatttatc agagcatatt | 360 |
| aaaaaccctg gattcaactt aattacaaag gttgttatag aaaagaaga gcccgtggac | 420 |
| ccgtgcttca gagccaactg cgagtaccag tgccagcccc tgaaccaaac tagctacctc | 480 |
| tgcgtctgcg ccgagggctt cgcgcccatt ccccacgagc cgcacaggtg ccagatgttt | 540 |
| tgcaaccaga ctgcctgtcc agccgactgc gaccccaaca cccaggctag ctgtgagtgc | 600 |
| cctgaaggct acatcctgga cgacggtttc atctgcacgg acatcgacga gtgcgaaaac | 660 |
| ggcggcttct gctccggggt gtgccacaac ctccccggta ccttcgagtg catctgcggg | 720 |
| cccgactcgg cccttgcccg ccacattggc accgactgtg actccggc | 768 |

<210> SEQ ID NO 20
<211> LENGTH: 1617
<212> TYPE: DNA
<213> ORGANISM: Artificial Sequence

```
<220> FEATURE:
<223> OTHER INFORMATION: Variant of tPA (tenecteplase)

<400> SEQUENCE: 20
caagagattc atgctagatt cagaagaggt gctagatcct accaggtcat ttgtagagat      60
gaaaagacac aaatgatcta tcaacagcac cagtcatggc ttagacctgt tttgagaagt     120
aacagagtcg agtactgttg gtgcaattct ggtagagccc aatgtcatag tgttccagtc     180
aaatcatgta gtgaacctag atgctttaac ggtggaactt gtcaacaggc tttgtacttc     240
tctgatttcg tttgtcaatg cccagaggga ttcgctggta atgttgcga aattgacacc      300
agagctactt gttacgaaga tcagggaatc tcatatagag gtaattggtc tacagctgag     360
tccggagccg aatgtactca atggaattct ccgctttgg cccaaaaacc atactctggt      420
agaagacctg atgctattag acttggtttg ggaaaccaca attattgcag aaatccagac     480
agagattcta agccttggtg ttacgttttt aaggccggaa atattcaag tgaattctgt      540
tccaccctg catgctcaga gggtaacagt gattgttact ttggtaatgg atctgcttat      600
agaggaaccc attccttgac tgagtcaggt gccagttgtc ttccatggaa ctcaatgatt     660
ttgatcggaa aagtttacac tgcacaaaat cctagtgcac aggctcttgg tttgggaaag     720
cataactact gtagaaatcc agacggagat gccaaaccctt ggtgtcacgt tcttaagaac    780
agaagattga catgggaata ctgtgacgtc ccatcttgtt ccacctgcgg tttgagacaa     840
tactcacaac ctcagtttag aattaaaggt ggattgttcg ctgatatcgc ctctcatcca     900
tggcaggctg ccattttgc tgctgccgct gcttcccctg agagagatt cctttgtggt       960
ggaattttga tctcttcctg ctggattttg tccgcagctc actgttttca agaaagattc    1020
ccacctcatc accttacagt tatcttggga agaacctaca gagttgtccc aggtgaagag   1080
gaacagaagt ttgaggttga aaatacatt gtccataagg agttcgatga cgatacttat    1140
gacaatgata tcgcactttt gcaattgaag tctgattcaa gtagatgtgc tcaggaatct   1200
tccgttgtca gaactgtttg tttgccacct gctgaccttc aattgcctga ttggacagag   1260
tgtgaacttt ctggttacgg aaaacacgaa gccttgtctc catttttattc cgagagactt   1320
aaggaagcac atgttagatt gtatccttca agtagatgta catcccaaca ccttttgaac   1380
agaactgtca cagacaatat gttgtgtgct ggagatacca gatcaggtgg accacaagcc   1440
aacttgcatg acgcatgcca gggagatagt ggtggacctc ttgtttgttt gaatgacggt   1500
agaatgactc ttgtcggaat tatctcttgg ggtttgggat gtggtcaaaa agatgttcca   1560
ggtgtctaca ctaaggttac aaactatttg gactggatca gagataacat gagacca      1617

<210> SEQ ID NO 21
<211> LENGTH: 40
<212> TYPE: DNA
<213> ORGANISM: Artificial Sequence
<220> FEATURE:
<223> OTHER INFORMATION: primer_bind N_EGF_SK Fp 1

<400> SEQUENCE: 21
gaatatctcg agaaaagagt ggacccgtgc ttcagagcca                            40

<210> SEQ ID NO 22
<211> LENGTH: 48
<212> TYPE: DNA
<213> ORGANISM: Artificial Sequence
<220> FEATURE:
<223> OTHER INFORMATION: primer_bind N_EGF_SK Rp 2
```

<400> SEQUENCE: 22
gtctagcagc cactcaggtc cagcaatgcc ggagtcacag tcggtgcc 48

<210> SEQ ID NO 23
<211> LENGTH: 48
<212> TYPE: DNA
<213> ORGANISM: Artificial Sequence
<220> FEATURE:
<223> OTHER INFORMATION: primer_bind N_EGF_SK Fp3

<400> SEQUENCE: 23
ggcaccgact gtgactccgg cattgctgga cctgagtggc tgctagac 48

<210> SEQ ID NO 24
<211> LENGTH: 42
<212> TYPE: DNA
<213> ORGANISM: Artificial Sequence
<220> FEATURE:
<223> OTHER INFORMATION: primer_bind N_EGF_SK Rp 4

<400> SEQUENCE: 24
cctatacgcg gccgcttatt tgtcgttagg gttatcaggt at 42

<210> SEQ ID NO 25
<211> LENGTH: 42
<212> TYPE: DNA
<213> ORGANISM: Artificial Sequence
<220> FEATURE:
<223> OTHER INFORMATION: primer_bind SK_EGF Fp 1

<400> SEQUENCE: 25
gcatatctcg agaaaagaat tgctggacct gagtggctgc ta 42

<210> SEQ ID NO 26
<211> LENGTH: 60
<212> TYPE: DNA
<213> ORGANISM: Artificial Sequence
<220> FEATURE:
<223> OTHER INFORMATION: primer_bind SK_EGF Rp 2

<400> SEQUENCE: 26
gaagcacggg tccaccacaa tttgttgagc ttgtccgcca ccggctaaat gatagctagc 60

<210> SEQ ID NO 27
<211> LENGTH: 60
<212> TYPE: DNA
<213> ORGANISM: Artificial Sequence
<220> FEATURE:
<223> OTHER INFORMATION: primer_bind SK_EGF Fp 3

<400> SEQUENCE: 27
gctagctatc atttagccgg tggcggacaa gctcaacaaa ttgtggtgga cccgtgcttc 60

<210> SEQ ID NO 28
<211> LENGTH: 39
<212> TYPE: DNA
<213> ORGANISM: Artificial Sequence
<220> FEATURE:
<223> OTHER INFORMATION: primer_bind SK_EGF Rp 4

<400> SEQUENCE: 28
ccatatcgcg gccgcgccgg agtcacagtc ggtgccaat 39

<210> SEQ ID NO 29
<211> LENGTH: 42

```
<212> TYPE: DNA
<213> ORGANISM: Artificial Sequence
<220> FEATURE:
<223> OTHER INFORMATION: primer_bind ID a Fp 1

<400> SEQUENCE: 29
ggatatctcg agaaaagaat tgctggacct gagtggctgc ta                    42

<210> SEQ ID NO 30
<211> LENGTH: 42
<212> TYPE: DNA
<213> ORGANISM: Artificial Sequence
<220> FEATURE:
<223> OTHER INFORMATION: primer_bind ID a Rp 2

<400> SEQUENCE: 30
aagcacgggt ccacgggctc agatttcgct tggttttgta tt                    42

<210> SEQ ID NO 31
<211> LENGTH: 42
<212> TYPE: DNA
<213> ORGANISM: Artificial Sequence
<220> FEATURE:
<223> OTHER INFORMATION: primer_bind ID EGF Fp 3

<400> SEQUENCE: 31
aatacaaaac caagcgaaat ctgagcccgt ggacccgtgc tt                    42

<210> SEQ ID NO 32
<211> LENGTH: 44
<212> TYPE: DNA
<213> ORGANISM: Artificial Sequence
<220> FEATURE:
<223> OTHER INFORMATION: primer_bind ID EGF Rp 4

<400> SEQUENCE: 32
tacagtatat tccacatcaa cgccggagtc acagtcagtg ccaa                  44

<210> SEQ ID NO 33
<211> LENGTH: 44
<212> TYPE: DNA
<213> ORGANISM: Artificial Sequence
<220> FEATURE:
<223> OTHER INFORMATION: primer_bind ID C Fp 5

<400> SEQUENCE: 33
attggcactg actgtgactc cggcgttgat gtggaatata ctgt                  44

<210> SEQ ID NO 34
<211> LENGTH: 40
<212> TYPE: DNA
<213> ORGANISM: Artificial Sequence
<220> FEATURE:
<223> OTHER INFORMATION: primer_bind ID N3Rp 6

<400> SEQUENCE: 34
aaatatcgcg gccgctttgt cgttagggtt atcaggtata                       40

<210> SEQ ID NO 35
<211> LENGTH: 31
<212> TYPE: DNA
<213> ORGANISM: Artificial Sequence
<220> FEATURE:
<223> OTHER INFORMATION: primer_bind M repV Fp

<400> SEQUENCE: 35
```
cacaggtgtc aggtgttttg caatcagact g                                          31

<210> SEQ ID NO 36
<211> LENGTH: 31
<212> TYPE: DNA
<213> ORGANISM: Artificial Sequence
<220> FEATURE:
<223> OTHER INFORMATION: primer_bind M rep V Rp

<400> SEQUENCE: 36
cagtctgatt gcaaaacacc tgacacctgt g                                          31

<210> SEQ ID NO 37
<211> LENGTH: 42
<212> TYPE: DNA
<213> ORGANISM: Artificial Sequence
<220> FEATURE:
<223> OTHER INFORMATION: primer_bind M rep A Fp

<400> SEQUENCE: 37
ccgcacaggt gccaggcttt ttgcaaccag actgcttgtc ca                              42

<210> SEQ ID NO 38
<211> LENGTH: 42
<212> TYPE: DNA
<213> ORGANISM: Artificial Sequence
<220> FEATURE:
<223> OTHER INFORMATION: primer_bind M rep A Rp

<400> SEQUENCE: 38
tggacaagca gtctggttgc aaaaagcctg gcacctgtgc gg                              42

<210> SEQ ID NO 39
<211> LENGTH: 36
<212> TYPE: DNA
<213> ORGANISM: Artificial Sequence
<220> FEATURE:
<223> OTHER INFORMATION: primer_bind M rep Q Fp

<400> SEQUENCE: 39
cacaggtgtc agcaattttg caaccagaca gcctgt                                     36

<210> SEQ ID NO 40
<211> LENGTH: 36
<212> TYPE: DNA
<213> ORGANISM: Artificial Sequence
<220> FEATURE:
<223> OTHER INFORMATION: primer_bind M rep Q Rp

<400> SEQUENCE: 40
acaggctgtc tggttgcaaa attgctgaca cctgtg                                     36

<210> SEQ ID NO 41
<211> LENGTH: 42
<212> TYPE: DNA
<213> ORGANISM: Artificial Sequence
<220> FEATURE:
<223> OTHER INFORMATION: primer_bind N4SK_EGF Fp 1

<400> SEQUENCE: 41
gcataactcg agaaaagaga ggcttggctg ctagaccgtc ca                              42

<210> SEQ ID NO 42
<211> LENGTH: 39
<212> TYPE: DNA
<213> ORGANISM: Artificial Sequence
<220> FEATURE:
<223> OTHER INFORMATION: primer_bind N4SK_EGF Rp 2

<400> SEQUENCE: 42
ccatatcgcg gccgcgccgg agtcacagtc ggtgccaat                                39

<210> SEQ ID NO 43
<211> LENGTH: 42
<212> TYPE: DNA
<213> ORGANISM: Artificial Sequence
<220> FEATURE:
<223> OTHER INFORMATION: primer_bind N_EGF_TCS Fp 1

<400> SEQUENCE: 43
gcctaactcg agaaaagaga gcccgtggac ccgtgcttca ga                            42

<210> SEQ ID NO 44
<211> LENGTH: 42
<212> TYPE: DNA
<213> ORGANISM: Artificial Sequence
<220> FEATURE:
<223> OTHER INFORMATION: primer_bind N_EGF_TCS_Rp2

<400> SEQUENCE: 44
gacaattcta ggtttaatgc cagagtcaca gtcggtgcca at                            42

<210> SEQ ID NO 45
<211> LENGTH: 41
<212> TYPE: DNA
<213> ORGANISM: Artificial Sequence
<220> FEATURE:
<223> OTHER INFORMATION: primer_bind TCS_SK Fp 3

<400> SEQUENCE: 45
ggcattaaac ctagaattgt cggacctgag tggctgctag a                             41

<210> SEQ ID NO 46
<211> LENGTH: 42
<212> TYPE: DNA
<213> ORGANISM: Artificial Sequence
<220> FEATURE:
<223> OTHER INFORMATION: primer_bind SK Rp 4

<400> SEQUENCE: 46
cctatacgcg gccgcttatt tgtcgttagg gttatcaggt at                            42

<210> SEQ ID NO 47
<211> LENGTH: 42
<212> TYPE: DNA
<213> ORGANISM: Artificial Sequence
<220> FEATURE:
<223> OTHER INFORMATION: primer_bind ID N1C Fp1

<400> SEQUENCE: 47
ggatatctcg agaaaagaat tgctggacct gagtggctgc ta                            42

<210> SEQ ID NO 48
<211> LENGTH: 43
<212> TYPE: DNA
<213> ORGANISM: Artificial Sequence
<220> FEATURE:
<223> OTHER INFORMATION: primer_bind ID N1C Rp

<400> SEQUENCE: 48
ctctgaagca cgggtccacg ggctccaagt gactgcgatc aaa                           43

```
<210> SEQ ID NO 49
<211> LENGTH: 43
<212> TYPE: DNA
<213> ORGANISM: Artificial Sequence
<220> FEATURE:
<223> OTHER INFORMATION: primer_bind IDE4Fp3

<400> SEQUENCE: 49
tttgatcgca gtcacttgga gcccgtggac ccgtgcttca gag            43

<210> SEQ ID NO 50
<211> LENGTH: 40
<212> TYPE: DNA
<213> ORGANISM: Artificial Sequence
<220> FEATURE:
<223> OTHER INFORMATION: primer_bind IDE6Rp4

<400> SEQUENCE: 50
aacgtatttg atggtgaaca gtttgccgga gtcacagtcg                40

<210> SEQ ID NO 51
<211> LENGTH: 40
<212> TYPE: DNA
<213> ORGANISM: Artificial Sequence
<220> FEATURE:
<223> OTHER INFORMATION: primer_bind IDN3Fp5

<400> SEQUENCE: 51
cgactgtgac tccggcaaac tgttcaccat caaatacgtt                40

<210> SEQ ID NO 52
<211> LENGTH: 40
<212> TYPE: DNA
<213> ORGANISM: Artificial Sequence
<220> FEATURE:
<223> OTHER INFORMATION: primer_bind ID N3Rp6

<400> SEQUENCE: 52
aaatatcgcg gccgctttgt cgttagggtt atcaggtata                40

<210> SEQ ID NO 53
<211> LENGTH: 63
<212> TYPE: DNA
<213> ORGANISM: Artificial Sequence
<220> FEATURE:
<223> OTHER INFORMATION: primer_bind TG_ N_EGF_ Fp 1

<400> SEQUENCE: 53
ggtatcctcg agaaaagagt tcaagcgcaa cagatcgtgg aacccgtgga cccgtgcttc    60
aga                                                                63

<210> SEQ ID NO 54
<211> LENGTH: 34
<212> TYPE: DNA
<213> ORGANISM: Artificial Sequence
<220> FEATURE:
<223> OTHER INFORMATION: primer_bind Afl-II Rp2

<400> SEQUENCE: 54
ggttttgatt ttggacttaa gccttgctct gtct                      34

<210> SEQ ID NO 55
<211> LENGTH: 36
<212> TYPE: DNA
<213> ORGANISM: Artificial Sequence
```

<220> FEATURE:
<223> OTHER INFORMATION: primer_bind N_EGF_SAK Fp 1

<400> SEQUENCE: 55
atggatctcg agaaaagagt ggacccgtgc ttcaga                              36

<210> SEQ ID NO 56
<211> LENGTH: 44
<212> TYPE: DNA
<213> ORGANISM: Artificial Sequence
<220> FEATURE:
<223> OTHER INFORMATION: primer_bind N_EGF_SAK Rp 2

<400> SEQUENCE: 56
atattttctt tgtcgaatga acttgacatg ccggagtcac agtc                     44

<210> SEQ ID NO 57
<211> LENGTH: 45
<212> TYPE: DNA
<213> ORGANISM: Artificial Sequence
<220> FEATURE:
<223> OTHER INFORMATION: primer_bind N_EGF_SAK Fp3

<400> SEQUENCE: 57
gactgtgact ccggcatgtc aagttcattc gacaaggaa aatat                     45

<210> SEQ ID NO 58
<211> LENGTH: 40
<212> TYPE: DNA
<213> ORGANISM: Artificial Sequence
<220> FEATURE:
<223> OTHER INFORMATION: primer_bind N_EGF_SAK Rp 4

<400> SEQUENCE: 58
ttatatcgcg gccgcttatt tcttttctat aacaaccttt                          40

<210> SEQ ID NO 59
<211> LENGTH: 40
<212> TYPE: DNA
<213> ORGANISM: Artificial Sequence
<220> FEATURE:
<223> OTHER INFORMATION: primer_bind SAK_EGF Fp 1

<400> SEQUENCE: 59
atccctctcg agaaaagatc aagttcattc gacaaggaa                           40

<210> SEQ ID NO 60
<211> LENGTH: 52
<212> TYPE: DNA
<213> ORGANISM: Artificial Sequence
<220> FEATURE:
<223> OTHER INFORMATION: primer_bind SAK_EGF Rp 2

<400> SEQUENCE: 60
agttggctct gaagcacggg tccacgggct ctttcttttc tataacaacc tt            52

<210> SEQ ID NO 61
<211> LENGTH: 52
<212> TYPE: DNA
<213> ORGANISM: Artificial Sequence
<220> FEATURE:
<223> OTHER INFORMATION: primer_bind SAK_EGF Fp 3

<400> SEQUENCE: 61
aaggttgtta tagaaaagaa agagcccgtg gacccgtgct tcagagccaa ct            52

<210> SEQ ID NO 62
<211> LENGTH: 40
<212> TYPE: DNA
<213> ORGANISM: Artificial Sequence
<220> FEATURE:
<223> OTHER INFORMATION: primer_bind SAK_EGF Rp 4

<400> SEQUENCE: 62
ttttacgcgg ccgctcctga gtcacagtct gtgccaatgt                                40

<210> SEQ ID NO 63
<211> LENGTH: 38
<212> TYPE: DNA
<213> ORGANISM: Artificial Sequence
<220> FEATURE:
<223> OTHER INFORMATION: primer_bind BacFp 1

<400> SEQUENCE: 63
atataggcca tgggtggacc cgtgcttcag agccaact                                  38

<210> SEQ ID NO 64
<211> LENGTH: 35
<212> TYPE: DNA
<213> ORGANISM: Artificial Sequence
<220> FEATURE:
<223> OTHER INFORMATION: primer_bind BacRp 2

<400> SEQUENCE: 64
cctatatctc gagtttcttt tctataacaa ccttt                                     35

<210> SEQ ID NO 65
<211> LENGTH: 40
<212> TYPE: DNA
<213> ORGANISM: Artificial Sequence
<220> FEATURE:
<223> OTHER INFORMATION: primer_bind SAK_bac Fp1

<400> SEQUENCE: 65
atggatccat ggtcaagttc attcgacaaa ggaaaatata                                40

<210> SEQ ID NO 66
<211> LENGTH: 38
<212> TYPE: DNA
<213> ORGANISM: Artificial Sequence
<220> FEATURE:
<223> OTHER INFORMATION: primer_bind SAK_bac Rp2

<400> SEQUENCE: 66
tatattctcg agtcctgagt cacagtctgt gccaatgt                                  38

<210> SEQ ID NO 67
<211> LENGTH: 36
<212> TYPE: DNA
<213> ORGANISM: Artificial Sequence
<220> FEATURE:
<223> OTHER INFORMATION: primer_bind E 4 Fp 1

<400> SEQUENCE: 67
atggatctcg agaaaagagt ggacccgtgc ttcaga                                    36

<210> SEQ ID NO 68
<211> LENGTH: 43
<212> TYPE: DNA
<213> ORGANISM: Artificial Sequence
<220> FEATURE:
<223> OTHER INFORMATION: primer_bind E6 Rp 2

-continued

<400> SEQUENCE: 68
ccgacaattc taggtttaat gccggagtca cagtcagtgc caa         43

<210> SEQ ID NO 69
<211> LENGTH: 49
<212> TYPE: DNA
<213> ORGANISM: Artificial Sequence
<220> FEATURE:
<223> OTHER INFORMATION: primer_bind TCS SAK Fp 3

<400> SEQUENCE: 69
ggcattaaac ctagaattgt cggatcaagt tcattcgata aaggaaaat    49

<210> SEQ ID NO 70
<211> LENGTH: 40
<212> TYPE: DNA
<213> ORGANISM: Artificial Sequence
<220> FEATURE:
<223> OTHER INFORMATION: primer_bind TCS SAK Rp4

<400> SEQUENCE: 70
ttatatcgcg gccgcttatt tcttttctat aacaaccttt            40

<210> SEQ ID NO 71
<211> LENGTH: 48
<212> TYPE: DNA
<213> ORGANISM: Artificial Sequence
<220> FEATURE:
<223> OTHER INFORMATION: primer_bind tPA_Fp 1

<400> SEQUENCE: 71
ggataactcg agaaaagaga ggctcaagag attcatgcta gattcaga     48

<210> SEQ ID NO 72
<211> LENGTH: 44
<212> TYPE: DNA
<213> ORGANISM: Artificial Sequence
<220> FEATURE:
<223> OTHER INFORMATION: primer_bind tPA Rp 2

<400> SEQUENCE: 72
tcatatcgcg gccgctggtc tcatgttatc tctgatccag tcca         44

<210> SEQ ID NO 73
<211> LENGTH: 48
<212> TYPE: DNA
<213> ORGANISM: Artificial Sequence
<220> FEATURE:
<223> OTHER INFORMATION: primer_bind Fin Fp 1

<400> SEQUENCE: 73
ggataactcg agaaaagaga ggctcaagag attcatgcta gattcaga     48

<210> SEQ ID NO 74
<211> LENGTH: 42
<212> TYPE: DNA
<213> ORGANISM: Artificial Sequence
<220> FEATURE:
<223> OTHER INFORMATION: primer_bind Fin Rp2

<400> SEQUENCE: 74
ggctctaaag caagggtcaa ctgatttaac tggaacacta tg          42

<210> SEQ ID NO 75

```
<211> LENGTH: 42
<212> TYPE: DNA
<213> ORGANISM: Artificial Sequence
<220> FEATURE:
<223> OTHER INFORMATION: primer_bind EGF Fp3

<400> SEQUENCE: 75
catagtgttc cagttaaatc agttgaccct tgctttagag cc                              42

<210> SEQ ID NO 76
<211> LENGTH: 45
<212> TYPE: DNA
<213> ORGANISM: Artificial Sequence
<220> FEATURE:
<223> OTHER INFORMATION: primer_bind EGF RP 4

<400> SEQUENCE: 76
agctctggtt ccggaatcac agtcagtacc tatatgtctt gccaa                          45

<210> SEQ ID NO 77
<211> LENGTH: 45
<212> TYPE: DNA
<213> ORGANISM: Artificial Sequence
<220> FEATURE:
<223> OTHER INFORMATION: primer_bind K1 Fp 5

<400> SEQUENCE: 77
ttggcaagac atataggtac tgactgtgat tccggaacca gagct                          45

<210> SEQ ID NO 78
<211> LENGTH: 44
<212> TYPE: DNA
<213> ORGANISM: Artificial Sequence
<220> FEATURE:
<223> OTHER INFORMATION: primer_bind CD Rp 2

<400> SEQUENCE: 78
tcatatcgcg gccgctggtc tcatgttatc tctgatccag tcca                           44

<210> SEQ ID NO 79
<211> LENGTH: 48
<212> TYPE: DNA
<213> ORGANISM: Artificial Sequence
<220> FEATURE:
<223> OTHER INFORMATION: primer_bind Fg Fp 1

<400> SEQUENCE: 79
ggataactcg agaaaagaga ggctcaagag attcatgcta gattcaga                       48

<210> SEQ ID NO 80
<211> LENGTH: 42
<212> TYPE: DNA
<213> ORGANISM: Artificial Sequence
<220> FEATURE:
<223> OTHER INFORMATION: primer_bind Fg Rp2

<400> SEQUENCE: 80
tctaaagcaa gggtcaactg atttaactgg aacactatga ca                             42

<210> SEQ ID NO 81
<211> LENGTH: 42
<212> TYPE: DNA
<213> ORGANISM: Artificial Sequence
<220> FEATURE:
<223> OTHER INFORMATION: primer_bind EFI Fp3

<400> SEQUENCE: 81
```
tgtcatagtg ttccagttaa atcagttgac ccttgcttta ga                          42

<210> SEQ ID NO 82
<211> LENGTH: 45
<212> TYPE: DNA
<213> ORGANISM: Artificial Sequence
<220> FEATURE:
<223> OTHER INFORMATION: primer_bind EFI RP 4

<400> SEQUENCE: 82
atcactgttt ccggaatcac aatcagtacc aatatgtctt gccaa                       45

<210> SEQ ID NO 83
<211> LENGTH: 44
<212> TYPE: DNA
<213> ORGANISM: Artificial Sequence
<220> FEATURE:
<223> OTHER INFORMATION: primer_bind K2 Fp 5

<400> SEQUENCE: 83
ttggcaagac atattggtac tgattgtgat tccggaaaca gtga                        44

<210> SEQ ID NO 84
<211> LENGTH: 44
<212> TYPE: DNA
<213> ORGANISM: Artificial Sequence
<220> FEATURE:
<223> OTHER INFORMATION: primer_bind K2CD Rp 6

<400> SEQUENCE: 84
tcatatcgcg gccgctggtc tcatgttatc tctgatccag tcca                        44

<210> SEQ ID NO 85
<211> LENGTH: 42
<212> TYPE: DNA
<213> ORGANISM: Artificial Sequence
<220> FEATURE:
<223> OTHER INFORMATION: primer_bind N_EtPA Fp1

<400> SEQUENCE: 85
ggatatctcg agaaaagagt tgacccttgc ttcagagcca ac                          42

<210> SEQ ID NO 86
<211> LENGTH: 42
<212> TYPE: DNA
<213> ORGANISM: Artificial Sequence
<220> FEATURE:
<223> OTHER INFORMATION: primer_bind N_EtPA Rp 2

<400> SEQUENCE: 86
aaagtaacaa tcactatttg acttgactgg aacactatga ca                          42

<210> SEQ ID NO 87
<211> LENGTH: 42
<212> TYPE: DNA
<213> ORGANISM: Artificial Sequence
<220> FEATURE:
<223> OTHER INFORMATION: primer_bind EK2 CD Fp 3

<400> SEQUENCE: 87
tgtcatagtg ttccagtcaa gtcaaatagt gattgttact tt                          42

<210> SEQ ID NO 88
<211> LENGTH: 44
<212> TYPE: DNA

```
<213> ORGANISM: Artificial Sequence
<220> FEATURE:
<223> OTHER INFORMATION: primer_bind K2 CD Rp 4

<400> SEQUENCE: 88
tcatatcgcg gccgctggtc tcatgttatc tctgatccag tcca                    44

<210> SEQ ID NO 89
<211> LENGTH: 48
<212> TYPE: DNA
<213> ORGANISM: Artificial Sequence
<220> FEATURE:
<223> OTHER INFORMATION: primer_bind Finger  Fp1

<400> SEQUENCE: 89
ggataactcg agaaaagaga ggctcaagag attcatgcta gattcaga                48

<210> SEQ ID NO 90
<211> LENGTH: 42
<212> TYPE: DNA
<213> ORGANISM: Artificial Sequence
<220> FEATURE:
<223> OTHER INFORMATION: primer_bind Finger Rp 2

<400> SEQUENCE: 90
aaagtaacaa tcactatttg acttgactgg aacactatga ca                      42

<210> SEQ ID NO 91
<211> LENGTH: 42
<212> TYPE: DNA
<213> ORGANISM: Artificial Sequence
<220> FEATURE:
<223> OTHER INFORMATION: primer_bind K2 CD Fp 3

<400> SEQUENCE: 91
tgtcatagtg ttccagtcaa gtcaaatagt gattgttact tt                      42

<210> SEQ ID NO 92
<211> LENGTH: 43
<212> TYPE: DNA
<213> ORGANISM: Artificial Sequence
<220> FEATURE:
<223> OTHER INFORMATION: primer_bind EGF Rp 4

<400> SEQUENCE: 92
ccatatcgcg gccgcttaac ctgagtcaca atctgttcca ata                     43

<210> SEQ ID NO 93
<211> LENGTH: 42
<212> TYPE: DNA
<213> ORGANISM: Artificial Sequence
<220> FEATURE:
<223> OTHER INFORMATION: primer_bind EGF CD Fp1

<400> SEQUENCE: 93 gttgacccctt gctttagagc caactgtgaa taccaatgcc ag                     42

<210> SEQ ID NO 94
<211> LENGTH: 42
<212> TYPE: DNA
<213> ORGANISM: Artificial Sequence
<220> FEATURE:
<223> OTHER INFORMATION: primer_bind EF CD Rp 2

<400> SEQUENCE: 94
ctggcattgg tattcacagt tggctctaaa gcaagggtca ac                      42
```

<210> SEQ ID NO 95
<211> LENGTH: 42
<212> TYPE: DNA
<213> ORGANISM: Artificial Sequence
<220> FEATURE:
<223> OTHER INFORMATION: primer_bind K2 CD Fp 3

<400> SEQUENCE: 95 gttgacccctt gctttagagc caactgtgaa taccaatgcc ag       42

<210> SEQ ID NO 96
<211> LENGTH: 41
<212> TYPE: DNA
<213> ORGANISM: Artificial Sequence
<220> FEATURE:
<223> OTHER INFORMATION: primer_bind K2 CD Rp 4

<400> SEQUENCE: 96
tttatacgcg gccgctggtc tcatgttatc tctgatccag t         41

<210> SEQ ID NO 97
<211> LENGTH: 40
<212> TYPE: DNA
<213> ORGANISM: Artificial Sequence
<220> FEATURE:
<223> OTHER INFORMATION: primer_bind Met rep Val Fp

<400> SEQUENCE: 97
catgaaccac atagatgtca agtattctgc aaccagactg           40

<210> SEQ ID NO 98
<211> LENGTH: 40
<212> TYPE: DNA
<213> ORGANISM: Artificial Sequence
<220> FEATURE:
<223> OTHER INFORMATION: primer_bind Met rep Val Rp

<400> SEQUENCE: 98
cagtctggtt gcagaatact tgacatctat gtggttcatg           40

<210> SEQ ID NO 99
<211> LENGTH: 40
<212> TYPE: DNA
<213> ORGANISM: Artificial Sequence
<220> FEATURE:
<223> OTHER INFORMATION: primer_bind Met rep Ala Fp

<400> SEQUENCE: 99
catgaaccac atagatgtca agcattctgc aaccagactg           40

<210> SEQ ID NO 100
<211> LENGTH: 40
<212> TYPE: DNA
<213> ORGANISM: Artificial Sequence
<220> FEATURE:
<223> OTHER INFORMATION: primer_bind Met rep Ala Rp

<400> SEQUENCE: 100
cagtctggtt gcagaatgct tgacatctat gtggttcatg           40

<210> SEQ ID NO 101
<211> LENGTH: 40
<212> TYPE: DNA
<213> ORGANISM: Artificial Sequence
<220> FEATURE:

<223> OTHER INFORMATION: primer_bind Met rep Glu Fp

<400> SEQUENCE: 101
catgaaccac atagatgtca acaattctgc aaccagactg                                40

<210> SEQ ID NO 102
<211> LENGTH: 40
<212> TYPE: DNA
<213> ORGANISM: Artificial Sequence
<220> FEATURE:
<223> OTHER INFORMATION: primer_bind Met rep Glu Rp

<400> SEQUENCE: 102
cagtctggtt gcagaattgt tgacatctat gtggttcatg                                40

<210> SEQ ID NO 103
<211> LENGTH: 40
<212> TYPE: DNA
<213> ORGANISM: Artificial Sequence
<220> FEATURE:
<223> OTHER INFORMATION: primer_bind T 115 N Fp

<400> SEQUENCE: 103
cagggaatct catatagagg taattggtct acagctgagt                                40

<210> SEQ ID NO 104
<211> LENGTH: 40
<212> TYPE: DNA
<213> ORGANISM: Artificial Sequence
<220> FEATURE:
<223> OTHER INFORMATION: primer_bind T 115 N Rp

<400> SEQUENCE: 104
actcagctgt agaccaatta cctctatatg agattccctg                                40

<210> SEQ ID NO 105
<211> LENGTH: 31
<212> TYPE: DNA
<213> ORGANISM: Artificial Sequence
<220> FEATURE:
<223> OTHER INFORMATION: primer_bind N129 Q Fp

<400> SEQUENCE: 105
aatgtactaa ctggcaatct tccgctttgg c                                         31

<210> SEQ ID NO 106
<211> LENGTH: 31
<212> TYPE: DNA
<213> ORGANISM: Artificial Sequence
<220> FEATURE:
<223> OTHER INFORMATION: primer_bind N129 Q Rp

<400> SEQUENCE: 106
gccaaagcgg aagattgcca gttagtacat t                                         31

<210> SEQ ID NO 107
<211> LENGTH: 48
<212> TYPE: DNA
<213> ORGANISM: Artificial Sequence
<220> FEATURE:
<223> OTHER INFORMATION: primer_bind KH Fp 1

<400> SEQUENCE: 107
ggataactcg agaaaagaga ggctcaagag attcatgcta gattcaga                       48

-continued

<210> SEQ ID NO 108
<211> LENGTH: 33
<212> TYPE: DNA
<213> ORGANISM: Artificial Sequence
<220> FEATURE:
<223> OTHER INFORMATION: primer_bind KH Rp 2

<400> SEQUENCE: 108
agcagcggca gcagcaaaaa tggcagcctg cca                                33

<210> SEQ ID NO 109
<211> LENGTH: 37
<212> TYPE: DNA
<213> ORGANISM: Artificial Sequence
<220> FEATURE:
<223> OTHER INFORMATION: primer_bind KH Fp 3

<400> SEQUENCE: 109
gctgctgccg ctgcttcccc tggagagaga ttcctttt                           37

<210> SEQ ID NO 110
<211> LENGTH: 44
<212> TYPE: DNA
<213> ORGANISM: Artificial Sequence
<220> FEATURE:
<223> OTHER INFORMATION: primer_bind KH Rp4

<400> SEQUENCE: 110
tcatatcgcg gccgctggtc tcatgttatc tctgatccag tcca                    44

<210> SEQ ID NO 111
<211> LENGTH: 118
<212> TYPE: PRT
<213> ORGANISM: Homo sapiens

<400> SEQUENCE: 111

Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
                85                  90                  95

Phe Glu Cys Ile Cys Gly Pro Asp Ser Ala Leu Ala Arg His Ile Gly
            100                 105                 110

Thr Asp Cys Asp Ser Gly
        115

<210> SEQ ID NO 112
<211> LENGTH: 414
<212> TYPE: PRT
<213> ORGANISM: Streptococcus equisimilis

<400> SEQUENCE: 112

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp

```
            20                  25                  30
Ile Ser Leu Lys Phe Phe Glu Ile Asp Leu Thr Ser Arg Pro Ala His
        35                  40                  45
Gly Gly Lys Thr Glu Gln Gly Leu Ser Pro Lys Ser Lys Pro Phe Ala
    50                  55                  60
Thr Asp Ser Gly Ala Met Ser His Lys Leu Glu Lys Ala Asp Leu Leu
65                  70                  75                  80
Lys Ala Ile Gln Glu Gln Leu Ile Ala Asn Val His Ser Asn Asp Asp
                85                  90                  95
Tyr Phe Glu Val Ile Asp Phe Ala Ser Asp Ala Thr Ile Thr Asp Arg
            100                 105                 110
Asn Gly Lys Val Tyr Phe Ala Asp Lys Asp Gly Ser Val Thr Leu Pro
        115                 120                 125
Thr Gln Pro Val Gln Glu Phe Leu Leu Ser Gly His Val Arg Val Arg
    130                 135                 140
Pro Tyr Lys Glu Lys Pro Ile Gln Asn Gln Ala Lys Ser Val Asp Val
145                 150                 155                 160
Glu Tyr Thr Val Gln Phe Thr Pro Leu Asn Pro Asp Asp Phe Arg
                165                 170                 175
Pro Gly Leu Lys Asp Thr Lys Leu Leu Lys Thr Leu Ala Ile Gly Asp
            180                 185                 190
Thr Ile Thr Ser Gln Glu Leu Leu Ala Gln Ala Gln Ser Ile Leu Asn
        195                 200                 205
Lys Asn His Pro Gly Tyr Thr Ile Tyr Glu Arg Asp Ser Ser Ile Val
    210                 215                 220
Thr His Asp Asn Asp Ile Phe Arg Thr Ile Leu Pro Met Asp Gln Glu
225                 230                 235                 240
Phe Thr Tyr Arg Val Lys Asn Arg Glu Gln Ala Tyr Arg Ile Asn Lys
                245                 250                 255
Lys Ser Gly Leu Asn Glu Glu Ile Asn Asn Thr Asp Leu Ile Ser Glu
            260                 265                 270
Lys Tyr Tyr Val Leu Lys Lys Gly Glu Lys Pro Tyr Asp Pro Phe Asp
        275                 280                 285
Arg Ser His Leu Lys Leu Phe Thr Ile Lys Tyr Val Asp Val Asp Thr
    290                 295                 300
Asn Glu Leu Leu Lys Ser Glu Gln Leu Leu Thr Ala Ser Glu Arg Asn
305                 310                 315                 320
Leu Asp Phe Arg Asp Leu Tyr Asp Pro Arg Asp Lys Ala Lys Leu Leu
                325                 330                 335
Tyr Asn Asn Leu Asp Ala Phe Gly Ile Met Asp Tyr Thr Leu Thr Gly
            340                 345                 350
Lys Val Glu Asp Asn His Asp Asp Thr Asn Arg Ile Ile Thr Val Tyr
        355                 360                 365
Met Gly Lys Arg Pro Glu Gly Glu Asn Ala Ser Tyr His Leu Ala Tyr
    370                 375                 380
Asp Lys Asp Arg Tyr Thr Glu Glu Arg Glu Val Tyr Ser Tyr Leu
385                 390                 395                 400
Arg Tyr Thr Gly Thr Pro Ile Pro Asp Asn Pro Asn Asp Lys
                405                 410

<210> SEQ ID NO 113
<211> LENGTH: 532
<212> TYPE: PRT
<213> ORGANISM: Artificial Sequence
```

```
<220> FEATURE:
<223> OTHER INFORMATION: FUSION PROTIEN - N_EGF _SK

<400> SEQUENCE: 113

Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
                85                  90                  95

Phe Glu Cys Ile Cys Gly Pro Asp Ser Ala Leu Ala Arg His Ile Gly
            100                 105                 110

Thr Asp Cys Asp Ser Gly Ile Ala Gly Pro Glu Trp Leu Leu Asp Arg
        115                 120                 125

Pro Ser Val Asn Asn Ser Gln Leu Val Val Ser Val Ala Gly Thr Val
    130                 135                 140

Glu Gly Thr Asn Gln Asp Ile Ser Leu Lys Phe Phe Glu Ile Asp Leu
145                 150                 155                 160

Thr Ser Arg Pro Ala His Gly Gly Lys Thr Glu Gln Gly Leu Ser Pro
                165                 170                 175

Lys Ser Lys Pro Phe Ala Thr Asp Ser Gly Ala Met Ser His Lys Leu
            180                 185                 190

Glu Lys Ala Asp Leu Leu Lys Ala Ile Gln Glu Gln Leu Ile Ala Asn
        195                 200                 205

Val His Ser Asn Asp Asp Tyr Phe Glu Val Ile Asp Phe Ala Ser Asp
    210                 215                 220

Ala Thr Ile Thr Asp Arg Asn Gly Lys Val Tyr Phe Ala Asp Lys Asp
225                 230                 235                 240

Gly Ser Val Thr Leu Pro Thr Gln Pro Val Gln Glu Phe Leu Leu Ser
                245                 250                 255

Gly His Val Arg Val Arg Pro Tyr Lys Glu Lys Pro Ile Gln Asn Gln
            260                 265                 270

Ala Lys Ser Val Asp Val Glu Tyr Thr Val Gln Phe Thr Pro Leu Asn
        275                 280                 285

Pro Asp Asp Asp Phe Arg Pro Gly Leu Lys Asp Thr Lys Leu Leu Lys
    290                 295                 300

Thr Leu Ala Ile Gly Asp Thr Ile Thr Ser Gln Glu Leu Leu Ala Gln
305                 310                 315                 320

Ala Gln Ser Ile Leu Asn Lys Asn His Pro Gly Tyr Thr Ile Tyr Glu
                325                 330                 335

Arg Asp Ser Ser Ile Val Thr His Asp Asn Asp Ile Phe Arg Thr Ile
            340                 345                 350

Leu Pro Met Asp Gln Glu Phe Thr Tyr Arg Val Lys Asn Arg Glu Gln
        355                 360                 365

Ala Tyr Arg Ile Asn Lys Lys Ser Gly Leu Asn Glu Glu Ile Asn Asn
    370                 375                 380

Thr Asp Leu Ile Ser Glu Lys Tyr Tyr Val Leu Lys Lys Gly Glu Lys
385                 390                 395                 400
```

```
Pro Tyr Asp Pro Phe Asp Arg Ser His Leu Lys Leu Phe Thr Ile Lys
            405                 410                 415

Tyr Val Asp Val Asp Thr Asn Glu Leu Leu Lys Ser Glu Gln Leu Leu
        420                 425                 430

Thr Ala Ser Glu Arg Asn Leu Asp Phe Arg Asp Leu Tyr Asp Pro Arg
    435                 440                 445

Asp Lys Ala Lys Leu Leu Tyr Asn Asn Leu Asp Ala Phe Gly Ile Met
450                 455                 460

Asp Tyr Thr Leu Thr Gly Lys Val Glu Asp Asn His Asp Asp Thr Asn
465                 470                 475                 480

Arg Ile Ile Thr Val Tyr Met Gly Lys Arg Pro Glu Gly Glu Asn Ala
            485                 490                 495

Ser Tyr His Leu Ala Tyr Asp Lys Asp Arg Tyr Thr Glu Glu Glu Arg
        500                 505                 510

Glu Val Tyr Ser Tyr Leu Arg Tyr Thr Gly Thr Pro Ile Pro Asp Asn
    515                 520                 525

Pro Asn Asp Lys
    530

<210> SEQ ID NO 114
<211> LENGTH: 511
<212> TYPE: PRT
<213> ORGANISM: Artificial Sequence
<220> FEATURE:
<223> OTHER INFORMATION: FUSION PROTEIN - SK_EGF

<400> SEQUENCE: 114

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60

Thr Asp Ser Gly Ala Met Ser His Lys Leu Glu Lys Ala Asp Leu Leu
65                  70                  75                  80

Lys Ala Ile Gln Glu Gln Leu Ile Ala Asn Val His Ser Asn Asp Asp
            85                  90                  95

Tyr Phe Glu Val Ile Asp Phe Ala Ser Asp Ala Thr Ile Thr Asp Arg
        100                 105                 110

Asn Gly Lys Val Tyr Phe Ala Asp Lys Asp Gly Ser Val Thr Leu Pro
    115                 120                 125

Thr Gln Pro Val Gln Glu Phe Leu Leu Ser Gly His Val Arg Val Arg
130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Asp Phe Arg
            165                 170                 175

Pro Gly Leu Lys Asp Thr Lys Leu Leu Lys Thr Leu Ala Ile Gly Asp
        180                 185                 190

Thr Ile Thr Ser Gln Glu Leu Leu Ala Gln Ala Gln Ser Ile Leu Asn
    195                 200                 205

Lys Asn His Pro Gly Tyr Thr Ile Tyr Glu Arg Asp Ser Ser Ile Val
210                 215                 220
```

```
Thr His Asp Asn Asp Ile Phe Arg Thr Ile Leu Pro Met Asp Gln Glu
225                 230                 235                 240

Phe Thr Tyr Arg Val Lys Asn Arg Glu Gln Ala Tyr Arg Ile Asn Lys
            245                 250                 255

Lys Ser Gly Leu Asn Glu Glu Ile Asn Asn Thr Asp Leu Ile Ser Glu
        260                 265                 270

Lys Tyr Tyr Val Leu Lys Lys Gly Lys Pro Tyr Asp Pro Phe Asp
    275                 280                 285

Arg Ser His Leu Lys Leu Phe Thr Ile Lys Tyr Val Asp Val Asp Thr
        290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
            325                 330                 335

Tyr Asn Asn Leu Asp Ala Phe Gly Ile Met Asp Tyr Thr Leu Thr Gly
        340                 345                 350

Lys Val Glu Asp Asn His Asp Asp Thr Asn Arg Ile Ile Thr Val Tyr
    355                 360                 365

Met Gly Lys Arg Pro Glu Gly Glu Asn Ala Ser Tyr His Leu Ala Gly
370                 375                 380

Gly Gly Val Gln Ala Gln Gln Ile Val Val Asp Pro Cys Phe Arg Ala
385                 390                 395                 400

Asn Cys Glu Tyr Gln Cys Gln Pro Leu Asn Gln Thr Ser Tyr Leu Cys
            405                 410                 415

Val Cys Ala Glu Gly Phe Ala Pro Ile Pro His Glu Pro His Arg Cys
        420                 425                 430

Gln Met Phe Cys Asn Gln Thr Ala Cys Pro Ala Asp Cys Asp Pro Asn
    435                 440                 445

Thr Gln Ala Ser Cys Glu Cys Pro Glu Gly Tyr Ile Leu Asp Asp Gly
        450                 455                 460

Phe Ile Cys Thr Asp Ile Asp Glu Cys Glu Asn Gly Gly Phe Cys Ser
465                 470                 475                 480

Gly Val Cys His Asn Leu Pro Gly Thr Phe Glu Cys Ile Cys Gly Pro
            485                 490                 495

Asp Ser Ala Leu Ala Arg His Ile Gly Thr Asp Cys Asp Ser Gly
        500                 505                 510

<210> SEQ ID NO 115
<211> LENGTH: 629
<212> TYPE: PRT
<213> ORGANISM: Artificial Sequence
<220> FEATURE:
<223> OTHER INFORMATION: FUSION PROTEIN - N_EGF_SK_EGF

<400> SEQUENCE: 115

Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80
```

```
Glu Asn Gly Gly Phe Cys Ser Gly Val Cys His Asn Leu Pro Gly Thr
                    85                  90                  95

Phe Glu Cys Ile Cys Gly Pro Asp Ser Ala Leu Ala Arg His Ile Gly
                100                 105                 110

Thr Asp Cys Asp Ser Gly Ile Ala Gly Pro Glu Trp Leu Leu Asp Arg
            115                 120                 125

Pro Ser Val Asn Asn Ser Gln Leu Val Ser Val Ala Gly Thr Val
    130                 135                 140

Glu Gly Thr Asn Gln Asp Ile Ser Leu Lys Phe Phe Glu Ile Asp Leu
145                 150                 155                 160

Thr Ser Arg Pro Ala His Gly Gly Lys Thr Glu Gln Gly Leu Ser Pro
                165                 170                 175

Lys Ser Lys Pro Phe Ala Thr Asp Ser Gly Ala Met Ser His Lys Leu
            180                 185                 190

Glu Lys Ala Asp Leu Leu Lys Ala Ile Gln Glu Gln Leu Ile Ala Asn
            195                 200                 205

Val His Ser Asn Asp Asp Tyr Phe Glu Val Ile Asp Phe Ala Ser Asp
    210                 215                 220

Ala Thr Ile Thr Asp Arg Asn Gly Lys Val Tyr Phe Ala Asp Lys Asp
225                 230                 235                 240

Gly Ser Val Thr Leu Pro Thr Gln Pro Val Gln Glu Phe Leu Leu Ser
                245                 250                 255

Gly His Val Arg Val Arg Pro Tyr Lys Glu Lys Pro Ile Gln Asn Gln
                260                 265                 270

Ala Lys Ser Val Asp Val Glu Tyr Thr Val Gln Phe Thr Pro Leu Asn
            275                 280                 285

Pro Asp Asp Asp Phe Arg Pro Gly Leu Lys Asp Thr Lys Leu Leu Lys
    290                 295                 300

Thr Leu Ala Ile Gly Asp Thr Ile Thr Ser Gln Glu Leu Leu Ala Gln
305                 310                 315                 320

Ala Gln Ser Ile Leu Asn Lys Asn His Pro Gly Tyr Thr Ile Tyr Glu
                325                 330                 335

Arg Asp Ser Ser Ile Val Thr His Asp Asn Asp Ile Phe Arg Thr Ile
            340                 345                 350

Leu Pro Met Asp Gln Glu Phe Thr Tyr Arg Val Lys Asn Arg Glu Gln
            355                 360                 365

Ala Tyr Arg Ile Asn Lys Lys Ser Gly Leu Asn Glu Glu Ile Asn Asn
            370                 375                 380

Thr Asp Leu Ile Ser Glu Lys Tyr Tyr Val Leu Lys Lys Gly Glu Lys
385                 390                 395                 400

Pro Tyr Asp Pro Phe Asp Arg Ser His Leu Lys Leu Phe Thr Ile Lys
                405                 410                 415

Tyr Val Asp Val Asp Thr Asn Glu Leu Leu Lys Ser Glu Gln Leu Leu
            420                 425                 430

Thr Ala Ser Glu Arg Asn Leu Asp Phe Arg Asp Leu Tyr Asp Pro Arg
            435                 440                 445

Asp Lys Ala Lys Leu Leu Tyr Asn Asn Leu Asp Ala Phe Gly Ile Met
    450                 455                 460

Asp Tyr Thr Leu Thr Gly Lys Val Glu Asp Asn His Asp Asp Thr Asn
465                 470                 475                 480

Arg Ile Ile Thr Val Tyr Met Gly Lys Arg Pro Glu Gly Glu Asn Ala
                485                 490                 495
```

```
Ser Tyr His Leu Ala Gly Gly Val Gln Ala Gln Gln Ile Val Val
            500                 505                 510

Asp Pro Cys Phe Arg Ala Asn Cys Glu Tyr Gln Cys Gln Pro Leu Asn
515                 520                 525

Gln Thr Ser Tyr Leu Cys Val Cys Ala Glu Gly Phe Ala Pro Ile Pro
            530                 535                 540

His Glu Pro His Arg Cys Gln Met Phe Cys Asn Gln Thr Ala Cys Pro
545                 550                 555                 560

Ala Asp Cys Asp Pro Asn Thr Gln Ala Ser Cys Glu Cys Pro Glu Gly
                565                 570                 575

Tyr Ile Leu Asp Asp Gly Phe Ile Cys Thr Asp Ile Asp Glu Cys Glu
            580                 585                 590

Asn Gly Gly Phe Cys Ser Gly Val Cys His Asn Leu Pro Gly Thr Phe
595                 600                 605

Glu Cys Ile Cys Gly Pro Asp Ser Ala Leu Ala Arg His Ile Gly Thr
            610                 615                 620

Asp Cys Asp Ser Gly
625

<210> SEQ ID NO 116
<211> LENGTH: 534
<212> TYPE: PRT
<213> ORGANISM: Artificial Sequence
<220> FEATURE:
<223> OTHER INFORMATION: FUSION PROTEIN - INTERDOMAIN SK_EGF ALPHA AND
      BETA

<400> SEQUENCE: 116

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60

Thr Asp Ser Gly Ala Met Ser His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95

Tyr Phe Glu Val Ile Asp Phe Ala Ser Asp Ala Thr Ile Thr Asp Arg
            100                 105                 110

Asn Gly Lys Val Tyr Phe Ala Asp Lys Asp Gly Ser Val Thr Leu Pro
        115                 120                 125

Thr Gln Pro Val Gln Glu Phe Leu Leu Ser Gly His Val Arg Val Arg
    130                 135                 140

Pro Tyr Lys Glu Lys Pro Ile Gln Asn Gln Ala Lys Ser Glu Pro Val
145                 150                 155                 160

Asp Pro Cys Phe Arg Ala Asn Cys Glu Tyr Gln Cys Gln Pro Leu Asn
                165                 170                 175

Gln Thr Ser Tyr Leu Cys Val Cys Ala Glu Gly Phe Ala Pro Ile Pro
            180                 185                 190

His Glu Pro His Arg Cys Gln Met Phe Cys Asn Gln Thr Ala Cys Pro
        195                 200                 205

Ala Asp Cys Asp Pro Asn Thr Gln Ala Ser Cys Glu Cys Pro Glu Gly
    210                 215                 220
```

-continued

```
Tyr Ile Leu Asp Asp Gly Phe Ile Cys Thr Asp Ile Asp Glu Cys Glu
225                 230                 235                 240

Asn Gly Gly Phe Cys Ser Gly Val Cys His Asn Leu Pro Gly Thr Phe
            245                 250                 255

Glu Cys Ile Cys Gly Pro Asp Ser Ala Leu Ala Arg His Ile Gly Thr
        260                 265                 270

Asp Cys Asp Ser Gly Val Asp Val Glu Tyr Thr Val Gln Phe Thr Pro
    275                 280                 285

Leu Asn Pro Asp Asp Phe Arg Pro Gly Leu Lys Asp Thr Lys Leu
290                 295                 300

Leu Lys Thr Leu Ala Ile Gly Asp Thr Ile Thr Ser Gln Glu Leu Leu
305                 310                 315                 320

Ala Gln Ala Gln Ser Ile Leu Asn Lys Asn His Pro Gly Tyr Thr Ile
                325                 330                 335

Tyr Glu Arg Asp Ser Ser Ile Val Thr His Asp Asn Asp Ile Phe Arg
            340                 345                 350

Thr Ile Leu Pro Met Asp Gln Glu Phe Thr Tyr Arg Val Lys Asn Arg
        355                 360                 365

Glu Gln Ala Tyr Arg Ile Asn Lys Lys Ser Gly Leu Asn Glu Glu Ile
    370                 375                 380

Asn Asn Thr Asp Leu Ile Ser Glu Lys Tyr Tyr Val Leu Lys Lys Gly
385                 390                 395                 400

Glu Lys Pro Tyr Asp Pro Phe Asp Arg Ser His Leu Lys Leu Phe Thr
                405                 410                 415

Ile Lys Tyr Val Asp Val Asp Thr Asn Glu Leu Leu Lys Ser Glu Gln
            420                 425                 430

Leu Leu Thr Ala Ser Glu Arg Asn Leu Asp Phe Arg Asp Leu Tyr Asp
        435                 440                 445

Pro Arg Asp Lys Ala Lys Leu Leu Tyr Asn Asn Leu Asp Ala Phe Gly
    450                 455                 460

Ile Met Asp Tyr Thr Leu Thr Gly Lys Val Glu Asp Asn His Asp Asp
465                 470                 475                 480

Thr Asn Arg Ile Ile Thr Val Tyr Met Gly Lys Arg Pro Glu Gly Glu
                485                 490                 495

Asn Ala Ser Tyr His Leu Ala Tyr Asp Lys Asp Arg Tyr Thr Glu Glu
            500                 505                 510

Glu Arg Glu Val Tyr Ser Tyr Leu Arg Tyr Thr Gly Thr Pro Ile Pro
        515                 520                 525

Asp Asn Pro Asn Asp Lys
    530
```

<210> SEQ ID NO 117
<211> LENGTH: 643
<212> TYPE: PRT
<213> ORGANISM: Artificial Sequence
<220> FEATURE:
<223> OTHER INFORMATION: FUSION PROTEIN - TG_N_EGF_TCS_SK_EGF

<400> SEQUENCE: 117

```
Val Gln Ala Gln Gln Ile Val Val Asp Pro Cys Phe Arg Ala Asn Cys
1               5                   10                  15

Glu Tyr Gln Cys Gln Pro Leu Asn Gln Thr Ser Tyr Leu Cys Val Cys
            20                  25                  30

Ala Glu Gly Phe Ala Pro Ile Pro His Glu Pro His Arg Cys Gln Val
        35                  40                  45
```

-continued

Phe Cys Asn Gln Thr Ala Cys Pro Ala Asp Cys Asp Pro Asn Thr Gln
    50              55              60
Ala Ser Cys Glu Cys Pro Glu Gly Tyr Ile Leu Asp Asp Gly Phe Ile
65              70              75              80
Cys Thr Asp Ile Asp Glu Cys Glu Asn Gly Gly Phe Cys Ser Gly Val
                85              90              95
Cys His Asn Leu Pro Gly Thr Phe Glu Cys Ile Cys Gly Pro Asp Ser
            100             105             110
Ala Leu Ala Arg His Ile Gly Thr Asp Cys Asp Ser Gly Ile Lys Pro
        115             120             125
Arg Ile Val Gly Ile Ala Gly Pro Glu Trp Leu Leu Asp Arg Pro Ser
130             135             140
Val Asn Asn Ser Gln Leu Val Val Ser Val Ala Gly Thr Val Glu Gly
145             150             155             160
Thr Asn Gln Asp Ile Ser Leu Lys Phe Phe Glu Ile Asp Leu Thr Ser
                165             170             175
Arg Pro Ala His Gly Gly Lys Thr Glu Gln Gly Leu Ser Pro Lys Ser
            180             185             190
Lys Pro Phe Ala Thr Asp Ser Gly Ala Met Ser His Lys Leu Glu Lys
        195             200             205
Ala Asp Leu Leu Lys Ala Ile Gln Glu Gln Leu Ile Ala Asn Val His
    210             215             220
Ser Asn Asp Asp Tyr Phe Glu Val Ile Asp Phe Ala Ser Asp Ala Thr
225             230             235             240
Ile Thr Asp Arg Asn Gly Lys Val Tyr Phe Ala Asp Lys Asp Gly Ser
                245             250             255
Val Thr Leu Pro Thr Gln Pro Val Gln Glu Phe Leu Leu Ser Gly His
            260             265             270
Val Arg Val Arg Pro Tyr Lys Glu Lys Pro Ile Gln Asn Gln Ala Lys
        275             280             285
Ser Val Asp Val Glu Tyr Thr Val Gln Phe Thr Pro Leu Asn Pro Asp
    290             295             300
Asp Asp Phe Arg Pro Gly Leu Lys Asp Thr Lys Leu Leu Lys Thr Leu
305             310             315             320
Ala Ile Gly Asp Thr Ile Thr Ser Gln Glu Leu Leu Ala Gln Ala Gln
                325             330             335
Ser Ile Leu Asn Lys Asn His Pro Gly Tyr Thr Ile Tyr Glu Arg Asp
            340             345             350
Ser Ser Ile Val Thr His Asp Asn Asp Ile Phe Arg Thr Ile Leu Pro
        355             360             365
Met Asp Gln Glu Phe Thr Tyr Arg Val Lys Asn Arg Glu Gln Ala Tyr
    370             375             380
Arg Ile Asn Lys Lys Ser Gly Leu Asn Glu Glu Ile Asn Asn Thr Asp
385             390             395             400
Leu Ile Ser Glu Lys Tyr Tyr Val Leu Lys Gly Glu Lys Pro Tyr
                405             410             415
Asp Pro Phe Asp Arg Ser His Leu Lys Leu Phe Thr Ile Lys Tyr Val
            420             425             430
Asp Val Asp Thr Asn Glu Leu Leu Lys Ser Glu Gln Leu Leu Thr Ala
        435             440             445
Ser Glu Arg Asn Leu Asp Phe Arg Asp Leu Tyr Asp Pro Arg Asp Lys
    450             455             460

```
Ala Lys Leu Leu Tyr Asn Asn Leu Asp Ala Phe Gly Ile Met Asp Tyr
465                 470                 475                 480

Thr Leu Thr Gly Lys Val Glu Asp Asn His Asp Asp Thr Asn Arg Ile
                485                 490                 495

Ile Thr Val Tyr Met Gly Lys Arg Pro Glu Gly Glu Asn Ala Ser Tyr
            500                 505                 510

His Leu Ala Gly Gly Gly Val Gln Ala Gln Gln Ile Val Val Asp Pro
            515                 520                 525

Cys Phe Arg Ala Asn Cys Glu Tyr Gln Cys Gln Pro Leu Asn Gln Thr
        530                 535                 540

Ser Tyr Leu Cys Val Cys Ala Glu Gly Phe Ala Pro Ile Pro His Glu
545                 550                 555                 560

Pro His Arg Cys Gln Val Phe Cys Asn Gln Thr Ala Cys Pro Ala Asp
            565                 570                 575

Cys Asp Pro Asn Thr Gln Ala Ser Cys Glu Cys Pro Glu Gly Tyr Ile
            580                 585                 590

Leu Asp Asp Gly Phe Ile Cys Thr Asp Ile Asp Glu Cys Glu Asn Gly
        595                 600                 605

Gly Phe Cys Ser Gly Val Cys His Asn Leu Pro Gly Thr Phe Glu Cys
610                 615                 620

Ile Cys Gly Pro Asp Ser Ala Leu Ala Arg His Ile Gly Thr Asp Cys
625                 630                 635                 640

Asp Ser Gly

<210> SEQ ID NO 118
<211> LENGTH: 124
<212> TYPE: PRT
<213> ORGANISM: Artificial Sequence
<220> FEATURE:
<223> OTHER INFORMATION: FUSION PROTEIN - EGF _SAK

<400> SEQUENCE: 118

Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
                85                  90                  95

Phe Glu Cys Ile Cys Gly Pro Asp Ser Ala Leu Ala Arg His Ile Gly
            100                 105                 110

Thr Asp Cys Asp Ser Gly Gly Pro Gln Val Lys
            115                 120

<210> SEQ ID NO 119
<211> LENGTH: 256
<212> TYPE: PRT
<213> ORGANISM: Artificial Sequence
<220> FEATURE:
<223> OTHER INFORMATION: FUSION PROTEIN - SAK _EGF

<400> SEQUENCE: 119
```

```
Ser Ser Ser Phe Asp Lys Gly Lys Tyr Lys Gly Asp Asp Ala Ser
1               5                   10                  15

Tyr Phe Glu Pro Thr Gly Pro Tyr Leu Met Val Asn Val Thr Gly Val
            20                  25                  30

Asp Ser Lys Gly Asn Glu Leu Leu Ser Pro His Tyr Val Glu Phe Pro
        35                  40                  45

Ile Lys Pro Gly Thr Thr Leu Thr Lys Glu Lys Ile Glu Tyr Tyr Val
50                  55                  60

Glu Trp Ala Leu Asp Ala Thr Ala Tyr Lys Glu Phe Arg Val Val Glu
65                  70                  75                  80

Leu Asp Pro Ser Ala Lys Ile Glu Val Thr Tyr Tyr Asp Lys Asn Lys
                85                  90                  95

Lys Lys Glu Glu Thr Lys Ser Phe Pro Ile Thr Glu Lys Gly Phe Val
            100                 105                 110

Val Pro Asp Leu Ser Glu His Ile Lys Asn Pro Gly Phe Asn Leu Ile
        115                 120                 125

Thr Lys Val Val Ile Glu Lys Lys Glu Pro Val Asp Pro Cys Phe Arg
130                 135                 140

Ala Asn Cys Glu Tyr Gln Cys Gln Pro Leu Asn Gln Thr Ser Tyr Leu
145                 150                 155                 160

Cys Val Cys Ala Glu Gly Phe Ala Pro Ile Pro His Glu Pro His Arg
                165                 170                 175

Cys Gln Met Phe Cys Asn Gln Thr Ala Cys Pro Ala Asp Cys Asp Pro
            180                 185                 190

Asn Thr Gln Ala Ser Cys Glu Cys Pro Glu Gly Tyr Ile Leu Asp Asp
        195                 200                 205

Gly Phe Ile Cys Thr Asp Ile Asp Glu Cys Glu Asn Gly Gly Phe Cys
210                 215                 220

Ser Gly Val Cys His Asn Leu Pro Gly Thr Phe Glu Cys Ile Cys Gly
225                 230                 235                 240

Pro Asp Ser Ala Leu Ala Arg His Ile Gly Thr Asp Cys Asp Ser Gly
                245                 250                 255
```

<210> SEQ ID NO 120
<211> LENGTH: 539
<212> TYPE: PRT
<213> ORGANISM: Artificial Sequence
<220> FEATURE:
<223> OTHER INFORMATION: FROM CUSTOME SYNTHESIZED DNA - TPA =SEQ

<400> SEQUENCE: 120

```
Gln Glu Ile His Ala Arg Phe Arg Arg Gly Ala Arg Ser Tyr Gln Val
1               5                   10                  15

Ile Cys Arg Asp Glu Lys Thr Gln Met Ile Tyr Gln Gln His Gln Ser
            20                  25                  30

Trp Leu Arg Pro Val Leu Arg Ser Asn Arg Val Glu Tyr Cys Trp Cys
        35                  40                  45

Asn Ser Gly Arg Ala Gln Cys His Ser Val Pro Val Lys Ser Cys Ser
50                  55                  60

Glu Pro Arg Cys Phe Asn Gly Gly Thr Cys Gln Gln Ala Leu Tyr Phe
65                  70                  75                  80

Ser Asp Phe Val Cys Gln Cys Pro Glu Gly Phe Ala Gly Lys Cys Cys
                85                  90                  95

Glu Ile Asp Thr Arg Ala Thr Cys Tyr Glu Asp Gln Gly Ile Ser Tyr
            100                 105                 110
```

```
Arg Gly Thr Trp Ser Thr Ala Glu Ser Gly Ala Glu Cys Thr Asn Trp
        115                 120                 125
Asn Ser Ser Ala Leu Ala Gln Lys Pro Tyr Ser Gly Arg Arg Pro Asp
130                 135                 140
Ala Ile Arg Leu Gly Leu Gly Asn His Asn Tyr Cys Arg Asn Pro Asp
145                 150                 155                 160
Arg Asp Ser Lys Pro Trp Cys Tyr Val Phe Lys Ala Gly Lys Tyr Ser
                165                 170                 175
Ser Glu Phe Cys Ser Thr Pro Ala Cys Ser Glu Gly Asn Ser Asp Cys
            180                 185                 190
Tyr Phe Gly Asn Gly Ser Ala Tyr Arg Gly Thr His Ser Leu Thr Glu
        195                 200                 205
Ser Gly Ala Ser Cys Leu Pro Trp Asn Ser Met Ile Leu Ile Gly Lys
210                 215                 220
Val Tyr Thr Ala Gln Asn Pro Ser Ala Gln Ala Leu Gly Leu Gly Lys
225                 230                 235                 240
His Asn Tyr Cys Arg Asn Pro Asp Gly Asp Ala Lys Pro Trp Cys His
                245                 250                 255
Val Leu Lys Asn Arg Arg Leu Thr Trp Glu Tyr Cys Asp Val Pro Ser
            260                 265                 270
Cys Ser Thr Cys Gly Leu Arg Gln Tyr Ser Gln Pro Gln Phe Arg Ile
        275                 280                 285
Lys Gly Gly Leu Phe Ala Asp Ile Ala Ser His Pro Trp Gln Ala Ala
        290                 295                 300
Ile Phe Ala Lys His Arg Arg Ser Pro Gly Glu Arg Phe Leu Cys Gly
305                 310                 315                 320
Gly Ile Leu Ile Ser Ser Cys Trp Ile Leu Ser Ala Ala His Cys Phe
                325                 330                 335
Gln Glu Arg Phe Pro Pro His His Leu Thr Val Ile Leu Gly Arg Thr
            340                 345                 350
Tyr Arg Val Val Pro Gly Glu Glu Gln Lys Phe Glu Val Glu Lys
        355                 360                 365
Tyr Ile Val His Lys Glu Phe Asp Asp Asp Thr Tyr Asp Asn Asp Ile
        370                 375                 380
Ala Leu Leu Gln Leu Lys Ser Asp Ser Ser Arg Cys Ala Gln Glu Ser
385                 390                 395                 400
Ser Val Val Arg Thr Val Cys Leu Pro Pro Ala Asp Leu Gln Leu Pro
                405                 410                 415
Asp Trp Thr Glu Cys Glu Leu Ser Gly Tyr Gly Lys His Glu Ala Leu
            420                 425                 430
Ser Pro Phe Tyr Ser Glu Arg Leu Lys Glu Ala His Val Arg Leu Tyr
        435                 440                 445
Pro Ser Ser Arg Cys Thr Ser Gln His Leu Leu Asn Arg Thr Val Thr
450                 455                 460
Asp Asn Met Leu Cys Ala Gly Asp Thr Arg Ser Gly Gly Pro Gln Ala
465                 470                 475                 480
Asn Leu His Asp Ala Cys Gln Gly Asp Ser Gly Gly Pro Leu Val Cys
                485                 490                 495
Leu Asn Asp Gly Arg Met Thr Leu Val Gly Ile Ile Ser Trp Gly Leu
            500                 505                 510
Gly Cys Gly Gln Lys Asp Val Pro Gly Val Tyr Thr Lys Val Thr Asn
        515                 520                 525
Tyr Leu Asp Trp Ile Arg Asp Asn Met Arg Pro
```

<210> SEQ ID NO 121
<211> LENGTH: 775
<212> TYPE: PRT
<213> ORGANISM: Artificial Sequence
<220> FEATURE:
<223> OTHER INFORMATION: FUSION PROTEIN - N_EGF_TPA_EGF

<400> SEQUENCE: 121

```
Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
                85                  90                  95

Phe Glu Cys Ile Cys Gly Pro Asp Ser Ala Leu Ala Arg His Ile Gly
            100                 105                 110

Thr Asp Cys Asp Ser Gly Gln Glu Ile His Ala Arg Phe Arg Arg Gly
        115                 120                 125

Ala Arg Ser Tyr Gln Val Ile Cys Arg Asp Glu Lys Thr Gln Met Ile
    130                 135                 140

Tyr Gln Gln His Gln Ser Trp Leu Arg Pro Val Leu Arg Ser Asn Arg
145                 150                 155                 160

Val Glu Tyr Cys Trp Cys Asn Ser Gly Arg Ala Gln Cys His Ser Val
                165                 170                 175

Pro Val Lys Ser Cys Ser Glu Pro Arg Cys Phe Asn Gly Gly Thr Cys
            180                 185                 190

Gln Gln Ala Leu Tyr Phe Ser Asp Phe Val Cys Gln Cys Pro Glu Gly
        195                 200                 205

Phe Ala Gly Lys Cys Cys Glu Ile Asp Thr Arg Ala Thr Cys Tyr Glu
    210                 215                 220

Asp Gln Gly Ile Ser Tyr Arg Gly Thr Trp Ser Thr Ala Glu Ser Gly
225                 230                 235                 240

Ala Glu Cys Thr Asn Trp Asn Ser Ser Ala Leu Ala Gln Lys Pro Tyr
                245                 250                 255

Ser Gly Arg Arg Pro Asp Ala Ile Arg Leu Gly Leu Gly Asn His Asn
            260                 265                 270

Tyr Cys Arg Asn Pro Asp Arg Asp Ser Lys Pro Trp Cys Tyr Val Phe
        275                 280                 285

Lys Ala Gly Lys Tyr Ser Ser Glu Phe Cys Ser Thr Pro Ala Cys Ser
    290                 295                 300

Glu Gly Asn Ser Asp Cys Tyr Phe Gly Asn Gly Ser Ala Tyr Arg Gly
305                 310                 315                 320

Thr His Ser Leu Thr Glu Ser Gly Ala Ser Cys Leu Pro Trp Asn Ser
                325                 330                 335

Met Ile Leu Ile Gly Lys Val Tyr Thr Ala Gln Asn Pro Ser Ala Gln
            340                 345                 350

Ala Leu Gly Leu Gly Lys His Asn Tyr Cys Arg Asn Pro Asp Gly Asp
```

```
              355                 360                 365
Ala Lys Pro Trp Cys His Val Leu Lys Asn Arg Arg Leu Thr Trp Glu
370                 375                 380

Tyr Cys Asp Val Pro Ser Cys Ser Thr Cys Gly Leu Arg Gln Tyr Ser
385                 390                 395                 400

Gln Pro Gln Phe Arg Ile Lys Gly Gly Leu Phe Ala Asp Ile Ala Ser
                    405                 410                 415

His Pro Trp Gln Ala Ala Ile Phe Ala Lys His Arg Arg Ser Pro Gly
                420                 425                 430

Glu Arg Phe Leu Cys Gly Gly Ile Leu Ile Ser Ser Cys Trp Ile Leu
            435                 440                 445

Ser Ala Ala His Cys Phe Gln Glu Arg Phe Pro Pro His His Leu Thr
        450                 455                 460

Val Ile Leu Gly Arg Thr Tyr Arg Val Val Pro Gly Glu Glu Gln
465                 470                 475                 480

Lys Phe Glu Val Glu Lys Tyr Ile Val His Lys Glu Phe Asp Asp Asp
                485                 490                 495

Thr Tyr Asp Asn Asp Ile Ala Leu Leu Gln Leu Lys Ser Asp Ser Ser
                500                 505                 510

Arg Cys Ala Gln Glu Ser Ser Val Val Arg Thr Val Cys Leu Pro Pro
            515                 520                 525

Ala Asp Leu Gln Leu Pro Asp Trp Thr Glu Cys Glu Leu Ser Gly Tyr
        530                 535                 540

Gly Lys His Glu Ala Leu Ser Pro Phe Tyr Ser Glu Arg Leu Lys Glu
545                 550                 555                 560

Ala His Val Arg Leu Tyr Pro Ser Ser Arg Cys Thr Ser Gln His Leu
                565                 570                 575

Leu Asn Arg Thr Val Thr Asp Asn Met Leu Cys Ala Gly Asp Thr Arg
                580                 585                 590

Ser Gly Gly Pro Gln Ala Asn Leu His Asp Ala Cys Gln Gly Asp Ser
            595                 600                 605

Gly Gly Pro Leu Val Cys Leu Asn Asp Gly Arg Met Thr Leu Val Gly
        610                 615                 620

Ile Ile Ser Trp Gly Leu Gly Cys Gly Gln Lys Asp Val Pro Gly Val
625                 630                 635                 640

Tyr Thr Lys Val Thr Asn Tyr Leu Asp Trp Ile Arg Asp Asn Met Arg
                645                 650                 655

Pro Val Asp Pro Cys Phe Arg Ala Asn Cys Glu Tyr Gln Cys Gln Pro
                660                 665                 670

Leu Asn Gln Thr Ser Tyr Leu Cys Val Cys Ala Glu Gly Phe Ala Pro
            675                 680                 685

Ile Pro His Glu Pro His Arg Cys Gln Met Phe Cys Asn Gln Thr Ala
        690                 695                 700

Cys Pro Ala Asp Cys Asp Pro Asn Thr Gln Ala Ser Cys Glu Cys Pro
705                 710                 715                 720

Glu Gly Tyr Ile Leu Asp Asp Gly Phe Ile Cys Thr Asp Ile Asp Glu
                725                 730                 735

Cys Glu Asn Gly Gly Phe Cys Ser Gly Val Cys His Asn Leu Pro Gly
                740                 745                 750

Thr Phe Glu Cys Ile Cys Gly Pro Asp Ser Ala Leu Ala Arg His Ile
            755                 760                 765

Gly Thr Asp Cys Asp Ser Gly
770                 775
```

<210> SEQ ID NO 122
<211> LENGTH: 657
<212> TYPE: PRT
<213> ORGANISM: Artificial Sequence
<220> FEATURE:
<223> OTHER INFORMATION: FUSION PROTEIN - N_EGF_TPA

<400> SEQUENCE: 122

```
Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
                85                  90                  95

Phe Glu Cys Ile Cys Gly Pro Asp Ser Ala Leu Ala Arg His Ile Gly
            100                 105                 110

Thr Asp Cys Asp Ser Gly Gln Glu Ile His Ala Arg Phe Arg Arg Gly
        115                 120                 125

Ala Arg Ser Tyr Gln Val Ile Cys Arg Asp Glu Lys Thr Gln Met Ile
    130                 135                 140

Tyr Gln Gln His Gln Ser Trp Leu Arg Pro Val Leu Arg Ser Asn Arg
145                 150                 155                 160

Val Glu Tyr Cys Trp Cys Asn Ser Gly Arg Ala Gln Cys His Ser Val
                165                 170                 175

Pro Val Lys Ser Cys Ser Glu Pro Arg Cys Phe Asn Gly Gly Thr Cys
            180                 185                 190

Gln Gln Ala Leu Tyr Phe Ser Asp Phe Val Cys Gln Cys Pro Glu Gly
        195                 200                 205

Phe Ala Gly Lys Cys Cys Glu Ile Asp Thr Arg Ala Thr Cys Tyr Glu
    210                 215                 220

Asp Gln Gly Ile Ser Tyr Arg Gly Thr Trp Ser Thr Ala Glu Ser Gly
225                 230                 235                 240

Ala Glu Cys Thr Asn Trp Asn Ser Ser Ala Leu Ala Gln Lys Pro Tyr
                245                 250                 255

Ser Gly Arg Arg Pro Asp Ala Ile Arg Leu Gly Leu Gly Asn His Asn
            260                 265                 270

Tyr Cys Arg Asn Pro Asp Arg Asp Ser Lys Pro Trp Cys Tyr Val Phe
        275                 280                 285

Lys Ala Gly Lys Tyr Ser Ser Glu Phe Cys Ser Thr Pro Ala Cys Ser
    290                 295                 300

Glu Gly Asn Ser Asp Cys Tyr Phe Gly Asn Gly Ser Ala Tyr Arg Gly
305                 310                 315                 320

Thr His Ser Leu Thr Glu Ser Gly Ala Ser Cys Leu Pro Trp Asn Ser
                325                 330                 335

Met Ile Leu Ile Gly Lys Val Tyr Thr Ala Gln Asn Pro Ser Ala Gln
            340                 345                 350

Ala Leu Gly Leu Gly Lys His Asn Tyr Cys Arg Asn Pro Asp Gly Asp
        355                 360                 365
```

-continued

```
Ala Lys Pro Trp Cys His Val Leu Lys Asn Arg Arg Leu Thr Trp Glu
    370                 375                 380

Tyr Cys Asp Val Pro Ser Cys Ser Thr Cys Gly Leu Arg Gln Tyr Ser
385                 390                 395                 400

Gln Pro Gln Phe Arg Ile Lys Gly Gly Leu Phe Ala Asp Ile Ala Ser
                405                 410                 415

His Pro Trp Gln Ala Ala Ile Phe Ala Lys His Arg Arg Ser Pro Gly
            420                 425                 430

Glu Arg Phe Leu Cys Gly Gly Ile Leu Ile Ser Ser Cys Trp Ile Leu
        435                 440                 445

Ser Ala Ala His Cys Phe Gln Glu Arg Phe Pro Pro His His Leu Thr
    450                 455                 460

Val Ile Leu Gly Arg Thr Tyr Arg Val Val Pro Gly Glu Glu Glu Gln
465                 470                 475                 480

Lys Phe Glu Val Glu Lys Tyr Ile Val His Lys Glu Phe Asp Asp Asp
                485                 490                 495

Thr Tyr Asp Asn Asp Ile Ala Leu Leu Gln Leu Lys Ser Asp Ser Ser
            500                 505                 510

Arg Cys Ala Gln Glu Ser Ser Val Val Arg Thr Val Cys Leu Pro Pro
        515                 520                 525

Ala Asp Leu Gln Leu Pro Asp Trp Thr Glu Cys Glu Leu Ser Gly Tyr
    530                 535                 540

Gly Lys His Glu Ala Leu Ser Pro Phe Tyr Ser Glu Arg Leu Lys Glu
545                 550                 555                 560

Ala His Val Arg Leu Tyr Pro Ser Ser Arg Cys Thr Ser Gln His Leu
                565                 570                 575

Leu Asn Arg Thr Val Thr Asp Asn Met Leu Cys Ala Gly Asp Thr Arg
            580                 585                 590

Ser Gly Gly Pro Gln Ala Asn Leu His Asp Ala Cys Gln Gly Asp Ser
        595                 600                 605

Gly Gly Pro Leu Val Cys Leu Asn Asp Gly Arg Met Thr Leu Val Gly
    610                 615                 620

Ile Ile Ser Trp Gly Leu Gly Cys Gly Gln Lys Asp Val Pro Gly Val
625                 630                 635                 640

Tyr Thr Lys Val Thr Asn Tyr Leu Asp Trp Ile Arg Asp Asn Met Arg
                645                 650                 655

Pro

<210> SEQ ID NO 123
<211> LENGTH: 657
<212> TYPE: PRT
<213> ORGANISM: Artificial Sequence
<220> FEATURE:
<223> OTHER INFORMATION: FUSION PROTEIN - TPA_EGF

<400> SEQUENCE: 123

Gln Glu Ile His Ala Arg Phe Arg Arg Gly Ala Arg Ser Tyr Gln Val
1               5                   10                  15

Ile Cys Arg Asp Glu Lys Thr Gln Met Ile Tyr Gln Gln His Gln Ser
                20                  25                  30

Trp Leu Arg Pro Val Leu Arg Ser Asn Arg Val Glu Tyr Cys Trp Cys
            35                  40                  45

Asn Ser Gly Arg Ala Gln Cys His Ser Val Pro Val Lys Ser Cys Ser
        50                  55                  60
```

```
Glu Pro Arg Cys Phe Asn Gly Gly Thr Cys Gln Gln Ala Leu Tyr Phe
 65                  70                  75                  80

Ser Asp Phe Val Cys Gln Cys Pro Glu Gly Phe Ala Gly Lys Cys Cys
             85                  90                  95

Glu Ile Asp Thr Arg Ala Thr Cys Tyr Glu Asp Gln Gly Ile Ser Tyr
            100                 105                 110

Arg Gly Thr Trp Ser Thr Ala Glu Ser Gly Ala Glu Cys Thr Asn Trp
        115                 120                 125

Asn Ser Ser Ala Leu Ala Gln Lys Pro Tyr Ser Gly Arg Arg Pro Asp
    130                 135                 140

Ala Ile Arg Leu Gly Leu Gly Asn His Asn Tyr Cys Arg Asn Pro Asp
145                 150                 155                 160

Arg Asp Ser Lys Pro Trp Cys Tyr Val Phe Lys Ala Gly Lys Tyr Ser
                165                 170                 175

Ser Glu Phe Cys Ser Thr Pro Ala Cys Ser Glu Gly Asn Ser Asp Cys
            180                 185                 190

Tyr Phe Gly Asn Gly Ser Ala Tyr Arg Gly Thr His Ser Leu Thr Glu
        195                 200                 205

Ser Gly Ala Ser Cys Leu Pro Trp Asn Ser Met Ile Leu Ile Gly Lys
    210                 215                 220

Val Tyr Thr Ala Gln Asn Pro Ser Ala Gln Ala Leu Gly Leu Gly Lys
225                 230                 235                 240

His Asn Tyr Cys Arg Asn Pro Asp Gly Asp Ala Lys Pro Trp Cys His
                245                 250                 255

Val Leu Lys Asn Arg Arg Leu Thr Trp Glu Tyr Cys Asp Val Pro Ser
            260                 265                 270

Cys Ser Thr Cys Gly Leu Arg Gln Tyr Ser Gln Pro Gln Phe Arg Ile
        275                 280                 285

Lys Gly Gly Leu Phe Ala Asp Ile Ala Ser His Pro Trp Gln Ala Ala
    290                 295                 300

Ile Phe Ala Lys His Arg Arg Ser Pro Gly Glu Arg Phe Leu Cys Gly
305                 310                 315                 320

Gly Ile Leu Ile Ser Ser Cys Trp Ile Leu Ser Ala Ala His Cys Phe
                325                 330                 335

Gln Glu Arg Phe Pro Pro His His Leu Thr Val Ile Leu Gly Arg Thr
            340                 345                 350

Tyr Arg Val Val Pro Gly Glu Glu Gln Lys Phe Glu Val Glu Lys
        355                 360                 365

Tyr Ile Val His Lys Glu Phe Asp Asp Asp Thr Tyr Asp Asn Asp Ile
370                 375                 380

Ala Leu Leu Gln Leu Lys Ser Asp Ser Ser Arg Cys Ala Gln Glu Ser
385                 390                 395                 400

Ser Val Val Arg Thr Val Cys Leu Pro Pro Ala Asp Leu Gln Leu Pro
            405                 410                 415

Asp Trp Thr Glu Cys Glu Leu Ser Gly Tyr Gly Lys His Glu Ala Leu
        420                 425                 430

Ser Pro Phe Tyr Ser Glu Arg Leu Lys Glu Ala His Val Arg Leu Tyr
    435                 440                 445

Pro Ser Ser Arg Cys Thr Ser Gln His Leu Leu Asn Arg Thr Val Thr
                450                 455                 460

Asp Asn Met Leu Cys Ala Gly Asp Thr Arg Ser Gly Gly Pro Gln Ala
465                 470                 475                 480

Asn Leu His Asp Ala Cys Gln Gly Asp Ser Gly Gly Pro Leu Val Cys
```

```
                       485              490              495
Leu Asn Asp Gly Arg Met Thr Leu Val Gly Ile Ile Ser Trp Gly Leu
                500              505              510

Gly Cys Gly Gln Lys Asp Val Pro Gly Val Tyr Thr Lys Val Thr Asn
            515                 520                 525

Tyr Leu Asp Trp Ile Arg Asp Asn Met Arg Pro Val Asp Pro Cys Phe
        530                 535                 540

Arg Ala Asn Cys Glu Tyr Gln Cys Gln Pro Leu Asn Gln Thr Ser Tyr
545                 550                 555                 560

Leu Cys Val Cys Ala Glu Gly Phe Ala Pro Ile Pro His Glu Pro His
                565                 570                 575

Arg Cys Gln Met Phe Cys Asn Gln Thr Ala Cys Pro Ala Asp Cys Asp
            580                 585                 590

Pro Asn Thr Gln Ala Ser Cys Glu Cys Pro Glu Gly Tyr Ile Leu Asp
        595                 600                 605

Asp Gly Phe Ile Cys Thr Asp Ile Asp Glu Cys Glu Asn Gly Gly Phe
    610                 615                 620

Cys Ser Gly Val Cys His Asn Leu Pro Gly Thr Phe Glu Cys Ile Cys
625                 630                 635                 640

Gly Pro Asp Ser Ala Leu Ala Arg His Ile Gly Thr Asp Cys Asp Ser
                645                 650                 655

Gly

<210> SEQ ID NO 124
<211> LENGTH: 620
<212> TYPE: PRT
<213> ORGANISM: Artificial Sequence
<220> FEATURE:
<223> OTHER INFORMATION: FUSION PROTEIN - ID EGF TPA EGF DEL

<400> SEQUENCE: 124

Gln Glu Ile His Ala Arg Phe Arg Arg Gly Ala Arg Ser Tyr Gln Val
1               5                   10                  15

Ile Cys Arg Asp Glu Lys Thr Gln Met Ile Tyr Gln Gln His Gln Ser
                20                  25                  30

Trp Leu Arg Pro Val Leu Arg Ser Asn Arg Val Glu Tyr Cys Trp Cys
            35                  40                  45

Asn Ser Gly Arg Ala Gln Cys His Ser Val Pro Val Lys Ser Val Asp
        50                  55                  60

Pro Cys Phe Arg Ala Asn Cys Glu Tyr Gln Cys Gln Pro Leu Asn Gln
65                  70                  75                  80

Thr Ser Tyr Leu Cys Val Cys Ala Glu Gly Phe Ala Pro Ile Pro His
                85                  90                  95

Glu Pro His Arg Cys Gln Met Phe Cys Asn Gln Thr Ala Cys Pro Ala
            100                 105                 110

Asp Cys Asp Pro Asn Thr Gln Ala Ser Cys Glu Cys Pro Glu Gly Tyr
        115                 120                 125

Ile Leu Asp Asp Gly Phe Ile Cys Thr Asp Ile Asp Glu Cys Glu Asn
    130                 135                 140

Gly Gly Phe Cys Ser Gly Val Cys His Asn Leu Pro Gly Thr Phe Glu
145                 150                 155                 160

Cys Ile Cys Gly Pro Asp Ser Ala Leu Ala Arg His Ile Gly Thr Asp
                165                 170                 175

Cys Asp Ser Gly Thr Arg Ala Thr Cys Tyr Glu Asp Gln Gly Ile Ser
            180                 185                 190
```

```
Tyr Arg Gly Thr Trp Ser Thr Ala Glu Ser Gly Ala Glu Cys Thr Asn
            195                 200                 205

Trp Asn Ser Ser Ala Leu Ala Gln Lys Pro Tyr Ser Gly Arg Arg Pro
    210                 215                 220

Asp Ala Ile Arg Leu Gly Leu Gly Asn His Asn Tyr Cys Arg Asn Pro
225                 230                 235                 240

Asp Arg Asp Ser Lys Pro Trp Cys Tyr Val Phe Lys Ala Gly Lys Tyr
                245                 250                 255

Ser Ser Glu Phe Cys Ser Thr Pro Ala Cys Ser Glu Gly Asn Ser Asp
                260                 265                 270

Cys Tyr Phe Gly Asn Gly Ser Ala Tyr Arg Gly Thr His Ser Leu Thr
            275                 280                 285

Glu Ser Gly Ala Ser Cys Leu Pro Trp Asn Ser Met Ile Leu Ile Gly
    290                 295                 300

Lys Val Tyr Thr Ala Gln Asn Pro Ser Ala Gln Ala Leu Gly Leu Gly
305                 310                 315                 320

Lys His Asn Tyr Cys Arg Asn Pro Asp Gly Asp Ala Lys Pro Trp Cys
                325                 330                 335

His Val Leu Lys Asn Arg Arg Leu Thr Trp Glu Tyr Cys Asp Val Pro
            340                 345                 350

Ser Cys Ser Thr Cys Gly Leu Arg Gln Tyr Ser Gln Pro Gln Phe Arg
    355                 360                 365

Ile Lys Gly Gly Leu Phe Ala Asp Ile Ala Ser His Pro Trp Gln Ala
    370                 375                 380

Ala Ile Phe Ala Lys His Arg Arg Ser Pro Gly Glu Arg Phe Leu Cys
385                 390                 395                 400

Gly Gly Ile Leu Ile Ser Ser Cys Trp Ile Leu Ser Ala Ala His Cys
                405                 410                 415

Phe Gln Glu Arg Phe Pro Pro His His Leu Thr Val Ile Leu Gly Arg
            420                 425                 430

Thr Tyr Arg Val Val Pro Gly Glu Glu Glu Gln Lys Phe Glu Val Glu
    435                 440                 445

Lys Tyr Ile Val His Lys Glu Phe Asp Asp Thr Tyr Asp Asn Asp
    450                 455                 460

Ile Ala Leu Leu Gln Leu Lys Ser Asp Ser Ser Arg Cys Ala Gln Glu
465                 470                 475                 480

Ser Ser Val Val Arg Thr Val Cys Leu Pro Pro Ala Asp Leu Gln Leu
                485                 490                 495

Pro Asp Trp Thr Glu Cys Glu Leu Ser Gly Tyr Gly Lys His Glu Ala
            500                 505                 510

Leu Ser Pro Phe Tyr Ser Glu Arg Leu Lys Glu Ala His Val Arg Leu
    515                 520                 525

Tyr Pro Ser Ser Arg Cys Thr Ser Gln His Leu Leu Asn Arg Thr Val
    530                 535                 540

Thr Asp Asn Met Leu Cys Ala Gly Asp Thr Arg Ser Gly Gly Pro Gln
545                 550                 555                 560

Ala Asn Leu His Asp Ala Cys Gln Gly Asp Ser Gly Gly Pro Leu Val
                565                 570                 575

Cys Leu Asn Asp Gly Arg Met Thr Leu Val Gly Ile Ile Ser Trp Gly
            580                 585                 590

Leu Gly Cys Gly Gln Lys Asp Val Pro Gly Val Tyr Thr Lys Val Thr
    595                 600                 605
```

Asn Tyr Leu Asp Trp Ile Arg Asp Asn Met Arg Pro
        610                 615                 620

<210> SEQ ID NO 125
<211> LENGTH: 531
<212> TYPE: PRT
<213> ORGANISM: Artificial Sequence
<220> FEATURE:
<223> OTHER INFORMATION: FUSION PROTEIN - ID EGF TPA EGF k1 DEL

<400> SEQUENCE: 125

Gln Glu Ile His Ala Arg Phe Arg Arg Gly Ala Arg Ser Tyr Gln Val
1               5                   10                  15

Ile Cys Arg Asp Glu Lys Thr Gln Met Ile Tyr Gln Gln His Gln Ser
            20                  25                  30

Trp Leu Arg Pro Val Leu Arg Ser Asn Arg Val Glu Tyr Cys Trp Cys
        35                  40                  45

Asn Ser Gly Arg Ala Gln Cys His Ser Val Pro Val Lys Ser Val Asp
    50                  55                  60

Pro Cys Phe Arg Ala Asn Cys Glu Tyr Gln Cys Gln Pro Leu Asn Gln
65                  70                  75                  80

Thr Ser Tyr Leu Cys Val Cys Ala Glu Gly Phe Ala Pro Ile Pro His
                85                  90                  95

Glu Pro His Arg Cys Gln Met Phe Cys Asn Gln Thr Ala Cys Pro Ala
            100                 105                 110

Asp Cys Asp Pro Asn Thr Gln Ala Ser Cys Glu Cys Pro Glu Gly Tyr
        115                 120                 125

Ile Leu Asp Asp Gly Phe Ile Cys Thr Asp Ile Asp Glu Cys Glu Asn
    130                 135                 140

Gly Gly Phe Cys Ser Gly Val Cys His Asn Leu Pro Gly Thr Phe Glu
145                 150                 155                 160

Cys Ile Cys Gly Pro Asp Ser Ala Leu Ala Arg His Ile Gly Thr Asp
                165                 170                 175

Cys Asp Ser Gly Asn Ser Asp Cys Tyr Phe Gly Asn Gly Ser Ala Tyr
            180                 185                 190

Arg Gly Thr His Ser Leu Thr Glu Ser Gly Ala Ser Cys Leu Pro Trp
        195                 200                 205

Asn Ser Met Ile Leu Ile Gly Lys Val Tyr Thr Ala Gln Asn Pro Ser
    210                 215                 220

Ala Gln Ala Leu Gly Leu Gly Lys His Asn Tyr Cys Arg Asn Pro Asp
225                 230                 235                 240

Gly Asp Ala Lys Pro Trp Cys His Val Leu Lys Asn Arg Arg Leu Thr
                245                 250                 255

Trp Glu Tyr Cys Asp Val Pro Ser Cys Ser Thr Cys Gly Leu Arg Gln
            260                 265                 270

Tyr Ser Gln Pro Gln Phe Arg Ile Lys Gly Gly Leu Phe Ala Asp Ile
        275                 280                 285

Ala Ser His Pro Trp Gln Ala Ala Ile Phe Ala Lys His Arg Arg Ser
    290                 295                 300

Pro Gly Glu Arg Phe Leu Cys Gly Gly Ile Leu Ile Ser Ser Cys Trp
305                 310                 315                 320

Ile Leu Ser Ala Ala His Cys Phe Gln Glu Arg Phe Pro Pro His His
                325                 330                 335

Leu Thr Val Ile Leu Gly Arg Thr Tyr Arg Val Val Pro Gly Glu Glu
            340                 345                 350

```
Glu Gln Lys Phe Glu Val Glu Lys Tyr Ile Val His Lys Glu Phe Asp
            355                 360                 365

Asp Asp Thr Tyr Asp Asn Asp Ile Ala Leu Leu Gln Leu Lys Ser Asp
        370                 375                 380

Ser Ser Arg Cys Ala Gln Glu Ser Ser Val Val Arg Thr Val Cys Leu
385                 390                 395                 400

Pro Pro Ala Asp Leu Gln Leu Pro Asp Trp Thr Glu Cys Glu Leu Ser
            405                 410                 415

Gly Tyr Gly Lys His Glu Ala Leu Ser Pro Phe Tyr Ser Glu Arg Leu
        420                 425                 430

Lys Glu Ala His Val Arg Leu Tyr Pro Ser Ser Arg Cys Thr Ser Gln
            435                 440                 445

His Leu Leu Asn Arg Thr Val Thr Asp Asn Met Leu Cys Ala Gly Asp
        450                 455                 460

Thr Arg Ser Gly Gly Pro Gln Ala Asn Leu His Asp Ala Cys Gln Gly
465                 470                 475                 480

Asp Ser Gly Gly Pro Leu Val Cys Leu Asn Asp Gly Arg Met Thr Leu
            485                 490                 495

Val Gly Ile Ile Ser Trp Gly Leu Gly Cys Gly Gln Lys Asp Val Pro
        500                 505                 510

Gly Val Tyr Thr Lys Val Thr Asn Tyr Leu Asp Trp Ile Arg Asp Asn
            515                 520                 525

Met Arg Pro
    530

<210> SEQ ID NO 126
<211> LENGTH: 531
<212> TYPE: PRT
<213> ORGANISM: Artificial Sequence
<220> FEATURE:
<223> OTHER INFORMATION: FUSION ROTEIN - N_EGF_TPA EGF k1 DEL

<400> SEQUENCE: 126

Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
            85                  90                  95

Phe Glu Cys Ile Cys Gly Pro Asp Ser Ala Leu Ala Arg His Ile Gly
        100                 105                 110

Thr Asp Cys Asp Ser Gly Gln Glu Ile His Ala Arg Phe Arg Arg Gly
    115                 120                 125

Ala Arg Ser Tyr Gln Val Ile Cys Arg Asp Glu Lys Thr Gln Met Ile
130                 135                 140

Tyr Gln Gln His Gln Ser Trp Leu Arg Pro Val Leu Arg Ser Asn Arg
145                 150                 155                 160

Val Glu Tyr Cys Trp Cys Asn Ser Gly Arg Ala Gln Cys His Ser Val
            165                 170                 175
```

```
Pro Val Lys Ser Asn Ser Asp Cys Tyr Phe Gly Asn Gly Ser Ala Tyr
            180                 185                 190

Arg Gly Thr His Ser Leu Thr Glu Ser Gly Ala Ser Cys Leu Pro Trp
        195                 200                 205

Asn Ser Met Ile Leu Ile Gly Lys Val Tyr Thr Ala Gln Asn Pro Ser
    210                 215                 220

Ala Gln Ala Leu Gly Leu Gly Lys His Asn Tyr Cys Arg Asn Pro Asp
225                 230                 235                 240

Gly Asp Ala Lys Pro Trp Cys His Val Leu Lys Asn Arg Arg Leu Thr
                245                 250                 255

Trp Glu Tyr Cys Asp Val Pro Ser Cys Ser Thr Cys Gly Leu Arg Gln
            260                 265                 270

Tyr Ser Gln Pro Gln Phe Arg Ile Lys Gly Gly Leu Phe Ala Asp Ile
        275                 280                 285

Ala Ser His Pro Trp Gln Ala Ala Ile Phe Ala Lys His Arg Arg Ser
    290                 295                 300

Pro Gly Glu Arg Phe Leu Cys Gly Gly Ile Leu Ile Ser Ser Cys Trp
305                 310                 315                 320

Ile Leu Ser Ala Ala His Cys Phe Gln Glu Arg Phe Pro Pro His His
                325                 330                 335

Leu Thr Val Ile Leu Gly Arg Thr Tyr Arg Val Val Pro Gly Glu Glu
            340                 345                 350

Glu Gln Lys Phe Glu Val Glu Lys Tyr Ile Val His Lys Glu Phe Asp
        355                 360                 365

Asp Asp Thr Tyr Asp Asn Asp Ile Ala Leu Leu Gln Leu Lys Ser Asp
    370                 375                 380

Ser Ser Arg Cys Ala Gln Glu Ser Ser Val Val Arg Thr Val Cys Leu
385                 390                 395                 400

Pro Pro Ala Asp Leu Gln Leu Pro Asp Trp Thr Glu Cys Glu Leu Ser
                405                 410                 415

Gly Tyr Gly Lys His Glu Ala Leu Ser Pro Phe Tyr Ser Glu Arg Leu
            420                 425                 430

Lys Glu Ala His Val Arg Leu Tyr Pro Ser Ser Arg Cys Thr Ser Gln
        435                 440                 445

His Leu Leu Asn Arg Thr Val Thr Asp Asn Met Leu Cys Ala Gly Asp
    450                 455                 460

Thr Arg Ser Gly Gly Pro Gln Ala Asn Leu His Asp Ala Cys Gln Gly
465                 470                 475                 480

Asp Ser Gly Gly Pro Leu Val Cys Leu Asn Asp Gly Arg Met Thr Leu
                485                 490                 495

Val Gly Ile Ile Ser Trp Gly Leu Gly Cys Gly Gln Lys Asp Val Pro
            500                 505                 510

Gly Val Tyr Thr Lys Val Thr Asn Tyr Leu Asp Trp Ile Arg Asp Asn
        515                 520                 525

Met Arg Pro
    530

<210> SEQ ID NO 127
<211> LENGTH: 531
<212> TYPE: PRT
<213> ORGANISM: Artificial Sequence
<220> FEATURE:
<223> OTHER INFORMATION: FUSION PROTEIN - TPA _EGF egf AND K1 DEL

<400> SEQUENCE: 127
```

-continued

```
Gln Glu Ile His Ala Arg Phe Arg Arg Gly Ala Arg Ser Tyr Gln Val
1               5                   10                  15

Ile Cys Arg Asp Glu Lys Thr Gln Met Ile Tyr Gln Gln His Gln Ser
            20                  25                  30

Trp Leu Arg Pro Val Leu Arg Ser Asn Arg Val Glu Tyr Cys Trp Cys
        35                  40                  45

Asn Ser Gly Arg Ala Gln Cys His Ser Val Pro Val Lys Ser Asn Ser
    50                  55                  60

Asp Cys Tyr Phe Gly Asn Gly Ser Ala Tyr Arg Gly Thr His Ser Leu
65                  70                  75                  80

Thr Glu Ser Gly Ala Ser Cys Leu Pro Trp Asn Ser Met Ile Leu Ile
                85                  90                  95

Gly Lys Val Tyr Thr Ala Gln Asn Pro Ser Ala Gln Ala Leu Gly Leu
            100                 105                 110

Gly Lys His Asn Tyr Cys Arg Asn Pro Asp Gly Asp Ala Lys Pro Trp
        115                 120                 125

Cys His Val Leu Lys Asn Arg Arg Leu Thr Trp Glu Tyr Cys Asp Val
    130                 135                 140

Pro Ser Cys Ser Thr Cys Gly Leu Arg Gln Tyr Ser Gln Pro Gln Phe
145                 150                 155                 160

Arg Ile Lys Gly Gly Leu Phe Ala Asp Ile Ala Ser His Pro Trp Gln
                165                 170                 175

Ala Ala Ile Phe Ala Lys His Arg Arg Ser Pro Gly Glu Arg Phe Leu
            180                 185                 190

Cys Gly Gly Ile Leu Ile Ser Ser Cys Trp Ile Leu Ser Ala Ala His
        195                 200                 205

Cys Phe Gln Glu Arg Phe Pro Pro His His Leu Thr Val Ile Leu Gly
    210                 215                 220

Arg Thr Tyr Arg Val Val Pro Gly Glu Glu Glu Gln Lys Phe Glu Val
225                 230                 235                 240

Glu Lys Tyr Ile Val His Lys Glu Phe Asp Asp Asp Thr Tyr Asp Asn
                245                 250                 255

Asp Ile Ala Leu Leu Gln Leu Lys Ser Asp Ser Ser Arg Cys Ala Gln
            260                 265                 270

Glu Ser Ser Val Val Arg Thr Val Cys Leu Pro Pro Ala Asp Leu Gln
        275                 280                 285

Leu Pro Asp Trp Thr Glu Cys Glu Leu Ser Gly Tyr Gly Lys His Glu
    290                 295                 300

Ala Leu Ser Pro Phe Tyr Ser Glu Arg Leu Lys Glu Ala His Val Arg
305                 310                 315                 320

Leu Tyr Pro Ser Ser Arg Cys Thr Ser Gln His Leu Leu Asn Arg Thr
                325                 330                 335

Val Thr Asp Asn Met Leu Cys Ala Gly Asp Thr Arg Ser Gly Gly Pro
            340                 345                 350

Gln Ala Asn Leu His Asp Ala Cys Gln Gly Asp Ser Gly Gly Pro Leu
        355                 360                 365

Val Cys Leu Asn Asp Gly Arg Met Thr Leu Val Gly Ile Ile Ser Trp
    370                 375                 380

Gly Leu Gly Cys Gly Gln Lys Asp Val Pro Gly Val Tyr Thr Lys Val
385                 390                 395                 400

Thr Asn Tyr Leu Asp Trp Ile Arg Asp Asn Met Arg Pro Val Asp Pro
                405                 410                 415

Cys Phe Arg Ala Asn Cys Glu Tyr Gln Cys Gln Pro Leu Asn Gln Thr
```

```
                420                 425                 430

Ser Tyr Leu Cys Val Cys Ala Glu Gly Phe Ala Pro Ile Pro His Glu
            435                 440                 445

Pro His Arg Cys Gln Met Phe Cys Asn Gln Thr Ala Cys Pro Ala Asp
        450                 455                 460

Cys Asp Pro Asn Thr Gln Ala Ser Cys Glu Cys Pro Glu Gly Tyr Ile
465                 470                 475                 480

Leu Asp Asp Gly Phe Ile Cys Thr Asp Ile Asp Glu Cys Glu Asn Gly
                485                 490                 495

Gly Phe Cys Ser Gly Val Cys His Asn Leu Pro Gly Thr Phe Glu Cys
            500                 505                 510

Ile Cys Gly Pro Asp Ser Ala Leu Ala Arg His Ile Gly Thr Asp Cys
        515                 520                 525

Asp Ser Gly
        530

<210> SEQ ID NO 128
<211> LENGTH: 539
<212> TYPE: PRT
<213> ORGANISM: Artificial Sequence
<220> FEATURE:
<223> OTHER INFORMATION: tPA variant

<400> SEQUENCE: 128

Gln Glu Ile His Ala Arg Phe Arg Arg Gly Ala Arg Ser Tyr Gln Val
1               5                   10                  15

Ile Cys Arg Asp Glu Lys Thr Gln Met Ile Tyr Gln Gln His Gln Ser
            20                  25                  30

Trp Leu Arg Pro Val Leu Arg Ser Asn Arg Val Glu Tyr Cys Trp Cys
        35                  40                  45

Asn Ser Gly Arg Ala Gln Cys His Ser Val Pro Val Lys Ser Cys Ser
50                  55                  60

Glu Pro Arg Cys Phe Asn Gly Gly Thr Cys Gln Gln Ala Leu Tyr Phe
65                  70                  75                  80

Ser Asp Phe Val Cys Gln Cys Pro Glu Gly Phe Ala Gly Lys Cys Cys
                85                  90                  95

Glu Ile Asp Thr Arg Ala Thr Cys Tyr Glu Asp Gln Gly Ile Ser Tyr
            100                 105                 110

Arg Gly Asn Trp Ser Thr Ala Glu Ser Gly Ala Glu Cys Thr Asn Trp
        115                 120                 125

Gln Ser Ser Ala Leu Ala Gln Lys Pro Tyr Ser Gly Arg Arg Pro Asp
    130                 135                 140

Ala Ile Arg Leu Gly Leu Gly Asn His Asn Tyr Cys Arg Asn Pro Asp
145                 150                 155                 160

Arg Asp Ser Lys Pro Trp Cys Tyr Val Phe Lys Ala Gly Lys Tyr Ser
                165                 170                 175

Ser Glu Phe Cys Ser Thr Pro Ala Cys Ser Glu Gly Asn Ser Asp Cys
            180                 185                 190

Tyr Phe Gly Asn Gly Ser Ala Tyr Arg Gly Thr His Ser Leu Thr Glu
        195                 200                 205

Ser Gly Ala Ser Cys Leu Pro Trp Asn Ser Met Ile Leu Ile Gly Lys
    210                 215                 220

Val Tyr Thr Ala Gln Asn Pro Ser Ala Gln Ala Leu Gly Leu Gly Lys
225                 230                 235                 240

His Asn Tyr Cys Arg Asn Pro Asp Gly Asp Ala Lys Pro Trp Cys His
```

```
                    245                 250                 255
Val Leu Lys Asn Arg Leu Thr Trp Glu Tyr Cys Asp Val Pro Ser
            260                 265                 270

Cys Ser Thr Cys Gly Leu Arg Gln Tyr Ser Gln Pro Gln Phe Arg Ile
        275                 280                 285

Lys Gly Gly Leu Phe Ala Asp Ile Ala Ser His Pro Trp Gln Ala Ala
    290                 295                 300

Ile Phe Ala Lys His Arg Arg Ser Pro Gly Glu Arg Phe Leu Cys Gly
305                 310                 315                 320

Gly Ile Leu Ile Ser Ser Cys Trp Ile Leu Ser Ala Ala His Cys Phe
            325                 330                 335

Gln Glu Arg Phe Pro Pro His His Leu Thr Val Ile Leu Gly Arg Thr
        340                 345                 350

Tyr Arg Val Val Pro Gly Glu Glu Gln Lys Phe Glu Val Glu Lys
    355                 360                 365

Tyr Ile Val His Lys Glu Phe Asp Asp Thr Tyr Asp Asn Asp Ile
    370                 375                 380

Ala Leu Leu Gln Leu Lys Ser Asp Ser Ser Arg Cys Ala Gln Glu Ser
385                 390                 395                 400

Ser Val Val Arg Thr Val Cys Leu Pro Pro Ala Asp Leu Gln Leu Pro
            405                 410                 415

Asp Trp Thr Glu Cys Glu Leu Ser Gly Tyr Gly Lys His Glu Ala Leu
        420                 425                 430

Ser Pro Phe Tyr Ser Glu Arg Leu Lys Glu Ala His Val Arg Leu Tyr
    435                 440                 445

Pro Ser Ser Arg Cys Thr Ser Gln His Leu Leu Asn Arg Thr Val Thr
450                 455                 460

Asp Asn Met Leu Cys Ala Gly Asp Thr Arg Ser Gly Gly Pro Gln Ala
465                 470                 475                 480

Asn Leu His Asp Ala Cys Gln Gly Asp Ser Gly Gly Pro Leu Val Cys
            485                 490                 495

Leu Asn Asp Gly Arg Met Thr Leu Val Gly Ile Ile Ser Trp Gly Leu
        500                 505                 510

Gly Cys Gly Gln Lys Asp Val Pro Gly Val Tyr Thr Lys Val Thr Asn
    515                 520                 525

Tyr Leu Asp Trp Ile Arg Asp Asn Met Arg Pro
    530                 535

<210> SEQ ID NO 129
<211> LENGTH: 532
<212> TYPE: PRT
<213> ORGANISM: Artificial Sequence
<220> FEATURE:
<223> OTHER INFORMATION: Interdomain SK_EGFpolypeptide where EGF fused
      between beta and gamma domain of SK

<400> SEQUENCE: 129

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60
```

```
Thr Asp Ser Gly Ala Met Ser His Lys Leu Glu Lys Ala Asp Leu Leu
 65                  70                  75                  80

Lys Ala Ile Gln Glu Gln Leu Ile Ala Asn Val His Ser Asn Asp Asp
                 85                  90                  95

Tyr Phe Glu Val Ile Asp Phe Ala Ser Asp Ala Thr Ile Thr Asp Arg
            100                 105                 110

Asn Gly Lys Val Tyr Phe Ala Asp Lys Asp Gly Ser Val Thr Leu Pro
        115                 120                 125

Thr Gln Pro Val Gln Glu Phe Leu Leu Ser Gly His Val Arg Val Arg
    130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Phe Arg
            165                 170                 175

Pro Gly Leu Lys Asp Thr Lys Leu Leu Lys Thr Leu Ala Ile Gly Asp
        180                 185                 190

Thr Ile Thr Ser Gln Glu Leu Leu Ala Gln Ala Gln Ser Ile Leu Asn
    195                 200                 205

Lys Asn His Pro Gly Tyr Thr Ile Tyr Glu Arg Asp Ser Ser Ile Val
210                 215                 220

Thr His Asp Asn Asp Ile Phe Arg Thr Ile Leu Pro Met Asp Gln Glu
225                 230                 235                 240

Phe Thr Tyr Arg Val Lys Asn Arg Glu Gln Ala Tyr Arg Ile Asn Lys
            245                 250                 255

Lys Ser Gly Leu Asn Glu Glu Ile Asn Asn Thr Asp Leu Ile Ser Glu
        260                 265                 270

Lys Tyr Tyr Val Leu Lys Lys Gly Glu Lys Pro Tyr Asp Pro Phe Asp
    275                 280                 285

Arg Ser His Leu Val Asp Pro Cys Phe Arg Ala Asn Cys Glu Tyr Gln
    290                 295                 300

Cys Gln Pro Leu Asn Gln Thr Ser Tyr Leu Cys Val Cys Ala Glu Gly
305                 310                 315                 320

Phe Ala Pro Ile Pro His Glu Pro His Arg Cys Gln Met Phe Cys Asn
            325                 330                 335

Gln Thr Ala Cys Pro Ala Asp Cys Asp Pro Asn Thr Gln Ala Ser Cys
        340                 345                 350

Glu Cys Pro Glu Gly Tyr Ile Leu Asp Asp Gly Phe Ile Cys Thr Asp
    355                 360                 365

Ile Asp Glu Cys Glu Asn Gly Gly Phe Cys Ser Gly Val Cys His Asn
370                 375                 380

Leu Pro Gly Thr Phe Glu Cys Ile Cys Gly Pro Asp Ser Ala Leu Ala
385                 390                 395                 400

Arg His Ile Gly Thr Asp Cys Asp Ser Gly Lys Leu Phe Thr Ile Lys
            405                 410                 415

Tyr Val Asp Val Asp Thr Asn Glu Leu Leu Lys Ser Glu Gln Leu Leu
        420                 425                 430

Thr Ala Ser Glu Arg Asn Leu Asp Phe Arg Asp Leu Tyr Asp Pro Arg
    435                 440                 445

Asp Lys Ala Lys Leu Leu Tyr Asn Asn Leu Asp Ala Phe Gly Ile Met
    450                 455                 460

Asp Tyr Thr Leu Thr Gly Lys Val Glu Asp Asn His Asp Asp Thr Asn
465                 470                 475                 480

Arg Ile Ile Thr Val Tyr Met Gly Lys Arg Pro Glu Gly Glu Asn Ala
```

```
                        485                 490                 495
Ser Tyr His Leu Ala Tyr Asp Lys Asp Arg Tyr Thr Glu Glu Arg
                    500                 505                 510

Glu Val Tyr Ser Tyr Leu Arg Tyr Thr Gly Thr Pro Ile Pro Asp Asn
                515                 520                 525

Pro Asn Asp Lys
        530

<210> SEQ ID NO 130
<211> LENGTH: 136
<212> TYPE: PRT
<213> ORGANISM: Staphylococcus aureus

<400> SEQUENCE: 130

Ser Ser Ser Phe Asp Lys Gly Lys Tyr Lys Lys Gly Asp Asp Ala Ser
1               5                   10                  15

Tyr Phe Glu Pro Thr Gly Pro Tyr Leu Met Val Asn Val Thr Gly Val
            20                  25                  30

Asp Ser Lys Gly Asn Glu Leu Leu Ser Pro His Tyr Val Glu Phe Pro
        35                  40                  45

Ile Lys Pro Gly Thr Thr Leu Thr Lys Glu Lys Ile Glu Tyr Tyr Val
    50                  55                  60

Glu Trp Ala Leu Asp Ala Thr Ala Tyr Lys Glu Phe Arg Val Val Glu
65                  70                  75                  80

Leu Asp Pro Ser Ala Lys Ile Glu Val Thr Tyr Tyr Asp Lys Asn Lys
                85                  90                  95

Lys Lys Glu Glu Thr Lys Ser Phe Pro Ile Thr Glu Lys Gly Phe Val
            100                 105                 110

Val Pro Asp Leu Ser Glu His Ile Lys Asn Pro Gly Phe Asn Leu Ile
        115                 120                 125

Thr Lys Val Val Ile Glu Lys Lys
    130                 135

<210> SEQ ID NO 131
<211> LENGTH: 1800
<212> TYPE: DNA
<213> ORGANISM: Artificial Sequence
<220> FEATURE:
<223> OTHER INFORMATION: EGF 4,5,6 fused with truncated SK at both
      terminus by overlap extension

<400> SEQUENCE: 131
gtggacccgt gcttcagagc caactgcgag taccagtgcc agccctgaa ccaaactagc        60 tacctctgcg tctgcgccga gggcttcgcg cccattcccc acgagccgca caggtgccag      120
atgttttgca accagactgc ctgtccagcc gactgcgacc ccaacaccca ggctagctgt      180
gagtgccctg aaggctacat cctggacgac ggtttcatct gcacggacat cgacgagtgc      240
gaaaacggcg gcttctgctc cggggtgtgc acaacctcc ccgtaccctt cgagtgcatc       300
tgcgggcccg actcggccct tgcccgccac attggcaccg actgtgacag ccaattagtt      360
gttagcgttg ctggtactgt tgaggggacg aatcaagaca ttagtcttaa atttttgaa       420 atcgatctaa catcacgacc tgctcatgga ggaaagacag agcaaggctt aagtccaaaa      480
tcaaaaccat tgctactga tagtggcgcg atgtcacata acttgagaa agctgactta       540 ctaaaggcta ttcaagaaca attgatcgct aacgtccaca gtaacgacga ctactttgag      600
gtcattgatt ttgcaagcga tgcaaccatt actgatcgaa acggcaaggt ctactttgct      660
```

```
gacaaagatg gttcggtaac cttgccgacc caacctgtcc aagaattttt gctaagcgga      720
catgtgcgcg ttagaccata taaagaaaaa ccaatacaaa accaagcgaa atctgttgat      780
gtggaatata ctgtacagtt tactccctta aaccctgatg acgatttcag accaggtctc      840
aaagatacta agctattgaa aacactagct atcggtgaca ccatcacatc tcaagaatta      900
ctagctcaag cacaaagcat tttaaacaaa aaccacccag gctatacgat ttatgaacgt      960
gactcctcaa tcgtcactca tgacaatgac atttttccgta cgattttacc aatggatcaa     1020
gagtttactt accgtgttaa aaatcgggaa caagcttata ggatcaataa aaaatctggt     1080
ctgaatgaag aaataaacaa cactgacctg atctctgaga atattacgt ccttaaaaaa      1140 ggggaaaagc cgtatgatcc ctttgatcgc agtcacttga aactgttcac catcaaatac     1200
gttgatgtcg ataccaacga attgctaaaa agtgagcagc tcttaacagc tagcgaacgt     1260
aacttagact tcagagattt atacgatcct cgtgataagg ctaaactact ctacaacaat     1320
ctcgatgctt ttggtattat ggactatacc ttaactggaa aagtagagga taatcacgat     1380
gacaccaacc gtatcataac cgtttatatg ggcaagcgac ccgaaggaga gaatgctagc     1440
tatcatttag ccgtggaccc cgtgcttcaga gccaactgcg agtaccagtg ccagcccctg     1500
aaccaaacta gctacctctg cgtctgcgcc gagggcttcg cgcccattcc ccacgagccg     1560
cacaggtgcc agatgttttg caaccagact gcctgtccag ccgactgcga ccccaacacc     1620
caggctagct gtgagtgccc tgaaggctac atcctggacg acggtttcat ctgcacggac     1680
atcgacgagt gcgaaaacgg cggcttctgc tccggggtgt gccacaacct ccccggtacc     1740
ttcgagtgca tctgcgggcc cgactcggcc cttgcccgcc acattggcac cgactgtgac     1800
```

<210> SEQ ID NO 132
<211> LENGTH: 600
<212> TYPE: PRT
<213> ORGANISM: Artificial Sequence
<220> FEATURE:
<223> OTHER INFORMATION: Fusion sequence

<400> SEQUENCE: 132

```
Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
                85                  90                  95

Phe Glu Cys Ile Cys Gly Pro Asp Ser Ala Leu Ala Arg His Ile Gly
            100                 105                 110

Thr Asp Cys Asp Ser Gln Leu Val Val Ser Val Ala Gly Thr Val Glu
        115                 120                 125

Gly Thr Asn Gln Asp Ile Ser Leu Lys Phe Phe Glu Ile Asp Leu Thr
    130                 135                 140

Ser Arg Pro Ala His Gly Gly Lys Thr Glu Gln Gly Leu Ser Pro Lys
145                 150                 155                 160

Ser Lys Pro Phe Ala Thr Asp Ser Gly Ala Met Ser His Lys Leu Glu
```

-continued

```
                165                 170                 175
Lys Ala Asp Leu Leu Lys Ala Ile Gln Glu Gln Leu Ile Ala Asn Val
                180                 185                 190

His Ser Asn Asp Asp Tyr Phe Glu Val Ile Asp Phe Ala Ser Asp Ala
                195                 200                 205

Thr Ile Thr Asp Arg Asn Gly Lys Val Tyr Phe Ala Asp Lys Asp Gly
                210                 215                 220

Ser Val Thr Leu Pro Thr Gln Pro Val Gln Glu Phe Leu Leu Ser Gly
225                 230                 235                 240

His Val Arg Val Arg Pro Tyr Lys Glu Lys Pro Ile Gln Asn Gln Ala
                245                 250                 255

Lys Ser Val Asp Val Glu Tyr Thr Val Gln Phe Thr Pro Leu Asn Pro
                260                 265                 270

Asp Asp Asp Phe Arg Pro Gly Leu Lys Asp Thr Lys Leu Leu Lys Thr
                275                 280                 285

Leu Ala Ile Gly Asp Thr Ile Thr Ser Gln Glu Leu Leu Ala Gln Ala
                290                 295                 300

Gln Ser Ile Leu Asn Lys Asn His Pro Gly Tyr Thr Ile Tyr Glu Arg
305                 310                 315                 320

Asp Ser Ser Ile Val Thr His Asp Asn Asp Ile Phe Arg Thr Ile Leu
                325                 330                 335

Pro Met Asp Gln Glu Phe Thr Tyr Arg Val Lys Asn Arg Glu Gln Ala
                340                 345                 350

Tyr Arg Ile Asn Lys Lys Ser Gly Leu Asn Glu Glu Ile Asn Asn Thr
                355                 360                 365

Asp Leu Ile Ser Glu Lys Tyr Tyr Val Leu Lys Lys Gly Glu Lys Pro
                370                 375                 380

Tyr Asp Pro Phe Asp Arg Ser His Leu Lys Leu Phe Thr Ile Lys Tyr
385                 390                 395                 400

Val Asp Val Asp Thr Asn Glu Leu Leu Lys Ser Glu Gln Leu Leu Thr
                405                 410                 415

Ala Ser Glu Arg Asn Leu Asp Phe Arg Asp Leu Tyr Asp Pro Arg Asp
                420                 425                 430

Lys Ala Lys Leu Leu Tyr Asn Asn Leu Asp Ala Phe Gly Ile Met Asp
                435                 440                 445

Tyr Thr Leu Thr Gly Lys Val Glu Asp Asn His Asp Asp Thr Asn Arg
                450                 455                 460

Ile Ile Thr Val Tyr Met Gly Lys Arg Pro Glu Gly Glu Asn Ala Ser
465                 470                 475                 480

Tyr His Leu Ala Val Asp Pro Cys Phe Arg Ala Asn Cys Glu Tyr Gln
                485                 490                 495

Cys Gln Pro Leu Asn Gln Thr Ser Tyr Leu Cys Val Cys Ala Glu Gly
                500                 505                 510

Phe Ala Pro Ile Pro His Glu Pro His Arg Cys Gln Met Phe Cys Asn
                515                 520                 525

Gln Thr Ala Cys Pro Ala Asp Cys Asp Pro Asn Thr Gln Ala Ser Cys
                530                 535                 540

Glu Cys Pro Glu Gly Tyr Ile Leu Asp Asp Gly Phe Ile Cys Thr Asp
545                 550                 555                 560

Ile Asp Glu Cys Glu Asn Gly Gly Phe Cys Ser Gly Val Cys His Asn
                565                 570                 575

Leu Pro Gly Thr Phe Glu Cys Ile Cys Gly Pro Asp Ser Ala Leu Ala
                580                 585                 590
```

Arg His Ile Gly Thr Asp Cys Asp
        595                 600

<210> SEQ ID NO 133
<211> LENGTH: 1452
<212> TYPE: DNA
<213> ORGANISM: Artificial Sequence
<220> FEATURE:
<223> OTHER INFORMATION: EGF 4,5,6 with N-terminal truncated SK.

<400> SEQUENCE: 133

```
gtggacccgt gcttcagagc caactgcgag taccagtgcc agcccctgaa ccaaactagc     60
tacctctgcg tctgcgccga gggcttcgcg cccattcccc acgagccgca caggtgccag    120
atgttttgca accagactgc ctgtccagcc gactgcgacc ccaacaccca ggctagctgt    180
gagtgccctg aaggctacat cctggacgac ggtttcatct gcacggacat cgacgagtgc    240
gaaaacggcg gcttctgctc cggggtgtgc cacaacctcc ccggtaccct cgagtgcatc    300
tgcgggcccg actcggccct tgcccgccac attggcaccg actgtgacag ccaattagtt    360
gttagcgttg ctggtactgt tgaggggacg aatcaagaca ttagtcttaa attttttgaa    420
atcgatctaa catcacgacc tgctcatgga ggaaagacag agcaaggctt aagtccaaaa    480
tcaaaaccat ttgctactga tagtggcgcg atgtcacata acttgagaa agctgactta    540
ctaaaggcta ttcaagaaca attgatcgct aacgtccaca gtaacgacga ctactttgag    600
gtcattgatt ttgcaagcga tgcaaccatt actgatcgaa acggcaaggt ctactttgct    660
gacaaagatg gttcggtaac cttgccgacc caacctgtcc aagaattttt gctaagcgga    720
catgtgcgcg ttagaccata taagaaaaaa ccaatacaaa accaagcgaa atctgttgat    780
gtggaatata ctgtacagtt tactccctta aaccctgatg acgatttcag accaggtctc    840
aaagatacta agctattgaa aacactagct atcggtgaca ccatcacatc tcaagaatta    900
ctagctcaag cacaaagcat tttaaacaaa accacccag gctatacgat ttatgaacgt    960
gactcctcaa tcgtcactca tgacaatgac attttccgta cgattttacc aatggatcaa   1020
gagtttactt accgtgttaa aaatcgggaa caagcttata ggatcaataa aaaatctggt   1080
ctgaatgaag aaataaacaa cactgacctg atctctgaga atattacgt ccttaaaaaa    1140
ggggaaaagc cgtatgatcc ctttgatcgc agtcacttga aactgttcac catcaaatac   1200
gttgatgtcg ataccaacga attgctaaaa agtgagcagc tcttaacagc tagcgaacgt   1260
aacttagact tcagagattt atacgatcct cgtgataagg ctaaactact ctacaacaat   1320
ctcgatgctt ttggtattat ggactatacc ttaactggaa aagtagagga taatcacgat   1380
gacaccaacc gtatcataac cgtttatatg ggcaagcgac ccgaaggaga gaatgctagc   1440
tatcatttag cc                                                        1452
```

<210> SEQ ID NO 134
<211> LENGTH: 484
<212> TYPE: PRT
<213> ORGANISM: Artificial Sequence
<220> FEATURE:
<223> OTHER INFORMATION: EGF 4,5,6 fused with N-terminal truncated SK.

<400> SEQUENCE: 134

Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

-continued

```
Pro His Glu Pro His Arg Cys Gln Met Phe Cys Asn Gln Thr Ala Cys
         35                  40                  45

Pro Ala Asp Cys Asp Pro Asn Thr Gln Ala Ser Cys Glu Cys Pro Glu
         50                  55                  60

Gly Tyr Ile Leu Asp Asp Gly Phe Ile Cys Thr Asp Ile Asp Glu Cys
 65                  70                  75                  80

Glu Asn Gly Gly Phe Cys Ser Gly Val Cys His Asn Leu Pro Gly Thr
                 85                  90                  95

Phe Glu Cys Ile Cys Gly Pro Asp Ser Ala Leu Ala Arg His Ile Gly
                100                 105                 110

Thr Asp Cys Asp Ser Gln Leu Val Val Ser Val Ala Gly Thr Val Glu
            115                 120                 125

Gly Thr Asn Gln Asp Ile Ser Leu Lys Phe Phe Glu Ile Asp Leu Thr
        130                 135                 140

Ser Arg Pro Ala His Gly Gly Lys Thr Glu Gln Gly Leu Ser Pro Lys
145                 150                 155                 160

Ser Lys Pro Phe Ala Thr Asp Ser Gly Ala Met Ser His Lys Leu Glu
                165                 170                 175

Lys Ala Asp Leu Leu Lys Ala Ile Gln Glu Gln Leu Ile Ala Asn Val
                180                 185                 190

His Ser Asn Asp Asp Tyr Phe Glu Val Ile Asp Phe Ala Ser Asp Ala
            195                 200                 205

Thr Ile Thr Asp Arg Asn Gly Lys Val Tyr Phe Ala Asp Lys Asp Gly
        210                 215                 220

Ser Val Thr Leu Pro Thr Gln Pro Val Gln Glu Phe Leu Leu Ser Gly
225                 230                 235                 240

His Val Arg Val Arg Pro Tyr Lys Glu Lys Pro Ile Gln Asn Gln Ala
                245                 250                 255

Lys Ser Val Asp Val Glu Tyr Thr Val Gln Phe Thr Pro Leu Asn Pro
            260                 265                 270

Asp Asp Asp Phe Arg Pro Gly Leu Lys Asp Thr Lys Leu Leu Lys Thr
        275                 280                 285

Leu Ala Ile Gly Asp Thr Ile Thr Ser Gln Glu Leu Leu Ala Gln Ala
        290                 295                 300

Gln Ser Ile Leu Asn Lys Asn His Pro Gly Tyr Thr Ile Tyr Glu Arg
305                 310                 315                 320

Asp Ser Ser Ile Val Thr His Asp Asn Asp Ile Phe Arg Thr Ile Leu
                325                 330                 335

Pro Met Asp Gln Glu Phe Thr Tyr Arg Val Lys Asn Arg Glu Gln Ala
            340                 345                 350

Tyr Arg Ile Asn Lys Lys Ser Gly Leu Asn Glu Glu Ile Asn Asn Thr
        355                 360                 365

Asp Leu Ile Ser Glu Lys Tyr Tyr Val Leu Lys Lys Gly Glu Lys Pro
    370                 375                 380

Tyr Asp Pro Phe Asp Arg Ser His Leu Lys Leu Phe Thr Ile Lys Tyr
385                 390                 395                 400

Val Asp Val Asp Thr Asn Glu Leu Leu Lys Ser Glu Gln Leu Leu Thr
                405                 410                 415

Ala Ser Glu Arg Asn Leu Asp Phe Arg Asp Leu Tyr Asp Pro Arg Asp
            420                 425                 430

Lys Ala Lys Leu Leu Tyr Asn Asn Leu Asp Ala Phe Gly Ile Met Asp
        435                 440                 445
```

Tyr Thr Leu Thr Gly Lys Val Glu Asp Asn His Asp Asp Thr Asn Arg
                450                 455                 460

Ile Ile Thr Val Tyr Met Gly Lys Arg Pro Glu Gly Glu Asn Ala Ser
465                 470                 475                 480

Tyr His Leu Ala

<210> SEQ ID NO 135
<211> LENGTH: 1452
<212> TYPE: DNA
<213> ORGANISM: Artificial Sequence
<220> FEATURE:
<223> OTHER INFORMATION: SK (16-383) EGF 4,5,6

<400> SEQUENCE: 135

| | | | | |
|---|---|---|---|---|
| agccaattag | ttgttagcgt | tgctggtact | gttgagggga | cgaatcaaga | cattagtctt | 60 |
| aaatttttg | aaatcgatct | aacatcacga | cctgctcatg | gaggaaagac | agagcaaggc | 120 |
| ttaagtccaa | atcaaaaacc | atttgctact | gatagtggcg | cgatgtcaca | taaacttgag | 180 |
| aaagctgact | tactaaaggc | tattcaagaa | caattgatcg | ctaacgtcca | cagtaacgac | 240 |
| gactactttg | aggtcattga | ttttgcaagc | gatgcaacca | ttactgatcg | aaacggcaag | 300 |
| gtctactttg | ctgacaaaga | tggttcggta | accttgccga | cccaacctgt | ccaagaattt | 360 |
| ttgctaagcg | gacatgtgcg | cgttagacca | tataagaaaa | accaataca | aaaccaagcg | 420 |
| aaatctgttg | atgtggaata | tactgtacag | tttactccct | aaaccctga | tgacgatttc | 480 |
| agaccaggtc | tcaaagatac | taagctattg | aaaacactag | ctatcggtga | caccatcaca | 540 |
| tctcaagaat | tactagctca | agcacaaagc | attttaaaca | aaaccaccc | aggctatacg | 600 |
| atttatgaac | gtgactcctc | aatcgtcact | catgacaatg | acattttccg | tacgatttta | 660 |
| ccaatggatc | aagagtttac | ttaccgtgtt | aaaaatcggg | aacaagctta | taggatcaat | 720 |
| aaaaaatctg | gtctgaatga | agaaataaac | aacactgacc | tgatctctga | gaaatattac | 780 |
| gtccttaaaa | aaggggaaaa | gccgtatgat | ccctttgatc | gcagtcactt | gaaactgttc | 840 |
| accatcaaat | acgttgatgt | cgataccaac | gaattgctaa | aaagtgagca | gctcttaaca | 900 |
| gctagcgaac | gtaacttaga | cttcagagat | ttatacgatc | tcgtgataa | ggctaaacta | 960 |
| ctctacaaca | atctcgatgc | ttttggtatt | atggactata | ccttaactgg | aaaagtagag | 1020 |
| gataatcacg | atgacaccaa | ccgtatcata | accgtttata | tgggcaagcg | acccgaagga | 1080 |
| gagaatgcta | gctatcattt | agccgtggac | ccgtgcttca | gagccaactg | cgagtaccag | 1140 |
| tgccagcccc | tgaaccaaac | tagctacctc | tgcgtctgcg | ccgagggctt | cgcgcccatt | 1200 |
| ccccacgagc | cgcacaggtg | ccagatgttt | tgcaaccaga | ctgcctgtcc | agccgactgc | 1260 |
| gaccccaaca | cccaggctag | ctgtgagtgc | cctgaaggct | acatcctgga | cgacggtttc | 1320 |
| atctgcacgg | acatcgacga | gtgcgaaaac | ggcggcttct | gctccggggt | gtgccacaac | 1380 |
| ctccccggta | ccttcgagtg | catctgcggg | cccgactcgg | cccttgcccg | ccacattggc | 1440 |
| accgactgtg | ac | | | | | 1452 |

<210> SEQ ID NO 136
<211> LENGTH: 484
<212> TYPE: PRT
<213> ORGANISM: Artificial Sequence
<220> FEATURE:
<223> OTHER INFORMATION: SK (16-383) EGF 4,5,6

<400> SEQUENCE: 136

Ser Gln Leu Val Val Ser Val Ala Gly Thr Val Glu Gly Thr Asn Gln

-continued

```
1               5                   10                  15
Asp Ile Ser Leu Lys Phe Phe Glu Ile Asp Leu Thr Ser Arg Pro Ala
            20                  25                  30

His Gly Gly Lys Thr Glu Gln Gly Leu Ser Pro Lys Ser Lys Pro Phe
            35                  40                  45

Ala Thr Asp Ser Gly Ala Met Ser His Lys Leu Glu Lys Ala Asp Leu
            50                  55                  60

Leu Lys Ala Ile Gln Glu Gln Leu Ile Ala Asn Val His Ser Asn Asp
65                  70                  75                  80

Asp Tyr Phe Glu Val Ile Asp Phe Ala Ser Asp Ala Thr Ile Thr Asp
                    85                  90                  95

Arg Asn Gly Lys Val Tyr Phe Ala Asp Lys Asp Gly Ser Val Thr Leu
                    100                 105                 110

Pro Thr Gln Pro Val Gln Glu Phe Leu Leu Ser Gly His Val Arg Val
                    115                 120                 125

Arg Pro Tyr Lys Glu Lys Pro Ile Gln Asn Gln Ala Lys Ser Val Asp
            130                 135                 140

Val Glu Tyr Thr Val Gln Phe Thr Pro Leu Asn Pro Asp Asp Asp Phe
145                 150                 155                 160

Arg Pro Gly Leu Lys Asp Thr Lys Leu Leu Lys Thr Leu Ala Ile Gly
                    165                 170                 175

Asp Thr Ile Thr Ser Gln Glu Leu Leu Ala Gln Ala Gln Ser Ile Leu
                    180                 185                 190

Asn Lys Asn His Pro Gly Tyr Thr Ile Tyr Glu Arg Asp Ser Ser Ile
            195                 200                 205

Val Thr His Asp Asn Asp Ile Phe Arg Thr Ile Leu Pro Met Asp Gln
210                 215                 220

Glu Phe Thr Tyr Arg Val Lys Asn Arg Glu Gln Ala Tyr Arg Ile Asn
225                 230                 235                 240

Lys Lys Ser Gly Leu Asn Glu Glu Ile Asn Asn Thr Asp Leu Ile Ser
                    245                 250                 255

Glu Lys Tyr Tyr Val Leu Lys Lys Gly Glu Lys Pro Tyr Asp Pro Phe
                    260                 265                 270

Asp Arg Ser His Leu Lys Leu Phe Thr Ile Lys Tyr Val Asp Val Asp
            275                 280                 285

Thr Asn Glu Leu Leu Lys Ser Glu Gln Leu Leu Thr Ala Ser Glu Arg
            290                 295                 300

Asn Leu Asp Phe Arg Asp Leu Tyr Asp Pro Arg Asp Lys Ala Lys Leu
305                 310                 315                 320

Leu Tyr Asn Asn Leu Asp Ala Phe Gly Ile Met Asp Tyr Thr Leu Thr
                    325                 330                 335

Gly Lys Val Glu Asp Asn His Asp Thr Asn Arg Ile Ile Thr Val
            340                 345                 350

Tyr Met Gly Lys Arg Pro Glu Gly Glu Asn Ala Ser Tyr His Leu Ala
            355                 360                 365

Val Asp Pro Cys Phe Arg Ala Asn Cys Glu Tyr Gln Cys Gln Pro Leu
            370                 375                 380

Asn Gln Thr Ser Tyr Leu Cys Val Cys Ala Glu Gly Phe Ala Pro Ile
385                 390                 395                 400

Pro His Glu Pro His Arg Cys Gln Met Phe Cys Asn Gln Thr Ala Cys
                    405                 410                 415

Pro Ala Asp Cys Asp Pro Asn Thr Gln Ala Ser Cys Glu Cys Pro Glu
            420                 425                 430
```

```
Gly Tyr Ile Leu Asp Asp Gly Phe Ile Cys Thr Asp Ile Asp Glu Cys
            435                 440                 445

Glu Asn Gly Gly Phe Cys Ser Gly Val Cys His Asn Leu Pro Gly Thr
        450                 455                 460

Phe Glu Cys Ile Cys Gly Pro Asp Ser Ala Leu Ala Arg His Ile Gly
465                 470                 475                 480

Thr Asp Cys Asp

<210> SEQ ID NO 137
<211> LENGTH: 118
<212> TYPE: PRT
<213> ORGANISM: Artificial Sequence
<220> FEATURE:
<223> OTHER INFORMATION: Artificially synthesized

<400> SEQUENCE: 137

Val Asp Pro Cys Phe Arg Ala Asn Cys Glu Tyr Gln Cys Gln Pro Leu
1               5                   10                  15

Asn Gln Thr Ser Tyr Leu Cys Val Cys Ala Glu Gly Phe Ala Pro Ile
            20                  25                  30

Pro His Glu Pro His Arg Cys Gln Met Phe Cys Asn Gln Thr Ala Cys
        35                  40                  45

Pro Ala Asp Cys Asp Pro Asn Thr Gln Ala Ser Cys Glu Cys Pro Glu
    50                  55                  60

Gly Tyr Ile Leu Asp Asp Gly Phe Ile Cys Thr Asp Ile Asp Glu Cys
65                  70                  75                  80

Glu Asn Gly Gly Phe Cys Ser Gly Val Cys His Asn Leu Pro Gly Thr
            85                  90                  95

Phe Glu Cys Ile Cys Gly Pro Asp Ser Ala Leu Ala Arg His Ile Gly
            100                 105                 110

Thr Asp Cys Asp Ser Gly
            115
```

PROTEIN FUSION CONSTRUCTS POSSESSING THROMBOLYTIC AND ANTICOAGULANT PROPERTIES

SEQUENCE LISTING SUBMISSION VIA EFS-WEB

A computer readable text file, entitled "102082-5002_SequenceListing.txt," created on or about 23 Sep. 2013, with a file size of about 160 kb contains the sequence listing for this application and is hereby incorporated by reference in its entirety.

FIELD OF THE INVENTION

The present invention relates to thrombolytic drugs which include chimeric fusion proteins comprising a thrombolytic protein and the 4, 5, 6 epidermal growth factor-like domains (EGF 4,5,6) of thrombomodulin. The inventive fusion proteins possess plasminogen activation, thrombin inhibition, and anticoagulant protein C pathway activation activity. The inventive fusion proteins have therapeutic potential to break up thrombi and prevent reocclusion at the site of the clot.

BACKGROUND OF THE INVENTION

Thrombosis, the formation and development of a blood clot or thrombus within the vascular system, while a life saving process when it occurs during a hemorrhage, can be life threatening when it occurs at any other time. The thrombus can block a vessel and stop blood supply to an organ or other body part. If detached, the thrombus can become an embolus and occlude a vessel distant from the original site. Thrombotic disorders now constitute one of the major causes of mortality in both developing and developed countries world-wide. Although still the most preferred emergency ("SOS") medication against thrombotic circulatory disorders, the plasminogen activator protein drugs, such as streptokinase (SK), staphylokinase (SAK) and tissue plasminogen activator (tPA), are slowly losing their supremacy to emergency cardiac interventions such as stenting and bypass surgeries in the affluent countries because of bleeding risks associated with their use, and also the often-encountered problem of clot reformation at the same site of vascular injury due to thrombin activity and/or fresh generation of thrombin. Thus, there is an acute need to develop smarter and more effective thrombolytic drugs with additional features such as clot specificity and anti-thrombotic properties.

Blood clot formation is an end-result of a complex set of cascade reactions wherein several biochemical events cause the sealing, or repair, at the site of injury (Butenas and Mann 2002). On the basis of initiation of the blood coagulation cascade, pathways have been divided into extrinsic and intrinsic pathway, wherein the extrinsic pathway is initiated by the exposure of tissue factor (TF), whereas the intrinsic pathway is initiated by factor XII (Hageman factor), high molecular weight kininogen (HK), or prekallikrain. However, both cascade pathways ultimately join at the point of factor Xa generation, and subsequently follow common thrombin mediated fibrin generation (Cannon and Tracy 1995).

Thrombin generation is the central step of the blood coagulation process in vertebrates. During the thrombin generation process small amount of thrombin gets incorporated into the fibrin clot/network as it expands, and the catalytic site of this protease, being free in this absorbed thrombin, is able to amplify the clot growth (Liu, Nossel et al. 1979; Vali and Scheraga 1988). Thrombin interacts with diverse substrates and activates several clot promoting factors e.g. (a) it causes the activation of platelets by cleaving their cognate receptors (b) causes feed-back activation of factor V, VIII and XI (c) cause the activation of transglutminase, factor XIII and (d) converts fibrinogen into fibrin. Once the clot forms and stabilizes by inter-strand cross-linking, under the pathological conditions, it impedes the normal blood flow in vessels and leads to blockage of arteries and veins.

One of the most common, and preferred, medications against circulatory disorders emanating from pathological thrombus formation in animals/humans such as myocardial infarction, is the intravenous infusion of thrombolytic agents (Lijnen and Collen 1988; Collen and Lijnen 1990; Francis and Marder 1991). Available thrombolytics such as streptokinase (SK), urokinase (UK) and tissue type plasminogen activator (tPA) essentially operate through the same, plasmin-dependent mechanism (since these are plasminogen activators), where these cleave the scissile peptide between residues 561 and 562 of plasminogen and convert it into its proteolytically activated form, plasmin. Tissue type plasminogen activator and urokinase are proteases that specifically recognize the scissile peptide bond in human plasminogen (direct activators), whereas streptokinase and staphylokinase (which are protein 'co-factors' rather than proteases and thus 'indirect' activators; (see: (De Renzo, Boggiano et al. 1967; Buck, Hummel et al. 1968; McClintock and Bell 1971) first make tight 1:1 complexes with plasmin or plasminogen, and the resultant proteolytically active complex(es) cleave the scissile peptide bond of other, 'free' plasminogen molecules and exponentially generate plasmin (Reviewed by: (Wohl, Summaria et al. 1978; Castellino and Powell 1981; Wohl, Sinio et al. 1983; Davidson, Higgins et al. 1990). Of all the currently available clot-busters, that is, plasminogen activator protein drugs, streptokinase exhibits the highest thrombolytic power, although, being (like SAK) of bacterial origin, it has the limitation of engendering immune reactions in a small minority of patients. Nevertheless, it is widely used as an affordable thrombolytic because of its relatively low cost as compared to tPA and UK.

Successful thrombolytic therapy helps maintain normal blood flow and improves the survival in a significant number of patients (Verstraete 1990), but early re-occlusion or re-thrombosis, often at the same site, has continued to limit the successful application of thrombolytic drugs. Several studies demonstrate that early reocclusion occurs in up to 30% of patients after thrombolytic therapy (Ohman, Califf et al. 1990). The cause of rethrombosis or early reocclusion is explained by plasmin activity which increases the hyper coagulability of blood (Eisenberg, Miletich et al. 1988); it is proposed that plasmin activates contact factors (Ewald and Eisenberg 1995), factor V (Lee and Mann 1989) and likely also prothrombin (Seitz et al., 1993). Another suggested reason is the exposure of clot-bound thrombin subsequent to the latter's dissolution, which, in turn, generates more thrombin, with fibrin-bound thrombin being relatively resistant to antithrombin inhibitor/s (Hogg and Jackson 1989; Weitz, Hudoba et al. 1990); the 'released' thrombin again locally activates the procoagulant activity and starts to activate platelets (Kumar, Beguin et al. 1994; Puri, Kumar et al. 1995), thereby promoting a cycle of biochemical events leading to rethrombosis. Thus, inhibition of the thrombin at the site of injury both directly, and at the 'secondary' level of its procoagulant activity, should greatly thwart the above-described, unwanted chain of events. If such a property is integrated successfully in the same molecule as the thrombolytic drug, the advantages in terms of lives saved are obvious.

Plasminogen activators are a family of proteases which characteristically catalyse the enzymatic conversion of plasminogen to plasmin. TPA the enzymatic conversion of plasminogen to plasmin through the hydrolysis of a single Arginine-Valine bond.

Tissue plasminogen activator (also known as fibrinokinase, extrinsic plasminogen activator, t-PA or TPA) is a glycoprotein and has an approximate molecular weight (MW) of about 70,000 Daltons (68,000 Daltons). It is a serine protease which catalyses the enzymatic conversion of pro-enzyme plasminogen to active enzyme plasmin through the hydrolysis of a single Arginine-Valine bond. The catalytic site of t-PA is composed of amino acids His-322, Asp-371 and Ser-478. t-PA is a poor plasminogen activator in the absence of fibrin. The amino-terminal region is composed of several domains, which are homologous to other proteins. These distinct domains are involved in several functions of the enzyme, including binding to fibrin, fibrin-specific plasminogen activation, binding to endothelial cell receptors and rapid clearance in vivo. One such domain, comprising amino acid residues 50 to 87 (E domain) is homologous to Human Epidermal Growth Factor and seems to be involved in fibrin binding, fibrin affinity and in vivo clearance. The t-PA cDNA was cloned and subsequently expressed in Chinese hamster ovary (CHO) cells.

Tissue plasminogen activator (t-PA) is a component of the mammalian fibrinolytic system responsible for the specific activation of plasminogen associated with fibrin clots (i.e. it is capable of dissolving blood clots). Tissue plasminogen activator-mediated clot dissolution shows increased level of fibrinopeptide-A in plasma, which is a direct marker of clot-bound thrombin (Weitz, Leslie et al. 1998). A combination of tissue plasminogen activator and currently known anti-thrombin drugs such as heparin and hirudinis often used in medication but this anti-thrombin acts only on free thrombin, and the clot-bound thrombin is resistant towards heparin and other the inhibitors due to their low affinity. Besides, these drugs do not affect the indirect promoters of further thrombin generation (e.g. Factor V and Factor VIII). Hence, new chimeric proteins need to be designed which activate plasminogen along with inhibition of clot bound thrombin as well as the indirect promoters of thrombin, such as Factor V and Factor VIII.

Work on post-thrombolytic plasmin activity and consequent thrombin generation clearly suggests that there are potent factors which lead to the re-activation of the coagulation pathway even when the pathological clot has been cleared by a clot-buster drug. In addition, the generated thrombin is itself a potent coagulation pathway activator. It is remarkable that thrombin also performs an anti-coagulant function, which is an elegant example of the "self-limiting" control mechanisms of the hemostasis system such that there is no 'run away' coagulation throughout the vasculature. Free thrombin makes a 1:1 high-affinity, non-covalent complex with thrombomodulin, a cell surface protein (Kurosawa, Galvin et al. 1987). Once the thrombin-thrombomodulin complex is formed its substrate specificity is redirected from a pro-coagulant mode to an anti-coagulant one, whereby it activates the Protein C anticoagulant pathway. Thus, even though thrombin alone can activate protein C but once it complexes with thrombomodulin it accelerates protein C activation by nearly a 1000-fold (Esmon and Owen 1981; Owen and Esmon 1981)).

Mature thrombomodulin contains different domains responsible for different functions, namely thrombin inhibition and protein C activation which reside in the epidermal growth factor-like domains of this large protein. Epidermal growth factor-like (EGF) domains 5 and 6 are responsible mainly for thrombin affinity and EGF 4, 5 and 6 domains, activate protein C together (Kurosawa, Stearns et al. 1988; Stearns, Kurosawa et al. 1989). Thrombomodulin, or its isolated EGF domains 4, 5 and 6, are known to activate the protein C-centered anticoagulant pathway, and also directly inhibit thrombin's activity, but cannot dissolve the fibrin clots by themselves. For this, a thrombolytic agent is necessary. Both types of agents can, independently of each other, be used during cardiac thrombotic maladies, but the advantages of a single drug with both types of attributes (which has not been demonstrated so far) are obvious.

The term 'hemostasis' refers to the balance between anticoagulant and procoagulant activities in the blood/vascular system, wherein normally, the blood components, particularly platelets, do not interact abnormally with the blood vessels' inner lining. In case of injury or disease condition, platelets tend to adhere, and as a result, blood coagulation factors start to accumulate and get activated at the site of this injury, which, although a response to initiate repair at the site of injury, results in blood occlusion, thereby often precipitating thrombotic crises.

Blood coagulation and dissolution of a clot, inside blood vessels, are both necessary physiological processes for normal hemostasis. Clot formation and dissolution mechanisms inside the blood vessel are well known in the literature, and the role of different pro-coagulant proteins (clot promoting) and anti-coagulant proteins are now fairly also well-studied. Clot formation is the result of a complex set of reactions wherein thrombin plays a central role in initiation as well as coagulation cascade acceleration, with the end-result appearing in the form of a stable fibrin mesh.

Every modern thrombolytic/fibrinolytic therapy usually combines an anti-thrombotic medication as well (such as aspirin, heparin etc) which is required for the maintenance of normal equilibrium between the pro-coagulants and anti-coagulants during the clot lysis. During lysis, the transiently released thrombin initiates a self-generation loop to amplify clot growth; sometimes this results in a shift of the equilibrium towards the reformation of clot, or activation of the pro-coagulants/clot promoters.

Thrombolytics dissolve pathological clots by activating intrinsic plasminogen in the circulatory system. Among the available and therapeutically useful thrombolytics, streptokinase exhibits the highest thrombolytic potential but sometimes it leads to hemorrhage during the medication because of a lack of clot specificity. This problem is relatively less associated with other thrombolytics (tPA and SAK) because of their relatively increased fibrin clot specificity, but other shortcomings of these thrombolytics are lesser fibrinolytic potential and shorter in vivo half life. All the thrombolytics have essentially same mechanism of thrombolysis (plasminogen activation), but share a common problem, in that that after thrombolysis the generated thrombin often further amplifies thrombin generation by a feed-back mechanism controlled by blood coagulation factor Va and factor VIIIa. In the thrombolysis process, the clot-bound thrombin is also released into the circulation which is relatively resistant to in-built anti-thrombin and other externally provided thrombin inhibitory drugs. This clot-bound thrombin, present at the near vicinity of the 'original' injury also helps to generate even more thrombin in the vicinity of the clot/site of injury, particularly after incomplete removal of clot, which leads to the clinically grave, early re-occlusion problem.

Thombin generation during the lysis and activation of other intrinsic pro-coagulants is a normal part of the hemostasis equilibrium. Anti-thrombin agents like heparin, hirudin and chemically synthesized drugs can inhibit thrombin and prevent its subsequent transient effects, like suppression of hyper-responsive platelet formation process, inhibition of fibrinogen to fibrin conversion and other clot promoting activities which induces hyper-coagulibility in blood. Notably, however, all these direct inhibitors act on transiently generated thrombin, but not on those factors which actually speed up thrombin generation and play key roles in the pro-coagulant pathway. Thus, none of these drugs acts as efficaciously as desired on blood coagulation factors V and VIII, which play crucial role in thrombin generation and early re-occlusion.

The well-known cell surface molecule thrombomodulin, which makes 1:1 complexes with thrombin and directs its pro-coagulant function into a potent anti-coagulant, namely protein C activator. Both activated protein C and protein S degrade activated factor V and factor VIII (Esmon 1989).

Although all available thrombolytics do possess clot dissolving capability and their mechanism is well evident in literature, but during clot lysis, remnants of clot and plasmin lead to thrombin generation; at the same time, since these agents cannot inactivate the thrombin which makes a transient appearance during thelysis of the clot, the result is that reocclusion is a common problem subsequent to thrombolytic therapy. To date, no anti-thrombin drugs are available with a combination of thrombolytic and anti-thrombin properties, especially the pro-coagulant activity so as to inactivate the 'real culprit' which is chiefly responsible for re-thrombosis.

SUMMARY OF THE INVENTION

The present invention relates to the design of improved thrombolytic drugs, which, apart from being capable of plasminogen activation, also exhibit capabilities to inhibit thrombin generation. The presence of these dual properties in the same molecule is potentially of great benefit clinically since this helps to minimize the early re-occlusion problem after thrombolytic therapy. The invention discloses strategically designed chimeric polypeptides, where domains/segments with antithrombin-properties, derived from thrombomodulin, are fused with various thrombolytic proteins such that the resultant fusion/chimeric polypeptides exhibit clot dissolving (thrombolytic) as well as anti-thrombin properties at the same time. These novel fusion constructs have the ability to activate the thrombolytic system in a plasmin and/or thrombin dependent manner (which makes the constructs clot-specific, as fibrin clots are plasmin—as well as thrombin-rich, whereas free plasmin and thrombin are short-lived in the circulation, being rapidly inactivated by Serpins such as alpha-2 antiplasmin, anti-thrombin etc). These constructs also simultaneously inhibit the transiently generated thrombin released during clot lysis, and also initiate the in-built (intrinsic) anti-coagulant Protein C pathway during the medication with these agents in the event of thrombotic disorders such as stroke, myocardial infarction, deep vein thrombosis, etc.

Unlike the currently available thrombolytics, the present invention discloses new thrombolytic constructs which are capable of targeting factors Va and VIIIa of the coagulation cascade (besides the capability to activate the plasmin-dependent thrombolytic pathway) and also the intrinsically in-built anticoagulant Protein C pathway; this combinatorial presence of several desirable capabilities in the same drug molecule improves their overall efficacy, such that these can dissolve the pathological blood clots while minimizing one of the most potentially life-threatening, post-thrombolytic events, namely the relapse of the clotting process.

The approach is to design, test, and validate the creation of fusion proteins with both anti-thrombin and thrombolytic properties. The successful "functional" fusion of EGF 4,5,6- into a thrombolytic molecule can potentially target the latter towards thrombin-rich clots due to the former's intrinsic thrombin affinity. At the same time, if the said fusion, apart from retaining the two originally 'independent' parent biological activities (i.e. anti-thrombin and plasminogen activator activities), confers a pro-drug nature into the hybrid molecule in that it preferentially gets activated in the vicinity of the clot and not systemically, this would be another very useful and advantageous feature due to its targeted nature of action.

In the present invention, several hybrid protein molecules with a combination of thrombolytic property with thrombin inhibiting as well as protein C activation capability has been successfully functionalized by effective integration in the same molecule/s in order to vastly improve the efficacy of presently available thrombolytic drugs and help prevent the re-thrombosis phenomenon, since the presence of all these properties integrated into the same agent/molecule will impart both real-time (temporal) and spatial (in situ) beneficial action at the occluding fibrin blood clot in the various thrombotic pathological syndromes.

In the present invention, streptokinase, tissue plasminogen a activator and staphylokinase have been fused with EGF 4,5,6, to generate chimeric molecules having both the properties of initiation of plasmin dependent thrombolytic system and thrombin mediated Protein C anticoagulant pathway. Moreover, in some of embodiments of the present invention, the successful integration of thrombolysis, clot specificity, and antithrombin activities—which has not been reported so far is also achieved.

In different fusion constructs, the fusion junctions between the thrombolytic agents and the EGF domains were carefully designed using various preferred amino acid residues in the linkers, and different thrombin and/or plasmin cleavable sites were introduced, which gave different time-dependent plasminogen activation kinetics in vitro due to the proteolytic release of EGF 4,5,6 from the chimeras and consequent activation of the thrombolytic component. The presence of different thrombin cleavable site/s at the junction of thrombolytics and EGF 4,5,6 allows these two to separate from each other at the near-vicinity of thrombin rich clots by locally resident enzymes (thrombin or plasmin); thus after cleavage, each domain performs its function independently. Moreover, in some fusion constructs, transglutaminase-recognizable, cross-linking sequences have been introduced at strategic locations in the chimeric polypeptides so that the activated domains would bind covalently to the remnants of clot, in or around the epithelial tissues (whose damage led to the clot generation in the first place), due to the action of blood transglutminase, and thus continue to give the localized effect in terms of both plasminogen activation and thrombin inhibition long after the initial clot has dissolved. This would clearly lead to a 'healing' effect of the drug, an attribute that is unavailable in any thrombolytic protein drug currently being used.

BRIEF DESCRIPTION OF FIGURES

FIG. 1A is a schematic design A represents the DNA sequences encoding for EGF 4,5,6 in-fusion at the N-terminal end of SK (streptokinase).

FIG. 1B is a schematic design B represents the EGF 4,5,6 fusion at the C-terminal end of SK through an appropriate linker containing flexibility promoting residues (e.g., a triple-glycine stretch, GGG).

FIG. 1C is a schematic design C represents the EGF fusion simultaneously at N & C-terminii of SK along with a transglutaminase recognition site/stretch of residues.

FIG. 1D is a schematic design D represents the EGF 4,5,6 domains' fusion at the C-terminal end of SK, wherein 5 amino acids of SK were deleted.

FIG. 1I is a schematic design I represents the EGF domains' fusion simultaneously at the N & C-terminii of tPA (tissue plasminogen activator). In all figures and anywhere such terms occur in the specification, "egf" refers to the EGF-like domains of tPA, while "EGF456" refers to the EGF 4,5,6 domains of thrombomodulin.

FIG. 1J is a schematic design J represents the EGF 4,5,6 domains fusion at the C-terminal end of tPA.

FIG. 1K is a schematic design K represents the EGF 4,5,6 domain fusion at the N-terminal end of tPA.

FIG. 1Q is a schematic design Q represents the EGF 4,5,6 domains fusion with tPA, where intrinsic egf of tPA are replaced by EGF 4,5,6 domains.

FIG. 2. Is a schematic representation of PCR methods and cloning schemes used in the preparation of different fusion constructs.

FIG. 2A is a schematic design showing the PCR, restriction digestion and cloning strategies used in the construction of N_EGF_SK fusion gene block.

FIG. 2B is a schematic design showing the PCR, restriction digestion and cloning strategies used in the making of SK_EGF fusion gene block.

FIG. 2C is a schematic design showing the restriction digestion and cloning strategies used in the making of N_EGF_SK_EGF fusion gene block.

FIG. 2D is a schematic design showing the PCR, restriction digestion and cloning strategies used in the making of Inter-domain SK_EGF (EGF 4,5,6 fused between the α and β domains of SK) fusion gene block.

FIG. 2E is a schematic design showing the PCR, restriction digestion and cloning strategies used in the making of inter-domain SK_EGF (i.e. EGF 4,5,6 fused between the β and γ domains of SK) fusion gene block.

FIG. 2F is a schematic design showing the PCR, restriction digestion and cloning strategies used in the making of tPA gene block.

FIG. 2G is a schematic design showing the restriction digestion and cloning strategies used in the making of N_EGF_tPA and tPA_EGF fusion gene block.

FIG. 2H is a schematic design showing the PCR, restriction digestion and cloning strategies used in the making of tPA_EGF fusion gene block, where intrinsic egf and kringle 1 domains of tPA are selectively deleted.

FIG. 2I is a schematic design showing the PCR, restriction digestion and cloning strategies used in the making of N_EGF_tPA fusion gene block, where intrinsic egf and kringle 1 domain of tPA is deleted.

FIG. 2J is a schematic design showing the PCR, restriction digestion and cloning strategies used in the making of tPA_EGF fusion gene block, where intrinsic egf domain of tPA is replaced with EGF 4, 5, 6 domains.

FIG. 2K is a schematic design showing the PCR, restriction digestion and cloning strategies used in the making of tPA_EGF fusion gene block, where intrinsic egf and kringle 1 domain of tPA is replaced with EGF 4, 5, 6 domains.

DETAILED DESCRIPTION OF THE INVENTION

Figure 1E:
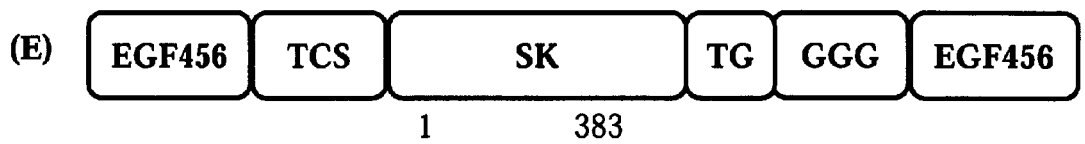
FIG. 1E is a schematic design E represents the simultaneous fusion of EGF 4,5,6 at the N and C-termini of SK, where a thrombin recognition and cleavable sequence (TCS) is present at the junction of EGF and SK.

The present invention relates to the design and preparation of new thrombolytic fusion polypeptides that exhibit distinct functional advantages over the available forms available presently, namely tissue plasminogen activator, SK and SAK or their derivatives/modified forms because the currently available forms only dissolve the fibrin clots through plasminogen activation and cannot prevent post thrombolytic consequences which lead to the early re-occlusion problem during thrombolytic therapy essentially due to thrombin generation.

The present invention discloses methods of making fusion constructs with direct and indirect plasminogen activators fused with the 4th, 5th, and $6^{th}$ EGF domains of thrombomodulin which retain the capability not only to activate plasminogen bit also inhibit thrombin directly as well as retain the ability for protein C activation through the anticoagulant pathway mediated by thrombin.

The terms "variant", "homolog", "derivative", "fragment" or "analog" in relation to the amino acid sequence of a protein include any substitution of, variation of, modification of, replacement of, deletion of or addition of one (or more) amino acid from or to the sequence providing the resultant protein or (poly)peptide has activity equivalent to that of the unmodified protein. In particular, the term "homolog" covers homology with respect to structure and/or function. With respect to sequence homology, preferably there is at least 70%, more preferably at least 80%, even more preferably at least 85% homology to the sequence of the unmodified protein. Preferably there is at least 90%, more preferably at least 95%, most preferably at least 98% homology to the sequence of the unmodified protein.

Typically, for the variant, homolog, derivative, fragment or analog of the present invention, the types of amino acid substitutions that could be made should maintain the hydrophobicity/hydrophilicity of the amino acid sequence. Amino acid substitutions may be made, for example from 1, 2 or 3 to 10, 20 or 30 substitutions provided that the modified sequence retains the ability to act in accordance with the present invention. Amino acid substitutions may include the use of non-naturally occurring analogues, for example to increase blood plasma half-life of a therapeutically administered polypeptide.

Conservative substitutions may be made, for example, as shown below. Amino acids in the same line may be substituted for each other:

ALIPHATIC Non-polar G A P I L V
Polar—uncharged C S T M N Q
Polar—charged D E K R AROMATIC H F W Y As indicated above, proteins of the invention are typically made by recombinant means, for example as described herein, and/or by using synthetic means using techniques well known to the skilled person such as solid phase synthesis.

As used herein a "deletion" is defined as a change in either nucleotide or amino acid sequence in which one or more nucleotides or amino acid residues, respectively, are absent.

As used herein an "insertion" or "addition" is a change in a nucleotide or amino acid sequence, which has resulted in the addition of one or more nucleotides or amino acid residues, respectively, as compared to the naturally occurring protein.

As used herein "substitution" results from the replacement of one or more nucleotides or amino acids by different nucleotides or amino acids, respectively.

As used herein, the terms "4, 5, and 6 epidermal growth factor-like domains" or "EGF 4,5,6" can be any one of the EGF 4, 5, or 6 domains of thrombomodulin, or can refer to all three EGF 4, 5, and 6 domains of thrombomodulin covalently bonded together as a peptide or peptide fragment. Each of the 4, 5, and 6 epidermal growth factor-like domains have homology to one or more domains of the epidermal growth factor (EGF) protein.

The present invention discloses a chimeric protein construct comprising the 4, 5, and 6 epidermal growth factor-like domains (EGF 4,5,6) of thrombomodulin fused to a thrombolytic protein selected from the group consisting of a streptokinase, a tissue plasminogen activator, a staphylokinase, a urokinase, and derivatives and analogs thereof.

In an embodiment of the present inventions is disclosed a chimeric protein construct, where thrombomodulin EGF 4,5,6 domains are fused to said thrombolytic protein, or derivative or analog thereof at the N-terminus, C-terminus, or both N- and C-termini of said thrombolytic protein, or derivative or analog thereof.

The present invention also discloses the design of genetic constructs with minimum essential antithrombotic parts of EGF fused with a thrombolytic protein (SK, tPA or SAK) at the portion encoding the N-terminal end of the thrombolytic protein, wherein translation (in the resultant 'chimeric' ORF) begins with the $4^{th}$ domain of EGF followed by the portion encoding for thrombolytic polypeptide synthesis. Thus, the mature polypeptide or folded protein contains not only the two different types of proteins but both the functionalities as well. These constructs with the thrombolytic protein are termed as EGF N-terminal fusion constructs.

In another embodiment, we have defined the design principle, and methods of construction, of EGF domains fused at the C-terminal side of the thrombolytic protein, by first fusing of the oligonucleotides blocks encoding the relevant portions (thrombolytic-EGF 4,5,6) such that the translation begins with the thrombolytic protein and terminates at the $6^{th}$ domain of EGF, and then expressing the oligonucleotide hybrid block in an expression system, purifying the hybrid and testing it for plasminogen activation as well as thrombin inhibition etc. Here, the translated polypeptide starts with a functionally active thrombolytic protein and has the EGF domains at the C-terminal end, thus also possessing antithrombin and protein C activation capabilities. Designs that lead to the preparation of functional polypeptides have also been disclosed wherein the chimeric polypeptide is inactive initially but attains its plasminogen activation capability upon proteolytic truncation with either plasmin or thrombin.

In another embodiment of the present invention is disclosed a thrombolytic protein comprising a streptokinase with one or more amino acid substitutions, insertions, deletions, or truncations, and wherein the construct possesses plasminogen activation, thrombin inhibition, and anticoagulant protein C pathway activation activity.

Another embodiment contains method of making N & C-terminal fusion constructs, where the thrombolytic protein contains the three EGF domains at the N- and C-termini of thrombolytic protein at the same time. These constructs were designed with the help of expression of oligonucleotide blocks with N-terminal and C-terminal EGF 4,5,6 fusion constructs joined via common restriction site and expression thereof using established methods of gene cloning etc.

In yet another embodiment, the design of intra-protein fusion carrying EGF domains within a thrombolytic such as streptokinase and tissue plasminogen activator, are disclosed.

In another embodiment, the hybrid/fusion construct had tissue plasminogen activator wherein the EGF 4,5,6 domains replaced the kringle 1 domain of tPA. This construct exhibited good plasminogen activity as well as antithrombin properties.

Another embodiment discloses the oxidation resistant forms of EGF domains where the methionine/s of EGF 4,5,6 were replaced with valine, alanine or glutamine amino acid residues in either the N-terminal, C-terminal and N & C-terminal (simultaneous) fusion constructs with thrombolytic (SK, tPA and SAK), described in the foregoing sections, via established methods of site directed mutagenesis.

In yet another embodiment of the invention is disclosed the thrombomodulin EGF 4,5,6 domains which are fused between the alpha and beta or beta and gamma domains of said streptokinase or between the alpha and beta or beta and gamma domains of a streptokinase derivative or analog, wherein the streptokinase derivative or analog comprises one or more mutations, additions, insertions, or truncations, and wherein said construct activates plasminogen, inhibits thrombin, and activates the anticoagulant protein C pathway.

In another embodiment of the present invention is disclosed a construct where the EGF 4,5,6 domains are fused in-frame to streptokinase, or a streptokinase derivative or analog, at one or more positions selected from the streptokinase N-terminus, streptokinase C-terminus, both N- and C-streptokinase termini, or at an inter-domain position of streptokinase.

In yet another embodiment of the present invention is disclosed a chimeric protein construct wherein the streptokinase derivative spans residues 5-383 or 5-414.

In further embodiment of the present invention is disclosed a chimeric protein construct wherein the streptokinase derivative spans residues 16-383.

In yet another embodiment of the present invention is disclosed a chimeric protein construct where the EGF 4,5,6 domains are fused in-frame at one or more positions selected from the streptokinase N-terminus, streptokinase C-terminus, or both N- and C-streptokinase termini, wherein the Met 41 of the EGF 4,5,6 domains is replaced by either valine, alanine, or glutamine; or the C-terminal Met 435 is replaced by valine, alanine, or glutamine; or in the simultaneous N- and C-terminal fusion constructs, Met 41 and Met 435 are independently replaced by either valine, alanine, or glutamine.

In another embodiment of the present invention is disclosed a chimeric protein construct further comprising transglutaminase recognition sequences.

In further embodiment of the present invention is disclosed a chimeric protein construct further comprising one or more thrombin cleavable sequences at the junction of the EGF 4,5,6 domain and the thrombolytic protein, or derivative or analog thereof.

In another embodiment, the hybrid/fusion constructs comprise a thrombin cleavable site at the junction of EGF 4,5,6 and their oxidation resistant forms.

In another embodiment, the hybrid/fusion construct contained EGF 4,5,6 domains are mutated to possess oxidation resistance due to methionine oxidation and consequent loss of activity during their preparation.

In another embodiment of the present invention is disclosed a chimeric protein construct comprising the EGF 4, 5, 6 domain of thrombomodulin fused to a tissue plasminogen activator (tPA) derivative, analog, or fragment at the N-terminus of the tPA derivative, analog, or fragment, at the C-terminus of the tPA derivative, analog, or fragment, at both termini of the tPA derivative, analog, or fragment, or internally within the tPA derivative, analog, or fragment.

In yet another embodiment of the present invention is disclosed a chimeric protein construct wherein the fusion between the EGF 4,5,6 domain and the tPA derivative, analog, or fragment further comprises one or more linker fragments.

In further embodiment of the present invention is disclosed a chimeric protein construct wherein the one or more linker fragments comprise one or more amino acids that promote flexibility of said construct.

In yet another embodiment of the present invention is disclosed a chimeric protein construct wherein the one or more amino acids is chosen from the group consisting of Gly, Asn, Pro, Ser, Gln, Arg and Lys.

In another embodiment of the present invention is disclosed a chimeric protein construct wherein the tPA derivative, analog or fragment comprises one or more mutations, additions, insertions, or truncations, and wherein said tPA derivative, analog or fragment activates plasminogen, inhibits thrombin, and activates anticoagulant protein C.

In yet another embodiment of the present invention is disclosed a chimeric protein construct comprising a fragment of tissue plasminogen activator (tPA), or a truncated or modified form thereof, fused to one or more thrombomodulin EGF 4,5,6 domains, such that the EGF domains of tPA are replaced by the one or more thrombomodulin EGF 4,5,6 domains, and wherein the construct has both antithrombin and plasminogen activation activity.

In further embodiment of the present invention is disclosed a chimeric protein construct comprising a fragment of tissue plasminogen activator (tPA), or a truncated or modified form thereof, fused to one or more thrombomodulin EGF 4,5,6 domains, such that the kringle 1 and EGF domains of tPA are replaced by the one or more thrombomodulin EGF 4,5,6 domains, and wherein the construct has both antithrombin and plasminogen activation activity.

In yet another embodiment of the present invention is disclosed a chimeric protein construct wherein the tPA EGF domains and kringle 1 domain are replaced by one or more thrombomodulin EGF 4,5,6 domains at the N-terminus or C-terminus of the tPA fragment.

In another embodiment of the present invention is disclosed a chimeric protein construct further comprising one or more linker fragments between the tPA fragment or truncated or modified form thereof and the thrombomodulin EGF 4,5,6 domains, the linker fragments comprising amino acid residues that promote flexibility of the construct so that the construct has thrombin inhibition, protein C activation, and plasminogen activation capabilities.

In yet another embodiment of the present invention is disclosed a chimeric protein construct wherein the methionine 41 of the EGF 4,5,6 component is replaced by either alanine, valine or glutamine.

In further embodiment of the present invention is disclosed a chimeric protein construct comprising an EGF 4,5,6 domain of thrombomodulin fused in-frame to the N-terminal or C-terminal end of staphylokinase (SAK).

In yet another embodiment of the present invention is disclosed a chimeric protein construct wherein the methionine 41 of the thrombomodulin EGF 4,5,6 domain is replaced by either alanine, valine or glutamine.

In another embodiment of the present invention is disclosed a chimeric protein construct further comprising thrombin cleavable sequences between the SAK and EGF 4,5,6 domain regions.

In yet another embodiment of the present invention is disclosed a chimeric protein construct further comprising transglutaminase cross-linking sequences.

In another embodiment of the present invention is disclosed a chimeric protein construct wherein said constructs are soluble in aqueous or saline solution.

In this invention, in another embodiment the recombinant chimeric proteins are expressed by plasmids under the control of tightly regulated promoters.

In an embodiment of this invention the various chimeric constructs were expressed through recombinant DNA technology in a suitable hosts such as bacteria, fungi, yeast or animal cells.

In another embodiment of the present invention is disclosed a chimeric protein construct which is secreted into an extracellular medium.

In another embodiment, tissue plasminogen activator and EGF 4,5,6 fusion constructs were expressed in prokaryotic and eukaryotic hosts from which the polypeptides were harvested to obtain the active hybrid constructs in pure form/s.

In another embodiment, various tissue plasminogen activator fusions with EGF constructs were also expressed in eukaryotic systems like animal cell lines, yeast expression system and plant cells where expression cassette was either integrated into host genome or remained in the cytoplasm as an episomal body. The expressed hybrid proteins may be glycosylated or non-glycosylated depending upon the host using for expression.

In another embodiment of the present invention is disclosed a method of treating thrombosis in a mammal, comprising administering to said mammal in need of treatment a therapeutically effective amount of a chimeric protein construct.

In another embodiment of the present invention is disclosed a method of inhibiting thrombin comprising the use of a chimeric protein construct.

In further embodiment of the present invention is disclosed a method of activating protein C comprising the use of a chimeric protein construct.

In yet another embodiment of the present invention is disclosed a method of providing both antithrombin and plasminogen activation comprising the use of a chimeric protein construct.

In another embodiment of the present invention is disclosed a pharmaceutical formulation comprising a pharmaceutically effective amount of a chimeric protein construct.

In another embodiment of the present invention is disclosed a method of thrombolysis in a mammal comprising administering to said mammal in need thereof a therapeutically effective amount of a chimeric protein construct.

In another embodiment, encoding DNA sequences of the hybrid constructs were optimized for the suitable expression host.

In another embodiment, a nucleic acid sequence encoding the chimeric protein construct mentioned above.

In another embodiment, a vector comprising a nucleic acid sequence.

In another embodiment, a host cell comprising a vector.

In another embodiment, a chimeric protein construct is prepared by expression of a nucleic acid sequence encoding said protein in a host cell expression system.

In another embodiment, a method of preparing a chimeric protein construct by expression of a nucleic acid sequence encoding said protein in a host cell expression system.

In another embodiment, the method in which the host cell expression system is a eukaryotic expression system.

In another embodiment, the method in which the host cell expression system is a bacterial expression system.

In another embodiment, the method, in which the bacteria is *E. coli*.

In another embodiment, the method in which the eukaryotic expression system is an animal cell, or a yeast cell.

In another embodiment, the method in which the yeast is *Pischia pastoris*.

In another embodiment, the method, wherein the chimeric protein construct is secreted from the host cell into an extracellular medium.

In another embodiment, the purified constructs are useful as therapeutic agents and in pharmaceutical compositions for treatment of mammals having various thrombotic conditions. Mammals may be humans, rodents, or domesticated animals.

In another embodiment, the purified constructs were used as therapeutic agents to alleviate various circulatory disorders with or without additional stabilizing agents and excipients.

According to another embodiment of the invention, the purified constructs are formulated into one or more pharmaceutical compositions. The pharmaceutical compositions with purified constructs, whether one or more, can be formulated in both solid form (i.e. freeze-dried in vials to later be reconstituted in a suitable solution) or also in liquid form.

In one particular embodiment, these compositions with the purified constructs constitute a kit for thrombolytic therapy or treatment which may optionally include other components, such as: containers with solutions for reconstituting the active ingredients, cannulas, drip bags with physiological serum for intravenous application and instructions for use, etc.

The pharmaceutical combinations may be formulated and used either in combination form (i.e. wherein all the active ingredients are combined into one formulation) or in individual form (i.e. wherein the active ingredients are not combined (or not all combined) into one formulation) as tablets, capsules or elixirs for oral administration; suppositories for rectal administration; sterile solutions, suspensions for injectable administration; and the like. The dose and method of administration can be tailored to achieve optimal efficacy but will depend on such factors as patient weight, diet, concurrent medication and other factors which those skilled in the medical arts will recognise.

Generally, with respect to the purified constructs (including uses, methods, pharmaceutical compositions and products) of the present invention, an amount between 0.1 to 1000 mg is administered (as a single dose or on a multi-dose, as-needed basis), dependent upon the potency of the purified construct used.

Preferred embodiments encompass pharmaceutical compositions prepared for storage and subsequent administration which comprise a therapeutically effective amount of the purified constructs or an enriched composition of the purified constructs, as described herein in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985).

Preservatives, stabilisers, dyes and even flavouring agents may be provided in the pharmaceutical composition. For example, sodium benzoate, sorbic acid and esters of p-hydroxybenzoic acid may be added as preservatives. In addition, antioxidants and suspending agents may be used.

In employing the purified constructs or their pharmaceutical compositions or products in a combination therapy in vivo, the compositions/products can be administered to the mammal in a variety of ways, including parenterally (e.g. intravenously, subcutaneously, intramuscularly, colonically, rectally, nasally, buccal, transdermally, vaginally or intraperitoneally), employing a variety of dosage forms.

As will be readily apparent to one skilled in the art, the useful in vivo dosage to be administered and the particular mode of administration will vary depending upon the mammalian species treated, the particular composition employed, and the specific use for which these compositions are employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved.

Generally, in carrying out the methods of this invention, the dosage for the purified constructs or pharmaceutical compositions can range broadly depending upon the desired effects and the therapeutic indication. Typically, suitable dosages of the purified constructs will be between about 0.1 and 1000 mg, preferably between about 10 and 500 mg, more preferably between about 10 and 150 mg, most preferably between about 10 and 120 mg. Administration is preferably parenteral, such as intravenous. Administration is also preferably as a single dose or on a multi-dose, as-needed basis. Administration is preferably parenteral, such as intravenous. Administration is also preferably as a single dose or on a multi-dose, as-needed basis.

Injectables can be prepared in conventional forms either as liquid solutions or suspensions, solid forms suitable for solution or suspension in liquid prior to injection, or as emulsions. Suitable excipients are, for example, water/saline, dextrose, mannitol, lactose, lecithin, albumin, sodium glutamate, cysteine hydrochloride or the like. In addition, if desired, the injectable pharmaceutical compositions may contain minor amounts of non-toxic auxiliary substances, such as wetting agents, pH buffering agents, and the like. If desired, absorption enhancing preparations (e.g. liposomes) may be utilised.

For parenteral administration, solutions of a pharmaceutically active agent used in accordance with this invention in either sesame or peanut oil or in aqueous propylene glycol may be employed. The aqueous solutions may be suitably buffered (preferably between pH 4 to pH 9) if necessary and the liquid diluent first rendered isotonic. For example, NIF is used in aqueous solution at a pH of around 7. However, NIF is stable in aqueous solution down to about pH 4. The preferred "partner compound", t-PA (or variants thereof, is generally used in aqueous solution at around pH 5. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

It should be noted that the pharmaceutical compositions and products of the present invention may be lyophilised for storage, prior to reconstitution and thereafter administration using methods well known to those skilled in the art. Whether stored as lyophile(s) or otherwise, the active components of the combinations of the present invention may be mixed together before lyophilisation or after reconstitution (for later co-administration) or stored individually (for later simultaneous, separate or sequential administration).

In one particular embodiment, administration is parenteral, for example by intravenous injection, or administered locally by catheterization for in situ administration in the near vicinity of the clot.

The quantities of purified constructs which may be present in the compositions of the pharmaceutical combination provided by this invention may vary within a broad range, but always in therapeutically effective quantities.

The dosage for each thrombolytic treatment protocol with the compositions of the pharmaceutical combination of this invention will depend on numerous factors, including the patient's age, condition, the severity of the clinical condition to be treated, the route and frequency of administration and of the purified construct which is going to be administered in each case.

In one aspect, this invention relates to a pharmaceutical combination or a kit of the invention, as have already been described, for thrombolytic therapy.

In another additional aspect, the invention also relates to a method of treatment and thrombolytic therapy consisting of administering to the patient a therapeutically effective quantity of one or more purified constructs. In this connection, the compositions according to the present invention are particularly eligible for treating ischemic heart disease and its complications, as well as ischemic cerebral strokes, rheumatoid diseases and other pathologies, in whose pathogenesis there take place an inflammatory reaction, ischemia of tissues, disturbances of hemorheology and vascular microcirculation because of thrombosis.

The present invention discloses fusion constructs of tissue plasminogen activator with EGF 4,5,6 domains of thrombomodulin with a six amino acid containing linker sequence. This linker sequence length and amino acid sequence order can be changed or modulated for further optimizing the functions of both the properties. Initially designed constructs with no linker sequence compared with linker-designed construct showed only a small fraction, roughly 20-25%, of the protein C activity in the different constructs containing optimized linkers.

In another embodiment, invention discloses the making of non natural fusion protein encoding gene blocks and their variants through the standard methods of genetic engineering.

Further, the inter-protein fusion linker sequences preferentially contained 3 or more glycine amino acid residues at the junction sites of the EGF 4,5,6 domains with the plasminogen activator component so as to provide the necessary flexibility to the $4^{th}$ domain of EGF which plays key role in Protein C binding and activation. Similarly, linkers were put just after the $6^{th}$ domain of EGF when these were fused at the N-terminal region of tPA so that it could facilitate thrombin binding. This was especially so in case where EGF4,5,6 was introduced between the ordered structures/domain of the tissue plasminogen activator. Thus the role of linkers was evident when two partners were fused to obtain preservation of the functionalities of both partner proteins.

The linker sequence was chosen in such a way wherein one positively charged amino acid (Lysine or Arginine) was placed in tandem with a Val residue but before the two or three glycine residues so that it could be cleaved by plasmin in the close vicinity of the clot where the chances of transient thrombin formation is very high during the lysis and both the domains could perform their work independently at the site of injury.

The Linker also contains one proline amino acid which actually helps to change the orientation of EGF 4,5,6 domains so that they can work optimally while binding to thrombin and activation protein C.

In another embodiment, the designed construct linker length can be increased or decreased as well as sequences of amino acids can be altered with natural and non natural amino acids in order to effect the rates of activation.

In another embodiment, thrombin cleavable sequence, transglutaminase recognition sequence and other blood protease susceptible sites can be introduced in the linkers without affecting fibrinolytic and antithrombotic function.

In another embodiment, invention discloses the expression and purification methods of various fusion polypeptides and their better variants.

In another embodiment, invention discloses various non natural polypeptides which show combined properties of thrombolytics and anti thrombin as well as protein C anticoagulant properties.

In another embodiment, oxidation resistant forms of EGF4,5,6 were fused with the functionally improved variants of tissue plasminogen activator which possess mutational variations compared with native tPA (e.g. DNA SEQ ID 20).

In another embodiment, oxidation resistant forms of EGF4,5,6 were fused with a plasmin resistant form of streptokinase.

In another embodiment, oxidation resistant forms of EGF 4,5,6 were fused with the thrombolytic protein where one or more cysteine residues were free.

In another embodiment, expressed fusion polypeptide are used for the treatment of cardiovascular diseases.

In another embodiment, suitable pharmaceutical composition possess expressed fusion polypeptide/s with FDA approved chemical stabilizer like mannitol, human serum albumin (HSA), etc and solubilizing agents.

Expressed fusion construct may formulate for the intravenous administration to human being may contains FDA approved stabilizers.

In another embodiment, EGF 4,5,6 and its variants can be fused with the urokinase type of plasminogen activator.

In another embodiment, different EGF fusion constructs can be made with those proteins which show 75-100% homology with SK, tPA, and SAK and showing 50-100% plasminogen activation potential compared to their native protein/s.

In another embodiment, variants of EGF4,5,6 fused with the SK, tPA and SAK where EGF 4,5.6 variants show 75-100% homology/similarity and 50-100% antithrombin and protein C activity as compare to independently expressed native EGF 4,5,6 domains.

Reagents

Genetic Constructs:

EGF 4,5,6 domain sequences were that of human thrombomodulinc DNA which was commercially custom-synthesized (GeneScript Inc., USA) for optimal expression in the yeast, *Pichia pastoris*. The synthetic gene segments were ligated in the correct order and cloned in a bacterial plasmid. The fusion constructs between EGF 4,5,6 domains of thrombomodulin, on the one hand, and a thrombolytic eg SAK, SK or tPA (or their derivatives/mutants) was carried out essentially by a combination of (a) custom-gene synthesis using chemical means, and (b) using the well established PCR technology for obtaining selected gene segments using specifically designed primers from the appropriate plasmids (see Methods used in Examples, below), followed by isolating the PCR-generated gene-segment blocks and 'fusing' them in-frame using specialized PCR methods such as Overlap Extension PCR etc. Generally, the regular PCR was done with a suitable, high processivity thermostable DNA polymerase (Pfu DNA polymerase from Fermantas Inc., or Stratagene Inc.), or high fidelity pfu turbo (Stratagene Inc.) enzyme. The hybrid DNA constructs were cloned/expressed in the T7 RNA polymerase promoter-based expression vector, pET-23d by transformation into the appropriate *Escherichia coli* strain—XL-Blue for routine plasmid sub-cloning without concomitant protein expression, and strain BL21 (DE3) strain for protein expression under the T7 RNA Pol promoter—which were procured from Novagen Inc. (Madison, Wis., USA), and also expressed in yeast (*Pichia pastoris*) under the methanol inducing promoter having in-frame α-mating factor signal sequence in the vector, pPIC-9K, and GS115 cells were used for expression (Invitrogen Life Technologies, California, USA). The various restriction endonucleases, T4 DNA ligase and other DNA modifying enzymes were acquired from New England Biolabs (Beverly, Mass.). Oligonucleotide primers were supplied by Biobasic, Inc., Canada. Purifications of DNA and extraction of PCR amplified products from agarose gels were performed using kits available from Qiagen GmbH (Germany). Automated DNA sequencing using fluorescent dyes was done on an Applied Biosystems 3130 xl genetic analyzer equipped with a 16-capillary set-up. Glu-plasminogen was either purchased from Roche Diagnostics GmbH (Penzberg, Germany) or purified from human plasma by affinity chromatography (Deutsch and Mertz, 1970). Human protein C, thrombin, hirudin were purchased from Calbiochem., USA, and standard thrombomodulin of rabbit, and recombinant thrombomodulin were both purchased from American Diagnostica Inc., USA. The N-terminal gas-phase amino acid sequencing was done with an Applied Biosystems sequencer, Model 491. Urokinase, EACA, sodium cyanoborohydride, and L-Lysine were purchased from Sigma Chemical Co., St. Louis, USA. Phenyl Agarose 6XL and DEAE Sepharose (Fast-Flow) were procured from GE-Amersham, Uppsala, Sweden, while Ni-NTA beads were from Qiagen. All other reagents were of the highest analytical grade available.

General Methods Used in Examples

1. Recombinant DNA Fusion Methods:

Various methods collectively referred to as Recombinant DNA technology are now well known in the field of molecular biology. Several techniques, standard protocols and their modified forms were have been very well described in several reference books, like Sambrook et al., Molecular Cloning: A laboratory Manual ($II^{nd}$ edition, Cold Spring Harbor Press, New York, 1989; McPherson, M. J., Quirke, P., and Taylor, G. R., [Ed.] PCR: A practical approach, IRL Press, Oxford, 1991). But several modifications were required in the designing of fusion construct where different publications from the published literature are cited for specific applications. In this invention, where we fused two genes, we took recourse the method known as the Ovelap Extension PCR of Ho et al., (Ho, Hunt et al. 1989), and Mehta and Singh (Mehta and Singh 1999). For small constructs amplification up to 2 Kb, pfu DNA polymerase (Fermentas Inc., USA) were used, and for longer PCR where high fidelity of polymerase action was required for the point mutation construction pfu turbo (Stratagene) was used for the amplification of 6-7 Kb long fragment amplification and site directed mutagenesis (Wang and Malcolm 1999).

2. Restriction Digestion and Ligation:

Restriction digestion and ligation enzymes were obtained from New England Biolabs, USA and 'fast digester' restriction enzymes of Fermantas Inc. were used according to the manufacturers' protocols. Mentioned with respect to almost all chimeric fusion construction examples, wherein ligation was carried out between the Xho I (tetra base cutter) and Not I (Hexa base cutter) digested vector and the insert/s, maximized the chances of directional cloning.

3. Electroporation of Ligation Mixtures in *E. coli* XL 1B Competent Cells and Transformation of Linearized Insert Containing Vector in pPIC-9K:

Ligation mixtures of reaction were electroporated into XL 1B competent cells (Sharma and Schimke 1996). High amount of DNA prepared from the Midi prep kit of Qiagen by following the instruction. In final steps of Midi Preparation DNA was eluted in high salt concentration, here we used 0.3 M sodium acetate of pH 5 at final concentration and 70% ethanol was used for the removal of excess salt (Sambrook et al., 1989), which may interfere in the digestion reactions. By this process we obtained 50-60 µg of DNA which were subjected for the linearization step, with the help of Bgl II enzyme, and after digestion again subjected to the sodium acetate and ethanol precipitation steps, and finally the dried pellet dissolved in 7-8 µl of autoclaved salt free water, where 1-3 µg/µl of DNA was obtained. Here 7-10 µg of DNA was used for the transformation in electrocompetent cells of His-GS 115 cells of Pichia pastoris, finally plated on minimal dextrose where only $His^{s+}$ transformants were grown on plates. The plasmid pPIC-9k is designed in such a way so that multicopy insertion of desired gene is possible through homologous recombination of with AOX 1 promotor (Ramchuran, Mateus et al., 2005). Multicopy target gene insertion can be monitored through the bacterial kanamycin resistance gene (Tn903) through monitoring the genticin resistant population with increasing antibiotic concentrations. Pichia can tolerate genticin resistance of 0.25 mg/ml as such, but 0.5 mg/ml and 4 mg/ml shows 1-2 copy and 7-12 copy insertion, respectively. Genticin resistance directly correlates with the multiple insertion of desired gene. Due to gene dosage effect it can be deduced that the higher secretion of desired gene products corresponds to a higher insertion number (Norden, Agemark et al. 2011).

4. Expression, Isolation and Refolding of Inclusion Bodies of Fusion Constructs.

Some constructs such as EGF-SAK an SAK-EGF were expressed under pET 23-d where the chimeric proteins accumulated in the form of inclusion bodies in the host E. coli Bl 21-DE 3 cells. Where inclusion bodies were formed maximum amount of over expressed protein was obtained (Misawa and Kumagai 1999; Zhang, Xu et al. 2009). The E. coli BL21 DE3 cell were used for the production of chimeric fusion protein' IBs, where 25 ml of LB (Luria Bertani) from overnight grown BL21 DE3 cell culture, was used as primary inoculum, which were transferred to 500 ml LB (secondary culture) media. Once the $OD_{600}$ reached 0.6-0.8 the protein production was induced with the help of 1 mM $IPT_G$. After induction, cells were kept under shaking conditions for 6 hrs at 40° C. After 6 hr incubation, cells were harvested by centrifugation at 6000 rpm for 10 minutes at 4° C. Finally, harvested cells were washed with 50 mM tris, 100 mM NaCl and 1 mM EDTA solution to remove the media components from cell mass. After washing, cells were suspended in washing solution to a final $OD_{600}$ between 35-40; at this dilution cells were subjected for sonication with probe-based sonicator where 30 sec on and off cycles were used for 45 minutes. After completion of lysis cycles, cell pellets were harvested by centrifugation at 12,000 rpm for 15 minutes. Obtained pellets were washed twice with 100 mM NaCl, 50 mM Tris Cl pH 7.4, 1 mM EDTA, 0.1% Triton X-100 and 2M urea-containing solution. Again these IBs were re-suspended in the solution and were harvested by centrifugation it 12000 rpm for 15 minutes. Harvested pellet was washed 2× with 100 mM NaCl, 50 mM Tris Cl pH 7.4 and 1 mM EDTA solution so that Triton X-100 was removed. Finally pellet was re-suspended in 8M urea (prepared in 20 mM Tris Cl pH 7.4) and 1 mM DTT for 2 hrs. Most of the dissolved inclusion bodies in this solution were separated from pellet by centrifugation at 12000 rpm for 20 minutes, and the final supernatant contained maximum portion of the chimeric fusion proteins. Now this protein fraction was subjected for refolding where it was diluted up to 0.2 mg/ml and refolded under the following conditions: 2M urea, oxidized and reduced glutathione mole-ratio 1.5:0.5 in 50 mM NaCl, 50 mM Tris-Cl, 2% glycerol at 4° C. for 36 hrs with very gentle stirring. After completion of this refolding step, the mixture was dialyzed against 20 mM Tris Cl pH 7.6, and 50 mM urea for 48 hrs and dialyzed reaction mixture was subjected to purification by tandem chromatographies using hydrophobic and ion exchange chromatography. Disulfide bond formation was monitored by DTNB reaction (Riener, Kada et al. 2002) which is a direct indicator of disulfide bond formation and refolding. Finally, the purified protein was subjected to different activity assays.

5. Casein-Plasminogen Overlay for the Detection of Plasminogen Activation:

In fusion constructs, at the preliminary level, plasminogen activation was screened by this method, where 5% (w/v) skimmed milk is boiled in water containing 15 mM NaCl, and 50 mM Tris along with 1% agarose. After cooling, ~200-400 µg of plasminogen were added in this mixture, and overlaid onto LB ampicillin containing plates with colonies/clones to be screened (Malke and Ferretti 1984). All the fused recombinant protein with plasminogen activation capability were easily detected by the zone of hydrolysis after incubation for periods varying between 1-2 h and up to 18 h, due to the formation of plasmin which degraded the casein, giving rise to easily visualized zones of clearance against a white background.

6. Screening of Best Produce Clones by Checking Plasminogen Activation Profiles:

After selecting higher copy number containing transformants by the use of genticin resistant marker were subjected for the actual screening of best producer clones. In this method primary culture raised in 2.5 ml of BMGY media (1% yeast extract, 2% peptone, 1× glycerol, 1× yeast nitrogen base without amino acids and 100 mM of potassium phosphate buffer pH 5.5) at 30° C. for 16-18 hrs. Once the optical density ($OD_{600}$) reached up to 3-4 units, we induced the culture by adding 7.5 ml of BMMY media (1% yeast extract, 2% peptone, 1× Methanol, 1× yeast nitrogen base without amino acids and 100 mM of potassium phosphate buffer, pH 5.5). These cultures are further induced for the production of recombinant production with final 0.5 v/v % methanol for 5 days, such that the recombinant fusion proteins were produced under the influence of the strong methanol induced promoter.

7. Zymography:

Extracellular secreted products and desired band of interest possessing plasminogen activation capability were detected by this method, where 10-12.5% SDS-page gels were run in non reducing sample buffer. After completion, excess of sodium dodecyl sulphate was remove by the washing in 2.5% triton X-100 solution. Then this gel was rinsed by 2-3 times with 50 mMTris, pH 7.4. This washed gel was placed on skimmed milk agarose and plasminogen containing solid surface (agar gel). After incubation for 5-7 hours the development of zones of hydrolysis become visible signifying Plasminogen activating capability in the resolved proteins.

8. Western Blotting Technique:

Detection of desired protein was done with the help of Western blotting. All the fusion constructs that were secreted into extracellular medium from Pichia pastoris cells were separated by the help of centrifugation at 6000 rpm and supernatants were taken for the desired product identification. Supernatant were directly taken as such for the western blotting or concentrated first by the 5 KDa or 10 KDa cut off range concentrators (Amicon) or subjected to the tri-chloro acetic acid precipitation, washed with acetone, and loaded onto 10-12.5% SDS polyacylamide gels. Proteins were transferred on nitrocellulose membrane with the help of Transfer buffer containing 25 mMtris, 175 mM glycine and 20% methanol. Gel blotting on membranes were done at 250 mA for 35 minutes. Blotted membranes were soaked on 10% skimmed milk overnight at 4° or incubated at 37° C. for 2 hours. This blot was further washed with phosphate buffered saline containing 0.1% tween-20 for three time, which removes the excess of skimmed milk. After that blot was submerged in primary antibody or polysera for 1 h at recommended dilution and washed with Tween-20 containing PBS, three times. Further this blot was incubated with the HRP conjugated secondary antibody followed by the PBS washing three times. Finally, blots were developed by the addition of DAB (di-amino benzidine) solution.

9. Lysine-Agarose Chromatography:

Various tissue plasminogen activator fusion construct with EGF 4,5,6 contains kringle domains which known for affinity toward the lysine residues (McCance, Menhart et al. 1994; Ye, Rahman et al. 2001). In this method, supernatant obtained from *Pichia pastoris* fermentation, having tissue plasminogen activator fusion polypeptide was dialyzed against the phosphate buffer pH 7.5 for 3-4 hrs and loaded on lysine-Sepaharose column pre-equilibrated with phosphate buffer (purchased from Amersham Biosciences, Uppasala, Sweden) with slow flow rate of approx. 0.5 ml/min. After completion of loading, column was again washed with 4-5 bed volumes of phosphate buffer and protein finally eluted in 0.3 M epsilon amino caproic acid and 100 mM NaCl solution (Qiu, Swartz et al. 1998).

10. Thrombin Affinity Chromatography:

Thrombin coupling was done on cyanogen bromide activated bead by previously described procedure (Salem, Maruyama et al. 1984). Here, proteins obtained from different steps of purification were finally subjected to thrombin affinity where columns were equilibrated in 50 mM Tris Cl pH 7.4 and dialyzed against 50 mM Tris Cl, pH 7.4 used for the loading at slow flow rate of approx. 0.5 ml/min; after completion of loading, the columns were washed with the same buffer. Finally protein was eluted by increasing gradient of NaCl (Salem, Maruyama et al. 1984). Different protein fractions were then tested for the protein C activation capability.

11. Hydrophobic Interaction Chromatography:

Purification of different fusion gene constructs of EGF-SK, EGF-tPA and EGF-SAK was done by different methods of chromatography, where hydrophobic and ion exchange chromatography was used for frequent purification of different fusion polypeptides (Goyal, Sahoo et al. 2007). In hydrophobic chromatography, phenyl sepharose (Amersham Biosciences, Uppasala, Sweden) 6% crossed linked beads with average particle size 100-300 μM size diameter were used for the column preparation. Simple XK16/20 column (Amersham Biosciences, Uppasala, Sweden) was packed with the help of peristaltic pump, approximately 25 ml phenyl Sepharose bed was made and equilibrated with 4-5 bed volumes of 0.3 M Na Cl and 50 mM tris, side by side supernatants obtained during the *Pichia pastoris* fermentation, containing the desired fusion constructs, were maintained in the same buffer strength and salt compositions as the equilibration buffer by dialysis. Equilibrated supernatant was loaded on packed column with 40 ml/hr flow rate, and after completion of supernatant loading, 4-5 bed volume of equilibration buffer was passed for removal of media components and nonspecifically bound impurities and finally desired fusion polypeptides were eluted in water. Eluted proteins were subjected for the second round of purification (see below), and tested for the plasminogen activation, thrombin inhibition and protein C activation assays.

12. DEAE (Diethylaminoethyl) Ion-Exchange Chromatography:

In this chromatographic procedure, DEAE Sepharose™ fast flow were packed in XK 16/20 column (Amersham Biosciences, Uppasala, Sweden) and in general the manufacturer's instructions were followed, where mostly, 20 ml swollen matrix was used for the packing. This column was equilibrated with the 20 mM Tris Cl buffer pH 7.4, and supernatants which was obtained from *Pichia pastoris*, after being extensively dialyzed against the 20 mM Tris Cl buffer pH 7.4, were loaded on equilibrated columns (in separate runs), or after being purified by the hydrophobic interaction chromatography (above), and with its ionic strength maintained same as that of the equilibration buffer, were loaded on the respective columns. After completion of loading, each column was washed with the 4-5 bed volume of equilibration buffer, which helps in the removal of non-specifically or loosely bound impurities and polypeptides. Elution of protein was done by applying increasing gradient of 1M NaCl over 5 bed-volumes of matrix. Protein quantization done with the help of the Bradford method (Bradford 1976) and compared with the standard curve of BSA. Finally purified protein was concentrated by 20 K Da cut-off concentrators (Amicon) and used for various analytical and functional assays.

13. Plasminogen Activation Assays for EFG-Thrombolytic Fusion Constructs:

All chimeric fusion polypeptides constructs contained a thrombolytic component (SK, SAK and tPA), so these constructs' capability to activate the plasminogen was measured by the release of color from chromogenic peptide substrate for plasmin. One-stage assays of streptokinase and all fusion constructs were carried out under conditions where 2 μM Human plasminogen, 50 mM Tris, 0.05% BSA and 5 mM of chromogenic substrate was used, and release of chromogenic substrate is monitored spectrophotometrically as function of time. It followed non linear regression, hence a plot between absorbance and time$^2$ followed straight line equation. Streptokinase immediately starts conversion of plasminogen into plasmin and shows virtually no delay in activation but in case of some of the fusion constructs, it takes a protracted time to activate the plasminogen into plasmin. This indicated that trace amount of plasmin makes the active complex as the zymogen activation of the plasminogen into plasmin (Pathway I) was not active. This was confirmed, when the progressive addition of trace (nanomolar) amounts of external plasmin progressively reduced the lag time. In case of Plasminogen activation by tissue plasminogen activator, a rapid and simple spectrophotometric method was followed, where simple chromogenic peptide (H-D-Val-Leu-Lys-pNA; S-2251; purchased from Chromogenix Inc.) was used for the detection of plasmin formed by the action of tissue plasminogen activator (Verheijen, Mullaart et al. 1982). This method also was used for validation of enhanced plasminogen activation in presence of fibrin and tissue plasminogen activation (van Zonneveld, Veerman et al. 1986). In this activation assay different purified amount of protein amount in incubated with 2 μM plasminogen, 0.05 M Tris Cl ph 7.2, 100 mM NaCl, 0.05% and 0.5 mM of S-2251 used in presence and absence of soluble fibrin (purchased from American Diagnostics, USA) and without fibrin. Absorbance at 405 monitored up to 2 hr with 1 minute interval time.

14. Clotting Time Experiments with Different Fusion Constructs:

In order to see the effect on thrombin-induced clot formation in presence of different chimeric constructs, a standard curve with different thrombin concentrations was made from which a 20 second clotting time with 6.6 IU of thrombin was obtained. Same amount of thrombin was then incubated with increasing concentrations of constructs to measure the concentrations where clotting time became double compared to the controls (Lougheed, Bowman et al. 1995).

15. Protein C Activation by Different Fusion/Chimeric Constructs:

Different fusion constructs of tissue plasminogen activator, staphylokinase and streptokinase were subjected for the thrombin mediated protein C activation assays in a dose-dependent manner. In this assay different amount of protein (in the nM range) were incubated with 10 nM of thrombin, in presence of 50 mM Tris-Cl, 5 mM $CaCl_2$, and 0.05% BSA at 37° C. for 20 min. After this time 0.504 of protein C was added into the wells and incubated for 20 minutes at 25° C. After that 0.5 mM hirudin was added to inhibit thrombin and incubation continued for 5 minutes at 25° C. and then chromogenic substrate was added at 0.5 mM final concentration, and the release of colored pNA was monitored at 405 nm with respect to time as detailed earlier (Eisenberg, Miletich et al. 1988; Ewald and Eisenberg 1995; Lougheed, Bowman et al. 1995; Meininger, Hunter et al. 1995; Dahlback and Villoutreix 2005).

EXAMPLES

The following examples are given by way of illustration of the present invention and therefore should not be construed to limit the scope of the present invention.

Example 1

Preparation of Various Fusion Genes Between Streptokinase and EGF 4,5,6 Domains (i) Hybrid Gene Constructs for Expression of EGF Domains Fused in Frame Upstream to the SK Encoding Open-Reading-Frame (ORF):

A double stranded (ds) DNA block, encoding EGF-SK protein fusion, in which the EGF 4,5,6 encoding sequences were fused in-frame at the N-terminal encoding side of the SK ORF, was constructed using primers N_EGF_SKFp 1 and N_EGF_SK Rp 2 (see table 1 for sequence of primers). The design and construction of a bacterial expression vector pET 23-d_SK has been described by Nihalani et al., 1998. It involved the cloning of the SK gene from *Streptococcus equisimilis* H46A in pBR 322 (Pratap et al., 1996), followed by sub-cloning into pET-23d, an expression vector containing a highly efficient ribosome binding site from the phage T7 major capsid protein (Studier and Moffatt, 1986), and further modification of the 5' end of the gene to minimize the propensity for formation of secondary structure. Streptokinase expressed from pET-23-d_SK construct is Met-SK. Further details are described in U.S. Pat. No. 7,163,817. This construct was used as a template for amplification of the SK gene (DNA SEQ ID 1, and corresponding protein SEQ ID 112).

A double-stranded polynucleotide block corresponding to EGF 4,5,6 domains (SEQ ID 2, and corresponding protein SEQ ID 111) was selectively amplified using as template a synthetic gene (DNA polynucleotide) corresponding to sequence ID 2 which was prepared by custom DNA synthesis and validated by automated DNA sequencing to sequence ID 2, after cloning in pET 23-d (Novagen) vector. Primer N_EGF_SK Fp1 also contained (see table 1 for detailed description of primers) aXho I restriction site at its 5' end so that the resultant gene block obtained after PCR could be docked into a yeast expression plasmid. Primer N_EGF_SK Rp 2 contained sequence at the 5' end (besides nucleotides hybridizing with the end of the $6^{th}$ domain of EGF 4,5,6) and also additional nucleotides which anneal with the 5 side of SK gene ORF. PCR cycle conditions were as follow: Hot start, complete denaturation at 95° C. for 5 minutes; denaturation at 95° C. for 45 seconds, followed by annealing at 45° C. for 45 seconds, extension at 72° C. for 1 minute, with a total no. of 28 cycles, and a final extension of 72° C. for 10 minutes for the completion of the amplification of any incomplete PCR products. For the amplification of the SK gene block, the primerN_EGF_SK Fp 3 (upstream) and primer N_EGF_SK_Rp 4 (downstream primer) (see table 1 for detailed description of primers) were used. PCR conditions were as follows: PCR conditions: Hot start, complete denaturation at 95° C. for 5 minutes, denaturation at 95° C. for 45 seconds, annealing at 45° C. for 45 seconds, extension at 72° C. for 3 minute, with a total no of 28 cycles and a final extension of 72° C. for 10 minutes for the complete amplification of any incomplete PCR products. Both PCR products were gel purified from agarose gels by gel extraction purification kit (Qiagen). These two purified PCR products were subjected to Splice Overlap Extension (SOE) PCR (see 'General Methods used in Examples' section, above, for details) in order to construct a contiguous EGF 4,5,6-SK hybrid gene construct in which EGF 4,5,6 encoding sequences were fused in-frame with SK gene encoding sequence ending with a terminator codon. This gene block was isolated front agarose gel in purified form and digested with Xho I and Not I restriction enzymes (R.E. enzymes) and ligated into similarly cut pET 23-d plasmid vector (refer to FIG. 1A and FIG. 2 A), which was then transformed into *E. coli* XL1B (rec A⁻ and end A⁻) cells in which the polypeptide is not expressed although plasmid DNA will be propagated. This plasmid was subjected to Sanger's di-deoxy method of sequencing in order to validate the DNA sequences of the EGF & SK components fused correctly (SEQ ID NO. 4, and corresponding protein SEQ ID 113). In this construct, Xho I and NotI digested cassette was isolated from agarose gel and 'docked' into pPIC-9K. In this resultant construct, the upstream EGF 4,5,6 sequences are placed in-frame with the α-secretory signal sequences as well as the Kex2 processing site, such that the hybrid gene construct, EG-4,5,6-SK is expressed in *Pichia pastoris*(strain GS115) from the alcohol oxidase promoter located in the vector after its integration into the host genome (Norden, Agemark et al. 2011). The hybrid polypeptide expressed from this expression vector is also efficiently transported across the membrane (see Examples below) and can be isolated there from in pure form.

(ii) Construction of SK-EFG4,5,6 Encoding Gene Construct, where EGF4,5,6 Encoding Domains Were Fused in Frame at the Downstream/C-Terminal Encoding End of SK Encoding Gene:

By using the set of SK_EGF Fp1 (upstream) and SK_EGF Rp2 (downstream) primers (see table 1 for primer sequence), nucleotide sequences corresponding to SK (DNA SEQ ID 1, and corresponding protein SEQ ID 114) were amplified using pET23-d-SK plasmid as template (see 'General Methods used in Examples'). Primer SK_EGF Fp1 contains a Xho I restriction site at its 5' end, whereas SK_EGF Rp2, at its 5' end, contains SK sequence up to 1149 bp followed by a triple glycine (Gly-Gly-Gly) encoding segment, as well as a transglutaminase recognition encoding sequence, finally ending with sequence overlapping with the 5' end encoding for the $4^{th}$ domain of EGF4,5,6. The resultant gene block contains the same Xho I restriction site at its 5' end, and downstream (3'-end) contains overlapping nucleotide sequence for the $4^{th}$ domain. In a second PCR, SK_EGF Fp3 and SK_EGF Rp4 (see table 1 for primer sequence) set of primers were used for the amplification of EGF4,5,6 domains from pET23-d_EGF4,5,6 (containing the Synthetic custom-made gene for EGF4,5,6) as template. Primer SK_EGF_Fp3 contained downstream sequence of SK, up to 1149 bp, followed by a triple glycine codon segment, and transglutaminase recognition site encoding sequence towards its 5' end; the other primer, namely SK_EGF_Rp4 contained partial sequence of the end of the $6^{th}$ domain of EGF4,5,6 and a Not I restriction site at its 5' end. After PCR, the resultant gene block 2, obtained by use of this set of primers, contains at its 5' end (upstream $1149^{th}$ bp of SK, followed by a triple glycine-encoding and transglutaminase recognition encoding sequences, and on the other hand, at its 3' end it contains a Not I restriction site to facilitate cloning into the pET-23-d vector. PCR conditions were as follows: Complete denaturation at 95° C. for 5 min, then 28 cycles of: 95° C. for 45 seconds, annealing of primers at 45° C. for 45 seconds, and 72° C. for 1 min; finally an extension at 72° for 10 min to complete any partial length PCR products.

Both the PCR blocks (PCR block of SK, and PCR block encoding EGF4,5,6 with partially overlapping sequences) were purified from gel by using QIagen gel extraction kit. These purified PCR products were subjected to splice overlap extension PCR in order to construct contiguous SK_GGG_transglutaminase_EGF4,5,6 hybrid gene construct, and finally amplified with the help of SK_EGF Fp1 and SK_EGF Rp4 (see table 1 for primer sequence) set of 'end' primers. Final PCR product was then digested with Xho I and Not I restriction enzymes (refer to FIG. 1B and FIG. 2B). After purification from gel, final digested and purified PCR block was ligated into pET23-d (previously similarly digested with Xho I and Not I, and gel purified). The resultant plasmid was termed pET23-d_SK_GGG_TG_EGF, which was propagated in *E. coli* XL1B (re-cA⁻, end A⁻) cells. This plasmid was subjected to Sanger's di-deoxy chain termination method and the complete cloned insert sequence was validated (DNA SEQ ID 6, and corresponding protein SEQ ID 114). From this plasmid construct, by using Xho1 and Not1 enzymes, the hybrid gene construct was isolated and ligated into pPIC-9K where the upstream XhoI site helped the SK-GGG-TG-EG4,5,6 block's in-frame docking into the α-secretory signal sequence upstream of the hybrid gene in the expression plasmid. This hybrid gene-construct was expressed in *Pichia pastoris* (GS 115) under the control of the alcohol oxidase promoter, after its integration into the host genome and selection of plasminogen activator-positive clones by functional screening.

Figure 1F:
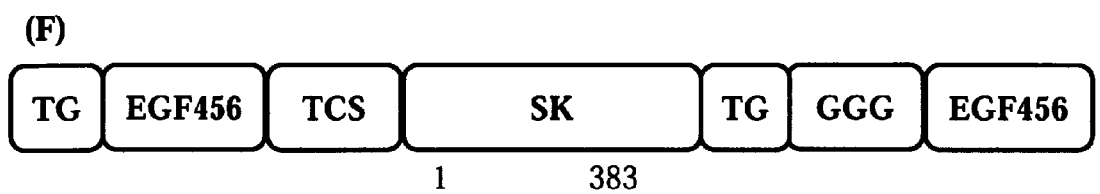
FIG. 1F is a schematic design F represents the simultaneous fusion of EGF 4,5,6 at N & C-termini of SK, where a thrombin recognition sequence is present at the junction of EGF and SK and a transglutaminase recognition sequence is present at the initial part (N-terminal end) of EGF.
Figure 1G:
FIG. 1G is a schematic design G represents the fusion of EGF domains at the junction of α and δ domains of SK.

(iii) Construction of DNA Hybrid Gene for the in Frame Insertion of the EGF 4,5,6 Domains into the Streptokinase Encoding Gene:

Construction of 'inter-domain SK'-EGF constructs in which the sequences for EGF4,5,6 were interspersed within the sequences of SK in a translationally in-frame manner, to give rise to hybrid gene construct/s, were also designed, and then made, with the use of suitable primes (see table no 1 for sequence of primers). The EGF sequence was inserted into the region of the SK gene encoding the inter-domain flexible segments (Wang et al., 1998; Yadav & Sahni, 2009), that is, either between the α and β domains, on the one hand, or between the β and γ domains, on the other. For this purpose, amplification of the DNA encoding the α-domain of SK was carried out first, employing the primer set IDα.Fp1 and IDα Rp 2 (for sequence details, please refer to table 1). Primer IDα.Fp1 contains an Xho I restriction site at its 5' end; on the other hand primer IDα Rp 2 contains an overlapping sequence for the $4^{th}$ domain of EGF at its 5' end. For this reaction, the following PCR conditions were used: Hot start, complete denaturation at 95° C. for 5 minutes, followed by 28 cycles of: denaturation at 95° C. for 45 seconds, annealing at 45° C. for 45 seconds, extension at 72° C. for 1.5 minute, and finally an 'extension segment' of 72° C. for 10 minutes to allow any incomplete PCR products to be completed. A DNA block encoding EGF 4,5,6 was also amplified separately using the primers set ID EGF Fp3 and IDEGF Rp4 (see table 1 for the sequence of these primers). Using this primer set a DNA block encoding EGF 4,5,6 sequence was obtained in which upstream sequence towards the 5' end partially overlapped with the downstream sequences of α-domain of SK; likewise the 3' end of this block contained sequence which were overlapping with the upstream sequence of the SK β-domain. A third PCR block encoding both γ and γ domains of SK was obtained by PCR using the primer set ID β Fp5 and ID γ Rp6 (see table 1 for sequence of these primers). For this reaction the following PCR conditions were used: Hot start, complete denaturation at 95° C. for 5 minutes, followed by denaturation at 95° C. for 45 seconds, annealing at 45° C. for 45 seconds, extension at 72° C. for 1.5 minute, with a total of 28 cycles, and a final extension of 72° C. for 10 minutes for the complete amplification of any incomplete PCR products. ID β Fp5 primer was designed such that 5' end of this was homologous with downstream sequences of the $6^{th}$ domain of EGF, whereas downstream primer ID γRp6 contained a terminator codon followed by a NotI restriction site. All three gene-blocks were purified from agarose gels with the help of gel purification kit (Qiagen) and subjected to a one-pot splice overlap extension reaction, in order to obtain a single contiguous gene product in which the order of gene segments was to be as follows: SKα-EGF 4,5,6-SKβ-SKγ. All three segments were added in 1:1:1 molar ratio in a simple PCR reaction where initial 10 cycles were done without the primers and next 18 cycles were done by adding 0.6 μM final concentration each of IDαFp1 and IDγRp6, in order to further amplify the three-fragment SOE intermediate. For this reaction, the following PCR conditions were used: Hot start, complete denaturation at 95° C. for 5 minutes, followed by (in each cycle) denaturation at 95° C. for 45 seconds, annealing at 45° C. for 45 seconds, extension at 72° C. for 3 minutes, and a final extension of 72° C. for 10 minutes for the completion of any incomplete PCR products. Final PCR product was gel purified and digested with Xho I and Not I restriction enzymes (refer to FIG. 1G and FIG. 2D). This hybrid gene construct was then ligated into pET 23-d vector and transformed into *E. coli* XL1B (rec A⁻ and end A⁻) competent cells, wherein the DNA could propagate without protein expression (since the host did not provide the required the phage-encoded RNA polymerase), which was subjected to Sanger's automated sequencing with the so-called di-deoxy chain termination method (DNA SEQ ID 3, and corresponding protein SEQ ID 116). The results completely validated the hybrid gene construct. After this, the hybrid gene cassette was isolated from the pET-23-d inter-domain SK_EGF plasmid by digesting it with Xho I and Not I enzymes. This cassette was then ligated into pPIC-9K upstream of, and in-frame with, the α-secretory signal sequence, and transformed into *Pichia pastoris* (GS115), cloned and selected as before by functional screening for plasminogen activation, the expression being under the influence of the alcohol oxidase promoter of the vector after integration in host genome after methanol induction as detailed in the Methods section.

(iv) Construction of Hybrid SK-EGF Gene in which the SK Component is Flanked on Both Sides by the EGF 4,5,6 Encoding Domains:

Another construct in which the SK encoding sequences were flanked on both sides by in-frame fused EGF 4,5,6 domains, was also constructed by taking pET23-d N_EGF_SK plasmid construct (see above, sub-sections i and ii), and subjecting it to Xho I and AflII (unique sites in the pET23-d N_EGF_SK construct) digestion, the same treatment also being given to pET-23-d-SK_EGF construct, and both digestion products resolved on agarose gels. The Xho I and Afl-II segment obtained from N_EGF_SK construct was ligated with the larger fragment of SK_EGF digestion, and the result of this gave the N_EGF_SK_EGF (DNA SEQ ID 7, and corresponding protein SEQ ID 115) in the pET23-d vector (refer to FIG. 1.C and FIG. 2.C). The expression cassette from this plasmid was isolated by Xho I and Not I digestions (this construct being first validated by DNA sequencing, as before) and ligated into pPIC-9K in-frame of the α-secretory signal sequence upstream of the EGF-SK-EGF hybrid cassette and expressed in pichia pastoris under the control of the alcohol oxidase promoter after integration in host genome, as before, after functional screening (see below).

(v) Construction of N_EGF_SK, SK_EGF and N_EGF_SK_EGF Encoding Gene Segments Containing Sequences Encoding Oxidation Resistant Polypeptide Segments Corresponding to EGF 4,5,6:

In N_EGF_SK, SK_EGF and N_EGF_SK_EGF polypeptides, the methionine residue present at the $41^{st}$ amino acid residue of EGF 4,5,6 domains, or the $434^{th}$ amino acid residue of SK_EGF, and $41^{st}$ and $434^{th}$ amino acid position N_EGF_SK_EGF, respectively, as part of the EGF4,5,6 domains are known for their oxidation proneness, which hampers the antithrombin activity especially the protein C activation function of these domains. Hence, keeping this in mind, in our design of the various SK-EGF fusion/gene fusion segments, we replaced this methionine with valine/alanine/glutamine amino acid residues at the gene level. This goal was achieved by the use of high fidelity enzyme pfu turbo DNA polymerase (Stratagene), as before, and introduction of site specific mutations in different templates using appropriate primers (Wang and Malcolm 1999). In order to make these constructs, three sets of primers were designed which allow the incorporation of either valine, alanine, or glutamine separately in different constructs at the position of the original Met residue in the EGF 4,5,6 domain/segment of the gene construct. The primers sets were named as follows:

i. M rep V Fp, and M rep V Rp (refer: table 1 for sequence of primer)
ii. M rep A Fp, and M rep A Rp (refer: table 1 for sequence of primer)
iii. M rep Q Fp, and M rep Q Rp (refer: table 1 for sequence of primer)

In the next step, pET 23-d_N_EGF_SK and pET 23-d_SK_EGF plasmids were used as template with above mentioned sets of primers. For each set of primers PCR cycle schemes were as follows: complete denaturation at 95° C., followed by denaturation at 95° C. for 45 seconds, annealing at 45° C. for 45 second, extension at 68° C. for 7 minutes for 28 cycles and extension for a further 10 min at 72° C. Final PCR blocks obtained by this reaction were digested with Dpn I restriction enzyme which cleaves methylated DNA and enhances the probability of getting positive clones after the transformation. This PCR product was transformed in to E. coli XL1Blue cells and plated on ampicillin containing LB agar plates and incubated at 37° C. for 16-18 h. A few clones were randomly picked and raised into 7-10 ml cultures in amipicillin-containing LB media. Plasmids were isolated and sequenced, to validate the presence of the desired mutation/s. By adopting this procedure, methionine was replaced with valine, alanine or glutamine amino acids at the gene level in both the constructs. These constructs were used to make valine, alanine and glutamine mutations in N_EGF_SK_EGF gene by standard sub-cloning procedures. Finally, these mutants were transferred to pPIC-9K and their expression was checked in GS115 strain of Pichia pastoris (see 'general methods used in examples').

(vi) Construction of ΔSK_EGF Construct with N-Terminal of SK with Five Amino Acid Deletion:

In this construct, the final objective involved was the removal of five amino acid at the N-terminal region of SK. These 5 amino acids-encoding nucleotides were removed with the help of PCR primers ΔSK_EGF Fp 1 and ΔSK_EGF Rp 2 (refer to table 1 for sequence of these primers) using pET 23-d_SK_GGG_TG_EGF (oxidation resistant, where met $41^{st}$ in EGF 4,5,6 segment was replaced by valine; see above) as a template. The primer Δ SK_EGF Fp1 contains a Xho I restriction site and overlapping sequence of SK started from $16^{th}$ base pair at its 5' end. ΔSK_EGF Rp 2 contains sequence of $6^{th}$ domain of EGF 4,5,6 and Not I site at its 5' end. PCR cycles were used for this reaction as follows: complete denaturation at 95° C. for 5 minutes, next 28 cycles: denaturation 95° C. for 45 seconds, annealing at 55° C. for 45 seconds, extension at 72° C. for 3 minutes and final extension done at 72° C. for 10 minutes for complete amplification of incomplete PCR products. Final PCR product was gel eluted and digested with the Xho I and Not I enzymes and ligated into pET 23-d vector, and sequenced for validation of complete and correct open reading frame. Finally ΔSK_EGF (refer to FIG. 1D) cassette was ligated in pPIC-9K and checked for its expression by standardized procedures as described earlier.

(vii) In-Frame Introduction of DNA Sequences Encoding for a Thrombin Cleavable Site at the Junction of Oxidation Resistant N_EGF_SK and N_EGF_SK_EGF Encoding Gene Blocks:

From the expression of N_EGF_SK, purification and kinetic analysis of plasminogen activation, which established a delayed nature of plasminogen activation, it was apparent that unlike native/unmodified SK, this construct could not activate human plasminogen directly, but required the presence of pre-formed plasmin. This automatically confers an advantage of clot-specific activation in such a construct since the clot in vivo is plasmin rich whereas the plasmin is rapidly inactivated in the general circulation. Similarly, fibrin clots are also thrombin-rich; hence, we mutated suitable sites in the construct to make it thrombin activatable as well. In order to do this, we mutated the inter-domain joining region of EGF and SK by a thrombin cleavable site, the result of which should give a thrombin cleavable activation switch in plasminogen activation. This can be monitored in one-stage assay by adding incrementally small amounts of thrombin and observing (as in the case of a similar plasmin-enrichment experiment described before) a progressive decrease of lag in plasminogen activation in N-terminal EGF4,5,6 fused SK construct. Thrombin cleavable sequence of factor XI was introduced at the junction of EGF and SK gene construct. This was achieved by the overlap extension PCR, where junction primers containing overlapping sequence and thrombin cleavable amino acid encoding nucleotides were used. In first PCR reaction, primers N_EGF_TCS Fp 1 and N_EGF_TCS Rp 2 (refer table 1 for the sequence of these primers) were used for the amplification of EGF 4,5,6 domains. The primer N_EGF_TCS Fp 1 contains a Xho I restriction site and sequence of $4^{th}$ domain of EGF at its 5' end; on the other hand N_EGF_TCS Rp2 contains $6^{th}$ domain sequence of EGF followed by thrombin cleavable site encoding sequence followed by upstream part of SK. PCR conditions were as follows: denaturation at 95° C. for 5 minutes, in next 28 cycles, denaturation at 95° C. for 45 seconds, annealing at 50° C. for 45 seconds, extension 72° C. for 1 minute and final extension done at 72° C. for 10 minutes in order to complete the incomplete PCR fragment. PCR block obtained by this reaction contains a Xho I restriction site at its 5' end and thrombin cleavable encoding nucleotide sequence and overlapping part of SK at 3' end. In next PCR reaction TCS_SK Fp 3 and SK Rp 4 (refer table 1 for the sequence of these primers) were used, where upstream primer (TCS_SK Fp 3) contains sequence of $6^{th}$ domain, overlapping part of EGF4,5,6, thrombin cleavable encoding nucleotide sequence, and SK encoding nucleotide sequence in 5' to 3' order; on the other side, SK Rp 4 contains a Not I cleavable site at its 5' end. PCR conditions were as follows: denaturation at 95° C. for 5 minutes, in next 28 cycles, denaturation at 95° C. for 45 seconds, annealing at 50° C. for 45 seconds, extension 72° C. for 1 minute and final extension at 72° C. for 10 minutes in order to complete the synthesis of any partial-length daughter fragments. The obtained PCR block should contain overlap sequence of $6^{th}$ domain and thrombin cleavable encoding nucleotides upstream, whereas downstream it should contain a Not I restriction site. Both PCR blocks were gel purified and mixed in 1:1 molar ratio in a single pot reaction, and amplified by the end-primers TCS Fp1 and SK Rp6, which gave the required N_EGF_TCS_SK PCR block (refer to FIG. 1.E) (TCS: thrombin cleavable sequence), which was gel purified and digested with Xho I and Not I enzymes, and finally ligated into similarly digested pET23-d by standard procedures. This construct sequence, after sub-cloning in E. coli XL Blue, was validated with respect to it open reading frame. This established that a Factor XI thrombin cleavable site with the following amino acid sequence at the junction of EGF4,5,6 and SK was created in the gene: Ile-Lys-Pro-Arg-Ile-Val-Gly. In this sequence, the thrombin specificity results in cleavage at the junction of Arginine and Isoleucine such that after thrombin's action, one amino acid was removed from the N-terminal end of SK and also, the second amino acid would be changed to valine (in native SK, the N-terminal residues are Ile-Ala-Gly-). After this, the N_EGF_TCS_SK cassette was ligated into pPIC-9K and its expression was carried out in Pichia pastoris. The thrombin cleavage was indeed found to be true in case of the purified construct, after treatment with thrombin, and confirmed by N-terminal protein sequencing.

Figure 1H:
FIG. 1H is a schematic design H represents the fusion of EGF domains as indicated at the junction of β and γ domains of SK.
Figure 1L:
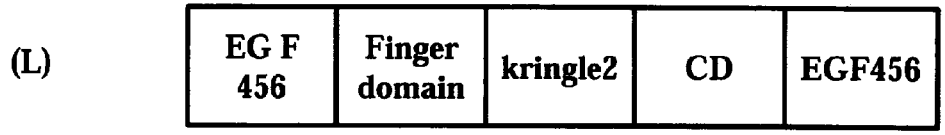
FIG. 1L is a schematic design L represents the EGF 4,5,6 domains' fusion at both N & C-termini of tPA (tissue plasminogen activator), where intrinsic egf of tPA is deleted.
Figure 1M:
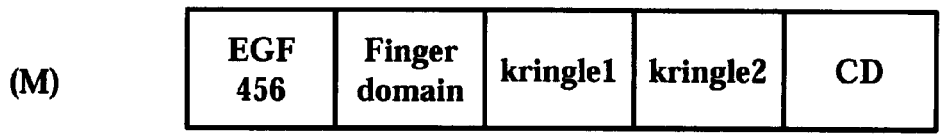
FIG. 1M is a schematic design M represents the EGF 4,5,6 fusion at the N-terminal end of tPA, where intrinsic egf of tPA is deleted.
Figure 1N:
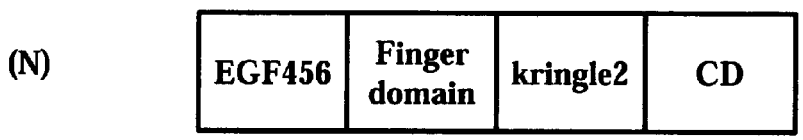
FIG. 1N is a schematic design N represents the EGF 4,5,6 fusion at the N-terminal end of tPA, where intrinsic egf and kringle 1 of tPA are deleted.
Figure 1O:
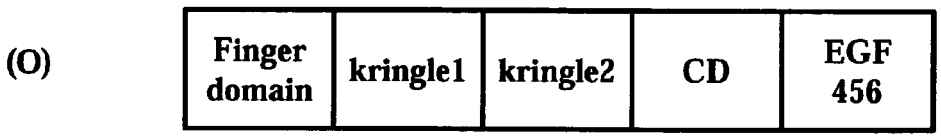
FIG. 1O is a schematic design O represents the EGF fusion at the C-terminal end of tPA, where intrinsic egf of tPA is deleted.

(viii) EGF4,5,6 Domains Fused Translationally in Frame at the Junction of the β and γ Domain of SK:

For this purpose, amplification of a β-domain was carried out employing primer ID αβ Fp1 & ID αβ Rp2 (refer table 1 for the sequence of these primers) by using pET23-d_SK as template. Primer ID αβ Fp1 contains Xho I restriction site at its 5' end, on the other hand ID αβ Rp2 contains downstream sequence of β domain of SK as well as partly overlapping sequence of $4^{th}$ domain of EGF4,5,6. PCR block obtained by these set of primer contain Xho I restriction site at upstream sequences, and downstream contain terminal sequences of β-domain and overlapping sequence of $4^{th}$ domain of EGF. In next step per block 2, which encodes for EGF4,5,6, were isolated by using IDE4Fp3 and IDE6Rp4 (refer table 1 for the sequence of these primers) set of primers. Primer IDE4Fp3 contains downstream sequence of β-domain of SK at its 5' end and IDE6Rp4 contains γ domain upstream overlapping sequence at its 5' end. PCR block 2 obtained by these set of primer contains overlapping sequence of downstream β-domain at 5' end and other end contains upstream sequence of γ domain. PCR conditions for this amplification as follows. Complete denaturation at 95° C. for 5 min. next 27 cycles 95° C.-45 second, annealing at 45° C. for 45 seconds, extension at 72° C. for 1 minute and final extension done 72° C.-10 minutes. In next step γ domain of SK was isolated by using IDγFp5 & ID γ Rp6 (refer table 1 for the sequence of these primers) set of primer. Primer ID γ Fp5 designed in such a way, where 5' end of IDγFp5' contains homologous downstream sequence of $6^{th}$ domain of EGF4,5,6, where as IDγRp6 contains termination codon followed by Not I restriction site. The following per scheme used for the amplification of block 3; Hot start for 5 minutes at 95° C., denaturation at 95° C. for 45 seconds, annealing at 47° C. for 45 seconds and extension done at 72° for 1.5 minutes. A total no of 28 cycles carried out, and a final extension of 10 minutes at 72° C. for completion of any incomplete amplified products. All the obtained PCR were gel purified by gel extraction kit (Qiagen) and quantitated by $A_{260}$ spectrophotometrically. In final pct reaction, all the three gene blocks subjected in a single pot for splice overlap extension reaction, in order to get single contiguous gene block in which order of resultant construct as follow: SKα-SKβ-EGF4,5,6-SKγ, all the three per mixed in 1:1:1 molar ratio in a polymerase chain reaction, where initial 10 cycles carried out without any primers and next 18 cycles done by adding 0.6 µM final concentration of IDαβFp1 & IDγRp6 primers, in order to amplify the three fragment intermediate complete gene block. PCR conditions were as follows: Hot start at 95° C. for 5 minutes, denaturation at 95° C. for 45 second, annealing at 45° C. for 45 seconds, and extension at 72° C. for 3 minutes, a total no. of 28 cycles were carried out where initial 10 cycle without primers and final amplification done at 72° for 10 minutes. Finally obtained gene block contains Xho I site at its 5' end and Not I site at it 3' end. This gene block digested with Xho I and Not I enzymes and clone to pET 23-d and pPIC 9K. Its expression, purification and characterization checked in pichia pastoris This gene block contain EGF 4,5,6 domains between the β and γ domain of SK (DNA SEQ ID 5, and corresponding protein SEQ ID 129; see FIG. 1H, and FIG. 2E).

(ix) Incorporation of a Transglutaminase Recognition Sequence at the N-Terminal Encoding End of N_EGF_TCS_SK Hybrid-Gene Block (Containing Methionine Oxidation Resistant Mutations):

For incorporation of a transglutaminase recognition sequence at the beginning or before the $4^{th}$ domain of EGF 4,5,6 domains in the EGF-SK constructs, primers TG_N_EGF_Fp 1 and Afl II Rp 2 (refer table 1 for detailed sequence of primer) were designed where TG Fp1 contains a Xho I restriction site, and nucleotide sequence encoding for the blood factor XIII transglutaminase recognition amino acid sequence at its upstream region, while primer Afl II Rp 2 contains nucleotide sequence of that region which contains Afl II restriction digestion site (165-$170^{th}$ nucleotide of SK contains Afl II restriction site which is situated at the centre of this primer). From these primers, we obtained by PCR a gene block that contains a Xho I restriction site, transglutaminase recognition encoding nucleotides, and sequence of $4^{th}$ domain of EGF4,5,6 with the downstream part of the block containing an Afl II restriction site. This gene block (oxidation resistant and thrombin cleavable sequence containing) was extracted from gel. Plasmids pET 23-d N_EGF_TCS_SK and pET 23-d N_EGF_TCS_SK_EGF were digested with Xho I and Afl II. Result of this gave the Xho I and Afl II gene block and larger and smaller parts from both the plasmid constructs. The digested gene block was ligated with the larger part of the constructs, and transformed into E. coli XL Blue to obtain the TG_N_EGF_TCS_SK and TG_N_EGF_TCS_SK_EGF (refer to FIG. 1F) containing plasmids. These were sequenced and validated for the correct open reading frames i.e. presence of transglutaminase encoding sequence in the context of the EGF-SK constructs described earlier. Both cassette were then ligated in Pichia pastoris and checked for their expression of these constructs (please refer to 'methods used in examples').

TABLE 1

Primers used for the various EGF 4, 5, 6 and streptokinase gene fusion constructs preparations.

| S. No. | SEQ ID Nos. | Name of primer | Primers Sequence |
|---|---|---|---|
| 1 | SEQ ID 21 | N_EGF_SK Fp 1 | 5' GAATATCTCGAGAAAAGAGTGGACCCGTGCTTCA-GAGCCA 3' |
| 2 | SEQ ID 22 | N_EGF_SK Rp 2 | 5' GTCTAGCAGCCACTCAGGTCCAGCAATGCCGGAGTCA CAGTCGGTGCC 3' |
| 3 | SEQ ID 23 | N_EGF_SK Fp3 | 5' GGCACCGACTGTGACTCCGGCATTGCTGGACCTG AGTGGCTGCTAGAC 3' |
| 4 | SEQ ID 24 | N_EGF_SK Rp 4 | 5' CCTATACGCGGCCGCTTATTTGTCGTTAGGGTTAT-CAGGTAT 3' |
| 5 | SEQ ID 25 | SK_EGF Fp 1 | 5' GCATATCTCGAGAAAA-GAATTGCTGGACCTGAGTGGCTGCTA 3' |
| 6 | SEQ ID 26 | SK_EGF Rp 2 | 5' GAAGCACGGGTCCACCACAATTTGTTGAGCTTGTCCG CCACCGGCTAAATGATAGCTAGC 3' |
| 7 | SEQ ID 27 | SK_EGF Fp 3 | 5' GCTAGCTATCATTTAGCCGGTGGCGGACAAGCTCAAC AAATTGTGGTGGACCCGTGCTTC 3' |
| 8 | SEQ ID 28 | SK_EGF Rp 4 | 5' CCATATCGCGGCCGCGCCGGAGTCA-CAGTCGGTGCCAAT 3' |
| 9 | SEQ ID 29 | ID α Fp 1 | 5' GGATATCTCGAGAAAA-GAATTGCTGGACCTGAGTGGCTGCTA '3 |
| 10 | SEQ ID 30 | ID α Rp 2 | 5' AAGCACGGGTCCACGGGCTCA-GATTTCGCTTGGTTTTGTATT 3' |
| 11 | SEQ ID 31 | ID EGF Fp 3 | 5' AATACAAAACCAAGCGAAATCTGAGCCCGTGGACCCG TGCTT 3' |
| 12 | SEQ ID 32 | ID EGF Rp 4 | 5' TACAGTATATTCCACATCAACGCCGGAGTCACAGTCA GTGCCAA 3' |
| 13 | SEQ ID 33 | ID β Fp 5 | 5' ATTGGCACTGACTGTGACTCCGGCGTTGATGTGGAAT ATACTGT 3' |
| 14 | SEQ ID 34 | ID γ Rp 6 | 5' AAATATCGCGGCCGCTTTGTCGTTAGGGTTATCAGG-TATA 3' |
| 15 | SEQ ID 35 | M repV Fp | 5' CACAGGTGTCAGGTGTTTTGCAATCAGACTG 3' |
| 16 | SEQ ID 36 | M rep V Rp | 5' CAGTCTGATTGCAAAACACCTGACACCTGTG 3' |
| 17 | SEQ ID 37 | M rep A Fp | 5' CCGCACAGGTGCCAGGCTTTTTGCAACCAGACTG CTTGTCCA 3' |
| 18 | SEQ ID 38 | M rep A Rp | 5' TGGACAAG-CAGTCTGGTTGCAAAAAGCCTGGCACCTGTGCGG 3' |
| 19 | SEQ ID 39 | M rep Q Fp | 5' CACAGGTGTCAGCAATTTTGCAACCAGA-CAGCCTGT 3' |
| 20 | SEQ ID 40 | M rep Q Rp | 5' ACAGGCTGTCTGGTTGCAAAATTGCTGA-CACCTGTG 3' |
| 21 | SEQ ID 41 | ΔSK_EGF Fp 1 | 5' GCATAACTCGAGAAAAGAGAGGCTTGGCTGCTA-GACCGTCCA 3' |
| 22 | SEQ ID 42 | ΔSK_EGF Rp 2 | 5' CCATATCGCGGCCGCGCCGGAGTCA-CAGTCGGTGCCAAT 3' |
| 23 | SEQ ID 43 | N_EGF_TCS Fp 1 | 5' GCCTAACTCGAGAAAAGA-GAGCCCGTGGACCCGTGCTTCAGA 3' |
| 24 | SEQ ID 44 | N_EGF_TCS_Rp2 | 5' GACAATTCTAGGTTTAATGCCAGAGTCA-CAGTCGGTGCCAAT 3' |
| 25 | SEQ ID 45 | TCS_SK Fp 3 | 5' GGCATTAAACCTA-GAATTGTCGGACCTGAGTGGCTGCTAGA 3' |

TABLE 1 -continued

Primers used for the various EGF 4, 5, 6 and streptokinase gene fusion constructs preparations.

| S. No. | SEQ ID Nos. | Name of primer | Primers Sequence |
|---|---|---|---|
| 26 | SEQ ID 46 | SK Rp 4 | 5' CCTATACGCGGCCGCTTATTTGTCGTTAGGGTTAT-CAGGTAT 3' |
| 27 | SEQ ID 47 | ID αβ Fp1 | 5' GGATATCTCGAGAAAA-GAATTGCTGGACCTGAGTGGCTGCTA '3 |
| 28 | SEQ ID 48 | ID αβ Rp2 | 5' CTCTGAAGCACGGGTCCACGGGCTCCAAGTGACTGCG ATCAAA 3' |
| 29 | SEQ ID 49 | IDE4Fp3 | 5' TTTGATCGCAGTCACTTGGAGCCCGTGGACCCGTGCTT CAGAG 3' |
| 30 | SEQ ID 50 | IDE6Rp4 | 5' AACGTATTTGATGGTGAACAGTTTGCCGGAGTCA CAGTCG 3' |
| 31 | SEQ ID 51 | IDγFp5 | 5' CGACTGTGACTCCGGCAAACTGTTCACCATCAAATAC GTT 3' |
| 32 | SEQ ID 52 | ID γ Rp6 | 5' AAATATCGCGGCCGCTTTGTCGTTAGGGTTATCAGG-TATA 3' |
| 33 | SEQ ID 53 | TG_N_EGF_Fp 1 | 5' GGTATCCTCGAGAAAAGAGTTCAAGCGCAACAGA TCGTGGAACCCGTGGACCCGTGCTTCAGA 3' |
| 34 | SEQ ID 54 | Afl-II Rp2 | 5' GGTTTTGATTTTGGACTTAAGCCTTGCTCTGTCT 3' |

Example 2

Expression and Functional Characterization of Various EGF-SK Hybrid Polypeptides The different gene blocks described in Example 1, e.g. N_EGF-SK, SK-EGF and N_EGF_SK_EGF, and another class of inter-domain fusion constructs, like interdomain EGF_α β SK, interdomain EGF_β γSK, truncated ΔSK_EGF, and oxidation resistant forms of N_EGF_SK, SK_EGF and N_EGF_SK_EGF, with transglutaminase and thrombin cleavage sites etc incorporated, and all cloned in the expression vector pPIC-9K, and also validated with respect to express functionally active hybrid gene products expected from the sequence of the respective gene-fusions, were then isolated from relatively larger-volume cultures prior to their further characterization. As described in Example 1, *Pichia* clones were routinely tested initially by the casein overlay method for plasminogen activation capability, and several (10-20 each) positives were then grown on BMGY and BMMY media (BMGY=1% yeast extract, 2% peptone, 1× glycerol, 1× yeast nitrogen base without amino acids and 100 mM of potassium phosphate buffer pH 5.5, and BMMY=1% yeast extract, 2% peptone, 1× Methanol, 1× yeast nitrogen base without amino acids and 100 mM of potassium phosphate buffer, pH 5.5) and then inducing with methanol as described earlier under 'Methods', and the cell-free supernatants were used for casein overlay assays (for re-confirmation) as well as plasminogen activation (spectrophotometric) assays in presence of peptide chromogenic substrate. Those found to be relatively high producers were then grown on one-liter level and proteins purified by hydrophobic interaction (e.g. phenyl-agarose) and ion-exchange (DEAE-agarose) chromatographies in tandem (details are described under the section 'general methods used in examples'). The hybrid SK-EGF polypeptides obtained by these two methods of purification were generally 90-95% pure by SDS-PAGE. All the purified constructs were tested for plasminogen activation capability (single-stage assays using human plasminogen) as well as thrombin inhibition assays for measuring clotting time, as well as chromogenic assays for Protein C activation (see 'methods used in examples'). While SK_EGF and oxidation resistant SK_EGF showed kinetics of PG activation closely similar to SK but with a 2-3 minute additional lag in activation kinetics, in case of N_EGF_SK, and oxidation resistant N_EGF_SK, N_EGF_TCS_SK and TG_N_EGF_SK the lag in the activation was highly pronounced (20-25 minutes) after which the plasminogen activation kinetics was native-SK like. This suggested that the initial activation of the PG by the constructs was delayed whereas in the case of unmodified SK, it is virtually instantaneous. However, once the SK construct was activated, albeit after the lag, it exhibited full plasminogen activating characteristics. A slightly greater lag (30-35 minutes) found in the bi-polar EGF fusion protein, namely N_EGF_SK_EGF, oxidation resistant N_EGF_SK_EGF, N_EGF_TCS_SK_EGF and its variant TG_N_EGF_TCS_SK_EGF. However as stated before, after abolishment of lag, the rate of plasminogen activation per milligram of protein (specific activity) was similar to that of unmodified SK. The reason for the lag in N_EGF_SK, N_EGF_SK_EGF and similar kind of construct was found to be the abolishment of the self activation mechanism of the zymogen (Bajaj and Castellino 1977; Boxrud, Verhamme et al. 2004; Aneja, Datt et al. 2009). This was established by the observation that there was a progressive loss of lag by slight addition of small quantities (in nanomolar amounts) of Plasmin into the reaction assays. In addition, there was no lag when the pre-formed plasmin complexes of these constructs were used in assays clearly suggesting that instead of an instantaneous plasminogen activation mechanism observed with SK, the fusion constructs with the lag were now capable of plasminogen activation only once they were complexed with plasmin. A similar plasmin dependent activation was also found in the inter-domain α β EGF_SK construct; however, after activation its overall specific activity was found to be only 40-50% that of unmodified streptokinase. Remarkably, in case of the other inter-domain construct, where the EGF 4,5,6 segments were placed at the junction of the β and γ domain of SK, the purified protein showed less than 5% plasminogen activity compared to unmodified SK. This clearly shows that any fusion of EGF with SK is not automatically functional, but only the correctly designed ones are so. These can be selected out by screening (when the designing has been done either empirically or by virtue of structural assumptions) using the plate/spectrophotometric assays for plasminogen activation, thrombin inhibition etc which can be easily adapted for a high-throughput screening system. Thus, any designed site-specific substitution, deletion or domain-additive mutants of SK, or naturally occurring variants of streptokinase, can be used to get similar SK-EGF proteins by the approach adopted here.

The purified constructs were also tested for the measurement of inhibition of thrombin by the clotting time assay using human blood factors (see Methods used in Examples, previously described). Remarkably all of the constructs showed significant increase in clotting time in these assays (approximately 2.5-3 fold) over that of control assays which did not have any construct, or had native SK, as another control. Moreover, the increase in clotting time was found to follow a linear dose-dependent behavior over the low nanomolar range of concentration, which was closely similar to that observed with EGF4,5,6 domains obtained by expression in *Pichia*, used as a positive control. These results established that the EGF fusion constructs which had plasminogen activation capability (as also the one which had very low activity) also exhibited strong thrombin inhibiting capabilities as well.

Example 3

Construction of DNAs Encoding Various EGF 4,5,6 and tPA Hybrid Genes

A DNA segment encoding EGF4,5,6 sequence (SEQ ID 2, and corresponding protein SEQ ID 111) fused in frame with encoding tpA (SEQ ID 9, and corresponding protein SEQ ID 120) and another segment of DNA fused in frame encoding EGF4,5,6 (SEQ ID 8, and corresponding protein SEQ ID 111) was chemically synthesized purify and cloned in pUC19. It was sequenced to establish its validity (SEQ ID 8, and corresponding protein SEQ ID 111). This construct refer to as EGF-tpA-EGF (SEQ ID 10, and corresponding protein SEQ ID 121). In addition to this gene construct wherein EGF4,5,6 domains gene encoding segments were fused either at the N-terminal site of tPA (SEQ ID 11, and corresponding protein SEQ ID122) or fused at the C-terminal of tpA (SEQ ID 12, and corresponding protein SEQ ID 123). The tPA encoding sequences were first amplified by primer tPAFp 1 and tPA Rp2 (refer to table 2 for primer sequence) primers. The PCR conditions use for this reaction are as follows: Hot start, complete denaturation at 95° C. for 5 minutes, denaturation at 95° C. for 45 seconds, annealing at 55° C. for 45 seconds, extension at 72° C. for 4 minute, a total no of 28 cycles and a final extension of 72° C. for 10 minutes for the complete amplification of incomplete PCR products. Thus primers used for this reaction tPAFp 1 contains Xho I restriction site at its 5' end and tPARp 2 contains Not I restriction site. Obtained PCR product was digested with the Xho I and Not I restriction enzymes and ligated in to pET 23-d. Final construct formed by this process was named as pET 23-d tPA (refer to FIG. 2F), and sequenced to validate the tPA open reading frame. In order to make N-terminal (N_EGF_tPA) and C-terminal (tPA_EGF) fusions, a simple restriction digestion and ligation scheme was followed. To make both the constructs in a single step, pET23-d tPA and pUC-19_N_EGF_tPA_EGF were cleaved with Xho I and BSrG I, both being unique cutters; this gave the smaller and larger fragments. Smaller fragment of pUC-19_N_EGF_tPA_EGF digestion contains N_EGF_tPA sequence, which was ligated with the lager fragment of pET23-d_tPA, step that gave the N_EGF_tPA (DNA SEQ ID 11, and corresponding protein SEQ ID 122) construct. tPA_EGF (DNA SEQ ID 12, and corresponding protein SEQ ID 123) construct was made by ligation of larger fragment of pUC-19_N_EGF_tPA_EGF with smaller fragment of pET 23-d_tPA, which gave tPA_EGF (refer to FIG. 1J) for this construction. N_EGF_tPA (refer to FIG. 1K) and tPA_EGF (refer to FIG. 2G) were digested with the Xho I and Not I restriction enzymes and the isolated insert fragment was ligated into pPIC-9K, where construct was placed in-frame to the α-secretory signal sequence. All these constructs were expressed in *Pichiapastrois* (GS115) under the influence of methanol inducing promoter located in the vector after integration to the host genome.

TABLE 2

Primers used for the various EGF 4, 5, 6 and tissue plasminogen activator gene fusion construct preparations.

| S. No. | SEQ ID Nos. | Primer Name | Primers Sequence |
|---|---|---|---|
| 1 | SEQ ID 71 | tPA_Fp 1 | 5' GGATAACTCGAGAAAAGAGAGGCTCAAGAGATTCATGCTA-GATTCAGA 3' |
| 2 | SEQ ID 72 | tPA Rp 2 | 5' TCATATCGCGGCCGCTGGTCTCATGTTATCTCTGATCCAGTCCA 3' |
| 3 | SEQ ID 73 | Fin Fp 1 | 5' GGATAACTCGAGAAAAGAGAGGCTCAAGAGATTCATGCTA-GATTCAGA 3' |
| 4 | SEQ ID 74 | Fin Rp2 | 5' GGCTCTAAAGCAAGGGTCAACTGATTTAACTGGAACAC-TATG 3' |
| 5 | SEQ ID 75 | EGF Fp3 | 5' CATAGTGTTCCAGTTAAATCAGTTGACCCTTGCTTTAGAGCC 3' |
| 6 | SEQ ID 76 | EGF RP 4 | 5 AGCTCTGGTTCCGGAATCACAGTCAGTACCTA-TATGTCTTGCCAA 3 |

TABLE 2-continued

Primers used for the various EGF 4, 5, 6 and tissue plasminogen activator gene fusion construct preparations.

| S. No. | SEQ ID Nos. | Primer Name | Primers Sequence |
|---|---|---|---|
| 7 | SEQ ID 77 | K1 Fp 5 | 5' TTGGCAAGACATATAGGTACTGACTGTGATTCCGGAACCA-GAGCT 3' |
| 8 | SEQ ID 78 | CD Rp 2 | 5' TCATATCGCGGCCGCTGGTCTCATGTTATCTCTGATCCAGTCCA 3' |
| 9 | SEQ ID 79 | Fg Fp 1 | 5' GGATAACTCGAGAAAAGAGAGGCTCAAGAGATTCATGCTA-GATTCAGA 3' |
| 10 | SEQ ID 80 | Fg Rp2 | 5' TCTAAAGCAAGGGTCAACTGATTTAACTGGAACACTATGA-CA 3' |
| 11 | SEQ ID 81 | EFI Fp3 | 5' TGTCATAGTGTTCCAGTTAAATCAGTTGACCCTTGCTTTAGA 3' |
| 12 | SEQ ID 82 | EFI RP 4 | 5' ATCACTGTTTCCGGAATCACAATCAGTACCAATATGTCTTGCC AA 3' |
| 13 | SEQ ID 83 | K2 Fp 5 | 5' TTGGCAAGACATATTGGTACTGATTGTGATTCCGGAAACAGTG AT 3' |
| 14 | SEQ ID 84 | K2CD Rp 6 | 5' TCATATCGCGGCCGCTGGTCTCATGTTATCTCTGATCCAGTCCA 3' |
| 15 | SEQ ID 85 | N_EtPA Fp1 | 5' GGATATCTCGAGAAAAGAGTTGACCCTTGCTTCAGAGCCAAC 3' |
| 16 | SEQ ID 86 | N_EtPA Rp 2 | 5' AAAGTAACAATCACTATTTGACTTGACTGGAACACTATGACA 3' |
| 17 | SEQ ID 87 | EK2 CD Fp 3 | 5' TGTCATAGTGTTCCAGTCAAGTCAAATAGTGATTGTTACTTT 3' |
| 18 | SEQ ID 88 | K2 CD Rp 4 | 5' TCATATCGCGGCCGCTGGTCTCATGTTATCTCTGATCCAGTCCA 3' |
| 19 | SEQ ID 89 | Finger Fp1 | 5' GGATAACTCGAGAAAAGAGAGGCTCAAGAGATTCATGCTA-GATTCAGA 3' |
| 20 | SEQ ID 90 | Finger Rp 2 | 5' AAAGTAACAATCACTATTTGACTTGACTGGAACACTATGACA 3' |
| 21 | SEQ ID 91 | K2 CD Fp 3 | 5' TGTCATAGTGTTCCAGTCAAGTCAAATAGTGATTGTTACTTT 3' |
| 22 | SEQ ID 92 | EGF Rp 4 | 5' CCATATCGCGGCCGCTTAACCTGAGTCACAATCTGTTCCAATA 3' |
| 23 | SEQ ID 93 | EGF CD Fp1 | 5' GTTGACCCTTGCTTTAGAGCCAACTGTGAATACCAATGCCAG 3' |
| 24 | SEQ ID 94 | EF CD Rp 2 | 5' CTGGCATTGGTATTCACAGTTGGCTCTAAAGCAAGGGTCAAC 3' |
| 25 | SEQ ID 95 | K2 CD Fp 3 | 5' GTTGACCCTTGCTTTAGAGCCAACTGTGAATACCAATGCCAG 3' |
| 26 | SEQ ID 96 | K2 CD Rp 4 | 5' TTTATACGCGGCCGCTGGTCTCATGTTATCTCTGATCCAGT 3' |
| 27 | SEQ ID 97 | Met rep Val Fp | 5' CATGAACCACATAGATGTCAAGTATTCTGCAACCAGACTG 3' |
| 28 | SEQ ID 98 | Met rep Val Rp | 5' CAGTCTGGTTGCAGAATACTTGACATCTATGTGGTTCATG 3' |
| 29 | SEQ ID 99 | Met rep Ala Fp | 5' CATGAACCACATAGATGTCAAGCATTCTGCAACCAGACTG 3' |
| 30 | SEQ ID 100 | Met rep Ala Rp | 5' CAGTCTGGTTGCAGAATGCTTGACATCTATGTGGTTCATG 3' |

TABLE 2 -continued

Primers used for the various EGF 4, 5, 6 and tissue plasminogen activator gene fusion construct preparations.

| S. No. | SEQ ID Nos. | Primer Name | Primers Sequence |
|---|---|---|---|
| 31 | SEQ ID 101 | Met rep Glu Fp | 5' CATGAACCACATAGATGTCAACAATTCTGCAACCAGACTG 3' |
| 32 | SEQ ID 102 | Met rep Glu Rp | 5' CAGTCTGGTTGCAGAATTGTTGACATCTATGTGGTTCATG 3' |
| 33 | SEQ ID 103 | T 115 N Fp | 5' CAGGGAATCTCATATAGAGGTAATTGGTCTACAGCTGAGT 3' |
| 34 | SEQ ID 104 | T 115 N Rp | 5' ACTCAGCTGTAGACCAATTACCTCTATATGAGATTCCCTG 3' |
| 35 | SEQ ID 105 | N129 Q Fp | 5' AATGTACTAACTGGCAATCTTCCGCTTTGGC 3' |
| 36 | SEQ ID 106 | N129 Q Rp | 5' GCCAAAGCGGAAGATTGCCAGTTAGTACATT 3' |
| 37 | SEQ ID 107 | KH Fp 1 | 5' GGATAACTCGAGAAAAGAGAGGCTCAAGAGATTCATGCTA-GATTCAGA 3' |
| 38 | SEQ ID 108 | KH Rp 2 | 5' AGCAGCGGCAGCAGCAAAAATGGCAGCCTGCCA 3' |
| 39 | SEQ ID 109 | KH Fp 3 | 5' GCTGCTGCCGCTGCTTCCCCTGGAGAGAGATTCCTTT 3" |
| 40 | SEQ ID 110 | KH Rp4 | 5' TCATATCGCGGCCGCTGGTCTCATGTTATCTCTGATCCAGTCCA 3' |

Example 4

Construction of Various Hybrid Genes Between Tissue Plasminogen Activator and EGF 4,5,6 Domains of Human Thrombomodulin (i) Construction of Inter-Domain EGF 4,5,6-tPA Construct:

Tissue plasminogen activator contains different domains, in the following order: N-terminal peptide-finger domain-EGF like domain-kringle 1-kringle 2-catalytic domain. A new non-natural, hybrid design was constructed at gene level, where the intrinsic EGF domain/s of tPA were replaced by the EGF 4,5,6 domains of thrombomodulin. These constructs were made by the overlap extension PCR strategy used earlier for the generation of other hybrid genes.

(a) Construction of a Hybrid Gene Block, where the Intrinsic EGF Domain of tPA was Replaced with EGF4,5,6 Domains of Human Thrombomodulin:

In order to make this construct, pET 23-d_tPA (SEQ ID 9, and corresponding protein SEQ ID 120) was taken as reference where intrinsic egf coding region started from 187 bp to 297 bp. In the first step, the finger domain encoding DNA was isolated by the use of following primer Fin Fp 1 and Fin Rp2 (refer table 2 for the sequence of these primers), where upstream primer contains a Xho I restriction site at its 5' terminus, while on the other hand, the second primer contains downstream sequence encoding for finger domain with overlapping sequence for the $4^{th}$ domain of EGF4,5,6 domains. The PCR conditions were as follows: Complete denaturation at 95° C. for 5 minutes, followed next by 28 cycles: 95° C. for 45 seconds, annealing at 48° C. for 45 seconds, extension at 72° C. for 1 minute, and a final extension done at 72° C. for 10 minutes. In a second PCR, EGF 4,5,6 domain segment was amplified where EGF Fp 3 and EGF Rp 4 refer table 2 for the sequence of these primers) primer set was used. Primer EGF Fp3 contains downstream sequence of finger domain and $4^{th}$ domain of EGF; on the other hand, the downstream primer EGF Rp 4 contains overlapping sequence of kringle 1 at its 5' terminal end. The PCR conditions were as follows: Complete denaturation at 95° C. for 5 minutes, followed next by 28 cycles: 95° C. for 45 seconds, annealing at 48° C. for 45 seconds, extension at 72° C. for 1 minute, and finally ending with an extension segment at 72° C. for 10 minutes. Gene block obtained by this set of primers contains finger domain sequence at 5' terminus and overlapping sequence of kringle 1 at its 3' end. In a third PCR reaction, the sequence encoding for kringle 1 to the end of the catalytic domain was selectively amplified by the use of K1 Fp 5 and CD Rp 6 (refer table 2 for the sequence of these primers) set of primers. Primer K1 Fp1 contains overlapping sequence for the 6$^{th}$ domain of EGF4, 5,6 at its 5' terminus, and primer CD Rp 6 contains a termination codon and a Not I restriction site at the 5' end. PCR condition were as follows: Complete denaturation at 95° C. for 5 minutes, followed for the next 28 cycles which were: 95° C. for 45 seconds, annealing at 48° C. for 45 seconds, extension at 72° C. for 3 minutes, and final extension done at 72° C. for 10 minutes for all partial-length fragments' synthesis completion. Gene block obtained in this reaction contains the EGF 6$^{th}$ domain overlapping sequence at 5' terminus and also the catalytic domain encoding sequences, a termination codon and a Not I site at its 3' end. All the three PCR products were gel-purified and subjected in to a single-pot SOE for the amplification of the complete hybrid gene construct, where the order of assembly was to be as follows: finger domain-EGF4,5,6 domains-kringle 1-kringle 2 and tPA (refer to FIG. 1Q and FIG. 2J). catalytic domain. This was carried out with the help of Fin Fp 1 and CD Rp 6 (refer table 2 for the sequence of these primers) set of primers. Final PCR conditions were as follows: Complete denaturation at 95° C. for 5 minutes, with the next 28 cycles being: 95° C. for 45 seconds, annealing at 48° C. for 45 seconds, extension at 72° C. for 4 minutes, and final extension (single segment) at 72° C. for 10 minutes. This gene block was purified by gel extraction and digested with Xho I and Not I enzymes, and ligated with similarly digested and purified pET 23-d vector, and cloned into *E. coli* XL Blue as described before. A few random clones were subjected to Sanger's sequencing for the complete insert/gene block, and validated to contain the correct in-frame incorporation of EGF 4,5,6 domains into that of tPA (DNA SEQ ID 13, and corresponding protein SEQ ID 124). This gene block was then transferred to pPIC-9K vector, cloned into *Pichia pastoris*, as before, and screened for high levels of plasminogen activator activity as described under 'general methods used in Examples'.

Figure 1P:
FIG. 1P is a schematic design P represents the EGF domain 4,5,6 fusion at the C-terminal end of tPA, where intrinsic egf and kringle 1 of tPA are deleted.
Figure 1:
FIG. 1 is a schematic representation of different in-frame gene fusion constructs, where EGF 4,5,6 domains of thrombomodulin were fused with either DNA encoding for Streptokinase, Tissue plasminogen activator or Staphylokinase along with in-frame fused sequences coding for inter-domain linkers including ones with triple-Glycine (GGG), or transglutaminase-recognition signals (TG) to facilitate Coagulation Factor XIII-catalyzed covalent cross-linking of the hybrid protein with other tissues or the fibrin clot, as well as thrombin-cleavable sequence (TCS).
Figure 1R:
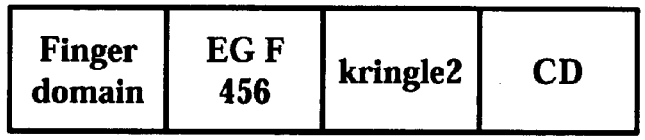
FIG. 1R is a schematic design R represents the EGF fusion with tPA, where intrinsic egf and kringle 1 of tPA are replaced by EGF 4,5,6 domains.
Figure 1S:
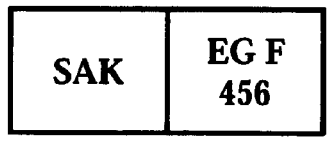
FIG. 1S is a schematic design S represents the fusion of EGF domains at the C-terminal end of SAK.

(b) Construction of Inter-Domain tPA and EGF Hybrid Gene Construct Where Intrinsic EGF and Kringle 1 Domains of tPA were Replaced with EGF 4,5,6 Domains of Human Thrombomodulin:

In order to make this construct, three different PCRs were done separately, where resultant gene blocks contained overlapping sequences at the terminals of each gene block, and they were then amplified in a single-pot SOE reaction in order to make the following hybrid construct: tPA finger domain-EGF4,5,6-tPAkringle 2-tPA catalytic (serine protease) domain (refer to FIG. 1R and FIG. 2H). In order to make this construct, pET 23-d_tPA (SEQ ID 9, and corresponding protein SEQ ID 120) was taken as the template where intrinsic egf- and kringle 1-encoding nucleotide region starts from 187 bp to 564 bp. In the first step, finger domain encoding segment was isolated by the use of the following primers: FgFp 1 and Fg Rp2 (refer table 2 for the sequence of these primers), where the upstream primer contain as Xho I restriction site at 5' terminus, while on the other hand, the second primer contains downstream sequences of finger domain and overlapping sequence of the 4$^{th}$ domain of EGF4,5,6 domains. The PCR condition were as follows: Complete denaturation at 95° C. for 5 minutes, with the next 28 cycles being: 95° C. for 45 seconds, annealing at 48° C. for 45 seconds, extension at 72° C. for 1 minute, and final extension being done at 72° C. for 10 minutes. In a second PCR, EGF 4,5,6 domains were amplified with primers EFI Fp 3 and EFI Rp 4 (refer table 2 for the sequence of these primers). Primer EFI Fp 3 contained downstream sequence of finger domain and 4$^{th}$ domain of EGF while on the other hand the downstream primer contained overlapping sequence of kringle 2 at its 5' terminal end. PCR conditions were as follows: Complete denaturation at 95° C. for 5 minutes, and next 28 cycles were: 95° C. for 45 seconds, annealing at 48° C. for 45 seconds, extension at 72° C. for 1 minute and final extension done at 72° C. for 10 minutes. The Gene block obtained by this set of primers contained finger domain sequence at the 5' terminus, and overlapping sequence of kringle 2 at its 3' end. In a third PCR reaction, sequences starting from kringle 2 to the tPA catalytic domain were amplified by the use of K2 Fp 5 and K2 CD Rp 6 (refer to table 2 for the sequence of these primers), a set of two primers. Primer K2 Fp5 contains overlapping sequence of 6$^{th}$ domain of EGF 4,5,6 at its 5' terminus and primer K2 CD Rp6 contains termination codon and Not I restriction site at the 5' end. PCR condition were as follows: A 'hot start' with complete denaturation at 95° C. for 5 minutes, with the next 28 cycles being −95° C. for 45 seconds, annealing at 48° C. for 45 seconds, extension at 72° C. for 3 minute—and a final extension being done at 72° C. for 10 minutes. The gene block obtained in this reaction contained the 6$^{th}$ domain overlapping sequence at its 5' terminus and the catalytic domain encoding sequence, followed by a termination codon, and a Not I site at its 3' end. All the three PCR products were gel-purified and subjected to single-pot SOE reaction with the Fg Fp 1 and K2CD Rp 6 set of primer (refer table 2 for the sequence of these primers) for the amplification for obtaining the complete hybrid gene construct, where the order of assembly of the various protein encoding segments was as follows (finally confirmed by DNA sequencing after cloning): finger domain-EGF4,5,6 domains-kringle 2 and catalytic domain (DNA SEQ ID 14, and corresponding protein SEQ ID 126). Final PCR conditions were as follows: Complete denaturation at 95° C. for 5 minutes, next 28 cycles being −95° C. for 45 seconds, annealing at 48° C. for 45 seconds, extension at 72° C. for 4 minutes, and a final extension done at 72° C. for 10 minutes. This gene block was purified by gel extraction and digested with Xho I and Not I enzymes and ligated with pET 23-d vector, and cloned in *E. coli* XL Blue, wherein the complete gene block was then sequenced and validated for the correct in-frame incorporation of EGF 4,5,6 domains into the partially truncated tPA gene. This final, hybrid gene-block was transferred to pPIC-9K vector and checked for its ORF expression in *pichia pastoris* using standardized procedures as described before.

(c) Construction of Hybrid Gene Blocks Encoding for Truncated Versions of tPA where EGF 4,5,6 Encoding Segments were Fused in-Frame at the N-Terminal and C-Terminal Encoding Ends of the Former:

These constructs were prepared by the help of previously made pET-23-d N_EGF_tPA (SEQ ID 11, and corresponding protein SEQ ID 121) and pET 23-d_tPA_EGF (SEQ ID 12, and corresponding protein SEQ ID 123) as templates. In both constructs, the intrinsic egf and kringle 1 domains were removed with the help of the overlapping PCR scheme. In order to remove intrinsic egf and kringel 1 domains of tPA from N_EGF_tPA (refer to FIG. 1.N) construct, two sets of primers were designed. The first set of primers, N_EtPAFp 1 and N_EtPA Rp2 (refer table 2 for the sequence of these primers) were used for the amplification of contiguous nucleotide sequences of EGF4,5,6 domains and tPA finger domain. In this case, upstream primer contained 4$^{th}$ domain sequence of EGF and Xho I restriction site at its 5' end, and primer N_EtPA Rp2 contained overlapping sequence of tPA kringle 2. A second set of primers, namely EK2 CD Fp3 and K2CD Rp 4 (refer table 2 for the sequence of these primers) was used for the amplification of kringle 2 and catalytic domain of tPA. Primer EK2 CD Fp 3 contained downstream overlapping sequence of finger domain at 5' end and other primer contains downstream sequence of tPA catalytic domain and a Not I restriction site (PCR conditions: Hot start, 95° C. for 5 minutes, 28 cycles of 95° C. for 45 seconds, 52° C. for 45 seconds, 72° C. for 2 minutes, and a final extension at 72° C. for 10 minutes). Resultant gene block obtained in this reaction contained tPA finger domain overlapping sequence at its 5' end and a Not I restriction site at its 3' end. Both PCR products were gel-purified and subjected for the construct of a complete gene block where intrinsic egf and kringle 1 were deleted with the help of primers N_EtPA Fp1 and K2 CD Rp4 (refer table 2 for the sequence of these primers), primer set. The resultant gene block was purified and digested with the Xho I and Not I restriction enzymes and ligated into pET 23-d vector, sub cloned in *E. coli*, and DNA-sequenced for the correct in-frame joining after removal of egf and kringle 1 from the tPA (DNA SEQ ID 15, and corresponding protein SEQ ID 126; FIG. 2.I) encoding gene-block. After validation by sequencing for the correct open reading frame of gene block, this cassette was ligated into pPIC-9K, transformed into *Pichia* as before, screened for activity, and checked for extracellular expression. In a similar way, intrinsic egf and kringel 1 were deleted from the tPA encoding gene block in the construct, tPA_EGF (see FIG. 1P and FIG. 2H). Here, pET 23-d-tPA_EGF plasmid DNA was used as template for the amplification of truncated tPA nucleotide sequence. Using the primer set, Finger Fp 1 and Finger Rp2 (refer table 2 for the sequence of these primers) for the amplification of finger domain, where Finger Fp 1 primer contained a Xho I restriction site at its 5' end and the other primer, Finger Rp2 contained downstream sequence of finger domain and overlapping sequence of kringle 2 of tPA. PCR conditions were as follows: complete denaturation at 95° C. for 5 minutes, followed by 30 cycles of: denaturation at 95° C. for 45 seconds, annealing at 44° C. for 45 seconds and extension 72° C. for 1 minute, ending with a final extension at 72° C. for 10 minutes. This gave the gene block containing tPA finger domain overlapping sequences, followed by an Xho I restriction site at its 5' end, and at its 3' end contained kringle 2 overlapping sequences. A second primer set was used for the amplification of kringle2-catalytic encoding domain and EGF 4,5,6 domains. The first primer, K2 CD Fp 3 (refer table 2 for the sequence of these primer), contained overlapping sequences to downstream end of tPA finger domain and a small part of kringle 2; on the other hand, the second primer EGF Rp 4 (refer table 2 for the sequence of these primer) contained downstream sequence of EGF and a Not I restriction site. PCR conditions were as follows: complete denaturation at 95° C. for 5 minutes, and 30 cycles of: denaturation at 95° C. for 45 seconds, annealing at 44° C. for 45 seconds and extension 72° C. for 1 minute, and final extension at 72° C. for 10 minutes. Both gene blocks were purified from gel and subjected to the overlap extension reaction in presence of primers Finger Fp1 and EGF Rp 4 (see Table 2 for the sequence of these primers), and the PCR product obtained from this was gel purified and ligated into pet 23-d in (DNA SEQ ID 16, and corresponding protein SEQ ID 127) *E. coli* as before, and sequenced to validate the complete gene block. Finally this gene block was ligated into pPIC-9K and transformed into *Pichia pastoris* for screening of expression and functional properties as described before.

(d) Incorporation of Different Mutations in Various EGF Containing Tissue Plasminogen Activator Gene Constructs:

In different fusion constructs of EGF 4,5,6 described above, and tPA, following amino acid changes were made: Threonine 115$^{th}$ amino acid changed by aspargine (T 115 N), Aspargine 129$^{th}$ amino acid changed by glutamine (N 129 Q) and KHRR encoding region of tPA 308-311 is replaced by a tetra-Alanine stretch of mutations (KHRR (308-311)AAAA) (DNA SEQ ID 20, and corresponding protein SEQ ID 128). These mutations are known to confer additional fibrin specificity to the resultant molecule, as well as increase the in vivo half life of the tPA (Keytt et al., 1994). For introduction of theses mutations, we used the site directed mutagenesis approach (refer to the 'methods used in examples') and incorporated these changes in the oxidation resistant (where the 129$^{th}$ methionine of EGF4,5,6 domain was replaced valine/alanine/glutamine) gene templates also. The following primers were used for the site directed mutagenesis: 1. T 115 N Fp and T115 N Rp (refer table 2 for sequence of these primers) 2. N129 Q Fp an N129 Q Rp. (refer table 2 for sequence of these primers)

In case of tPA mutations KHRR (where residues 308-311 of tPA were replaced by the tetra Alanine amino acid residues) overlapping extension PCR (refer to the methods used in examples) using KHFp 1 and KHRp 2 as end-primers (refer to table 2 for sequence of these primers i.e. at Serial Nos. 37 and 38) were used for the amplification of the 1-933 bp long stretch of polynucleotide, where KHFp 1 primer contains a Xho I restriction site, and upstream sequence of tPA; on the other hand, the primer KHRp2 contains a four-alanine mutation at its 5' end. The following PCR conditions were used: Hot start, complete denaturation at 95° C. for 5 minutes, followed by denaturation at 95° C. for 45 seconds, annealing at 45° C. for 45 seconds, extension at 72° C. for 1.5 minute, with a total of 28 cycles, and a final extension of 72° C. for 10 minutes for the complete amplification of any incomplete PCR products. Finally, the gene block obtained by this method contained a Xho I restriction site at the 5' end, and its 3' end contained a tetra-alamine mutation. In another set of PCR reaction, KHFp3 and KHRp 4 (refer table 2 for sequence of these primers) were used for the amplification of the DNA between 918$^{th}$ by to 1617$^{th}$ bp of tPA. Primer KHFp 3 contains a tetra alanine mutation at it 5' end, while the second primer, KHRp 4 contains a Xho I restriction site. Following PCR condition were used for the reaction: Hot start, complete denaturation at 95° C. for 5 minutes, followed by denaturation at 95° C. for 45 seconds, annealing at 45° C. for 45 seconds, extension at 72° C. for 1.5 minute, with a total of 28 cycles, and a final extension of 72° C. for 10 minutes for the complete amplification of any incomplete PCR products. The resultant gene block contains tetra-alanine mutation at its 5' end, and its 3' end contains a Not I restriction site. Both PCR products were gel purified and mixed into a common 'Overlap' PCR reaction single pot, where KHFp1 and KHRp 4 (refer to table 2 for the sequence of these primers) were used for the amplification of the whole gene block. Finally, the obtained gene block was transferred to pET 23-d and after validation of DNA sequence and correct open reading frame, transferred into pPIC9K where the hybrid polypeptide was expressed checked by standard conditions in *Pichia* (please refer to 'methods used in examples').

Example 5

Construction of Hybrid Genes Between Staphylokinase and Thrombomodulin Domains EGF 4,5,6

Figure 1T:
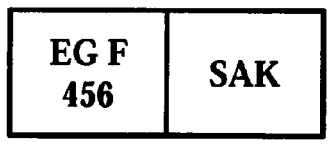
FIG. 1T is a schematic design T represents the fusion of EGF domains at the N-terminal end of SAK.
Figure 3:
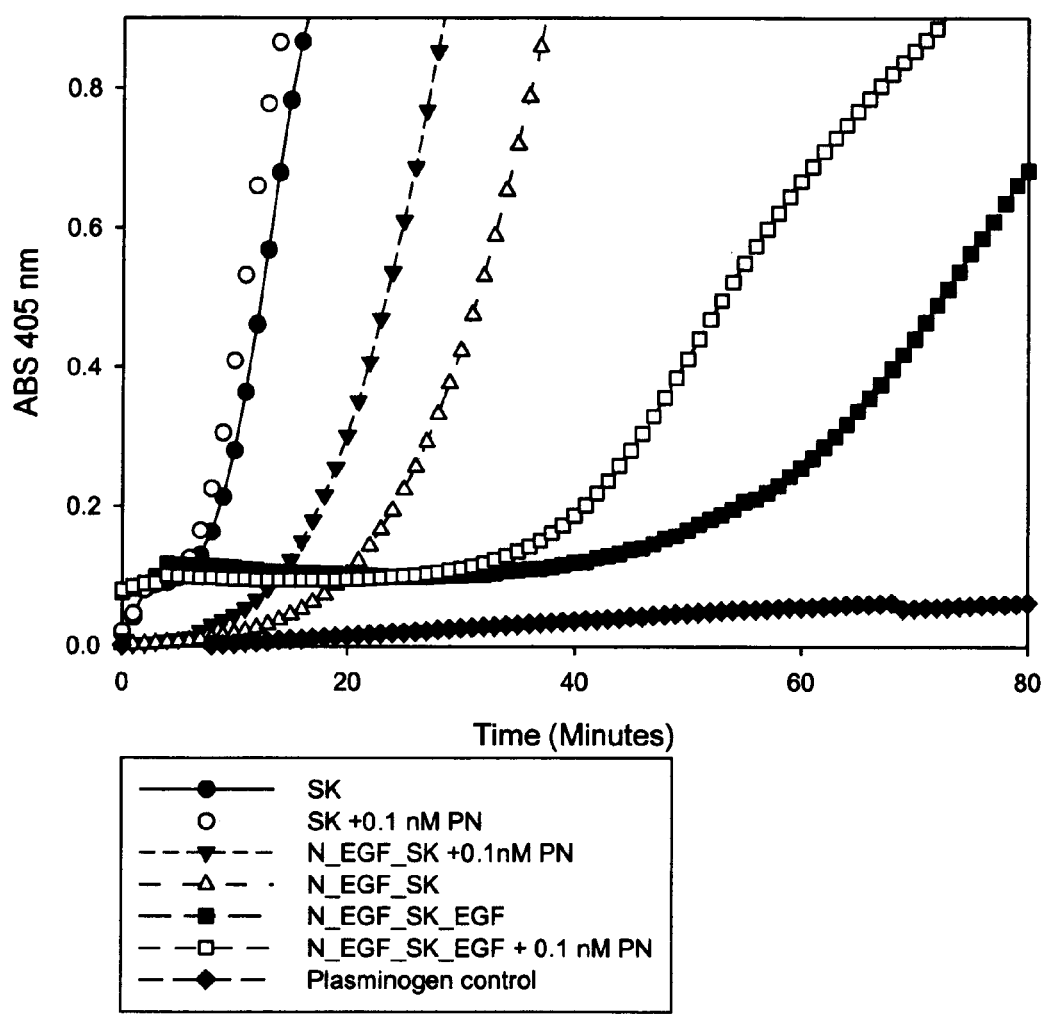
FIG. 3 Spectrophotometrically scans of plasminogen activation (Abs 405 nm) showing delayed plasminogen activation by N-terminal fused EGF 4,5,6 and SK constructs and decrease in the lag in presence of trace amounts of plasmin (see 'general methods used in examples' for details). Note that native SK does not show any significant lag in plasminogen activation.
Figure 4:
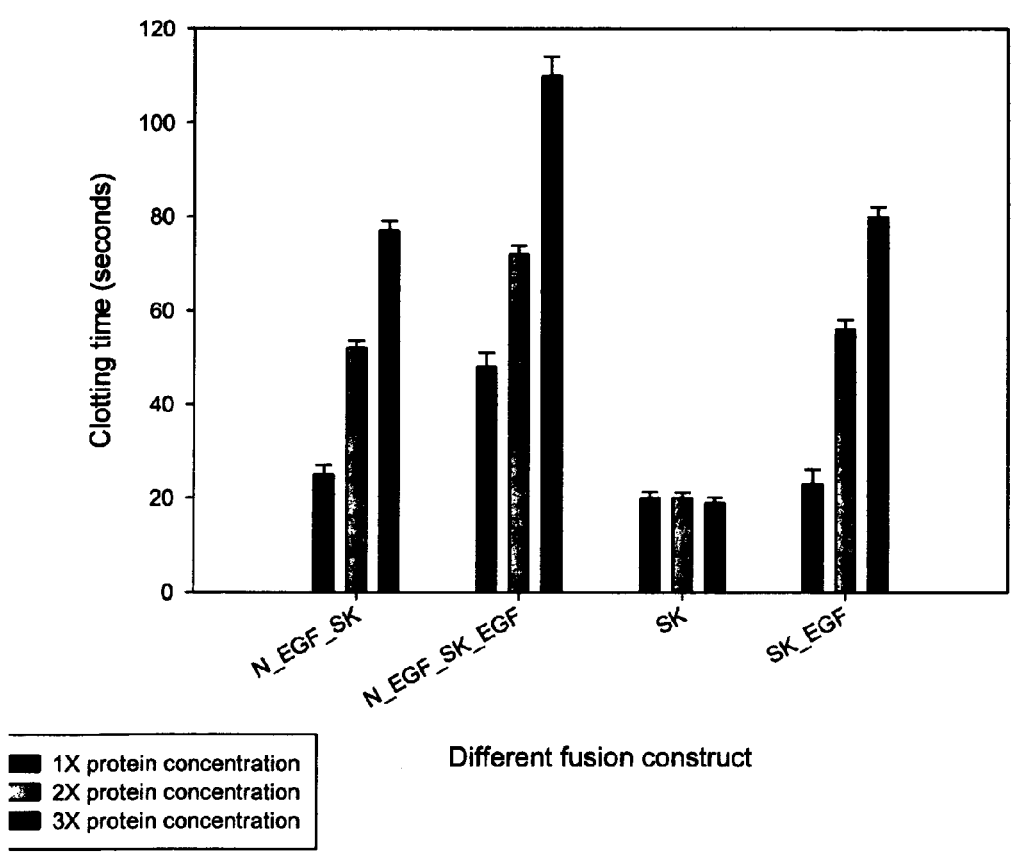
FIG. 4. Representation of the increased thrombin clotting time assay by varying amounts (60-180 nm) of different fusion constructs and controls as indicated.
Figure 5:
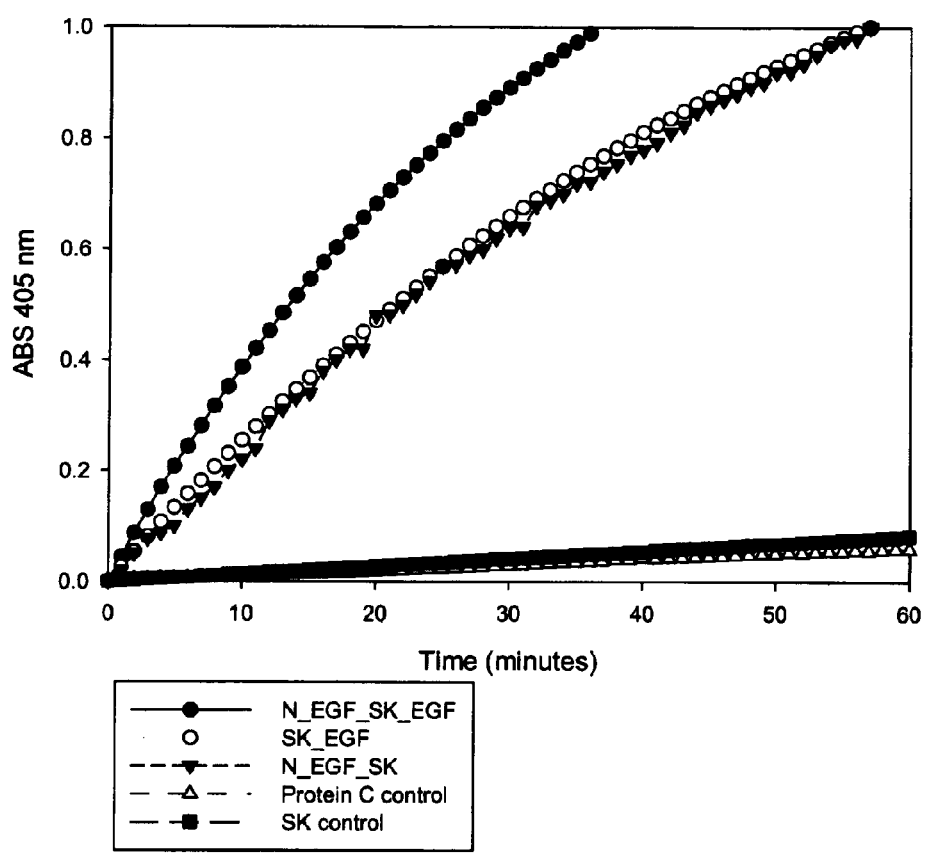
FIG. 5. Protein C activation profiles (see 'general methods' for details) in presence of different SK and EGF fusion constructs and suitable controls as indicated.
Figure 6:
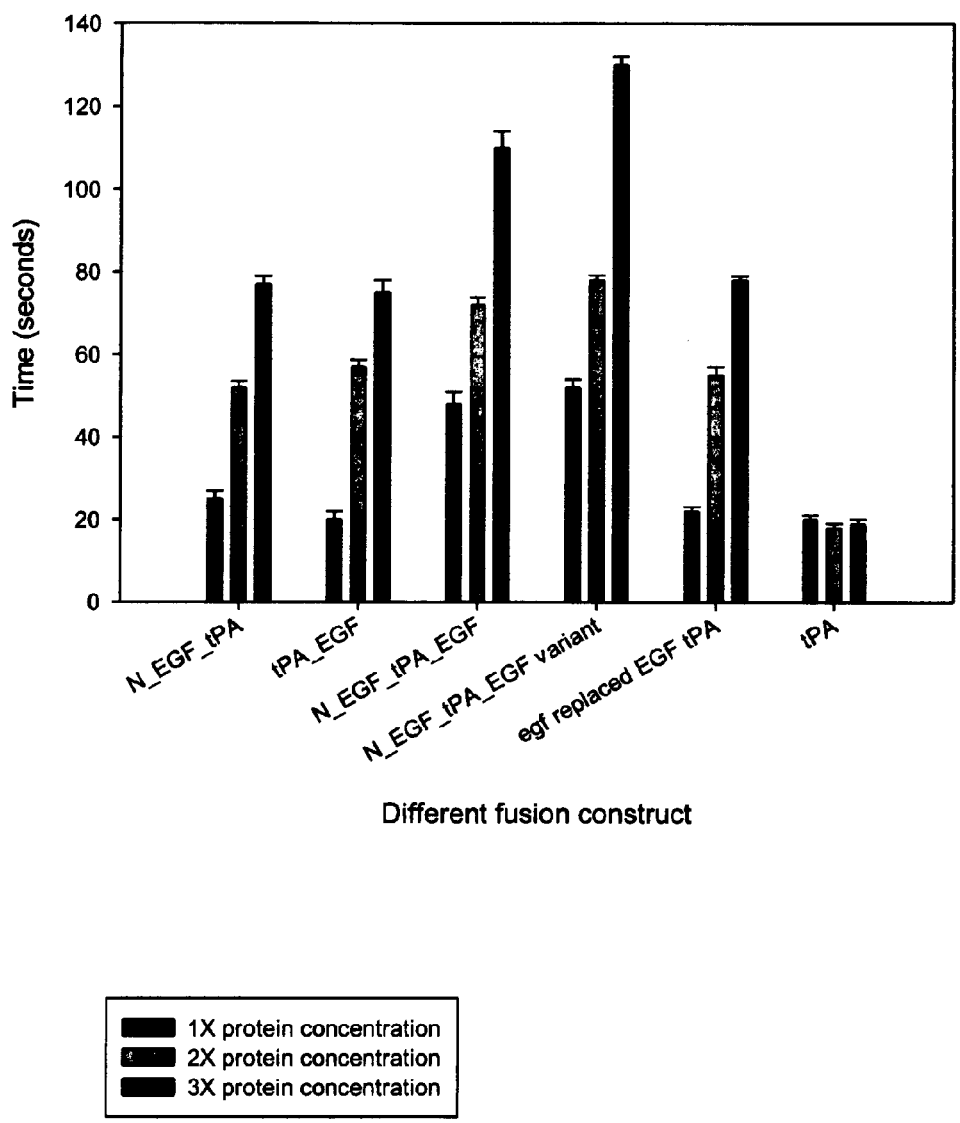
FIG. 6. Clotting time assay with different tPA fusion constructs (equimolar; 2 nm) and controls as indicated.
Figure 7:
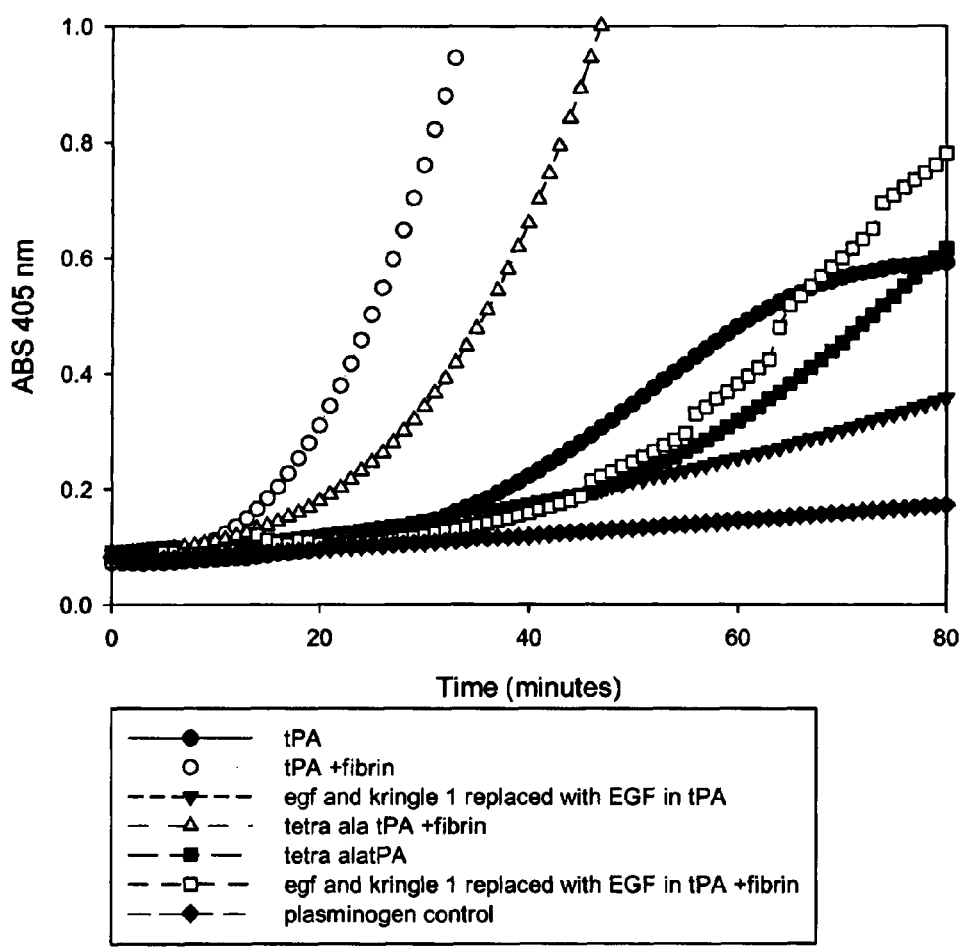
FIG. 7. Plasminogen activation in presence and absence of soluble fibrin with various tPA fusion constructs along with control as indicated.

Construction of SAK_EGF and EGF_SAK Encoding Hybrid Gene Blocks:

For the construction of EGF-SAK fusions, EGF 4,5,6 PCR block was isolated with the help of N_EGF_SAK Fp1 and N_EGF_SAK Rp 2 set (refer table 3 for the sequence of these primers) of primers, where pET 23-d_EGF 4,5,6 (Seq ID 2, and corresponding protein SEQ ID 111) was used as template. Here, N_EGF_SAK Fp 1 contained Xho I restriction site at its 5' end, while N_EGF_SAK Rp 2 contained overlapping sequence of SAK nucleotides at the 5' end. PCR conditions were as follows: complete denaturation at 95° C. for five minutes in the $1^{st}$ (hot start) cycle, with the next 28 cycles being: denaturation at 95° C. for 45 seconds, annealing at 50° C. for 45 seconds, extension at 72° C. for 1 minute, and final step was at 72° C. for 10 minutes for completion of any uncompleted PCR products. The PCR product contained a Xho I restriction site at its 5' end, and 3' end contained overlapping sequence of SAK. In a second step, SAK PCR block was amplified with the help of N_EGF_SAK Fp3 and N_EGF_SAK Rp 4 set of primers and pGMEX_SAK (SEQ ID 17, and corresponding protein SEQ ID 130) construct was used as template. In this reaction, primer N_EGF_SAK Fp 3 contained downstream overlapping sequence of the $6^{th}$ domain of EGF 4,5,6; N_EGF_SAK Rp 4 contained a termination codon followed by a Not I restriction site. PCR conditions were as follows: complete denaturation at 95° C. for five minutes in the $1^{st}$ cycle, followed next by 28 cycles of denaturation at 95° C. for 45 seconds, annealing at 50° C. for 45 seconds, extension at 72° C. for 1 minute, and final step at 72° C. for 10 minute for completion of uncompleted PCR products. This gave the gene block which had $6^{th}$ EGF domain overlapping sequences at the 5' end, and 3' end contained a termination codon followed by a Not I restriction site. Both the PCR products were gel-extracted and purified with the help of gel purification kit and mixed into a single SOE PCR reaction in 1:1 molar ratio with N_EGF_SAK upstream Fp 1 and N_EGF_SAK Rp 4 downstream primers being used for the hybrid gene intermediate (obtained by overlap extension) amplification. As a result of this, we got a contiguous gene fragment which contained the N_EGF_SAK (DNA SEQ ID 18, and corresponding protein SEQ ID 118) sequence. This gene block was then digested with Xho I and Not I, and transferred into pPIC-9K vector. DNA sequencing validated in-frame fusion expected in the EGF_SAK (refer to FIG. 1T) construct and absence of any other mutations. This construct was transformed into the GS 115 strain of *Pichia pastoris* and checked for expression under the influence of the alcohol oxidase promoter after integration into host genome, as before.

The construction of SAK_EGF (refer to FIG. 1. S) construct was carried out in a similar way where EGF4,5,6 domain segment was fused at the C-terminal end of SAK. In the first step, SAK gene block was isolated with the help of SAK_EGF Fp 1 and SAK_EGF Rp 2 set of primer. Primer SAK_EGF Fp 1 contains aXho I restriction site at the 5' end; on the other hand SAK_EGF Rp 2 contains overlapping sequence of $4^{th}$ domain of EGF 4,5,6. The resultant gene block contains Xho I site among its upstream sequences and overlapping $4^{th}$ domain EGF sequence at its downstream ones. In a second step, SAK gene block was isolated by the use of SAK_EGF Fp 3 and SAK_EGF Rp 4 primers, where the SAK_EGF Fp3 contains overlapping sequence of SAK, and SAK_EGF Rp 4 contains termination codon and a Not I restriction site. The gene block isolated from PCR using these set of primers contained SAK overlapping sequence upstream, and termination codon and Not I site at its downstream end. Both gene blocks were purified from agarosegel and mixed into a single SOE reaction with the SAK_EGF Fp 1 and SAK_EGF Rp 4 in order to obtain the complete SAK_EGF (DNA SEQ ID 19, and corresponding protein SEQ ID 119) gene block. Thus, the final PCR product gave a hybrid gene block containing the SAK_EGF sequence which was purified from gel and digested with Xho I and Not I restriction enzymes and transferred into pPIC-9K, after sequencing correct in-frame validation done. This construct transform into GS 115 strain of *Pichia pastoris* where, after genome integration by standardized procedures, its expression (which was checked by SDS-PAGE as well as casein-overlay plasminogen activator assays) under the influence of the alcohol oxidase promoter situated in the expression plasmid pPIC-9K. Whole SAK_EGF construct was incorporated in-frame upstream of the α-secretory signal sequence which helps in transport of hybrid gene product across the membrane into the medium.

Bacterial Expression of N_EGF_SAK and SAK_EGF:

The above-described N_EGF_SAK and SAK_EGF DNA constructs were also expressed under the influence of IPTG inducible lac promoter. In order to make these constructs, the pPIC-9K_N_EGF_SAK and pPIC-9K_SAK_EGF plasmids were used as template.

(i) Construction of Bacterial Expression Cassette of N_EGF_SAK Gene Block:

N_EGF_SAK gene block was first amplified with the help of BacFp 1 and BacRp 2 primers by using pPIC-9K N_EGF_SAK as template. Bac Fp1 primer contained a Nco I site at its 5' end, to help in providing a required AUG codon in the beginning of the gene block, and provide the initiator Met residue encoding codon in the mRNA. Primer BacRp 2 contained a Xho I restriction site to facilitate in-frame introduction of 6 histidine amino acid-encoding nucleotides at the end of the transcribed mRNA before the ter codon that helps in detection of gene product and its purification. This gene block was isolated from the gel and digested with Nco I and Xho I restriction enzymes, finally ligated with T7 promoter based pET 23-d vector and transformed into *E. coli*. These two sites, which are unique, help the hybrid gene construct's insertion under the influence of T7 RNA polymerase promoter (Studier and Moffatt, 1986). This construct pET 23-d N_EGF_SAK_SAK was transformed into XL 1B cells (rec A⁻ and end A⁻) where plasmid propagates and sequenced. Now this plasmid transfer to BL21 (DE3) cells (expression host), where induction of T7 RNA polymerase was done by IPTG and expression in intra-cellular form as inclusion bodies (please refer to 'methods used in examples' for expression conditions, isolation of inclusion bodies and refolding protocols). Finally, the refolded protein was obtained in highly purified form through chromatography and subjected to activity assays.

(ii) Construction of SAK_EGF Gene Block for Bacterial Expression:

SAK_EGF construct was prepared by the help of SAK_EGF Fp1 and SAK_EGF Rp 2 primers, where pPIC-9K_SAK_EGF was taken as the template for amplification. The primer SAK_bac Fp1 contained a Nco I restriction site at the 5' end to help in the introduction of a AUG codon; on the other hand, SAK_bac Rp2 contained a Xho I restriction site to facilitate the introduction of 6 histidine amino acid-coding nucleotides prior to the termination codon at the downstream end of the intended SAK_EGF gene-construct. The PCR conditions were as follows: complete denaturation at 95° C. for five minutes in $1^{st}$ cycle, next 28 cycles were: denaturation at 95° C. for 45 seconds, annealing at 50° C. for 45 seconds, extension at 72° C. for 1.5 minute, and a final step 72° C. for 10 minute for completion of partial-length PCR products. Resultant gene block contained a Nco I site at its upstream end, and Xho I site present at its downstream end, and was purified by gel extraction and ligated into pET 23-d vector. This ligation product was transformed into *E. coli* XL1B (rec A⁻ and end A⁻) cells by electroporation and the resultant plasmids sequenced for the validation of correct open reading frame. Propagation of plasmid was done in XL1B cells but for expression of hybrid gene product plasmid was transformed into *E. coli* BL 21 (DE 3) cell (Novagen Inc.). Finally, protein was expressed in presence of IPTG, which forms inclusion bodies which were isolated and refolded in presence of oxidized and reduced glutathione as detailed under 'methods used in examples', and subjected to plasminogen activator and thrombin inhibition activity assays as for the EGF_SAK construct, above.

(iii) Introduction of Thrombin Cleavable Sequences at the Junction of EGF and SAK:

Thrombin cleavable sequences were introduced at the junction of EGF and SAK in the N-terminal fusion construct. For this construct, EGF_SAK DNA in the plasmid pET-23-d was taken as template for EGF and SAK amplification. Thrombin cleavable primers were designed. For EGF amplification, named E 4 Fp 1 and E6 Rp 2 (refer to table 3 for sequence of these primers at Serial No's. 13 and 14) primers were used. E4 Fp 1 primer contains Xho I restriction site and upstream sequence of EGF4,5,6 domains at its 5' end; on the other hand E6 Rp2 contains downstream sequence of EGF 4,5,6 and thrombin cleavable nucleotide sequence at its 5' end. Following PCR conditions were used for the amplification: complete denaturation at 95° C., followed by next 28 cycles: 95° C. for 45 seconds, annealing at 45° C. for 45 second, extension at 72° C. for 1 minutes, and finally, an extension for a further 10 min at 72° C. Gene block obtained by this PCR reaction contains sequence encoding in-frame for the 4$^{th}$ domain of EGF at its 5' end, and its 3' end contains downstream sequence of EGF4,5,6 and a thrombin cleavable sequence. In a second PCR reaction, the SAK gene block was amplified with the help of TCS SAK Fp 3 and TCS SAK Rp4 (refer to table 3 for sequence of these primers i.e. S. No. 15,16). TCS SAK Fp3 contains a thrombin cleavable sequence and upstream sequence of SAK nucleotide; similarly the other primer TCS SAK Rp4 contains downstream sequence of SAK and termination codon, followed by a Not I restriction site. The resultant, amplified gene block contains thrombin cleavable nucleotide sequence at its 5' end and termination codon and Not I site situated at its 3' end. The following PCR conditions were used for the amplification of the SAK gene block: complete denaturation at 95° C., followed by next 28 cycles as follows: denaturation at 95° C. for 45 seconds, annealing at 45° C. for 45 seconds, extension at 72° C. for 1 minutes, and final extension for a further 10 min at 72° C. Both the PCR products were gel-eluted and subjected in a common Overlap Extension PCR reaction for the amplification of EGF_TCS_SAK gene block with the help of E4 Fp 1 and TCS SAK Rp 4 (refer to table 3 for sequence of these primers i.e. at S. No. 13 and 16 of the table) under the following conditions: complete denaturation at 95° C., followed by denaturation at 95° C. for 45 seconds, annealing at 45° C. for 45 seconds, extension at 72° C. for 2 minutes for 28 cycles and a final extension for a further 10 min at 72° C. The obtained gene block contained a Xho I restriction site at its 5' end and a Not I site at its 3' end. This PCR product was digested with Xho I and Not I enzymes, and ligated into pPIC-9K after being sequenced for correct in-frame insertion of thrombin cleavable sequence subsequent to cloning in pET 23-d.

TABLE 3

Primers used for the various EGF 4, 5, 6 and SAK fusion construct preparations.

| S No. | SEQ ID Nos. | Primer Name | Primer Sequence |
|---|---|---|---|
| 1 | SEQ ID 55 | N_EGF_SAK Fp 1 | 5' ATGGATCTCGAGAAAAGAGTGGACCCGTGCTTCAGA 3' |
| 2 | SEQ ID 56 | N_EGF_SAL Rp 2 | 5' ATATTTTCTTTGTCGAATGAACTTGACATGCCGGAGTCACAGTC 3' |
| 3 | SEQ ID 57 | N_EGF_SAK Fp3 | 5' GACTGTGACTCCGGCATGTCAAGTTCATTCGACAAAGGAAAATAT 3' |
| 4 | SEQ ID 58 | N_EGF_SAK Rp 4 | 5' TTATATCGCGGCCGCTTATTTCTTTTCTATAACAACCTTT 3' |
| 5 | SEQ ID 59 | SAK_EGF Fp 1 | 5' ATCCCTCTCGAGAAAAGATCAAGTTCATTCGACAAAGGAA 3' |
| 6 | SEQ ID 60 | SAK_EGF Rp 2 | 5' AGTTGGCTCTGAAGCACGGGTCCACGGGCTCTTTCTTTTCTA TAACAACCTT 3' |
| 7 | SEQ ID 61 | SAK_EGF Fp 3 | 5' AAGGTTGTTATAGAAAAGAAAGAGCCCGTGGACCCGTGCTT CAGAGCCAACT 3' |
| 8 | SEQ ID 62 | SAK_EGF Rp 4 | 5' TTTTACGCGGCCGCTCCTGAGTCACAGTCTGTGCCAATGT 3' |
| 9 | SEQ ID 63 | BacFp 1 | 5' ATATAGGCCATGGGTGGACCCGTGCTTCAGAGCCAACT 3' |

TABLE 3 -continued

Primers used for the various EGF 4, 5, 6 and SAK fusion construct preparations.

| S No. | SEQ ID Nos. | Primer Name | Primer Sequence |
|---|---|---|---|
| 10 | SEQ ID 64 | BacRp 2 | 5' CCTATATCTCGAGTTTCTTTTCTATAACAACCTTT 3' |
| 11 | SEQ ID 65 | SAK_bac Fp1 | 5' ATGGATCCATGGTCAAGTTCATTCGACAAAGGAAAATATA 3' |
| 12 | SEQ ID 66 | SAK_bac Rp2 | 5' TATATTCTCGAGTCCTGAGTCACAGTCTGTGCCAATGT 3' |
| 13 | SEQ ID 67 | E 4 Fp 1 | 5' ATGGATCTCGAGAAAAGAGTGGACCCGTGCTTCAGA 3' |
| 14 | SEQ ID 68 | E6 Rp 2 | 5' CCGACAATTCTAGGTTTAATGCCGGAGTCACAGT-CAGTGCCAA 3' |
| 15 | SEQ ID 69 | TCS SAK Fp 3 | 5' GGCATTAAACCTAGAATTGTCGGATCAAGTTCATTCGATAA AGGAAAAT 3 |
| 16 | SEQ ID 70 | TCS SAK Rp4 | 5' TTATATCGCGGCCGCTTATTTCTTTTCTATAACAACCTTT 3' |

Example 6

Biological Activities of tPA-EGF and SAK-EGF Fusion Constructs

The different hybrid gene constructs of EGF and tPA, where chemically synthesized (N_EGF_tPA_EGF), hybrid tPA fusion constructs (where EGF 4,5,6 was inserted to replace the intrinsic domains of tPA i.e. egf and Kringle 1), internally deleted forms of tPA and EGF fusions (where intrinsic egf and kringle 1 were deleted and EGF 4,5,6 fused at either N and C terminii), and oxidation resistant variants of above-mentioned constructs were cloned in-frame upstream of α-secretory signal sequence of pPIC-9K vector essentially as described before. Each construct was separately checked by the restriction endonucleases and validated by DNA sequencing. All these constructs were individually transferred to Pichia pastoris (GS 115) by electroporation (please refer to 'general methods used in examples' section). Individual clones were grown on BMGY and BMMY media (BMGY=1% yeast extract, 2% peptone, 1× glycerol, 1× yeast nitrogen base without amino acids and 100 mM of potassium phosphate buffer pH 5.5 and BMMY=1% yeast extract, 2% peptone, 1× Methanol, 1× yeast nitrogen base without amino acids and 100 mM of potassium phosphate buffer pH 5.5) for 5 days along with by inducing with methanol and supernatants were tested by casein overlay method for plasminogen activation ability (refer to 'methods used in examples' section); apart from this, the supernatant of each positive clone tested for plasminogen activation in one-stage assay. Then each hyper-active clone was grown at one-liter level, where the presence of tPA polypeptide in each protein was validated by Western blotting, and followed by lysine affinity and ion-exchange chromatography (for detailed protocol refer to 'methods used in examples'). Different fusion constructs obtained by chromatography were 92-95% pure by SDS-PAGE. These purified proteins were subjected for the plasminogen activation assays. The specific activity of each purified protein was closely similar to pichia derived native tissue plasminogen activator. However, constructs where the finger, egf, and kringle 1 and kringle 2 domains were deleted and replaced by EGF 4,5,6 domains showed comparatively weaker zones of hydrolysis by the Casein Overlay method, and also generally exhibited relatively lowered plasminogen activator activity by the quantitative micro-titer plate-based assay using plasminogen and chromogenic substrate. Moreover, the extent of stimulation in activity seen in presence of soluble fibrin in the internally deleted constructs were much lower as compared to tPA/tPA mutants where the fusions of EGF were at the former's terminii. In case of the tPA mutant (containing the Threonine $115^{th}$ amino acid changed into aspargine (T 115 N), Aspargine $129^{th}$ amino acid changed to glutamine (N 129 Q) and KHRR encoding region of tPA i.e. residues 308-311 being replaced by a tetra-Alanine stretch of mutations (KHRR (308-311→AAAA; see Example, above), the plasminogen activator activity was native-like in terms of both 'basal' activity as well as its stimulation in presence of soluble fibrin. At the same time, this construct exhibited the highest thrombin inhibiting property using well defined assays (see 'Methods used in Examples' section) of thrombin inhibition and protein C activation. In contrast, thrombin inhibition, as checked by the clotting time assay, wherein fibrin mesh formation in presence or absence of native tPA up to high micro molar concentrations was essentially unaltered compared to buffer controls, the addition of nanomolar concentrations of different purified chimeric constructs including the 'tetra-ala' mutant above, or where EGF 4,5,6 was incorporated in different places internally or at the ends in tPA, gave significantly increased clotting time in a dose-dependent manner. The observed increase in clotting was more prominent in N_EGF_tPA_EGF construct compared to EGF domains fused at either end. This type of effect was also observed in thrombin mediated protein C activation assays, where amount of protein C generated by N_EGF_tPA_EG was 2-4 fold higher than the single EGF 4,5,6 domain containing tPA fusion constructs and the internally fused EGF-tPA constructs in general. In another set of results, where oxidation resistant forms with methionine substitutions in the EGF portion of the EGF-tPA fusions were compared for their thrombin mediated protein C activation capability, the oxidation resistant forms where methionine was replaced with Valine invariably showed 15-20% higher protein C activation.

In a similar way staphylokinase and EGF fusion constructs were prepared and expressed in Pichia pastoris as well as in B121 DE3 cells. Streptokinase expression in Pichia pastoris and glycosylation of its $26^{th}$ amino acid have been reported in literature, where this glycosylation seems to hamper the plasminogen a activation function, but if cultures were grown in presence of tunicamycin containing media, the same plasminogen activation profile like native bacterial purified SAK is obtained. Keeping this fact in consideration, the same gene blocks were prepared and designed for both bacterial and pichia expression. Using SAK and EGF fusion gene blocks for SAK-EGF fusions at the N-terminal and C-terminal ends, the initial expression was carried out in E. coli BL 21 DE cells where they the polypeptide synthesis was induced by 1 mM concentration of IPTG (please refer to 'methods used in examples'). Finally, EGF_SAK and SAK_EGF were obtained in form of inclusion bodies where refolding conditions for these polypeptides were optimized with different ratio of oxidized and reduced glutathione as well as other solution conditions (please refer to 'methods used in examples'); side by side, both the constructs were expressed in Pichia pastoris in presence of tunicamycin. Finally, fusion polypeptides obtained through both methods were purified and subjected to the plasminogen activation, thrombin inhibition and protein C activation assays. Plasminogen activation of pichia-derived, on the one hand, and refolded fusion constructs obtained from E. coli IBs, on the other, were essentially the same, but in case of thrombin inhibition and protein C activation the pichia derived EGF_SAK and SAK_EGF polypeptides were only approx. 2-fold more active compared to the E. coli derived protein. The underlying reason viz. methionine oxidation of EGF in presence of oxidizing conditions particularly during the refolding was validated by quantitative amino acid analysis. The oxidation and activity dimunition problem was solved by putting valine in place of methionine by site directed mutagenesis in the EGF section of the hybrids, as described in the earlier Examples, above.

ADVANTAGES OF THE PRESENT INVENTION

The present invention has advantages over anti-thrombin thrombolytics used in the art. In the past, attempts were made to make anti-thrombin thrombolytics where Kringle of tissue plasminogen activator, peptidic sequences containing arginine (R), glycine (G) and aspartic (D), and the anti-thrombin part of hirudin were introduced at the C-terminal of staphylokinase, the premise being that this form of staphylokinase would help in platelet inhibition by the 'RGD peptide', increased fibrin affinity by the tPA derived kringle, and the thrombin inactivating hirudin part conferring the anti-thrombin property through inhibition of the transiently formed thrombin at the early stages (Szemraj, Walkowiak et al. 2005). Efforts were also made to combat re-occlusion problem after thrombolysis through recombinant lipoprotein associated cogulation inhibitors (LACI) to effect inhibition of tissue factor and factor VII (Haskel, Torr et al. 1991). This helps in making inactive complex with tissue factor but cannot thwart transient and clot-bound thrombin.

In this invention, however, strategically designed new-generation thrombolytics which contain plasminogen activation as well as thrombin inhibition properties of both kinds (early-stage transient thrombin, as well as the procoagulant generated Protein C pathway) have been designed and validated.

Presently available medication for myocardial infarction/circulatory diseases require co-administration of heparin, hirudin and other thrombin inhibitors but available/marketed thrombin inhibitors target transiently generated thrombin, and do not inhibit the feed-back generation of thrombin.

In contrast to presently available medication, we have strategically designed new class of improved thrombolytics that perform both the thrombin inhibitory functions simultaneously apart from their plasminogen activation property specificity and thereby help to prevent unwanted side effects during clot lysis without not only not compromising their original properties such as fibrin enhancement (as in case of tPA) but also additional properties (such as plasmin- and thrombin dependent activation in cases where none existed in the 'parent' molecules). In cases where there is non-specific plasminogen activation in the original molecule (as is the case of streptokinase) we have designed hybrid constructs that exhibit clot specificity apart from the antithrombin properties.

In the present invention, we have disclosed non-natural chimeric versions of thrombolytics like streptokinase, staphylokinase and tissue plasminogen activator which contain both fibrinolytic and anti-thrombin potential. The already known 'parent' molecules of these constructs, including the second- and third-generation engineered ones, can dissolve clots but cannot suppress thrombin's activity which is primarily responsible for re-thrombosis. The present constructs not only dissolve the fibrin clots but also directly suppress thrombin and also activate protein C when thrombin shifts the equilibrium through the intrinsic thrombomodulin-catalyzed anticoagulant pathway.

In accordance with the present invention, in one embodiment, EGF 4,5,6 domains were introduced at the different domain junctions within the streptokinase molecule, after placement of suitable linkers, or in place of a natural inter-domain linker. Different active constructs were then selected on the basis of plasminogen activation profile as well as thrombin inhibition properties. Similarly, various muteins of SK fused with the EGF domains in various combinations/motifs were created, expressed and then screened using a simple assay system where functionally surviving chimeras were selected out having the desired properties.

An interesting and useful phenomenon observed in streptokinase (the drug molecule with highest thrombolytic potential) when EGF 4,5,6 was fused at its N-terminal end was that the chimeric construct showed delayed plasminogen activation kinetics and this delayed activation was significantly reduced if small amounts of plasmin were present in the reaction mixture. The serendipitous observation that these chimeric constructs exhibited plasmin-dependent activation (as opposed to 'spontaneous' zymogenic activation of plasminogen by unmodified native streptokinase) also makes the resultant molecules clot specific in that these will be circulating initially in an inactive state (since there is usually no free plasmin in blood, as it is rapidly inactivated by the anti-plasmin serpins) but upon encountering the clot-bound plasmin, will be activated due to its plasmin dependent mechanism of action. This would greatly minimize the hemorrhage risk of SK and confer additional advantages on a widely used drug, besides the one conferred by the functional fusion of the EGF domains.

Other interesting constructs in accordance with the present invention were obtained by the fusion of EGF 4,5,6 domains at the inter-domain junction of alpha (α) and beta (β) domain, on the one hand, and beta (β) and gamma (γ) domains of streptokinase, on the other. Amongst these constructs we found plasminogen activation as well as anti-thrombin activity only where we fused EGF between the alpha and beta domains. Interestingly, the fusion construct where EGF domains were introduced between the beta and gamma domains failed to show any plasmin activity. These results suggest that it is not predictable a priori whether a given domain fusion design will allow the 'parent' properties to co-exist unless actually tested by experimentation.

An advantage that was observed in the N-terminal EGF-SK fusion construct, and N-terminal fusion of EGF domains with truncated SK (residues 5-383) constructs was their clear plasmin dependent activation property apart from thrombin inactivation, which is potentially of great advantage for clot specific thrombolysis and thrombin inactivation.

When EGF 4,5,6 domains were fused with N-terminal and C-terminal regions of staphylokinase, it was observed that the N-terminal part was removed during the 1:1 plasmin complex formation, which is likely to be helpful in the independent function of EGF domain during the lysis as also in generating a high level of clot specificity. In the case of C-terminal EGF fusion, it was found to remain attached to SAK. In both cases, thus, plasminogen activation and anti-thrombotic properties were found to be integrated successfully in the chimeric polypeptides.

Compositions including compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. A biomolecule such as a precursor protein or precursor nucleic acid can be a prodrug.

Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation. The scope of the invention shall be limited only by the claims.

REFERENCES

Aneja, R., M. Datt, et al. (2009). "Identification of a new exosite involved in catalytic turnover by the streptokinase-plasmin activator complex during human plasminogen activation." *J Biol Chem* 284(47): 32642-32650.

Bajaj, A. P. and F. J. Castellino (1977). "Activation of human plasminogen by equimolar levels of streptokinase." *J Biol Chem* 252(2): 492-498.

Boxrud, P. D., I. M. Verhamme, et al. (2004). "Resolution of conformational activation in the kinetic mechanism of plasminogen activation by streptokinase." *J Biol Chem* 279(35): 36633-36641.

Bradford, M. M. (1976). "A rapid and sensitive method for the quantitation of microgram quantities of protein utilizing the principle of protein-dye binding." *Anal Biochem* 72: 248-254.

Buck, F. F., B. C. Hummel, et al. (1968). "Interaction of streptokinase and human plasminogen. V. Studies on the nature and mechanism of formation of the enzymatic site of the activator complex." *J Biol Chem* 243(13): 3648-3654.

Butenas, S. and K. G. Mann (2002). "Blood coagulation." *Biochemistry (Mosc)* 67(1): 3-12.

Cannon, C. P. and R. Tracy (1995). "Clotting for the Clinician: An Overview of Thrombosis and Antithrombotic Therapy." *J Thromb Thrombolysis* 2(2): 95-106.

Castellino, F. J. and J. R. Powell (1981). "Human plasminogen." *Methods Enzymol* 80 Pt C: 365-378.

Collen, D. and H. R. Lijnen (1990). "Molecular mechanisms of thrombolysis: implications for therapy." *Biochem Pharmacol* 40(2): 177-186.

Dahlback, B. and B. O. Villoutreix (2005). "The anticoagulant protein C pathway." *FEBS Lett* 579(15): 3310-3316.

Davidson, D. J., D. L. Higgins, et al. (1990). "Plasminogen activator activities of equimolar complexes of streptokinase with variant recombinant plasminogens." *Biochemistry* 29(14): 3585-3590.

De Renzo, E. C., E. Boggiano, et al. (1967). "Interaction of streptokinase and human plasminogen. IV. Further gel electrophoretic studies on the combination of streptokinase with human plasminogen or human plasmin." *J Biol Chem* 242(10): 2428-2434.

Eisenberg, P. R., J. P. Miletich, et al. (1988). "Differential effects of activation of prothrombin by streptokinase compared with urokinase and tissue-type plasminogen activator (t-PA)." *Thromb Res* 50(5): 707-717.

Esmon, C. T. (1989). "The roles of protein C and thrombomodulin in the regulation of blood coagulation." *J Biol Chem* 264(9): 4743-4746.

Esmon, C. T. and W. G. Owen (1981). "Identification of an endothelial cell cofactor for thrombin-catalyzed activation of protein C." *Proc Natl Acad Sci USA* 78(4): 2249-2252.

Ewald, G. A. and P. R. Eisenberg (1995). "Plasmin-mediated activation of contact system in response to pharmacological thrombolysis." *Circulation* 91(1): 28-36.

Francis, C. W. and V. J. Marder (1991). "Fibrinolytic therapy for venous thrombosis." *Prog Cardiovasc Dis* 34(3): 193-204.

Goyal, D., D. K. Sahoo, et al. (2007). "Hydrophobic interaction expanded bed adsorption chromatography (HI-EBAC)

based facile purification of recombinant streptokinase from *E. coli* inclusion bodies." *J Chromatogr B Analyt Technol Biomed Life Sci* 850(1-2): 384-391.

Grella, D. K. and F. J. Castellino (1997). "Activation of human plasminogen by staphylokinase. Direct evidence that preformed plasmin is necessary for activation to occur." *Blood* 89(5): 1585-1589.

Haskel, E. J., S. R. Torr, et al. (1991). "Prevention of arterial reocclusion after thrombolysis with recombinant lipoprotein-associated coagulation inhibitor." *Circulation* 84(2): 821-827.

Ho, S. N., H. D. Hunt, et al. (1989). "Site-directed mutagenesis by overlap extension using the polymerase chain reaction." *Gene* 77(1): 51-59.

Hogg, P. J. and C. M. Jackson (1989). "Fibrin monomer protects thrombin from inactivation by heparin-antithrombin III: implications for heparin efficacy." *Proc Natl Acad Sci USA* 86(10): 3619-3623.

Huntington, J. A. (2003). "Mechanisms of glycosaminoglycan activation of the serpins in hemostasis." *J Thromb Haemost* 1(7): 1535-1549.

Kumar, R., S. Beguin, et al. (1994). "The influence of fibrinogen and fibrin on thrombin generation—evidence for feedback activation of the clotting system by clot bound thrombin." *Thromb Haemost* 72(5): 713-721.

Kurosawa, S., J. B. Galvin, et al. (1987). "Proteolytic formation and properties of functional domains of thrombomodulin." *J Biol Chem* 262(5): 2206-2212.

Kurosawa, S., D. J. Stearns, et al. (1988). "A 10-kDa cyanogen bromide fragment from the epidermal growth factor homology domain of rabbit thrombomodulin contains the primary thrombin binding site." *J Biol Chem* 263(13): 5993-5996.

Lee, C. D. and K. G. Mann (1989). "Activation/inactivation of human factor V by plasmin." *Blood* 73(1): 185-190.

Lijnen, H. R. and D. Collen (1988). "New strategies in the development of thrombolytic agents." *Blut* 57(4): 147-162.

Liu, C. Y., H. L. Nossel, et al. (1979). "The binding of thrombin by fibrin." *J Biol Chem* 254(20): 10421-10425.

Lougheed, J. C., C. L. Bowman, et al. (1995). "Thrombin inhibition by cyclic peptides from thrombomodulin." *Protein Sci* 4(4): 773-780.

Loy, J. A., X. Lin, et al. (2001). "Domain interactions between streptokinase and human plasminogen." *Biochemistry* 40(48): 14686-14695.

Malke, H. and J. J. Ferretti (1984). "Streptokinase: cloning, expression, and excretion by *Escherichia coli.*" *Proc Natl Acad Sci USA* 81(11): 3557-3561.

McCance, S. G., N. Menhart, et al. (1994). "Amino acid residues of the kringle-4 and kringle-5 domains of human plasminogen that stabilize their interactions with omega-amino acid ligands." *J Biol Chem* 269(51): 32405-32410.

McClintock, D. K. and P. H. Bell (1971). "The mechanism of activation of human plasminogen by streptokinase." *Biochem Biophys Res Commun* 43(3): 694-702.

Mehta, R. K. and J. Singh (1999). "Bridge-overlap-extension PCR method for constructing chimeric genes." *Biotechniques* 26(6): 1082-1086.

Meininger, D. P., M. J. Hunter, et al. (1995). "Synthesis, activity, and preliminary structure of the fourth EGF-like domain of thrombomodulin." *Protein Sci* 4(9): 1683-1695.

Misawa, S. and I. Kumagai (1999). "Refolding of therapeutic proteins produced in *Escherichia coli* as inclusion bodies." *Biopolymers* 51(4): 297-307.

Norden, K., M. Agemark, et al. (2011). "Increasing gene dosage greatly enhances recombinant expression of aquaporins in *Pichia pastoris.*" *BMC Biotechnol* 11(1): 47.

Ohman, E. M., R. M. Califf, et al. (1990). "Consequences of reocclusion after successful reperfusion therapy in acute myocardial infarction. TAMI Study Group." *Circulation* 82(3): 781-791.

Owen, W. G. and C. T. Esmon (1981). "Functional properties of an endothelial cell cofactor for thrombin-catalyzed activation of protein C." *J Biol Chem* 256(11): 5532-5535.

Parry, M. A., X. C. Zhang, et al. (2000). "Molecular mechanisms of plasminogen activation: bacterial cofactors provide clues." *Trends Biochem Sci* 25(2): 53-59.

Puri, R. N., A. Kumar, et al. (1995). "Inhibition of ADP-induced platelet responses by covalent modification of aggregin, a putative ADP receptor, by 8-(4-bromo-2,3-dioxobutylthio) ADP." *J Biol Chem* 270(41): 24482-24488.

Qiu, J., J. R. Swartz, et al. (1998). "Expression of active human tissue-type plasminogen activator in *Escherichia coli.*" *Appl Environ Microbiol* 64(12): 4891-4896.

Ramchuran, S. O., B. Mateus, et al. (2005). "The methylotrophic yeast *Pichia pastoris* as a host for the expression and production of thermostable xylanase from the bacterium *Rhodothermus marinus.*" *FEMS Yeast Res* 5(9): 839-850.

Riener, C. K., G. Kada, et al. (2002). "Quick measurement of protein sulfhydryls with Ellman's reagent and with 4,4'-dithiodipyridine." *Anal Bioanal Chem* 373(4-5): 266-276.

Salem, H. H., I. Maruyama, et al. (1984). "Isolation and characterization of thrombomodulin from human placenta." *J Biol Chem* 259(19): 12246-12251.

Sazonova, I. Y., A. K. Houng, et al. (2001). "The mechanism of a bacterial plasminogen activator intermediate between streptokinase and staphylokinase." *J Biol Chem* 276(16): 12609-12613.

Schaller, J. and S. S. Gerber (2011). "The plasmin-antiplasmin system: structural and functional aspects." *Cell Mol Life Sci* 68(5): 785-801.

Sharma, R. C. and R. T. Schimke (1996). "Preparation of electrocompetent *E. coli* using salt-free growth medium." *Biotechniques* 20(1): 42-44.

Stearns, D. J., S. Kurosawa, et al. (1989). "Microthrombomodulin. Residues 310-486 from the epidermal growth factor precursor homology domain of thrombomodulin will accelerate protein C activation." *J Biol Chem* 264(6): 3352-3356.

Szemraj, J., B. Walkowiak, et al. (2005). "A new recombinant thrombolytic and antithrombotic agent with higher fibrin affinity—a staphylokinase variant. I. In vitro study." *J Thromb Haemost* 3(10): 2156-2165.

Vali, Z. and H. A. Scheraga (1988). "Localization of the binding site on fibrin for the secondary binding site of thrombin." *Biochemistry* 27(6): 1956-1963.

van Zonneveld, A. J., H. Veerman, et al. (1986). "Autonomous functions of structural domains on human tissue-type plasminogen activator." *Proc Natl Acad Sci USA* 83(13): 4670-4674.

Verheijen, J. H., E. Mullaart, et al. (1982). "A simple, sensitive spectrophotometric assay for extrinsic (tissue-type) plasminogen activator applicable to measurements in plasma." *Thromb Haemost* 48(3): 266-269.

Verstraete, M. (1990). "Thrombolytic treatment in acute myocardial infarction." *Circulation* 82(3 Suppl): I196-109.

Wang, W. and B. A. Malcolm (1999). "Two-stage PCR protocol allowing introduction of multiple mutations, deletions and insertions using QuikChange Site-Directed Mutagenesis." *Biotechniques* 26(4): 680-682.

Wang, X., X. Lin, et al. (1998). "Crystal structure of the catalytic domain of human plasmin complexed with streptokinase." *Science* 281(5383): 1662-1665.

Wang, X., J. Tang, et al. (1999). "Crystal structure of streptokinase beta-domain." *FEBS Lett* 459(1): 85-89.

Weitz, J. I., M. Hudoba, et al. (1990). "Clot-bound thrombin is protected from inhibition by heparin-antithrombin III but is susceptible to inactivation by antithrombin III-independent inhibitors." *J Clin Invest* 86(2): 385-391.

Weitz, J. I., B. Leslie, et al. (1998). "Thrombin binds to soluble fibrin degradation products where it is protected from inhibition by heparin-antithrombin but susceptible to inactivation by antithrombin-independent inhibitors." *Circulation* 97(6): 544-552.

Wohl, R. C., L. Sinio, et al. (1983). "Comparative activation kinetics of mammalian plasminogens." *Biochim Biophys Acta* 745(1): 20-31.

Wohl, R. C., L. Summaria, et al. (1978). "Steady state kinetics of activation of human and bovine plasminogens by streptokinase and its equimolar complexes with various activated forms of human plasminogen." *J Biol Chem* 253(5): 1402-1407.

Yadav, S. and G. Sahni (2010). "Probing the primary structural determinants of streptokinase inter-domain linkers by site-specific substitution and deletion mutagenesis." *Biochim Biophys Acta* 1804(9): 1730-1737.

Ye, Q., M. N. Rahman, et al. (2001). "High-resolution crystal structure of apolipoprotein(a) kringle IV type 7: insights into ligand binding." *Protein Sci* 10(6): 1124-1129.

Zhang, T., X. Xu, et al. (2009). "Modeling of protein refolding from inclusion bodies." *Acta Biochim Biophys Sin (Shanghai)* 41(12): 1044-1052.

We claim:

1. A chimeric protein construct comprising streptokinase produced by *Streptococcus equisimilis*, or a streptokinase homolog with at least 90% homology to the amino acid sequence of SEQ ID NO: 112, and further comprising the 4, 5, and 6 epidermal growth factor-like domains (EGF 4,5,6) of thrombomodulin.

2. The chimeric protein construct according to claim 1, where said thrombomodulin EGF 4,5,6 domains are present at the N-terminus, C-terminus, or both N- and C-termini of said streptokinase or said streptokinase homolog.

3. The chimeric protein construct according to claim 2 wherein said construct comprises a sequence with at least 90% homology to SEQ ID NO: 111 and wherein the Met 41 of the EGF 4,5,6 domains of SEQ ID NO: 111 is replaced by either valine, alanine, or glutamine; or the C-terminal Met 435 of SEQ ID NO: 111 is replaced by valine, alanine, or glutamine; or in the simultaneous N- and C-terminal fusion constructs, Met 41 and Met 435 are independently replaced by either valine, alanine, or glutamine.

4. The chimeric protein construct according to claim 1, wherein said construct possesses plasmin-dependent plasminogen activation, thrombin inhibition, and anticoagulant protein C pathway activation activity.

5. The chimeric protein construct according to claim 1, wherein the streptokinase homolog spans residues 5-383 or 5-414 of SEQ ID NO: 112.

6. The chimeric protein construct according to claim 1, wherein the streptokinase homolog spans residues 16-383 of SEQ ID NO: 112.

7. The chimeric protein construct according to claim 1 further comprising at least one transglutaminase recognition sequence.

8. The chimeric protein construct according to claim 1 further comprising one or more thrombin cleavable sequences at the junction of the EGF 4,5,6 domain and streptokinase or said streptokinase homolog.

9. The chimeric protein construct according to claim 1, wherein said constructs are soluble in aqueous or saline solution.

10. The chimeric construct according to claim 1 that is prepared by expression in a bacterial system.

11. The chimeric construct according to claim 1 that is prepared by expression in a eukaryotic system.

12. The chimeric construct according to claim 11, wherein the eukaryotic expression system is selected from the group consisting of an animal cell and a yeast cell.

13. The chimeric protein construct according to claim 12 wherein the chimeric protein construct is secreted into an extracellular medium.

14. The chimeric construct according to claim 12, wherein the yeast cell is *Pichia pastoris*.

15. The chimeric protein construct according to claim 1 that is prepared by expression of a nucleic acid sequence encoding said protein in a host cell expression system.

16. The chimeric construct according to claim 1, wherein the chimeric construct is encoded by a nucleic acid sequence selected from SEQ ID NOS: 4, 6, and 7.

17. The chimeric protein construct of claim 1, wherein said protein construct comprises an amino acid sequence at least 90% identical to the amino acid sequence of SEQ ID NO: 113.

18. The chimeric protein construct of claim 17, wherein said protein construct comprises an amino acid sequence at least 95% identical to the amino acid sequence of SEQ ID NO: 113.

19. The chimeric protein construct of claim 18, wherein said protein construct comprises the amino acid sequence of SEQ ID NO: 113.

20. The chimeric protein construct of claim 19, wherein said protein construct consists of the amino acid sequence of SEQ ID NO:113.

21. A nucleic acid sequence encoding a chimeric protein construct according to claim 1.

22. A vector comprising a nucleic acid sequence of claim 21.

23. A host cell comprising a vector of claim 22.

24. A chimeric protein construct of streptokinase in combination with the 4, 5, and 6 epidermal growth factor-like domains (EGF 4,5,6) of thrombomodulin, said construct comprising an amino acid sequence with at least 90% homology to the amino acid sequence of SEQ ID NO:113.

25. The chimeric protein construct according to claim 24, wherein said construct comprises the amino acid sequence of SEQ ID NO:113.

26. The chimeric protein construct according to claim 24, further comprising at least one transglutaminase recognition sequence.

27. The chimeric protein construct according to claim 24, further comprising one or more thrombin cleavable sequences at the junction of streptokinase and the EGF 4,5,6 domain.

28. The chimeric protein construct according to claim 24, wherein said construct is soluble in aqueous or saline solution.

29. The chimeric protein construct according to claim 24, prepared by expression in a bacterial system.

30. The chimeric protein construct according to claim 24, prepared by expression in a eukaryotic system.

31. The chimeric construct according to claim 30, wherein the yeast cell is *Pichia pastoris*.

32. The chimeric construct according to claim 30, wherein the eukaryotic expression system is selected from the group consisting of an animal cell and a yeast cell.

33. The chimeric protein construct according to claim 30, wherein the chimeric protein construct is secreted into an extracellular medium.

34. The chimeric protein construct according to claim 24, prepared by expression of a nucleic acid sequence encoding said protein in a host cell expression system.

35. A nucleic acid sequence encoding the chimeric protein construct of claim 24.

36. A vector comprising the nucleic acid sequence of claim 35.

37. A host cell comprising the vector of claim 36.

38. A nucleic acid encoding a chimeric protein construct, said nucleic acid comprising a nucleic acid sequence with at least 90% identity to a nucleic acid sequence selected from SEQ ID NOS: 4, 6, and 7.

* * * * *